United States Patent
Kim et al.

(10) Patent No.: US 9,834,550 B2
(45) Date of Patent: Dec. 5, 2017

(54) PYRIDOPYRIMIDINONE COMPOUNDS FOR MODULATING THE CATALYTIC ACTIVITY OF HISTONE LYSINE DEMETHYLASES (KDMS)

(71) Applicant: Dong-A Socio Holdings Co., Ltd., Seoul (KR)

(72) Inventors: Myeong-seop Kim, Suwon (KR); Taesun Park, Yongin (KR); Taeyoung Yoon, Seoul (KR); Seung Min Yang, Yongin (KR); Hae-Sun Kim, Yongin (KR); Jun Gyu Kim, Seoul (KR)

(73) Assignee: DONG-A ST CO., LTD., Seoul (KR)

( * ) Notice: Subject to any disclaimer, the term of this patent is extended or adjusted under 35 U.S.C. 154(b) by 0 days.

(21) Appl. No.: 14/923,525

(22) Filed: Oct. 27, 2015

(65) Prior Publication Data
US 2016/0122343 A1 May 5, 2016

Related U.S. Application Data

(60) Provisional application No. 62/069,915, filed on Oct. 29, 2014.

(51) Int. Cl.
*A61K 31/519* (2006.01)
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................. C07D 471/04
See application file for complete search history.

(56) References Cited

U.S. PATENT DOCUMENTS

| | | | |
|---|---|---|---|
| 7,361,662 | B2 | 4/2008 | Rault |
| 2014/0371214 | A1 | 12/2014 | Labelle |

FOREIGN PATENT DOCUMENTS

| | | | |
|---|---|---|---|
| CN | 103694255 | * | 4/2014 |
| WO | 00-64424 | | 11/2000 |
| WO | 2007-117161 | | 10/2007 |
| WO | 2013-012915 | | 1/2013 |
| WO | 2014-052699 | | 4/2014 |
| WO | 2014/053491 | | 4/2014 |
| WO | 2014/055634 | | 4/2014 |
| WO | 2014-087165 | | 6/2014 |
| WO | 2014/139326 | | 9/2014 |
| WO | 2014/151106 | | 9/2014 |
| WO | 2014/164708 | | 9/2014 |
| WO | 2015/035062 | | 3/2015 |
| WO | 2015-148597 | | 10/2015 |

OTHER PUBLICATIONS

Shilatifard, "Chromatin Modifications by Methylation and Ubiquitination: Implications in the Regulation of Gene Expression", A. Annu. Rev. Biochem., Feb. 22, 2006, 75, 243-269.
Martin, C. and Zhang, Y. "The Diverse Functions of Histone Lysine Methylation", Nat. Rev. Mol. Cell Biol., Nov. 2005, 6, 838-849.
Spannhoff, A. et al. "The Emerging Therapeutic Potential of Histone Methyltransferase and Demethylase Inhibitors", ChemMedChem, Oct. 2009, 4, 1568-1582.
Cloos, P. A. et al. "Erasing the methyl mark: histone demethylases at the center of cellular differentiation and disease", Genes Dev., May 1, 2008, 22, 1115-1140.
Scoumanne, A. and Chen X. J., "The Lysine-specific Demethylase 1 Is Required for Cell Proliferation in Both p53-dependent and-independent Manners", Biol. Chem., Apr. 4, 2007, 282, 15471-15475.
Tzatsos, A. et al., "KDM2B promotes pancreatic cancer via Polycomb-dependent and -independent transcriptional programs", J. Clin. Invest., Feb. 1, 2013, 123, 727-739.
Liu, G. et al., "Genomic amplification and oncogenic properties of the GASC1 histone demethylase gene in breast cancer", Oncogene, Dec. 17, 2009, 28, 4491-4500.
Wissmann, M. et al., "Cooperative demethylation by JMJD2C and LSD1 promotes androgen receptor-dependent gene expression", NatureCell Biol., Mar. 2007, 9, 347-353.
Zeng, J. et al., "The Histone Demethylase RBP2 Is Overexpressed in Gastric Cancer and Its Inhibition Triggers Senescence of Cancer Cells", Gastroenterology, Mar. 2010, 138, 981-992.
Hidalgo, A. et al., "Microarray comparative genomic hybridization detection of chromosomal imbalances in uterine cervix carcinoma", BMC Cancer, Jul. 9, 2005, 5, 77.
Lu, P. J. et al., "A Novel Gene (PLU-1) Containing Highly Conserved Putative DNA/Chromatin Binding Motifs Is Specifically Up-regulated in Breast Cancer", J. Biol. Chem., May 28, 1999, 274, 15633-15645.
Xiang, Y. et al., "JARID1B is a histone H3 lysine 4 demethylase up-regulated in prostate cancer", Proc. Natl. Acad. Sci. USA, Dec. 4, 2007, 104, 19226-19231.
Hayami, S. et al., "Overexpression of the JmjC histone demethylase KDM5B in human carcinogenesis: involvement in the proliferation of cancer cells through the E2F/RB pathway", Mol. Cancer, Mar. 13, 2010, 9, 59.

(Continued)

*Primary Examiner* — Brian McDowell
(74) *Attorney, Agent, or Firm* — Lex IP Meister, PLLC

(57) ABSTRACT

The present invention provides a compound of Formula (I) being capable of modulating the activity of histone lysine demethylase (KDM), pharmaceutical compositions thereof, methods to prepare the said compounds, and the use of such compounds as a medicament. The compound of Formula (I) acts as KDM inhibitor with marked potency, thereby having an outstanding potential for a pharmaceutical intervention of cancer and any other diseases related to KDM dysregulation.

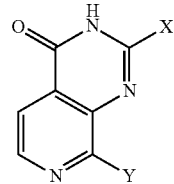

<Formula (I)>

5 Claims, 1 Drawing Sheet

(56) References Cited

OTHER PUBLICATIONS zur Hausen, H., "Papillomaviruses in the causation of human cancers—a brief historical account", Virilogy, Jan. 8, 2009, 384, 260-265.
Sharma, S. et al., "A Chromatin-Mediated Reversible Drug-Tolerant State in Cancer Cell Subpopulations", Cell, Apr. 2, 2010, 141, 69-80.
Roesch, A. et al., "Overcoming Intrinsic Multidrug Resistance in Melanoma by Blocking the Mitochondrial Respiratory Chain of Slow-Cycling JARID1Bhigh Cells", Cancer Cell, Jun. 10, 2013, 23, 811-825.
Dalgliesh, G. L. et al., "Systematic sequencing of renal carcinoma reveals inactivation of histone modifying genes", Nature, Jan. 21, 2010, 463, 360-363.
Perinchery, G. et al., "Deletion of Y-Chromosome Specific Genes in Human Prostate Cancer", J. Urol., Apr. 2000, 163, 1339-1342.
Arteaga, M. F. et al., "The Histone Demethylase PHF8 Governs Retinoic Acid Response in Acute Promyelocytic Leukemia", Cancer Cell, Mar. 18, 2013, 23, 376-389.
He, J. et al., "KDM2b/JHDM1b, an H3K36me2-specific demethylase, is required for initiation and maintenance of acute myeloid leukemia", Blood, Apr. 7, 2011, 117, 3869-3880.
Hayakawa, M. et al., "Synthesis and biological evaluation of 4-morpholino-2-phenylquinazolines and related derivatives as novel P13 kinase p110α inhibitors", Bioorganic & Medicinal Chemistry, [Epub.] Jul. 11, 2006, vol. 14, pp. 6847-6858. See p. 6849, compound 13d.
Chemical Abstract compounds, STN express. RN 1437483-85-6(Entered STN: Jun. 13, 2013), RN 1437481-06-5 (Entered STN: Jun. 13, 2013), RN 1437434-95-1(Entered STN: Jun. 13, 2013), RN 1437433-79-8(Entered STN: Jun. 13, 2013).
Kumpan, K. et al., "Structure-based design, synthesis and evaluation in vitro of arylnaphthyridinones, arylpyridopyrimidinones and their tetrahydro derivatives as inhibitors of the tankyrases", Bioorganic & Medicinal Chemistr, [Epub.] May 13, 2015, vol. 23, pp. 3013-3032. See abstract; and p. 3017, scheme 3, compounds 15a,b,d, 16a,b,d,e.
Patent Cooperation Treaty, International Search Report, PCT/KR2015/011386, dated Oct. 27, 2015.
Patent Cooperation Treaty, Written Opinion of the International Searching Authority, PCT/KR2015/011386, dated Oct. 27, 2015.

* cited by examiner

PYRIDOPYRIMIDINONE COMPOUNDS FOR MODULATING THE CATALYTIC ACTIVITY OF HISTONE LYSINE DEMETHYLASES (KDMS)

CROSS REFERENCE TO RELATED APPLICATION

This application claims the benefit of U.S. Provisional Application Ser. No. 62/069,915, filed on Oct. 29, 2014, the contents of which are incorporated by reference herein in their entireties.

TECHNICAL FIELD

The present invention provides compounds that are capable of modulating the activity of histone lysine demethylase (KDM), pharmaceutical compositions thereof, methods to prepare the said compounds, and the use of such compounds as a medicament.

BACKGROUND

The nucleosome is a basic unit to build up the extremely complicating chromatin structure inside the cells of eukaryotes. In the nucleosome, the genomic DNA is wrapped around a histone octamer which is composed of two copies of four different core histone subunits, H2A, H2B, H3 and H4. Mutations in the genomic DNA sequence could cause aberrant expressions of essential proteins that are required to maintain homeostasis of life, leading to serious illness such as birth defects, diabetes, neurological disorders and cancer. However, it has been shown for the past few decades that, even without the sequence alterations, the production and biological functions of the proteins can also be perturbed by newly termed "epigenetic" changes in the genomic DNA and histones. DNA methylation and histone post-translational modifications are two major epigenetic events that are commonly occurred in most of living organisms. In humans, about 70% of cytosines within CpG dinucleotides are usually methylated and the N-terminal tails of the histones are subjected to several covalent modifications including methylation, acetylation, phophorylation, ubiquitination and sumoylation (Shilatifard, A. *Annu. Rev. Biochem.* (2006) 75, 243-269). At some specific lysine residues of the histones, one, two or three methyl groups can be added or removed by two distinct classes of enzymes, histone methyltransferases (HMTs) and histone demethylases (KDMs), respectively. These methylation states play an essential role in regulating gene expression in a context-dependent manner. For instance, di/tri methylation on the lysine 4, 36 or 79 of the histone H3 is generally attributed to an active mark for gene expression. In contrast, di/tri methylation on the lysine 9, 27 of the H3 is usually linked with a closed chromatin conformation (heterochromatin), leading to repression of gene expression (Martin, C. & Zhang, Y *Nat. Rev. Mol. Cell Biol.* (2005) 6, 838-849).

More than 30 KDMs have been found in mammals and KDMs can be classified into two families based on the underlying mechanism by which they remove methyl groups from the histone tails; LSD1 (lysine specific demethylase 1) and JmjC-containing KDMs. LSD1, the first hisone demethylase discovered in 2004, erases mono- and di-methyl marks on the H3K4 and H3K9 using flavin as a cofactor. As a protonated amine in the substrate is required for its demethylation pathway, LSD1 cannot act on tri-methylated lysines. The existence of different class of KDMs that could remove a trimethyl mark was, therefore, predicted and identified later as catalytic JmjC-domain containing proteins. Compared with LSD1, these proteins contain much more diverse subfamilies including KDM2, KDM3, KDM4, KDM5, KDM6 and PHF2/8, all of which utilize Fe(II) and α-ketoglutarate (αKG) as cofactors (Spannhoff, A. et al. *ChemMedChem* (2009) 4, 1568-1582)

Many studies have shown that KDMs are implicated in the etiology of cancer, one of the most devastating human diseases (Cloos, P. A. et al. *Genes Dev.* (2008) 22, 1115-1140). LSD1 is overexpressed in various types of cancer cells including prostate, lung and breast cancer in which LSD1 may enhance oncogenic properties of the cells by modulating the expression of pro-survival genes and tumor suppressor genes such as p53 (Scoumanne, A. & Chen X. *J. Biol. Chem.* (2007) 282, 15471-15475)

Small hairpin RNA (shRNA)-mediated depletion of KDM2B (also known as FBXL10) attenuated the growth of acute myeloid leukemia (AML) cell line, in which KDM2B is overexpressed (He, J. et al. *Blood* (2011) 117, 3869-3880). Alterations in the expression of Polycomb target genes may account for this anti-proliferative effect on the basis of a recent finding that KDM2B regulated the expression (Tzatsos, A. et al. *J. Clin. Invest.* (2013) 123, 727-739).

Initially identified as a putative oncogene GASC1 (gene amplified in squamous cell carcinoma 1), KDM4C, which removes di- and tri-methyl marks from H3K9 as well as H3K36, is genomically amplified in breast carcinoma and prostate carcinoma and required for the growth of these malignant cells (Liu, G. et al. *Oncogene* (2009) 28, 4491-4500; Wissmann, M. et al. *Nature Cell Biol.* (2007) 9, 347-353).

The family of KDM5/JARID1 (Jumonji AT-rich interactive domain 1) in human comprises four members, KDM5A/RBP2, KDM5B/PLU-1, KDM5C/SMCX and KDM5D/SMCY, which share highly conserved structural motifs that include a JmjN domain, a catalytic JmjC domain, an ARID DNA binding domain, a zinc finger and two to three PHD (plant homeodomain) fingers. These subfamily members are shown to be involved in the pathogenesis of cancer.

Aberrantly high expression of KDM5A is often found in gastric and cervical cancers (Zeng, J. et al. *Gastroenterology* (2010), 138, 981-992; Hidalgo, A. et al. *BMC Cancer* (2005) 5, 77), and KDM5B is also up-regulated in several malignancies such as breast, prostate, lung cancers and melanoma (Lu, P. J. et al. *J. Biol. Chem.* (1999) 274, 15633-15645; Xiang, Y. et al. *Proc. Natl. Acad. Sci. USA* (2007) 104, 19226-19231; Hayami, S. et al. *Mol. Cancer* (2010) 9, 59; zur Hansen, H. *Virilogy* (2009) 384, 260-265). Acquired drug resistance in cancer is often linked to the presence of cancer stem cells which are capable of reforming tumor cells. Recent studies demonstrated that, in drug-resistant lung cancer cells and melanoma cells, disruption of KDM5A or KDM5B enzymatic function by RNA interference reduced the cancer stem cell-like properties and increased drug sensitivity, thus exerting an anti-proliferative effect on those cells (Sharma, S. et al. *Cell* (2010) 141, 69-80; Roesch, A. et al. *Cancer Cell* (2013) 23, 811-825).

KDM5C seems to be associated with mental retardation and some forms of cancer. Gene expression analysis for clear cell renal cell carcinoma (ccRCC) revealed that truncation mutation of KDM5C was found in 3% of ccRCC tumors and most of the mutation was occurred concomitantly with VHL (Von Hippel-Lindau tumor suppressor) mutations (Dalgliesh, G. L. et al. *Nature* (2010) 463, 360-363).

Although direct linkage between KDM5D and cancer has yet to be known, one study shows that 52% of tested prostate cancer cases contain deletion of KDM5D gene, implying an association of KDM5D with the disease (Perinchery, G. et al. *J. Urol.* (2000) 163, 1339-1342).

Similar to KDM5A and KDM5B, KDM7B (also known as PHF8) enzymatically active on H3K9me1/2 and H4K20me1 is exhibited to govern an anti-cancer drug (retinoic acid) response in acute promyelocytic leukemia (Arteaga, M. F. et al. *Cancer Cell* (2013) 23, 376-389).

Taken together, deregulation of KDM is involved in initiation, maintenance, progression and other pathogenesis of cancer, suggesting KDM is a very promising therapeutic target for the intervention of the disease. The present invention is directed to KDM inhibitory compounds with marked potency, thereby having an outstanding potential for a pharmaceutical intervention of cancer and any other diseases related to KDM dysregulation.

INFORMATION DISCLOSURE

Several kinase inhibitory compounds containing an aminopyridine scaffold have been previously described in the publication US 2008/7361662B2, but they have different moieties onto the scaffold from the present invention. To date, no compound of this class has been approved for anti-cancer therapy in human. Several KDM-inhibitory compounds have been previously described in the publications WO 2014/055634, US 2014/0371214, WO 2014/053491, WO 2014/139326, WO 2014/151106, WO 2014/164708 and WO 2015/035062, but they are chemically and structurally different compounds from the present invention.

SUMMARY OF THE INVENTION

Accordingly, a first aspect of the present invention relates to a compound of the Formula (I)

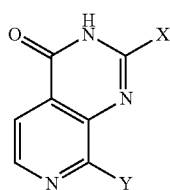

Formula (I)

wherein,

X is selected from the group consisting of hydrogen, cycloalkyl, heterocyclyl, aryl, heteroaryl, —CH($R^1$)NH—$R^2$ and —CH($R^1$)O—$R^2$, which cycloalkyl, heterocyclyl, aryl and heteroaryl may optionally be substituted with one or more $R^3$;

Y is absent or —CH$_2$NH-A-Z—;

A is selected from the group consisting of a single bond, $C_{1-8}$ alkylene, $C_{2-8}$ alkenylene, $C_{2-8}$ alkynylene, $C_{3-10}$ cycloalkylene, heterocyclylene, —C(=O)— and —CH($R^3$)C(=O)—, which alkylene, alkenylene, alkynylene, cycloalkylene and heterocyclylene may optionally be substituted with one or more $R^4$;

Z is selected from the group consisting of hydrogen, —N($R^4$)($R^5$), $C_{1-8}$ alkyl, $C_{2-8}$ alkenyl, $C_{2-8}$ alkynyl, $C_{3-10}$ cycloalkyl, heterocyclyl, aryl, arylalkyl and heteroaryl, which alkyl, alkenyl, alkynyl, cycloalkyl, heterocyclyl, aryl, arylalkyl and heteroaryl may optionally be substituted with one or more $R^3$;

$R^1$ is selected from the group consisting of hydrogen, $C_{1-8}$ alkyl, $C_{1-4}$ aminoalkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, arylalkyl, heterocyclyl and heteroarylalkyl, which heterocyclyl may optionally be substituted with one or more selected from the group consisting of halogen and $C_{1-8}$alkyl;

$R^2$ is selected from the group consisting of aryl, arylalkyl and heteroaryl, which aryl, arylalkyl and heteroaryl may optionally be substituted with one or more selected from hydrogen, halogen, $C_{1-8}$ alkyl, $C_{2-8}$ alkenyl, $C_{2-8}$ alkynyl, $C_{3-10}$ cycloalkyl, —CF$_3$, —CN, —NO$_2$, —C(=O)—O($R^4$), —C(=O)—N($R^4$)($R^5$), —O($R^4$), —OCF$_3$, —S($R^4$), —SO$_3$, —SO$_2$($R^4$), —N($R^4$)($R^5$), $C_{1-8}$ alkoxy$C_{1-8}$ alkyl, —$C_{1-8}$ alkyl-C(=O)$R^4$, —C(=O)$R^4$, —$C_{1-8}$ alkyl-$R^4$, —NH—C(=O)$R^4$ and —$C_{1-8}$alkyl-NR$^4$R$^5$;

$R^3$ is selected from the group consisting of hydrogen, $C_{1-8}$ alkyl, $C_{1-4}$ aminoalkyl, $C_{1-4}$ hydroxyalkyl, $C_{2-8}$ alkenyl, $C_{2-8}$ alkynyl, $C_{3-10}$ cycloalkyl, oxo, C(=O)—O($R^4$), —C(=O)—N($R^4$)($R^5$)—O($R^4$), —S($R^4$), —SO$_2$($R^4$) and —N($R^4$)($R^5$); or, alternatively two vicinal substituents are forming aryl or heteroaryl ring, which is substituted with one or more $R^4$.

$R^4$ or $R^5$ is independently selected from the group consisting of hydrogen, $C_{1-6}$ alkyl, $C_{1-4}$ aminoalkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, cycloalkylalkyl, heterocyclyl, heterocyclylalkyl, heteroarylalkyl and arylalkyl, which alkyl, alkenyl, alkynyl, cycloalkyl, heterocyclyl, heteroaryl, aryl, cycloalkylalkyl, heterocyclylalkyl, heteroarylalkyl and arylalkyl may optionally be substituted with one or more independently selected $R^1$; or, alternatively germinal $R^4$ and $R^5$ are forming N-containing heterocyclyl, which is substituted with one or more $R^1$.

BRIEF DESCRIPTION OF THE DRAWINGS

In FIG. 1, Reference refers to 8-(((piperidin-4-ylmethyl)amino)methyl)pyrido[3,4-d]pyrimidin-4(3H)-one.

In FIG. 2, Nicotinic Acid means 2-((((1-benz ylpiperidin-4-yl)methyl)amino)methyl)isonicotinic acid

DETAILED DESCRIPTION

Figure 1:
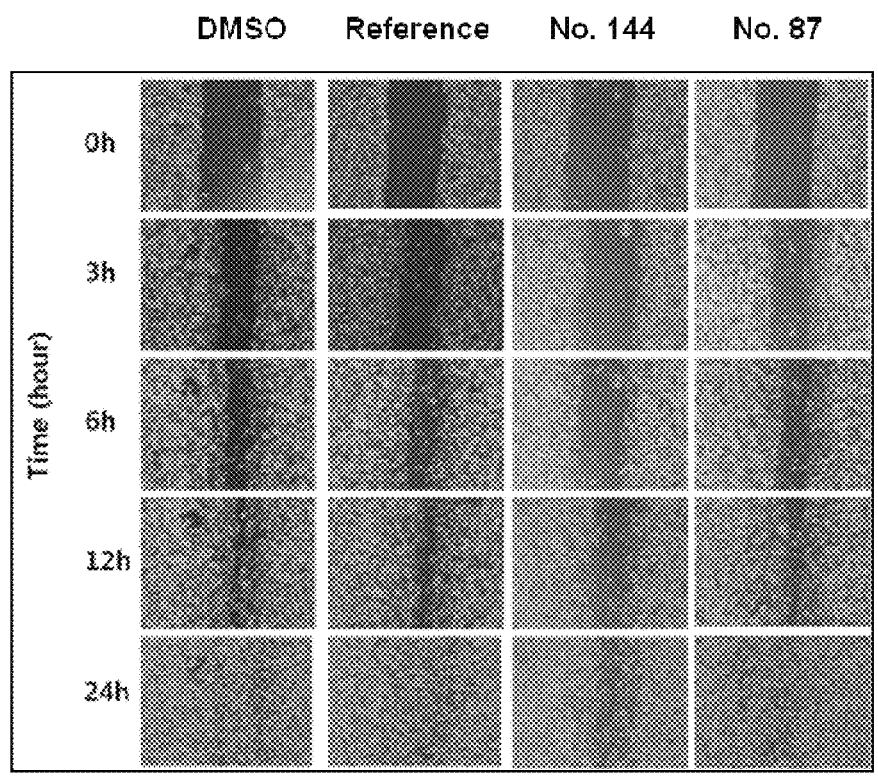
FIG. 1 is the microscopic photo for showing the results of wound healing assay of the present compounds.

The term 'halogen' as used herein refers to fluorine, chlorine, bromine or iodine.

The term 'alkyl' as used herein refers to a straight chain or branched chain hydrocarbon residue, unless otherwise stated. The examples of the C1-8 alkyl include methyl, ethyl, propyl, isopropyl, butyl, isobutyl, pentyl, hexyl, heptyl, octyl and the like.

The term 'alkoxy' as used herein includes an alkyl-oxygen radical having alkyl as defined above, unless otherwise stated. The examples of the $C_{1-8}$alkoxy include methoxy, ethoxy, propoxy, butoxy, pentoxy, and the like.

The term 'heterocycle' or 'heterocyclic' as used herein refers to a 4 to 13 membered non-aromatic compound including 1 to 3 hetero atoms selected from the group consisting of N, O and S, unless otherwise stated.

The term 'heteroaryl' as used herein refers to a 4 to 13 membered heteroaromatic compound including 1 to 3 hetero atoms selected from the group consisting of N, O and S, unless otherwise stated.

The term 'aryl' as used herein refers to a $C_{6-12}$ aromatic compound, unless otherwise stated.

In a preferred embodiment of the present invention, X is selected from hydrogen, $C_{3-8}$ cycloalkyl, 4 to 10-membered heterocyclyl having 1 to 3 hetero atoms selected from the group consisting of N, O and S, phenyl, 4 to 10-membered heteroaryl having 1 to 3 hetero atoms selected from the group consisting of N, O and S, —CH($R^1$)NH—$R^2$ and CH($R^1$)O—$R^2$, which heterocyclyl may optionally be substituted with $R^3$;

In a preferred embodiment of the present invention, A is selected from the group consisting of a single bond, $C_{1-8}$ alkylene, $C_{2-8}$ alkenylene, $C_{2-8}$ alkynylene, $C_{3-10}$ cycloalkylene, heterocyclylene, —C(=O)— and —CH($R^3$)C(=O)—, which alkylene, alkenylene, alkynylene, cycloalkylene and heterocyclylene may optionally be substituted with one or more $R^4$;

In a preferred embodiment of the present invention, Z is selected from the group consisting of hydrogen, —N($R^4$)($R^5$), $C_{1-6}$ alkyl, $C_{2-6}$ alkenyl, $C_{2-6}$ alkynyl, $C_{3-8}$ cycloalkyl, aryl, arylalkyl, phenyl, 4 to 10-membered heterocyclyl having 1 to 3 hetero atoms selected from the group consisting of N, O and S and 4 to 10-membered heteroaryl having 1 to 3 hetero atoms selected from the group consisting of N, O and S, which alkyl, alkenyl, alkynyl, cycloalkyl, heterocyclyl, heteroaryl and aryl may optionally be substituted independently with one or more $R^3$;

In a preferred embodiment of the present invention, $R^1$ is selected from the group consisting of hydrogen, $C_{1-6}$ alkyl, $C_{1-3}$ aminoalkyl, $C_{1-3}$ fluoroalkyl, $C_{1-3}$ hydroxyalkyl, $C_{2-6}$ alkenyl, $C_{2-6}$ alkynyl, $C_{3-8}$ cycloalkyl, benyzyl, 4-10 membered heteroarylalkyl and 4-10 membered heterocyclyl having 1 to 3 hetero atoms selected from the group consisting of N, O and S, which heteroarylalkyl, and heterocyclyl may optionally be substituted with one or more independently selected from the group consisting of halogen and $C_{1-6}$alkyl;

In a preferred embodiment of the present invention, $R^2$ is selected from the group consisting of phenyl, benzyl or 4-10 membered heteroaryl having 1 to 3 hetero atoms selected from the group consisting of N, O or S, which phenyl, benzyl and heteroaryl may optionally be substituted with one or more independently selected from hydrogen, halogen, $C_{1-6}$ alkyl, $C_{2-6}$ alkenyl, $C_{2-6}$ alkynyl, $C_{3-8}$ cycloalkyl, —$CF_3$, —CN, —$NO_2$, —C(=O)—O($R^4$), —C(=O)—N($R^4$)($R^5$), —O($R^4$), —$OCF_3$, —S($R^4$), —$SO_3$, —$SO_2$($R^4$), —N($R^4$)($R^5$), $C_{1-6}$alkoxy$C_{1-6}$alkyl, —$C_{1-6}$alkyl-C(=O)$R^4$, —C(=O)$R^4$, —$C_{1-6}$alkyl-$R^4$, —NH—C(=O)$R^4$ and —$C_{1-6}$alkyl-N$R^4R^5$;

In a preferred embodiment of the present invention, $R^3$ is selected from the group consisting of hydrogen, $C_{1-6}$ alkyl, $C_{1-4}$ aminoalkyl, $C_{1-4}$ hydroxyalkyl, $C_{2-6}$ alkenyl, $C_{2-6}$ alkynyl, $C_{3-8}$ cycloalkyl, oxo, C(=O)—O($R^4$), —C(=O)—N($R^4$)($R^5$)—O($R^4$), —S($R^4$), —$SO_2$($R^4$) and —N($R^4$)($R^5$); or, alternatively two vicinal substituents are forming phenyl or 4-10 membered heteroaryl ring, which is substituted with one or more $R^4$;

In a preferred embodiment of the present invention, $R^4$ or $R^5$ is independently selected from the group consisting of hydrogen, $C_{1-6}$ alkyl, $C_{1-4}$ aminoalkyl, $C_{1-4}$ fluoroalkyl, $C_{1-4}$ hydroxyalkyl, $C_{2-6}$ alkenyl, $C_{2-6}$ alkynyl, $C_{3-8}$ cycloalkyl, $C_{3-8}$ cycloalkyl$C_{1-4}$ alkyl, 4-10 membered heterocyclyl having 1 to 3 hetero atoms selected from the group consisting of N, O and S, 4-10 membered heterocyclyl $C_{1-4}$ alkyl having 1 to 3 hetero atoms selected from the group consisting of N, O and S, 4-10 membered heteroarylalkyl $C_{1-4}$ alkyl having 1 to 3 hetero atoms selected from the group consisting of N, O and S, and benzyl, which alkyl, alkenyl, alkynyl, cycloalkyl, heterocyclyl, heteroaryl, aryl, cycloalkylalkyl, heterocyclylalkyl, heteroarylalkyl and arylalkyl may optionally be substituted with one or more independently selected $R^1$; or, alternatively germinal $R^4$ and $R^5$ are forming 4-10 membered N-containing heterocyclyl, which is substituted with one or more $R^1$.

In a more preferred embodiment of the present invention, X is hydrogen, cyclopentyl, tetrahydrofuran, benzofuran, dihydrobenzofuran, chromane, dihydroindene, tetrahydronaphthalen, —CH($R^1$)NH—$R^2$ or CH($R^1$)O—$R^2$, which benzofuran may optionally be substituted with piperidinoethylaminocarbonyl or methoxycarbonyl;

In a more preferred embodiment of the present invention, A is a single bond, methylene, ethylene, propylene, butylene, —C(=O)— or —$CH_2$C(=O)—, which methylene, ethylene, propylene and butylene may be optionally substituted with $CH_3$;

In a more preferred embodiment of the present invention, Z is hydrogen, amino, benzyl, pyridine, cyclohexyl, diethylamino, azetidine, pyrrolidine, furane, thiophene, oxazole, isoxazole, pyrazole, imidazole, piperidine, piperazine, pyrimidine, pyrazine, morpholine, tetrahydrofuran, tetrahydropyrane, dihydropyrrolopyridine, or piperidinylmethyl, which substituted with one or more independently selected from oxo, Cl, $CH_3$, ethyl, isopropyl, butyl, hydroxyethyl, methoxyethyl, cyclopropyl, benzyl, methylpiperidine, —C(=O)—N($CH_3$)$_2$, diethylamino, dimethylamino, metylamino, methylpyrrolidinylmethyl, piperidine, benzylpyrrolidine and pyrrolididinyltetrahydrofuran or dimethylaminoethyl;

In a more preferred embodiment of the present invention, $R^1$ is hydrogen or methyl;

In a more preferred embodiment of the present invention, $R^2$ is phenyl which may optionally be substituted with one or more independently selected from the group consisting of fluoro, chloro, cyano, nitro, methyl, ethyl, butyl, trifluoromethyl, methoxy, cyclopentyl, cyclohexyl, methoxyethyl, —C(=O)—$CH_3$, —($CH_2$)$_2$—C(=O)—$CH_3$, —NH—C(=O)—$CH_3$, pyridine, phenoxy, benzoyl, phenyl, propoxypiperidinylmethyl, methoxycarbonyl, benzyl optionally substituted with methyl, propoxypiperidinomethyl, aminomethyl optionally substituted with tetrahydropyranyl, benzyl, tetrahydropyranmethyl or morpholinoethyl, aminocarbonyl optionally substituted with piperidinoethyl, hydroxyethylpiperidinomethyl, methoxyethylpiperidinomethyl, methylpiperidinomethyl, benzylpiperidinomethyl, morpholinoethyl, benzyl, cyclohexylmethyl, pyridinomethyl, dimethylaminopropyl, cyclopentyl, acetylpiperidinomethyl, piperidinomethyl, aminocyclohexyl, tetrahydropyranomethyl or piperidinoethyl, pyrrolidinocarbonyl, piperidinocarbonyl optionally substituted with benzyl or propoxy, piperazinocarbonyl, morpholinocarbonyl, morpholinoethylaminocarbonyl, phenoxy, benzyloxy optionally substituted with methoxy, benzoyl, or phenyl; piperidine optionally substituted with methyl or benzyl; pyridine optionally substituted with fluoro, bromo or methyl; pyrazine optionally substituted with bromo; indene; benzyl optionally substituted with chloro;

In a far more preferred embodiment of the present invention, the compound represented by the above Formula (I) may be selected from the group consisting of the compounds shown in Table 1 below.

TABLE 1

| No. | Chemical Structure | Chemical Name |
| --- | --- | --- |
| 1 | 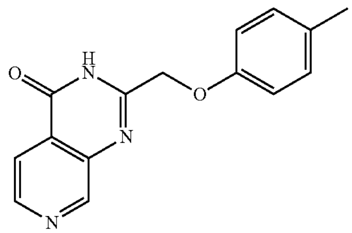 [SMILES: Cc1ccc(OCc2nc3cnccc3c(=O)[nH]2)cc1] | 2-((p-tolyloxy)methyl)pyrido[3,4-d]pyrimidin-4(3H)-one |
| 2 | 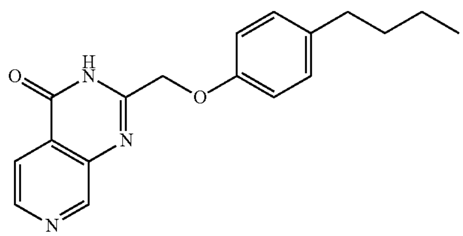 [SMILES: CCCCc1ccc(OCc2nc3cnccc3c(=O)[nH]2)cc1] | 2-((4-butylphenoxy)methyl)pyrido[3,4-d]pyrimidin-4(3H)-one |
| 3 | 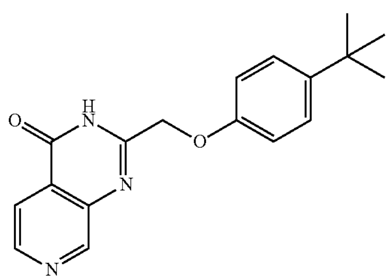 [SMILES: CC(C)(C)c1ccc(OCc2nc3cnccc3c(=O)[nH]2)cc1] | 2-((4-(tert-butyl)phenoxy)methyl)pyrido[3,4-d]pyrimidin-4(3H)-one |
| 4 | 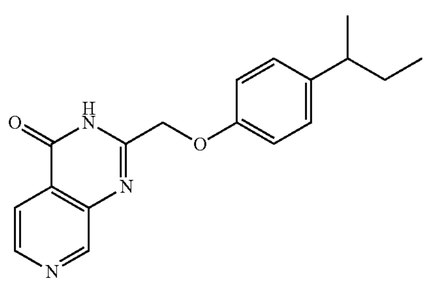 [SMILES: CCC(C)c1ccc(OCc2nc3cnccc3c(=O)[nH]2)cc1] | 2-((4-(sec-butyl)phenoxy)methyl)pyrido[3,4-d]pyrimidin-4(3H)-one |
| 5 | 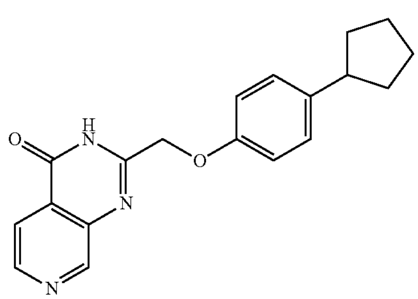 [SMILES: O=c1[nH]c(COc2ccc(C3CCCC3)cc2)nc2cnccc12] | 2-((4-cyclopentylphenoxy)methyl)pyrido[3,4-d]pyrimidin-4(3H)-one |

TABLE 1-continued

| No. | Chemical Structure | Chemical Name |
|---|---|---|
| 6 | 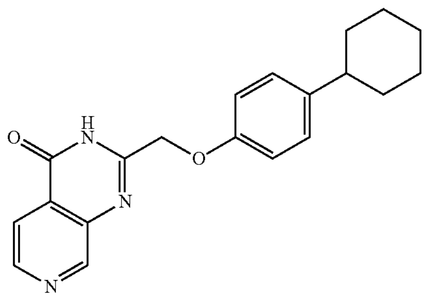 [SMILES: O=c1[nH]c(COc2ccc(C3CCCCC3)cc2)nc2cnccc12] | 2-((4-cyclohexylphenoxy)methyl)pyrido[3,4-d]pyrimidin-4(3H)-one |
| 7 | 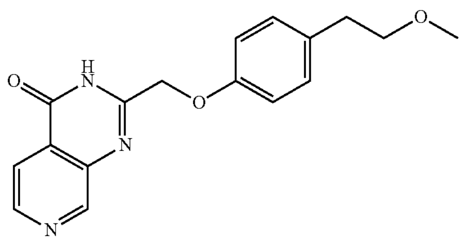 [SMILES: COCCc1ccc(OCc2nc3cnccc3c(=O)[nH]2)cc1] | 2-((4-(2-methoxyethyl)phenoxy)methyl)pyrido[3,4-d]pyrimidin-4(3H)-one |
| 8 | 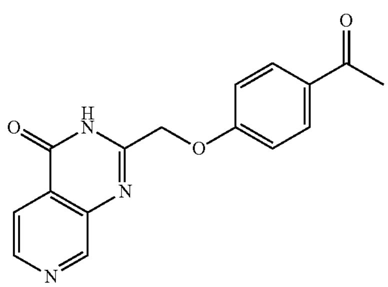 [SMILES: CC(=O)c1ccc(OCc2nc3cnccc3c(=O)[nH]2)cc1] | 2-((4-acetylphenoxy)methyl)pyrido[3,4-d]pyrimidin-4(3H)-one |
| 9 | 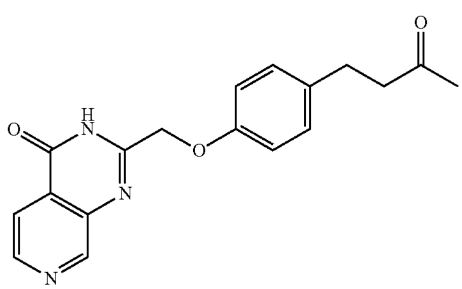 [SMILES: CC(=O)CCc1ccc(OCc2nc3cnccc3c(=O)[nH]2)cc1] | 2-((4-(3-oxobutyl)phenoxy)methyl)pyrido[3,4-d]pyrimidin-4(3H)-one |
| 10 | 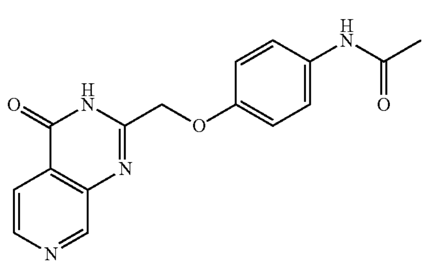 [SMILES: CC(=O)Nc1ccc(OCc2nc3cnccc3c(=O)[nH]2)cc1] | N-(4-((4-oxo-3,4-dihydropyrido[3,4-d]pyrimidin-2-yl)methoxy)phenyl)acetamide |
| 11 | 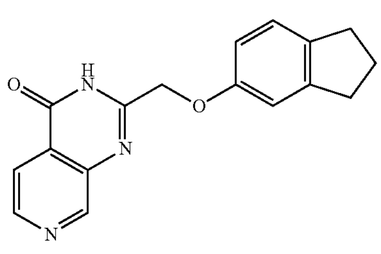 [SMILES: O=c1[nH]c(COc2ccc3c(c2)CCC3)nc2cnccc12] | 2-(((2,3-dihydro-1H-inden-5-yl)oxy)methyl)pyrido[3,4-d]pyrimidin-4(3H)-one |

TABLE 1-continued

| No. | Chemical Structure | Chemical Name |
|---|---|---|
| 12 | 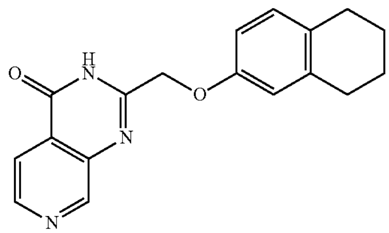 [SMILES: O=c1[nH]c(COc2ccc3c(c2)CCCC3)nc2cnccc12] | 2-(((5,6,7,8-tetrahydronaphthalen-2-yl)oxy)methyl)pyrido[3,4-d]pyrimidin-4(3H)-one |
| 13 | 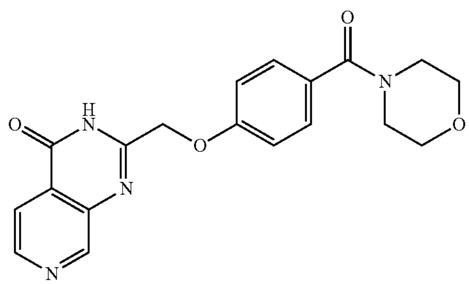 [SMILES: O=C(c1ccc(OCc2nc3cnccc3c(=O)[nH]2)cc1)N1CCOCC1] | 2-((4-(morpholine-4-carbonyl)phenoxy)methyl)pyrido[3,4-d]pyrimidin-4(3H)-one |
| 14 | 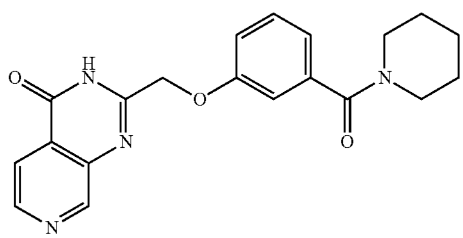 [SMILES: O=C(c1cccc(OCc2nc3cnccc3c(=O)[nH]2)c1)N1CCCCC1] | 2-((3-(piperidine-1-carbonyl)phenoxy)methyl)pyrido[3,4-d]pyrimidin-4(3H)-one |
| 15 | 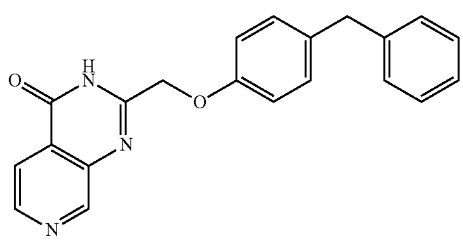 [SMILES: O=c1[nH]c(COc2ccc(Cc3ccccc3)cc2)nc2cnccc12] | 2-((4-benzylphenoxy)methyl)pyrido[3,4-d]pyrimidin-4(3H)-one |
| 16 | 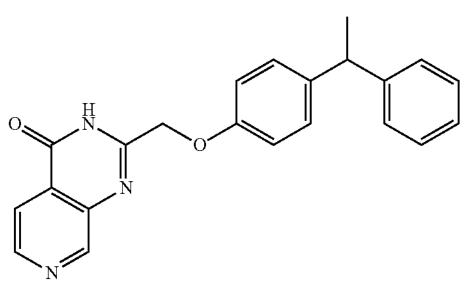 [SMILES: CC(c1ccccc1)c1ccc(OCc2nc3cnccc3c(=O)[nH]2)cc1] | 2-((4-(1-phenylethyl)phenoxy)methyl)pyrido[3,4-d]pyrimidin-4(3H)-one |
| 17 | 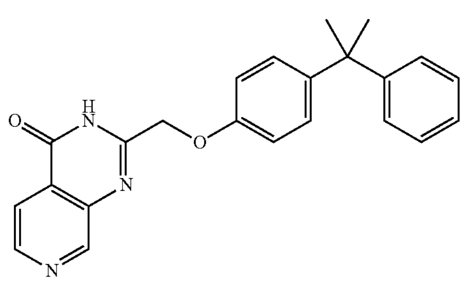 [SMILES: CC(C)(c1ccccc1)c1ccc(OCc2nc3cnccc3c(=O)[nH]2)cc1] | 2-((4-(2-phenylpropan-2-yl)phenoxy)methyl)pyrido[3,4-d]pyrimidin-4(3H)-one |

TABLE 1-continued

| No. | Chemical Structure | Chemical Name |
|---|---|---|
| 18 | 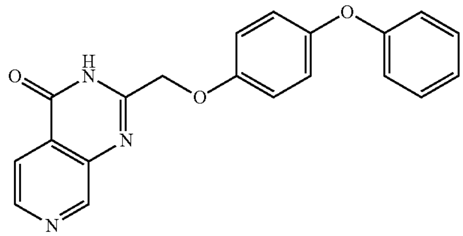 [SMILES: O=c1[nH]c(COc2ccc(Oc3ccccc3)cc2)nc2cnccc12] | 2-((4-phenoxyphenoxy)methyl)pyrido[3,4-d]pyrimidin-4(3H)-one |
| 19 | 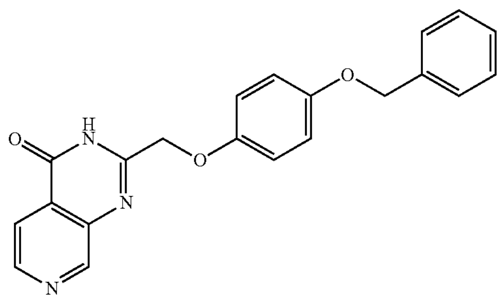 [SMILES: O=c1[nH]c(COc2ccc(OCc3ccccc3)cc2)nc2cnccc12] | 2-((4-(benzyloxy)phenoxy)methyl)pyrido[3,4-d]pyrimidin-4(3H)-one |
| 20 | 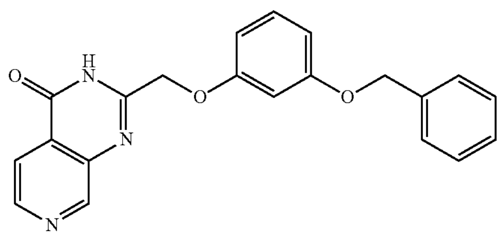 [SMILES: O=c1[nH]c(COc2cccc(OCc3ccccc3)c2)nc2cnccc12] | 2-((3-(benzyloxy)phenoxy)methyl)pyrido[3,4-d]pyrimidin-4(3H)-one |
| 21 | 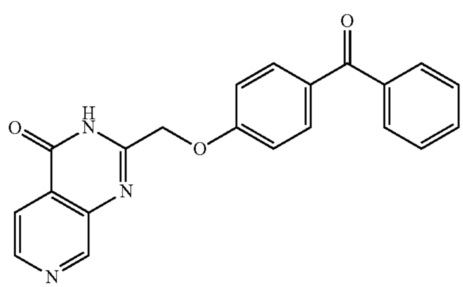 [SMILES: O=C(c1ccccc1)c1ccc(OCc2nc3cnccc3c(=O)[nH]2)cc1] | 2-((4-benzoylphenoxy)methyl)pyrido[3,4-d]pyrimidin-4(3H)-one |
| 22 | 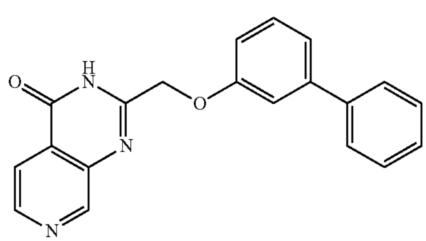 [SMILES: O=c1[nH]c(COc2cccc(-c3ccccc3)c2)nc2cnccc12] | 2-(([1,1'-biphenyl]-3-yloxy)methyl)pyrido[3,4-d]pyrimidin-4(3H)-one |
| 23 | 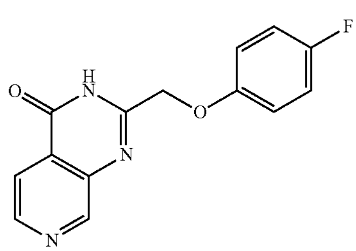 | 2-((4-fluorophenoxy)methyl)pyrido[3,4-d]pyrimidin-4(3H)-one |

TABLE 1-continued

| No. | Chemical Structure | Chemical Name |
|---|---|---|
| 24 | 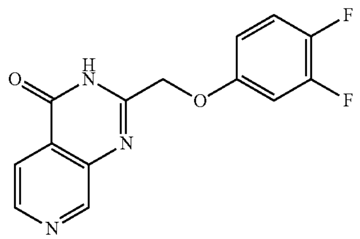 [SMILES: O=c1[nH]c(COc2ccc(F)c(F)c2)nc2cnccc12] | 2-((3,4-difluorophenoxy)methyl)pyrido[3,4-d]pyrimidin-4(3H)-one |
| 25 | 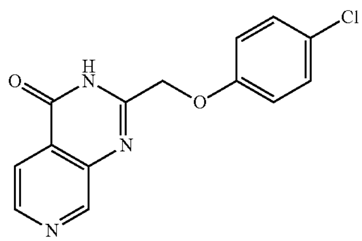 | 2-((4-chlorophenoxy)methyl)pyrido[3,4-d]pyrimidin-4(3H)-one |
| 26 | 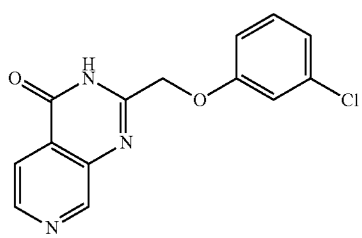 [SMILES: O=c1[nH]c(COc2cccc(Cl)c2)nc2cnccc12] | 2-((3-chlorophenoxy)methyl)pyrido[3,4-d]pyrimidin-4(3H)-one |
| 27 | 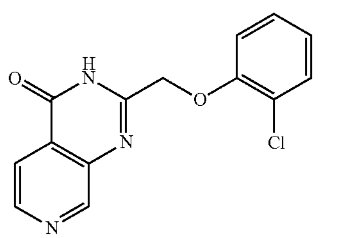 [SMILES: O=c1[nH]c(COc2ccccc2Cl)nc2cnccc12] | 2-((2-chlorophenoxy)methyl)pyrido[3,4-d]pyrimidin-4(3H)-one |
| 28 | 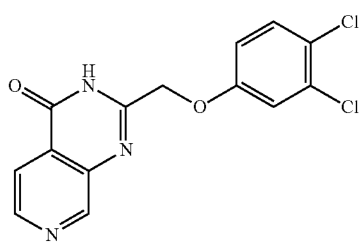 [SMILES: O=c1[nH]c(COc2ccc(Cl)c(Cl)c2)nc2cnccc12] | 2-((3,4-dichlorophenoxy)methyl)pyrido[3,4-d]pyrimidin-4(3H)-one |
| 29 | 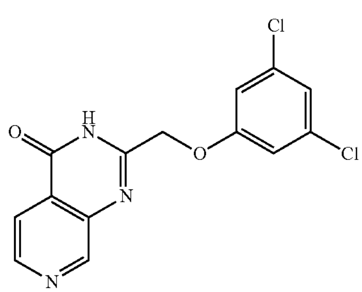 [SMILES: O=c1[nH]c(COc2cc(Cl)cc(Cl)c2)nc2cnccc12] | 2-((3,5-dichlorophenoxy)methyl)pyrido[3,4-d]pyrimidin-4(3H)-one |

TABLE 1-continued

| No. | Chemical Structure | Chemical Name |
|---|---|---|
| 30 | 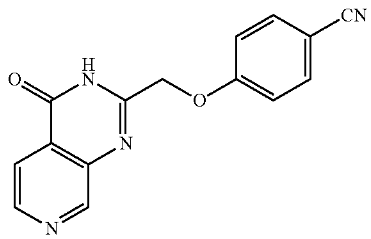 [SMILES: N#Cc1ccc(OCc2nc3cnccc3c(=O)[nH]2)cc1] | 4-((4-oxo-3,4-dihydropyrido[3,4-d]pyrimidin-2-yl)methoxy)benzonitrile |
| 31 | 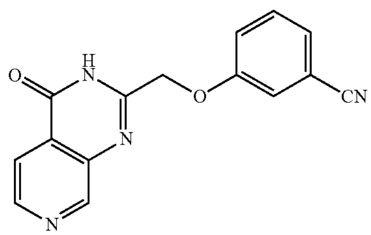 [SMILES: N#Cc1cccc(OCc2nc3cnccc3c(=O)[nH]2)c1] | 3-((4-oxo-3,4-dihydropyrido[3,4-d]pyrimidin-2-yl)methoxy)benzonitrile |
| 32 | 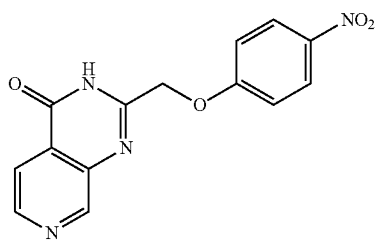 [SMILES: O=c1[nH]c(COc2ccc([N+](=O)[O-])cc2)nc2cnccc12] | 2-((4-nitrophenoxy)methyl)pyrido[3,4-d]pyrimidin-4(3H)-one |
| 33 | 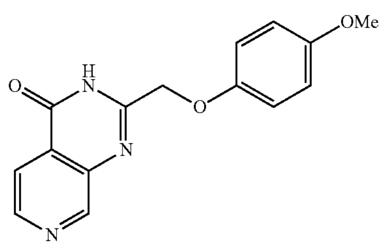 [SMILES: COc1ccc(OCc2nc3cnccc3c(=O)[nH]2)cc1] | 2-((4-methoxyphenoxy)methyl)pyrido[3,4-d]pyrimidin-4(3H)-one |
| 34 | 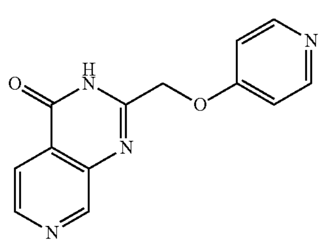 [SMILES: O=c1[nH]c(COc2ccncc2)nc2cnccc12] | 2-((pyridin-4-yloxy)methyl)pyrido[3,4-d]pyrimidin-4(3H)-one |
| 35 | 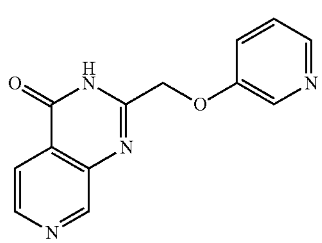 [SMILES: O=c1[nH]c(COc2cccnc2)nc2cnccc12] | 2-((pyridin-3-yloxy)methyl)pyrido[3,4-d]pyrimidin-4(3H)-one |

TABLE 1-continued

| No. | Chemical Structure | Chemical Name |
|---|---|---|
| 36 | 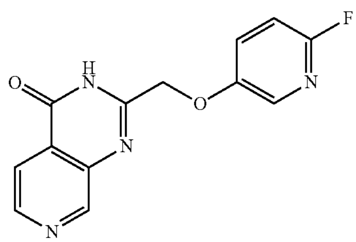 [SMILES: O=c1[nH]c(COc2ccc(F)nc2)nc2cnccc12] | 2-(((6-fluoropyridin-3-yl)oxy)methyl)pyrido[3,4-d]pyrimidin-4(3H)-one |
| 37 | 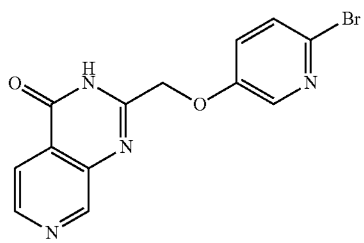 [SMILES: O=c1[nH]c(COc2ccc(Br)nc2)nc2cnccc12] | 2-(((6-bromopyridin-3-yl)oxy)methyl)pyrido[3,4-d]pyrimidin-4(3H)-one |
| 38 | 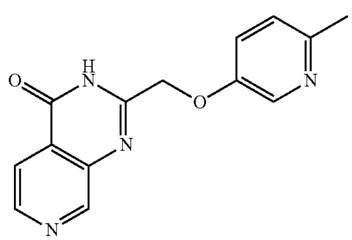 | 2-(((6-methylpyridin-3-yl)oxy)methyl)pyrido[3,4-d]pyrimidin-4(3H)-one |
| 39 | 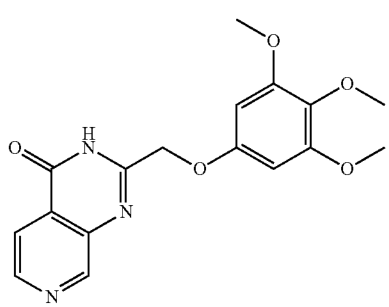 [SMILES: COc1cc(OCc2nc3cnccc3c(=O)[nH]2)cc(OC)c1OC] | 2-((3,4,5-trimethoxyphenoxy)methyl)pyrido[3,4-d]pyrimidin-4(3H)-one |
| 40 | 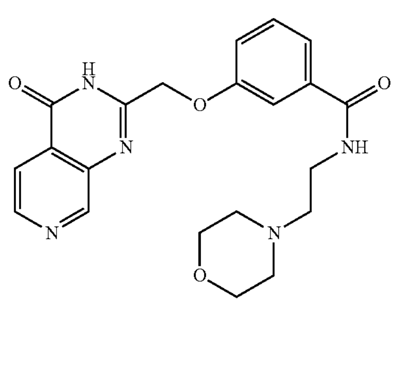 [SMILES: O=C(NCCN1CCOCC1)c1cccc(OCc2nc3cnccc3c(=O)[nH]2)c1] | N-(2-morpholinoethyl)-3-((4-oxo-3,4-dihydropyrido[3,4-d]pyrimidin-2-yl)methoxy)benzamide |

TABLE 1-continued

| No. | Chemical Structure | Chemical Name |
|---|---|---|
| 41 | 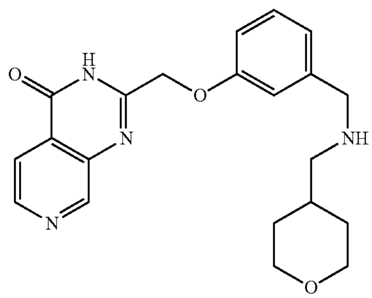 [SMILES: O=c1[nH]c(COc2cccc(CNCC3CCOCC3)c2)nc2cnccc12] | 2-((3-((((tetrahydro-2H-pyran-4-yl)methyl)amino)methyl)phenoxy)methyl)pyrido[3,4-d]pyrimidin-4(3H)-one |
| 42 | 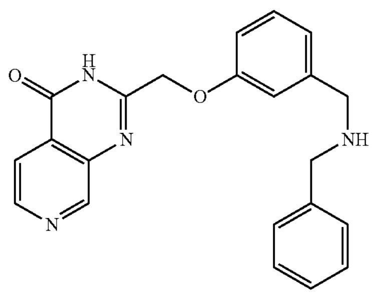 [SMILES: O=c1[nH]c(COc2cccc(CNCc3ccccc3)c2)nc2cnccc12] | 2-((3-((benzylamino)methyl)phenoxy)methyl)pyrido[3,4-d]pyrimidin-4(3H)-one |
| 43 | 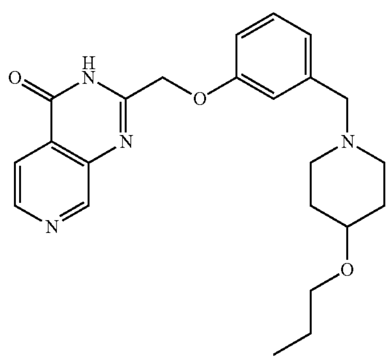 [SMILES: CCCOC1CCN(Cc2cccc(OCc3nc4cnccc4c(=O)[nH]3)c2)CC1] | 2-((3-((4-propoxypiperidin-1-yl)methyl)phenoxy)methyl)pyrido[3,4-d]pyrimidin-4(3H)-one |
| 44 | 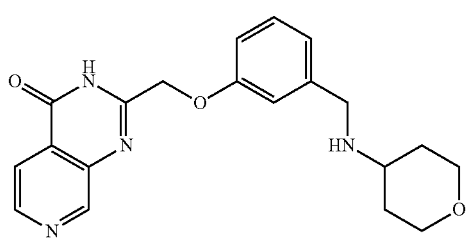 [SMILES: O=c1[nH]c(COc2cccc(CNC3CCOCC3)c2)nc2cnccc12] | 2-((3-(((tetrahydro-2H-pyran-4-yl)amino)methyl)phenoxy)methyl)pyrido[3,4-d]pyrimidin-4(3H)-one |
| 45 | 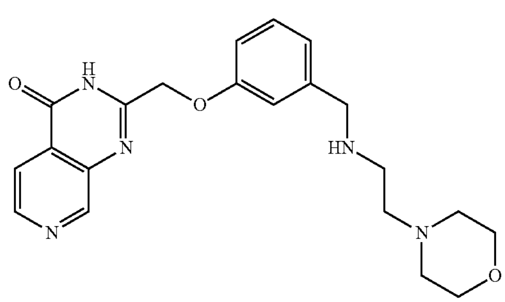 [SMILES: O=c1[nH]c(COc2cccc(CNCCN3CCOCC3)c2)nc2cnccc12] | 2-((3-(((2-morpholinoethyl)amino)methyl)phenoxy)methyl)pyrido[3,4-d]pyrimidin-4(3H)-one |

TABLE 1-continued

| No. | Chemical Structure | Chemical Name |
|---|---|---|
| 46 | 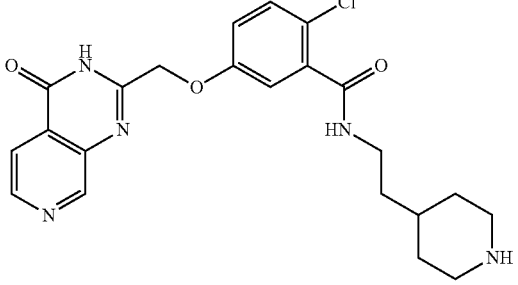 | 2-chloro-5-((4-oxo-3,4-dihydropyrido[3,4-d]pyrimidin-2-yl)methoxy)-N-(2-(piperidin-4-yl)ethyl)benzamide |
| 47 | 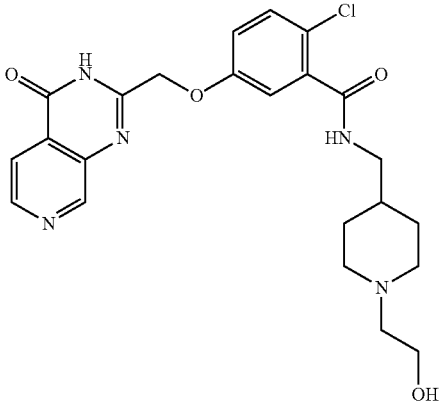 [SMILES: O=C(NCC1CCN(CCO)CC1)c1cc(OCc2nc3cnccc3c(=O)[nH]2)ccc1Cl] | 2-chloro-N-((1-(2-hydroxyethyl)piperidin-4-yl)methyl)-5-((4-oxo-3,4-dihydropyrido[3,4-d]pyrimidin-2-yl)methoxy)benzamide |
| 48 | 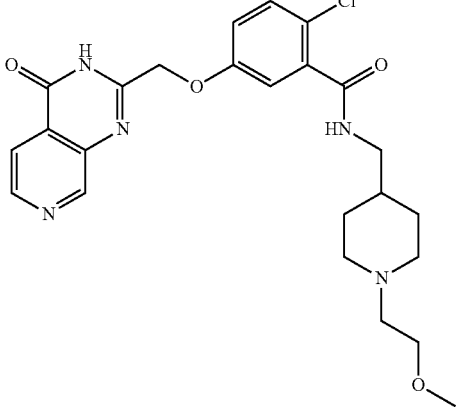 | 2-chloro-N-((1-(2-methoxyethyl)piperidin-4-yl)methyl)-5-((4-oxo-3,4-dihydropyrido[3,4-d]pyrimidin-2-yl)methoxy)benzamide |
| 49 | 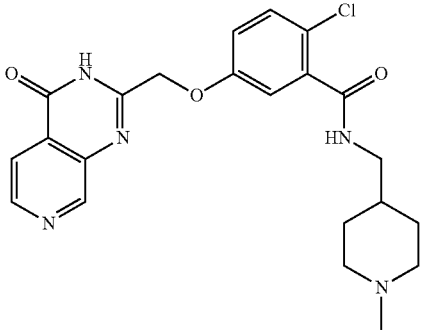 [SMILES: CN1CCC(CNC(=O)c2cc(OCc3nc4cnccc4c(=O)[nH]3)ccc2Cl)CC1] | 2-chloro-N-((1-methylpiperidin-4-yl)methyl)-5-((4-oxo-3,4-dihydropyrido[3,4-d]pyrimidin-2-yl)methoxy)benzamide |

TABLE 1-continued

| No. | Chemical Structure | Chemical Name |
|---|---|---|
| 50 | 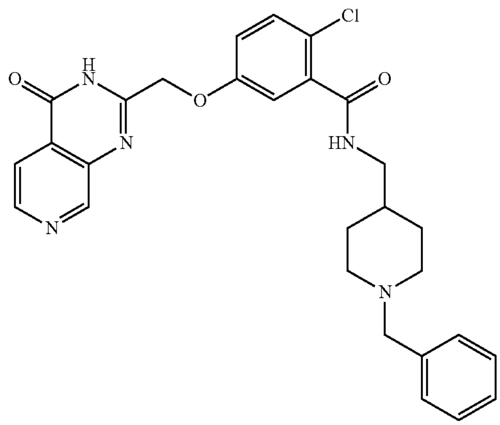 [SMILES: O=C(NCC1CCN(Cc2ccccc2)CC1)c1cc(OCc2nc3cnccc3c(=O)[nH]2)ccc1Cl] | N-((1-benzylpiperidin-4-yl)methyl)-2-chloro-5-((4-oxo-3,4-dihydropyrido[3,4-d]pyrimidin-2-yl)methoxy)benzamide |
| 51 | 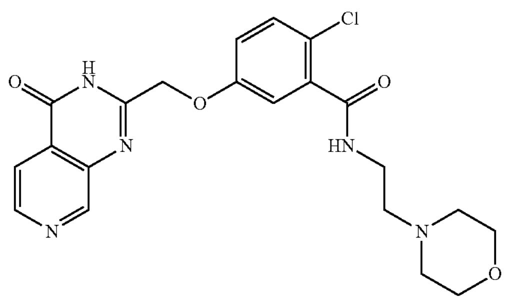 [SMILES: O=C(NCCN1CCOCC1)c1cc(OCc2nc3cnccc3c(=O)[nH]2)ccc1Cl] | 2-chloro-N-(2-morpholinoethyl)-5-((4-oxo-3,4-dihydropyrido[3,4-d]pyrimidin-2-yl)methoxy)benzamide |
| 52 | 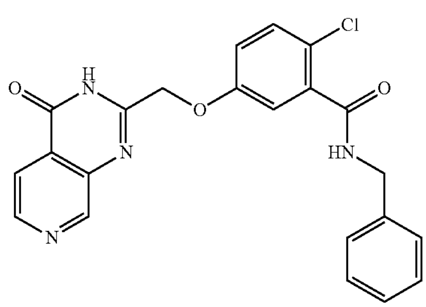 [SMILES: O=C(NCc1ccccc1)c1cc(OCc2nc3cnccc3c(=O)[nH]2)ccc1Cl] | N-benzyl-2-chloro-5-((4-oxo-3,4-dihydropyrido[3,4-d]pyrimidin-2-yl)methoxy)benzamide |
| 53 | 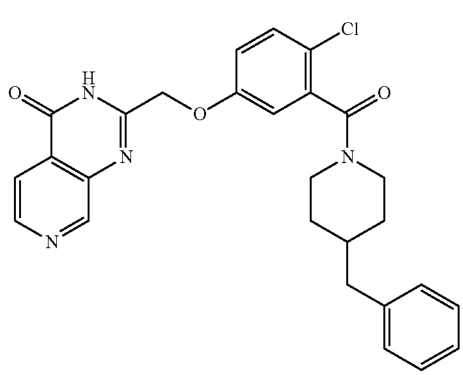 [SMILES: O=C(c1cc(OCc2nc3cnccc3c(=O)[nH]2)ccc1Cl)N1CCC(Cc2ccccc2)CC1] | 2-((3-(4-benzylpiperidine-1-carbonyl)-4-chlorophenoxy)methyl)pyrido[3,4-d]pyrimidin-4(3H)-one |

TABLE 1-continued

| No. | Chemical Structure | Chemical Name |
|---|---|---|
| 54 | 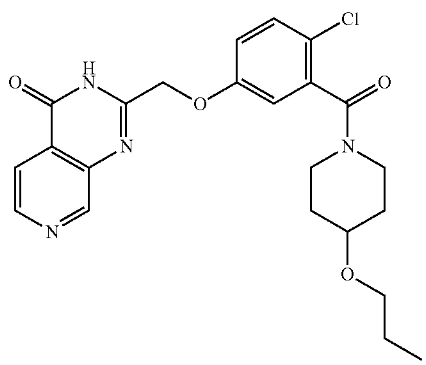 [SMILES: CCCOC1CCN(C(=O)c2cc(OCc3nc4cnccc4c(=O)[nH]3)ccc2Cl)CC1] | 2-((4-chloro-3-(4-propoxypiperidine-1-carbonyl)phenoxy)methyl)pyrido[3,4-d]pyrimidin-4(3H)-one |
| 55 | 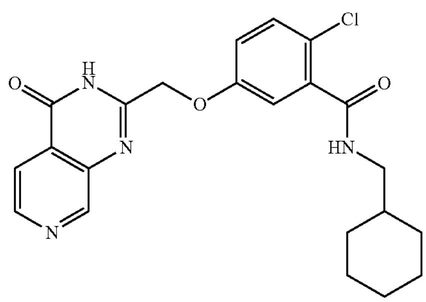 [SMILES: O=C(NCC1CCCCC1)c1cc(OCc2nc3cnccc3c(=O)[nH]2)ccc1Cl] | 2-chloro-N-(cyclohexylmethyl)-5-((4-oxo-3,4-dihydropyrido[3,4-d]pyrimidin-2-yl)methoxy)benzamide |
| 56 | 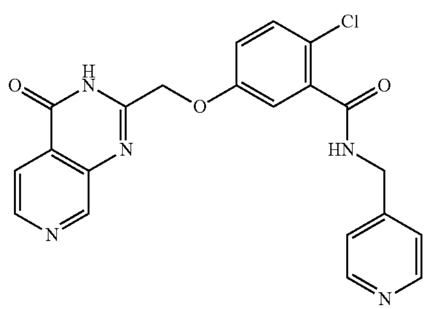 [SMILES: O=C(NCc1ccncc1)c1cc(OCc2nc3cnccc3c(=O)[nH]2)ccc1Cl] | 2-chloro-5-((4-oxo-3,4-dihydropyrido[3,4-d]pyrimidin-2-yl)methoxy)-N-(pyridin-4-ylmethyl)benzamide |
| 57 | 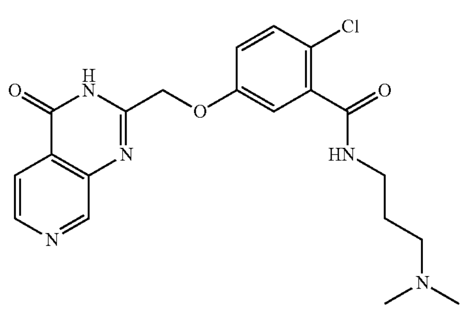 [SMILES: CN(C)CCCNC(=O)c1cc(OCc2nc3cnccc3c(=O)[nH]2)ccc1Cl] | 2-chloro-N-(3-(dimethylamino)propyl)-5-((4-oxo-3,4-dihydropyrido[3,4-d]pyrimidin-2-yl)methoxy)benzamide |
| 58 | 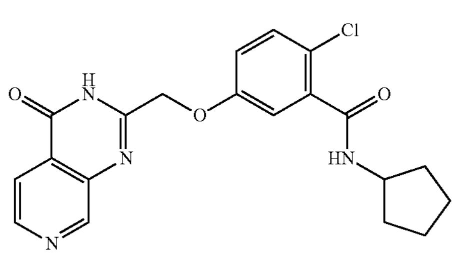 [SMILES: O=C(NC1CCCC1)c1cc(OCc2nc3cnccc3c(=O)[nH]2)ccc1Cl] | 2-chloro-N-cyclopentyl-5-((4-oxo-3,4-dihydropyrido[3,4-d]pyrimidin-2-yl)methoxy)benzamide |

TABLE 1-continued

| No. | Chemical Structure | Chemical Name |
|---|---|---|
| 59 | 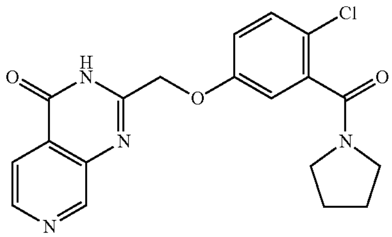 [SMILES: O=C(c1cc(OCc2nc3cnccc3c(=O)[nH]2)ccc1Cl)N1CCCC1] | 2-((4-chloro-3-(pyrrolidine-1-carbonyl)phenoxy)methyl)pyrido[3,4-d]pyrimidin-4(3H)-one |
| 60 | 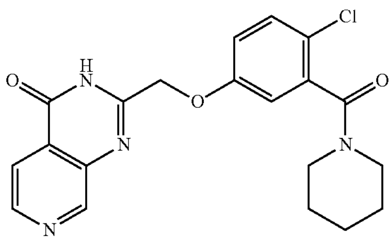 [SMILES: O=C(c1cc(OCc2nc3cnccc3c(=O)[nH]2)ccc1Cl)N1CCCCC1] | 2-((4-chloro-3-(piperidine-1-carbonyl)phenoxy)methyl)pyrido[3,4-d]pyrimidin-4(3H)-one |
| 61 | 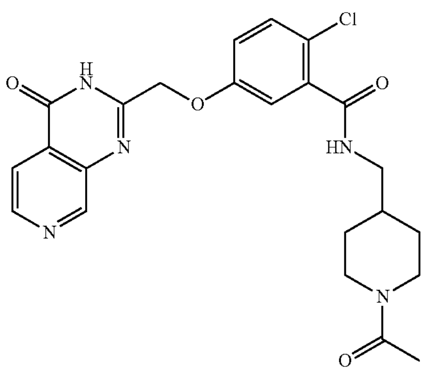 [SMILES: CC(=O)N1CCC(CNC(=O)c2cc(OCc3nc4cnccc4c(=O)[nH]3)ccc2Cl)CC1] | N-((1-acetylpiperidin-4-yl)methyl)-2-chloro-5-((4-oxo-3,4-dihydropyrido[3,4-d]pyrimidin-2-yl)methoxy)benzamide |
| 62 | 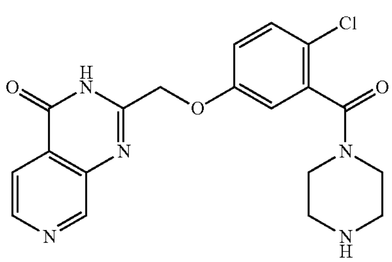 [SMILES: O=C(c1cc(OCc2nc3cnccc3c(=O)[nH]2)ccc1Cl)N1CCNCC1] | 2-((4-chloro-3-(piperazine-1-carbonyl)phenoxy)methyl)pyrido[3,4-d]pyrimidin-4(3H)-one |
| 63 | 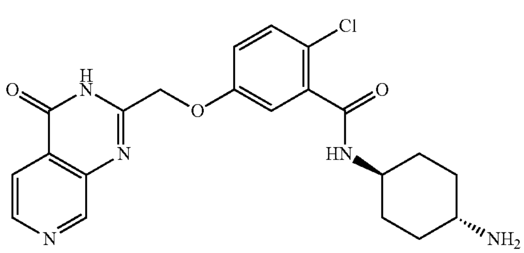 [SMILES: N[C@H]1CC[C@H](NC(=O)c2cc(OCc3nc4cnccc4c(=O)[nH]3)ccc2Cl)CC1] | N-(trans-1,4-aminocyclohexyl)-2-chloro-5-((4-oxo-3,4-dihydropyrido[3,4-d]pyrimidin-2-yl)methoxy)benzamide |

TABLE 1-continued

| No. | Chemical Structure | Chemical Name |
|---|---|---|
| 64 | 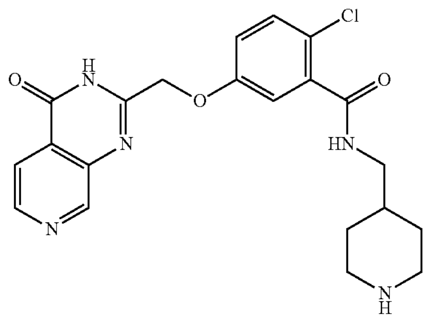 [SMILES: O=C(NCC1CCNCC1)c1cc(OCc2nc3cnccc3c(=O)[nH]2)ccc1Cl] | 2-chloro-5-((4-oxo-3,4-dihydropyrido[3,4-d]pyrimidin-2-yl)methoxy)-N-(piperidin-4-ylmethyl)benzamide |
| 65 | 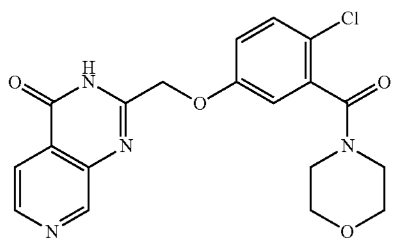 [SMILES: O=C(c1cc(OCc2nc3cnccc3c(=O)[nH]2)ccc1Cl)N1CCOCC1] | 2-((4-chloro-3-(morpholine-4-carbonyl)phenoxy)methyl)pyrido[3,4-d]pyrimidin-4(3H)-one |
| 66 | 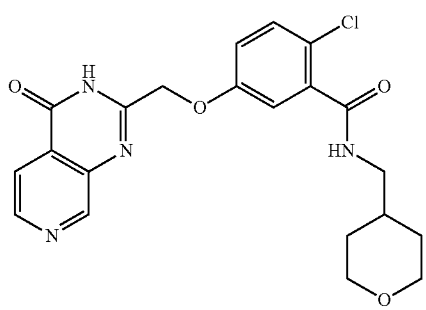 [SMILES: O=C(NCC1CCOCC1)c1cc(OCc2nc3cnccc3c(=O)[nH]2)ccc1Cl] | 2-chloro-5-((4-oxo-3,4-dihydropyrido[3,4-d]pyrimidin-2-yl)methoxy)-N-((tetrahydro-2H-pyran-4-yl)methyl)benzamide |
| 67 | 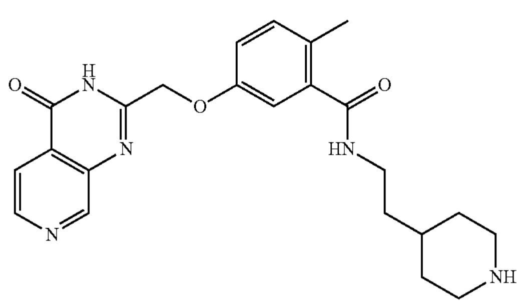 [SMILES: Cc1ccc(OCc2nc3cnccc3c(=O)[nH]2)cc1C(=O)NCCC1CCNCC1] | 2-methyl-5-((4-oxo-3,4-dihydropyrido[3,4-d]pyrimidin-2-yl)methoxy)-N-(2-(piperidin-4-yl)ethyl)benzamide |
| 68 | 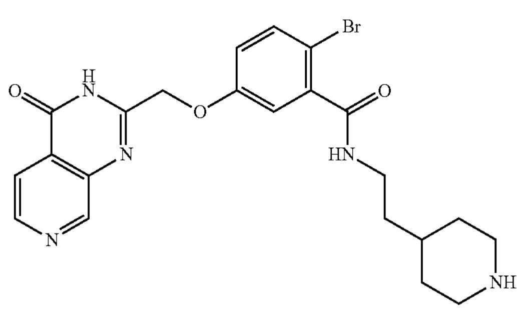 | 2-bromo-5-((4-oxo-3,4-dihydropyrido[3,4-d]pyrimidin-2-yl)methoxy)-N-(2-(piperidin-4-yl)ethyl)benzamide |

TABLE 1-continued

| No. | Chemical Structure | Chemical Name |
|---|---|---|
| 69 | 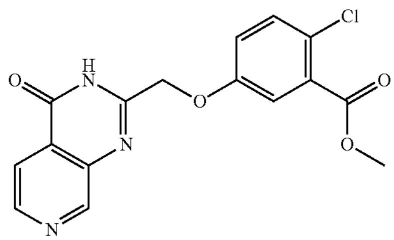 | methyl 2-chloro-5-((4-oxo-3,4-dihydropyrido[3,4-d]pyrimidin-2-yl)methoxy)benzoate |
| 70 | 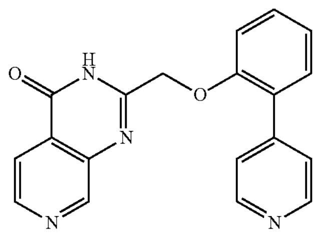 [SMILES: O=c1[nH]c(COc2ccccc2-c2ccncc2)nc2cnccc12] | 2-((2-(pyridin-4-yl)phenoxy)methyl)pyrido[3,4-d]pyrimidin-4(3H)-one |
| 71 | 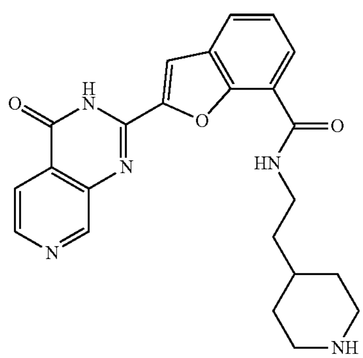 [SMILES: O=C(NCCC1CCNCC1)c1cccc2cc(-c3nc4cnccc4c(=O)[nH]3)oc12] | 2-(4-oxo-3,4-dihydropyrido[3,4-d]pyrimidin-2-yl)-N-(2-(piperidin-4-yl)ethyl)benzofuran-7-carboxamide |
| 72 | 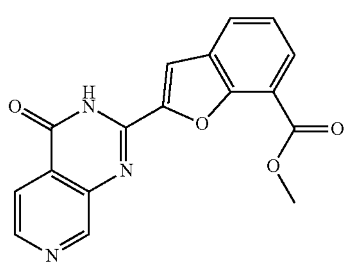 [SMILES: COC(=O)c1cccc2cc(-c3nc4cnccc4c(=O)[nH]3)oc12] | methyl 2-(4-oxo-3,4-dihydropyrido[3,4-d]pyrimidin-2-yl)benzofuran-7-carboxylate |
| 73 | 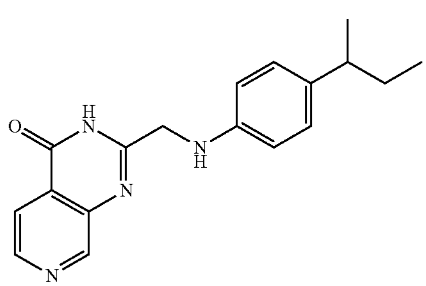 [SMILES: CCC(C)c1ccc(NCc2nc3cnccc3c(=O)[nH]2)cc1] | 2-(((4-(sec-butyl)phenyl)amino)methyl)pyrido[3,4-d]pyrimidin-4(3H)-one |

TABLE 1-continued

| No. | Chemical Structure | Chemical Name |
|---|---|---|
| 74 | 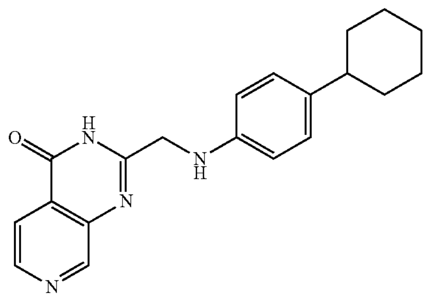 | 2-(((4-cyclohexylphenyl)amino)methyl)pyrido[3,4-d]pyrimidin-4(3H)-one |
| 75 | 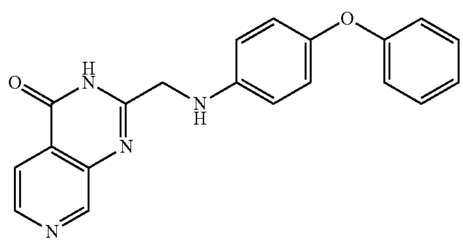 | 2-(((4-phenoxyphenyl)amino)methyl)pyrido[3,4-d]pyrimidin-4(3H)-one |
| 76 | 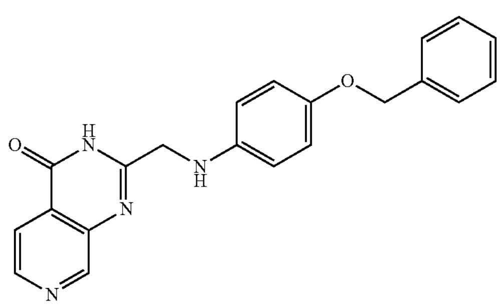 | 2-(((4-(benzyloxy)phenyl)amino)methyl)pyrido[3,4-d]pyrimidin-4(3H)-one |
| 77 | 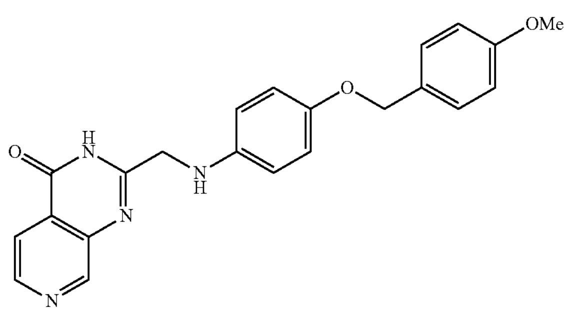 [SMILES: COc1ccc(COc2ccc(NCc3nc4cnccc4c(=O)[nH]3)cc2)cc1] | 2-(((4-((4-methoxybenzyl)oxy)phenyl)amino)methyl)pyrido[3,4-d]pyrimidin-4(3H)-one |
| 78 | 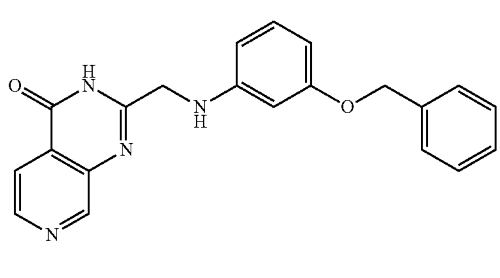 | 2-(((3-(benzyloxy)phenyl)amino)methyl)pyrido[3,4-d]pyrimidin-4(3H)-one |

TABLE 1-continued

| No. | Chemical Structure | Chemical Name |
|---|---|---|
| 79 | 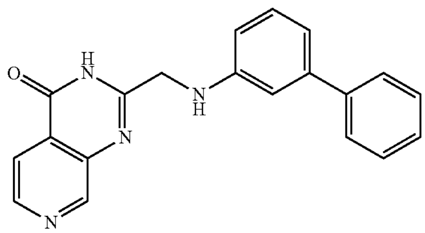 [SMILES: O=c1[nH]c(CNc2cccc(-c3ccccc3)c2)nc2cnccc12] | 2-(([1,1'-biphenyl]-3-ylamino)methyl)pyrido[3,4-d]pyrimidin-4(3H)-one |
| 80 | 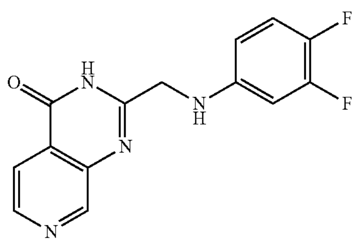 [SMILES: O=c1[nH]c(CNc2ccc(F)c(F)c2)nc2cnccc12] | 2-(((3,4-difluorophenyl)amino)methyl)pyrido[3,4-d]pyrimidin-4(3H)-one |
| 81 | 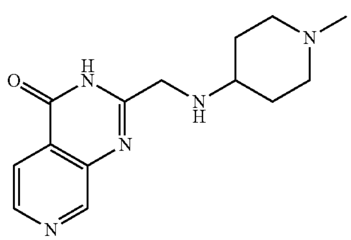 [SMILES: CN1CCC(NCc2nc3cnccc3c(=O)[nH]2)CC1] | 2-(((1-methylpiperidin-4-yl)amino)methyl)pyrido[3,4-d]pyrimidin-4(3H)-one |
| 82 | 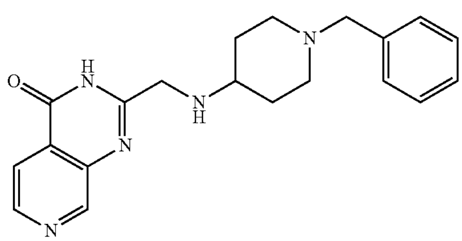 [SMILES: O=c1[nH]c(CNC2CCN(Cc3ccccc3)CC2)nc2cnccc12] | 2-(((1-benzylpiperidin-4-yl)amino)methyl)pyrido[3,4-d]pyrimidin-4(3H)-one |
| 83 | 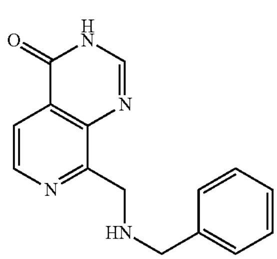 [SMILES: O=c1[nH]cnc2c(CNCc3ccccc3)nccc12] | 8-((benzylamino)methyl)pyrido[3,4-d]pyrimidin-4(3H)-one |
| 84 | 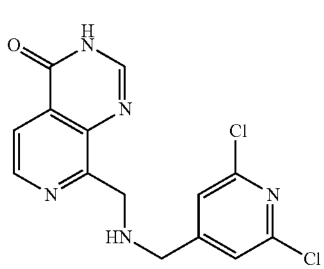 [SMILES: O=c1[nH]cnc2c(CNCc3cc(Cl)nc(Cl)c3)nccc12] | 8-((((2,6-dichloropyridin-4-yl)methyl)amino)methyl)pyrido[3,4-d]pyrimidin-4(3H)-one |

TABLE 1-continued

| No. | Chemical Structure | Chemical Name |
|---|---|---|
| 85 | 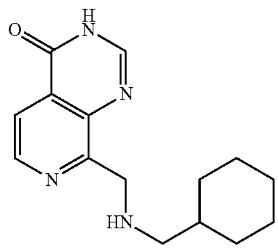 [SMILES: O=c1[nH]cnc2c(CNCC3CCCCC3)nccc12] | 8-(((cyclohexylmethyl)amino)methyl)pyrido[3,4-d]pyrimidin-4(3H)-one |
| 86 | 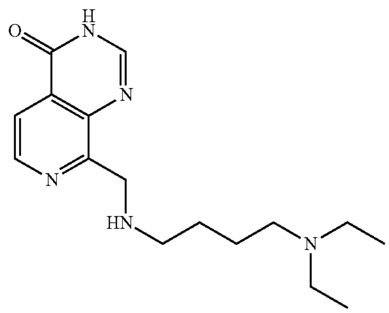 [SMILES: CCN(CC)CCCCNCc1nccc2c(=O)[nH]cnc12] | 8-(((4-(diethylamino)butyl)amino)methyl)pyrido[3,4-d]pyrimidin-4(3H)-one |
| 87 | 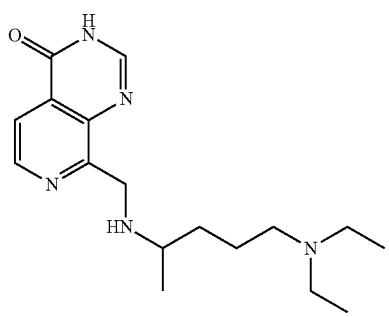 [SMILES: CCN(CC)CCCC(C)NCc1nccc2c(=O)[nH]cnc12] | 8-(((5-(diethylamino)pentan-2-yl)amino)methyl)pyrido[3,4-d]pyrimidin-4(3H)-one |
| 88 | 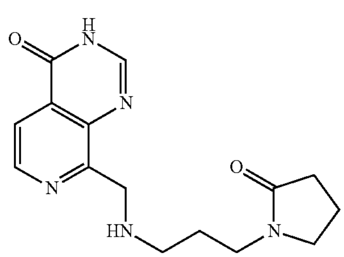 [SMILES: O=C1CCCN1CCCNCc1nccc2c(=O)[nH]cnc12] | 8-(((3-(2-oxopyrrolidin-1-yl)propyl)amino)methyl)pyrido[3,4-d]pyrimidin-4(3H)-one |
| 89 | 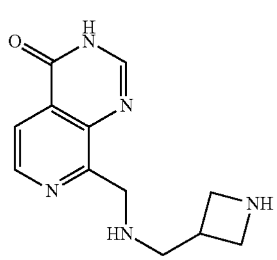 [SMILES: O=c1[nH]cnc2c(CNCC3CNC3)nccc12] | 8-(((azetidin-3-ylmethyl)amino)methyl)pyrido[3,4-d]pyrimidin-4(3H)-one |

TABLE 1-continued

| No. | Chemical Structure | Chemical Name |
|---|---|---|
| 90 | 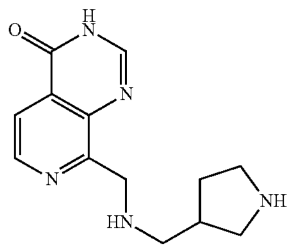 [SMILES: O=c1[nH]cnc2c(CNCC3CCNC3)nccc12] | 8-(((pyrrolidin-3-ylmethyl)amino)methyl)pyrido[3,4-d]pyrimidin-4(3H)-one |
| 91 | 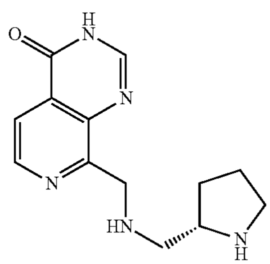 [SMILES: O=c1[nH]cnc2c(CNC[C@@H]3CCCN3)nccc12] | (S)-8-(((pyrrolidin-2-ylmethyl)amino)methyl)pyrido[3,4-d]pyrimidin-4(3H)-one |
| 92 | 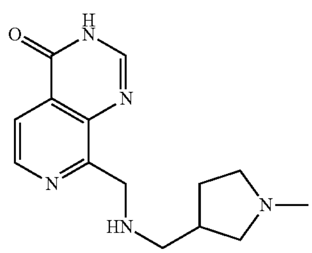 [SMILES: CN1CCC(CNCc2nccc3c(=O)[nH]cnc23)C1] | 8-((((1-methylpyrrolidin-3-yl)methyl)amino)methyl)pyrido[3,4-d]pyrimidin-4(3H)-one |
| 93 | 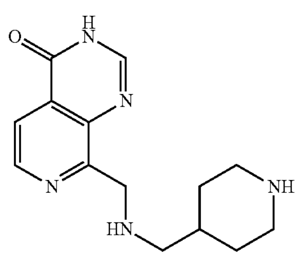 [SMILES: O=c1[nH]cnc2c(CNCC3CCNCC3)nccc12] | 8-(((piperidin-4-ylmethyl)amino)methyl)pyrido[3,4-d]pyrimidin-4(3H)-one |
| 94 | 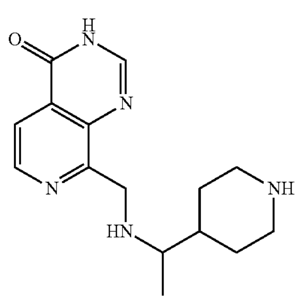 [SMILES: CC(NCc1nccc2c(=O)[nH]cnc12)C1CCNCC1] | 8-(((1-(piperidin-4-yl)ethyl)amino)methyl)pyrido[3,4-d]pyrimidin-4(3H)-one |
| 95 | 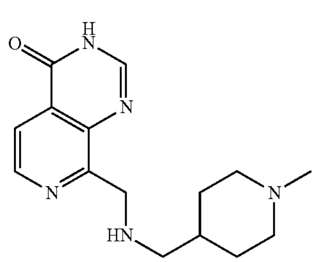 [SMILES: CN1CCC(CNCc2nccc3c(=O)[nH]cnc23)CC1] | 8-((((1-methylpiperidin-4-yl)methyl)amino)methyl)pyrido[3,4-d]pyrimidin-4(3H)-one |

TABLE 1-continued

| No. | Chemical Structure | Chemical Name |
|---|---|---|
| 96 | 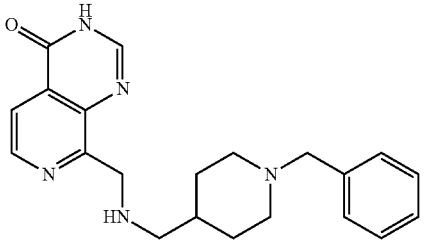 [SMILES: O=c1[nH]cnc2c(CNCC3CCN(Cc4ccccc4)CC3)nccc12] | 8-((((1-benzylpiperidin-4-yl)methyl)amino)methyl)pyrido[3,4-d]pyrimidin-4(3H)-one |
| 97 | 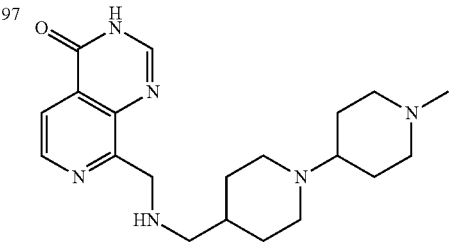 | 8-((((1'-methyl-[1,4'-bipiperidin]-4-yl)methyl)amino)methyl)pyrido[3,4-d]pyrimidin-4(3H)-one |
| 98 | 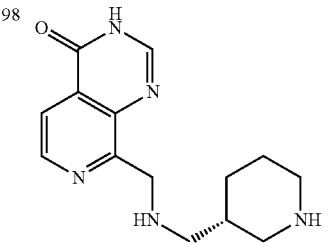 | (R)-8-(((piperidin-3-ylmethyl)amino)methyl)pyrido[3,4-d]pyrimidin-4(3H)-one |
| 99 | 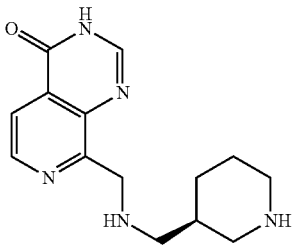 [SMILES: O=c1[nH]cnc2c(CNC[C@H]3CCCNC3)nccc12] | (S)-8-(((piperidin-3-ylmethyl)amino)methyl)pyrido[3,4-d]pyrimidin-4(3H)-one |
| 100 | 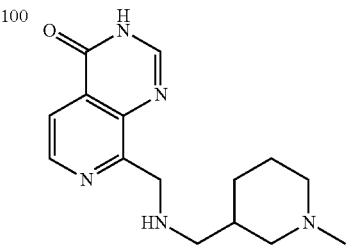 | 8-((((1-methylpiperidin-3-yl)methyl)amino)methyl)pyrido[3,4-d]pyrimidin-4(3H)-one |
| 101 | 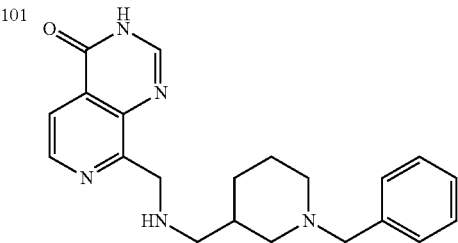 | 8-((((1-benzylpiperidin-3-yl)methyl)amino)methyl)pyrido[3,4-d]pyrimidin-4(3H)-one |

TABLE 1-continued

| No. | Chemical Structure | Chemical Name |
|---|---|---|
| 102 | 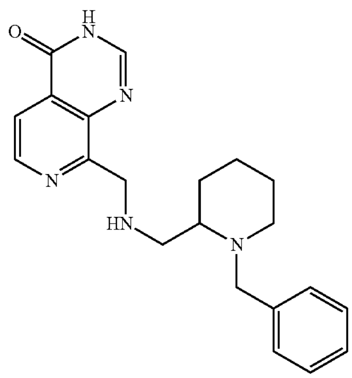 [SMILES: O=c1[nH]cnc2c(CNCC3CCCCN3Cc3ccccc3)nccc12] | 8-((((1-benzylpiperidin-2-yl)methyl)amino)methyl)pyrido[3,4-d]pyrimidin-4(3H)-one |
| 103 | 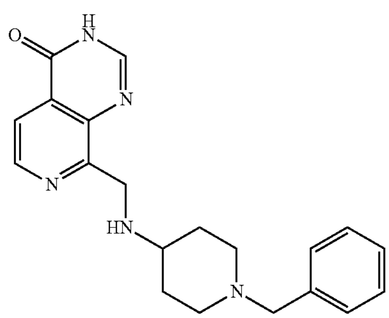 [SMILES: O=c1[nH]cnc2c(CNC3CCN(Cc4ccccc4)CC3)nccc12] | 8-(((1-benzylpiperidin-4-yl)amino)methyl)pyrido[3,4-d]pyrimidin-4(3H)-one |
| 104 | 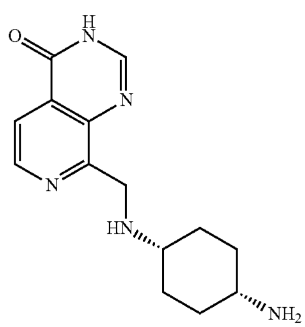 [SMILES: N[C@H]1CC[C@@H](NCc2nccc3c(=O)[nH]cnc23)CC1] | 8-((((1s,4s)-4-aminocyclohexyl)amino)methyl)pyrido[3,4-d]pyrimidin-4(3H)-one |
| 105 | 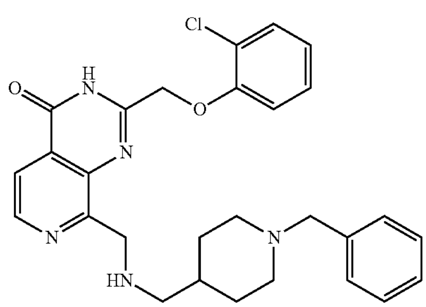 [SMILES: O=c1[nH]c(COc2ccccc2Cl)nc2c(CNCC3CCN(Cc4ccccc4)CC3)nccc12] | 8-((((1-benzylpiperidin-4-yl)methyl)amino)methyl)-2-((2-chlorophenoxy)methyl)pyrido[3,4-d]pyrimidin-4(3H)-one |

TABLE 1-continued

| No. | Chemical Structure | Chemical Name |
|---|---|---|
| 106 | 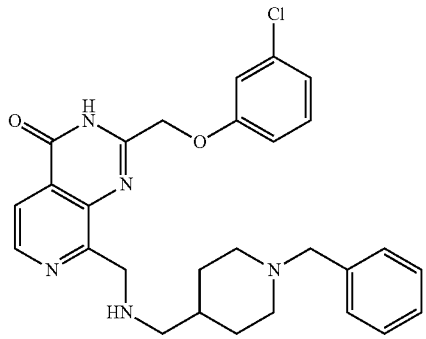 [SMILES: O=c1[nH]c(COc2cccc(Cl)c2)nc2c(CNCC3CCN(Cc4ccccc4)CC3)nccc12] | 8-((((1-benzylpiperidin-4-yl)methyl)amino)methyl)-2-((3-chlorophenoxy)methyl)pyrido[3,4-d]pyrimidin-4(3H)-one |
| 107 | 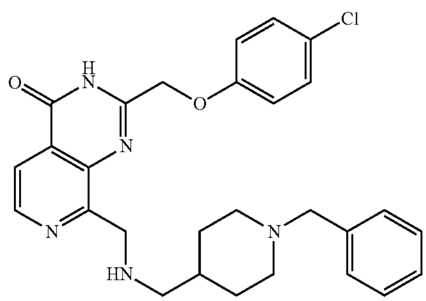 | 8-((((1-benzylpiperidin-4-yl)methyl)amino)methyl)-2-((4-chlorophenoxy)methyl)pyrido[3,4-d]pyrimidin-4(3H)-one |
| 108 | 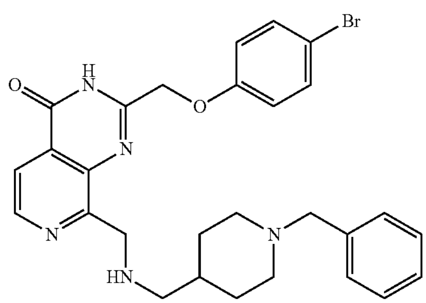 | 8-((((1-benzylpiperidin-4-yl)methyl)amino)methyl)-2-((4-bromophenoxy)methyl)pyrido[3,4-d]pyrimidin-4(3H)-one |
| 109 | 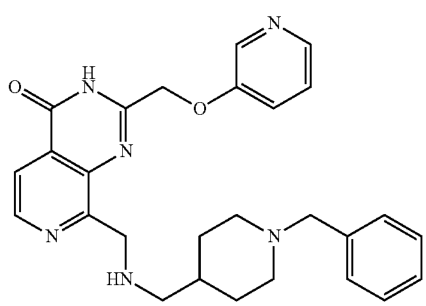 [SMILES: O=c1[nH]c(COc2cccnc2)nc2c(CNCC3CCN(Cc4ccccc4)CC3)nccc12] | 8-((((1-benzylpiperidin-4-yl)methyl)amino)methyl)-2-((pyridin-3-yloxy)methyl)pyrido[3,4-d]pyrimidin-4(3H)-one |
| 110 | 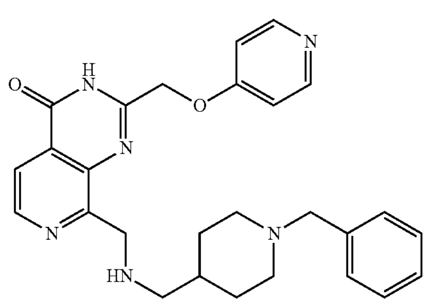 [SMILES: O=c1[nH]c(COc2ccncc2)nc2c(CNCC3CCN(Cc4ccccc4)CC3)nccc12] | 8-((((1-benzylpiperidin-4-yl)methyl)amino)methyl)-2-((pyridin-4-yloxy)methyl)pyrido[3,4-d]pyrimidin-4(3H)-one |

TABLE 1-continued

| No. | Chemical Structure | Chemical Name |
|---|---|---|
| 111 | 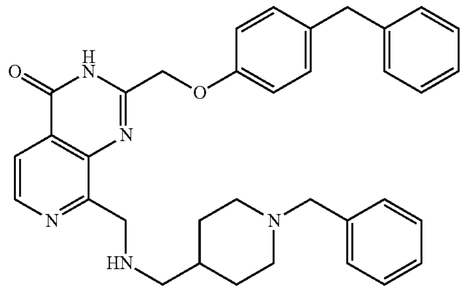 [SMILES: O=c1[nH]c(COc2ccc(Cc3ccccc3)cc2)nc2c(CNCC3CCN(Cc4ccccc4)CC3)nccc12] | 2-((4-benzylphenoxy)methyl)-8-((((1-benzylpiperidin-4-yl)methyl)amino)methyl)pyrido[3,4-d]pyrimidin-4(3H)-one |
| 112 | 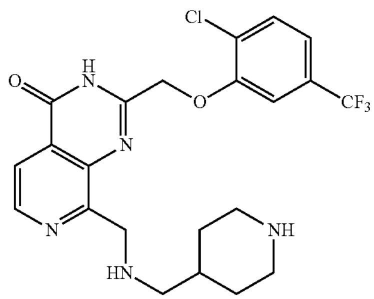 [SMILES: O=c1[nH]c(COc2cc(C(F)(F)F)ccc2Cl)nc2c(CNCC3CCNCC3)nccc12] | 2-((2-chloro-5-(trifluoromethyl)phenoxy)methyl)-8-(((piperidin-4-ylmethyl)amino)methyl)pyrido[3,4-d]pyrimidin-4(3H)-one |
| 113 | 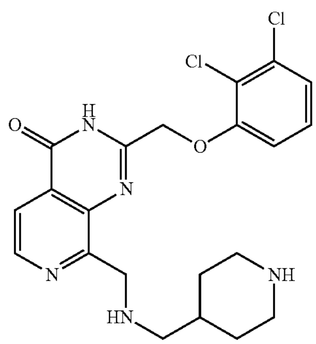 [SMILES: O=c1[nH]c(COc2cccc(Cl)c2Cl)nc2c(CNCC3CCNCC3)nccc12] | 2-((2,3-dichlorophenoxy)methyl)-8-(((piperidin-4-ylmethyl)amino)methyl)pyrido[3,4-d]pyrimidin-4(3H)-one |
| 114 | 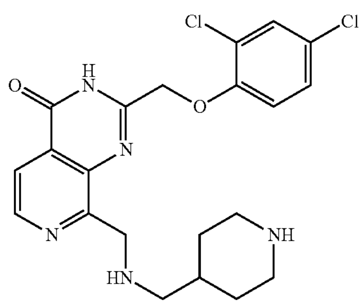 | 2-((2,4-dichlorophenoxy)methyl)-8-(((piperidin-4-ylmethyl)amino)methyl)pyrido[3,4-d]pyrimidin-4(3H)-one |
| 115 | 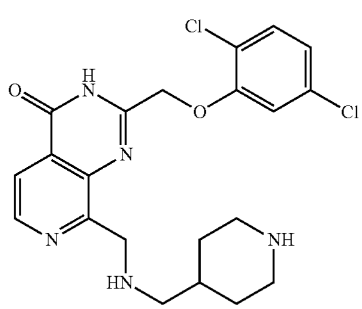 [SMILES: O=c1[nH]c(COc2cc(Cl)ccc2Cl)nc2c(CNCC3CCNCC3)nccc12] | 2-((2,5-dichlorophenoxy)methyl)-8-(((piperidin-4-ylmethyl)amino)methyl)pyrido[3,4-d]pyrimidin-4(3H)-one |

TABLE 1-continued

| No. | Chemical Structure | Chemical Name |
|---|---|---|
| 116 | 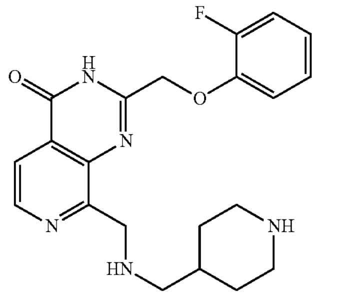 | 2-((2-fluorophenoxy)methyl)-8-(((piperidin-4-ylmethyl)amino)methyl)pyrido[3,4-d]pyrimidin-4(3H)-one |
| 117 | 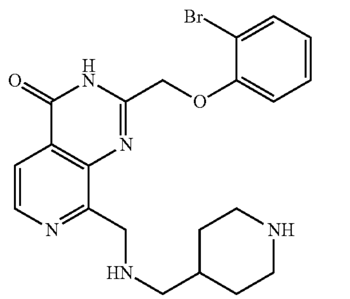 [SMILES: O=c1[nH]c(COc2ccccc2Br)nc2c(CNCC3CCNCC3)nccc12] | 2-((2-bromophenoxy)methyl)-8-(((piperidin-4-ylmethyl)amino)methyl)pyrido[3,4-d]pyrimidin-4(3H)-one |
| 118 | 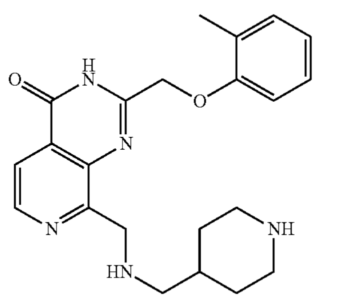 [SMILES: Cc1ccccc1OCc1nc2c(CNCC3CCNCC3)nccc2c(=O)[nH]1] | 8-(((piperidin-4-ylmethyl)amino)methyl)-2-((o-tolyloxy)methyl)pyrido[3,4-d]pyrimidin-4(3H)-one |
| 119 | 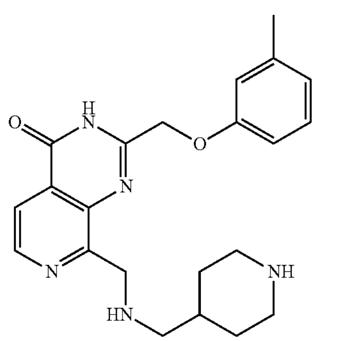 [SMILES: Cc1cccc(OCc2nc3c(CNCC4CCNCC4)nccc3c(=O)[nH]2)c1] | 8-(((piperidin-4-ylmethyl)amino)methyl)-2-((m-tolyloxy)methyl)pyrido[3,4-d]pyrimidin-4(3H)-one |
| 120 | 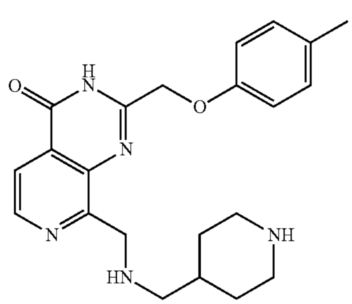 [SMILES: Cc1ccc(OCc2nc3c(CNCC4CCNCC4)nccc3c(=O)[nH]2)cc1] | 8-(((piperidin-4-ylmethyl)amino)methyl)-2-((p-tolyloxy)methyl)pyrido[3,4-d]pyrimidin-4(3H)-one |

TABLE 1-continued

| No. | Chemical Structure | Chemical Name |
|---|---|---|
| 121 | 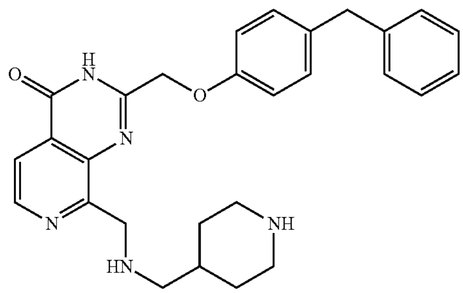 | 2-((4-benzylphenoxy)methyl)-8-(((piperidin-4-ylmethyl)amino)methyl)pyrido[3,4-d]pyrimidin-4(3H)-one |
| 122 | 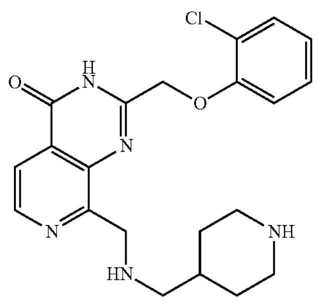 | 2-((2-chlorophenoxy)methyl)-8-(((piperidin-4-ylmethyl)amino)methyl)pyrido[3,4-d]pyrimidin-4(3H)-one |
| 123 | 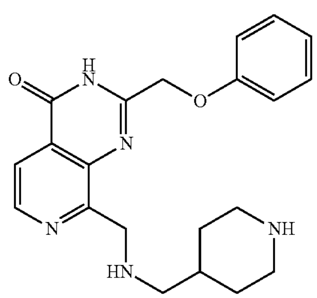 [SMILES: O=c1[nH]c(COc2ccccc2)nc2c(CNCC3CCNCC3)nccc12] | 2-(phenoxymethyl)-8-(((piperidin-4-ylmethyl)amino)methyl)pyrido[3,4-d]pyrimidin-4(3H)-one |
| 124 | 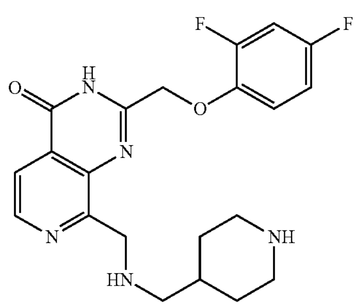 [SMILES: O=c1[nH]c(COc2ccc(F)cc2F)nc2c(CNCC3CCNCC3)nccc12] | 2-((2,4-difluorophenoxy)methyl)-8-(((piperidin-4-ylmethyl)amino)methyl)pyrido[3,4-d]pyrimidin-4(3H)-one |
| 125 | 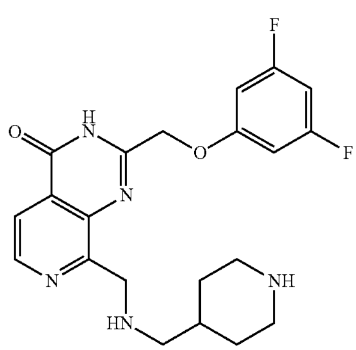 [SMILES: O=c1[nH]c(COc2cc(F)cc(F)c2)nc2c(CNCC3CCNCC3)nccc12] | 2-((3,5-difluorophenoxy)methyl)-8-(((piperidin-4-ylmethyl)amino)methyl)pyrido[3,4-d]pyrimidin-4(3H)-one |

TABLE 1-continued

| No. | Chemical Structure | Chemical Name |
|---|---|---|
| 126 | 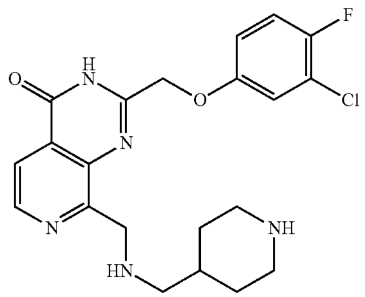 [SMILES: O=c1[nH]c(COc2ccc(F)c(Cl)c2)nc2c(CNCC3CCNCC3)nccc12] | 2-((3-chloro-4-fluorophenoxy)methyl)-8-(((piperidin-4-ylmethyl)amino)methyl)pyrido[3,4-d]pyrimidin-4(3H)-one |
| 127 | 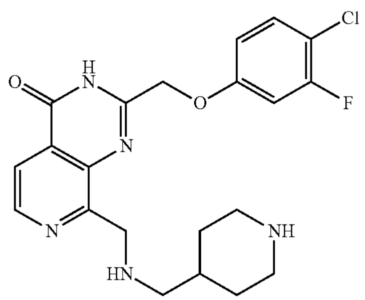 | 2-((4-chloro-3-fluorophenoxy)methyl)-8-(((piperidin-4-ylmethyl)amino)methyl)pyrido[3,4-d]pyrimidin-4(3H)-one |
| 128 | 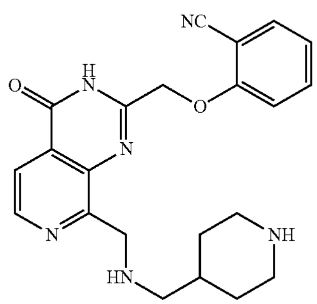 [SMILES: N#Cc1ccccc1OCc1nc2c(CNCC3CCNCC3)nccc2c(=O)[nH]1] | 2-((4-oxo-8-(((piperidin-4-ylmethyl)amino)methyl)-3,4-dihydropyrido[3,4-d]pyrimidin-2-yl)methoxy)benzonitrile |
| 129 | 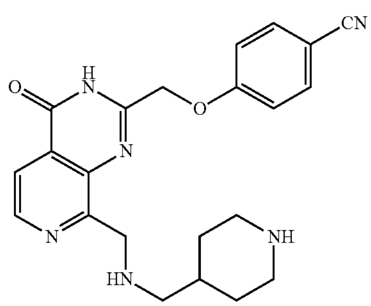 [SMILES: N#Cc1ccc(OCc2nc3c(CNCC4CCNCC4)nccc3c(=O)[nH]2)cc1] | 4-((4-oxo-8-(((piperidin-4-ylmethyl)amino)methyl)-3,4-dihydropyrido[3,4-d]pyrimidin-2-yl)methoxy)benzonitrile |
| 130 | 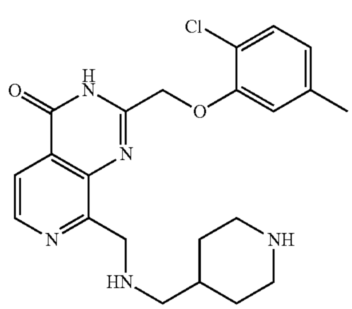 [SMILES: Cc1ccc(Cl)c(OCc2nc3c(CNCC4CCNCC4)nccc3c(=O)[nH]2)c1] | 2-((2-chloro-5-methylphenoxy)methyl)-8-(((piperidin-4-ylmethyl)amino)methyl)pyrido[3,4-d]pyrimidin-4(3H)-one |

TABLE 1-continued

| No. | Chemical Structure | Chemical Name |
|---|---|---|
| 131 | 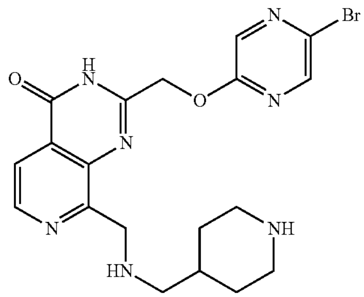 [SMILES: O=c1[nH]c(COc2cnc(Br)cn2)nc2c(CNCC3CCNCC3)nccc12] | 2-(((5-bromopyrazin-2-yl)oxy)methyl)-8-(((piperidin-4-ylmethyl)amino)methyl)pyrido[3,4-d]pyrimidin-4(3H)-one |
| 132 | 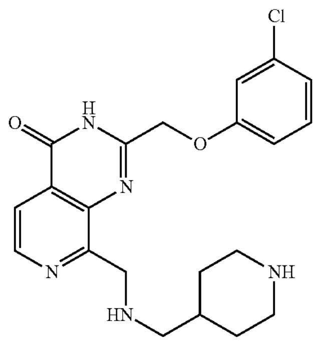 [SMILES: O=c1[nH]c(COc2cccc(Cl)c2)nc2c(CNCC3CCNCC3)nccc12] | 2-((3-chlorophenoxy)methyl)-8-(((piperidin-4-ylmethyl)amino)methyl)pyrido[3,4-d]pyrimidin-4(3H)-one |
| 133 | 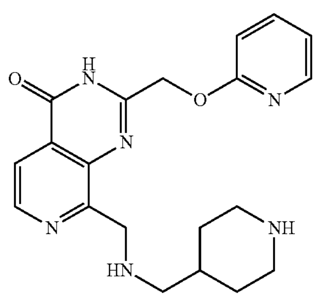 [SMILES: O=c1[nH]c(COc2ccccn2)nc2c(CNCC3CCNCC3)nccc12] | 8-(((piperidin-4-ylmethyl)amino)methyl)-2-((pyridin-2-yloxy)methyl)pyrido[3,4-d]pyrimidin-4(3H)-one |
| 134 | 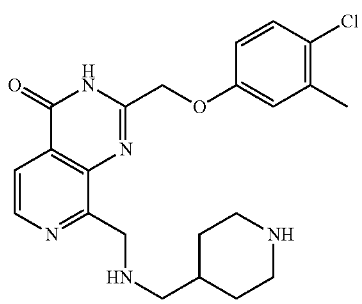 [SMILES: Cc1cc(OCc2nc3c(CNCC4CCNCC4)nccc3c(=O)[nH]2)ccc1Cl] | 2-((4-chloro-3-methylphenoxy)methyl)-8-(((piperidin-4-ylmethyl)amino)methyl)pyrido[3,4-d]pyrimidin-4(3H)-one |
| 135 | 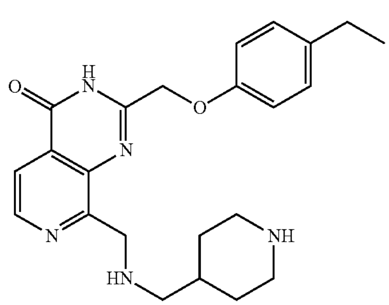 [SMILES: CCc1ccc(OCc2nc3c(CNCC4CCNCC4)nccc3c(=O)[nH]2)cc1] | 2-((4-ethylphenoxy)methyl)-8-(((piperidin-4-ylmethyl)amino)methyl)pyrido[3,4-d]pyrimidin-4(3H)-one |

TABLE 1-continued

| No. | Chemical Structure | Chemical Name |
|---|---|---|
| 136 | 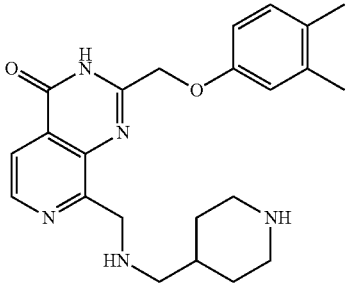 [SMILES: Cc1ccc(OCc2nc3c(CNCC4CCNCC4)nccc3c(=O)[nH]2)cc1C] | 2-((3,4-dimethylphenoxy)methyl)-8-(((piperidin-4-ylmethyl)amino)methyl)pyrido[3,4-d]pyrimidin-4(3H)-one |
| 137 | 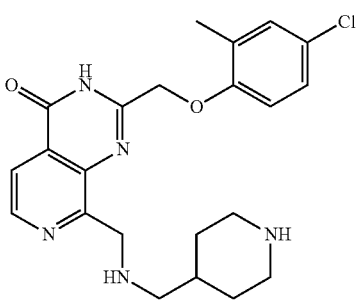 [SMILES: Cc1cc(Cl)ccc1OCc1nc2c(CNCC3CCNCC3)nccc2c(=O)[nH]1] | 2-((4-chloro-2-methylphenoxy)methyl)-8-(((piperidin-4-ylmethyl)amino)methyl)pyrido[3,4-d]pyrimidin-4(3H)-one |
| 138 | 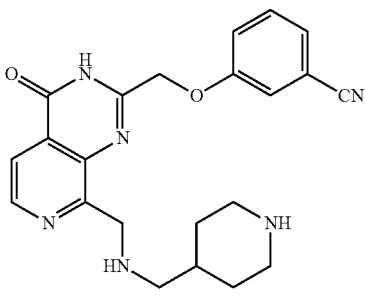 [SMILES: N#Cc1cccc(OCc2nc3c(CNCC4CCNCC4)nccc3c(=O)[nH]2)c1] | 3-((4-oxo-8-(((piperidin-4-ylmethyl)amino)methyl)-3,4-dihydropyrido[3,4-d]pyrimidin-2-yl)methoxy)benzonitrile |
| 139 | 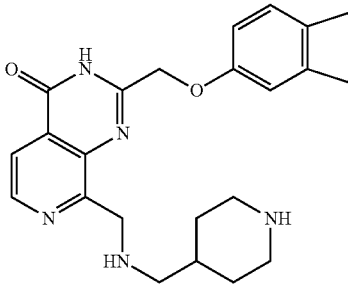 | 2-(((2,3-dihydro-1H-inden-5-yl)oxy)methyl)-8-(((piperidin-4-ylmethyl)amino)methyl)pyrido[3,4-d]pyrimidin-4(3H)-one |
| 140 | 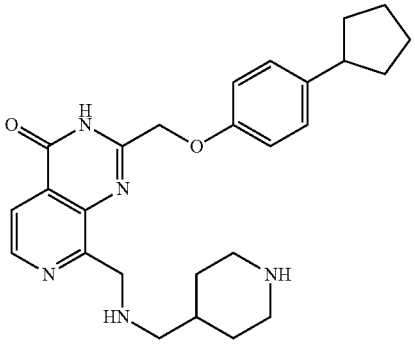 [SMILES: O=c1[nH]c(COc2ccc(C3CCCC3)cc2)nc2c(CNCC3CCNCC3)nccc12] | 2-((4-cyclopentylphenoxy)methyl)-8-(((piperidin-4-ylmethyl)amino)methyl)pyrido[3,4-d]pyrimidin-4(3H)-one |

TABLE 1-continued

| No. | Chemical Structure | Chemical Name |
|---|---|---|
| 141 | 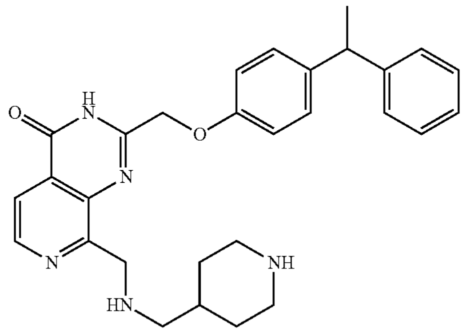 [SMILES: CC(c1ccccc1)c1ccc(OCc2nc3c(CNCC4CCNCC4)nccc3c(=O)[nH]2)cc1] | 2-((4-(1-phenylethyl)phenoxy)methyl)-8-(((piperidin-4-ylmethyl)amino)methyl)pyrido[3,4-d]pyrimidin-4(3H)-one |
| 142 | 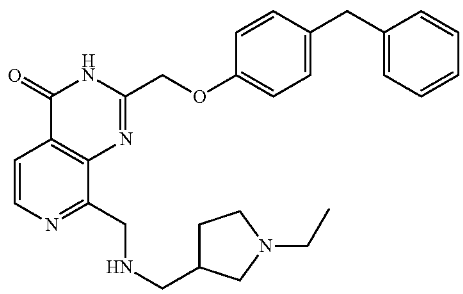 [SMILES: CCN1CCC(CNCc2nccc3c(=O)[nH]c(COc4ccc(Cc5ccccc5)cc4)nc23)C1] | 2-((4-benzylphenoxy)methyl)-8-((((1-ethylpyrrolidin-3-yl)methyl)amino)methyl)pyrido[3,4-d]pyrimidin-4(3H)-one |
| 143 | 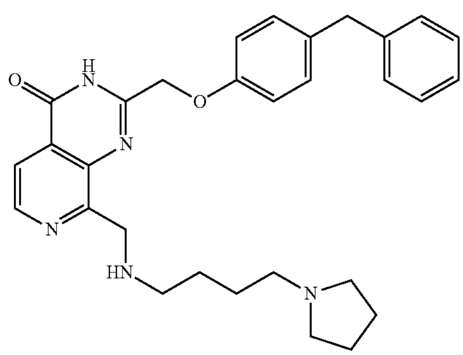 [SMILES: O=c1[nH]c(COc2ccc(Cc3ccccc3)cc2)nc2c(CNCCCCN3CCCC3)nccc12] | 2-((4-benzylphenoxy)methyl)-8-(((4-(pyrrolidin-1-yl)butyl)amino)methyl)pyrido[3,4-d]pyrimidin-4(3H)-one |
| 144 | 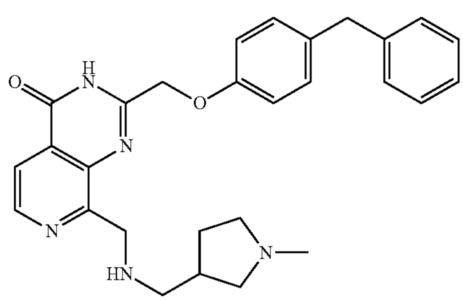 | 2-((4-benzylphenoxy)methyl)-8-((((1-methylpyrrolidin-3-yl)methyl)amino)methyl)pyrido[3,4-d]pyrimidin-4(3H)-one |
| 145 | 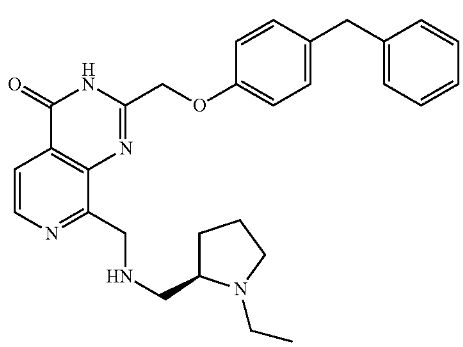 [SMILES: CCN1CCC[C@@H]1CNCc1nccc2c(=O)[nH]c(COc3ccc(Cc4ccccc4)cc3)nc12] | (R)-2-((4-benzylphenoxy)methyl)-8-((((1-ethylpyrrolidin-2-yl)methyl)amino)methyl)pyrido[3,4-d]pyrimidin-4(3H)-one |

TABLE 1-continued

| No. | Chemical Structure | Chemical Name |
|---|---|---|
| 146 | 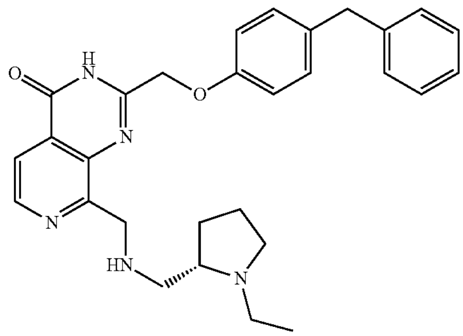 [SMILES: CCN1CCC[C@H]1CNCc1nccc2c(=O)[nH]c(COc3ccc(Cc4ccccc4)cc3)nc12] | (S)-2-((4-benzylphenoxy)methyl)-8-((((1-ethylpyrrolidin-2-yl)methyl)amino)methyl)pyrido[3,4-d]pyrimidin-4(3H)-one |
| 147 | 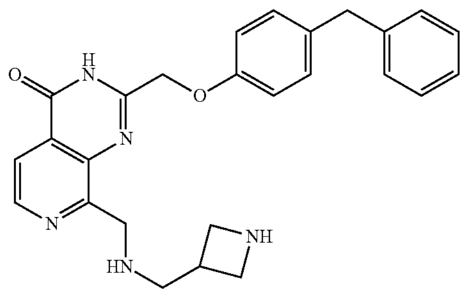 [SMILES: O=c1[nH]c(COc2ccc(Cc3ccccc3)cc2)nc2c(CNCC3CNC3)nccc12] | 8-(((azetidin-3-ylmethyl)amino)methyl)-2-((4-benzylphenoxy)methyl)pyrido[3,4-d]pyrimidin-4(3H)-one |
| 148 | 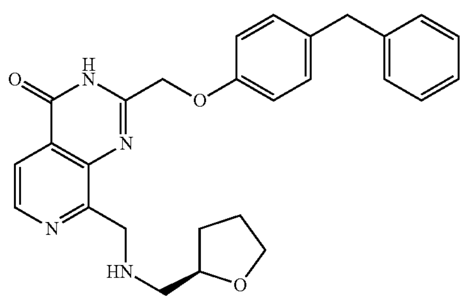 [SMILES: O=c1[nH]c(COc2ccc(Cc3ccccc3)cc2)nc2c(CNC[C@H]3CCCO3)nccc12] | (R)-2-((4-benzylphenoxy)methyl)-8-(((((tetrahydrofuran-2-yl)methyl)amino)methyl)pyrido[3,4-d]pyrimidin-4(3H)-one |
| 149 | 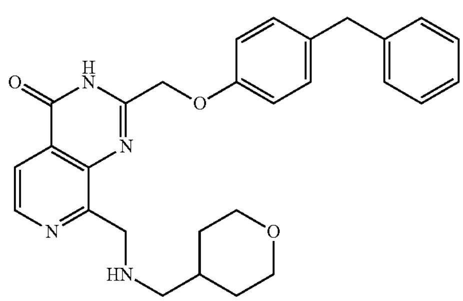 | 2-((4-benzylphenoxy)methyl)-8-(((((tetrahydro-2H-pyran-4-yl)methyl)amino)methyl)pyrido[3,4-d]pyrimidin-4(3H)-one |
| 150 | 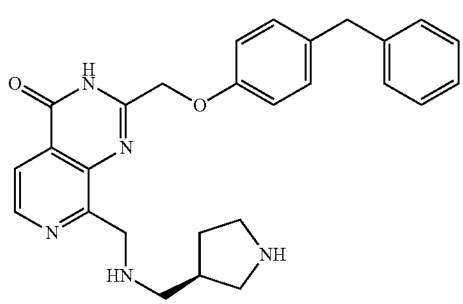 | (S)-2-((4-benzylphenoxy)methyl)-8-(((pyrrolidin-3-ylmethyl)amino)methyl)pyrido[3,4-d]pyrimidin-4(3H)-one |

TABLE 1-continued

| No. | Chemical Structure | Chemical Name |
|---|---|---|
| 151 | 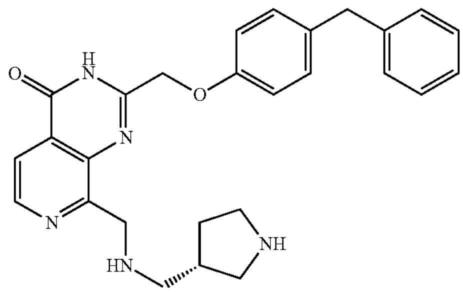 [SMILES: O=c1[nH]c(COc2ccc(Cc3ccccc3)cc2)nc2c(CNC[C@@H]3CCNC3)nccc12] | (R)-2-((4-benzylphenoxy)methyl)-8-(((pyrrolidin-3-ylmethyl)amino)methyl)pyrido[3,4-d]pyrimidin-4(3H)-one |
| 152 | 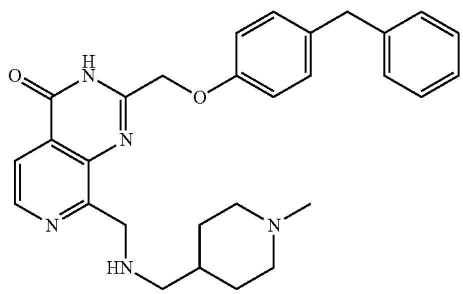 | 2-((4-benzylphenoxy)methyl)-8-(((((1-methylpiperidin-4-yl)methyl)amino)methyl)pyrido[3,4-d]pyrimidin-4(3H)-one |
| 153 | 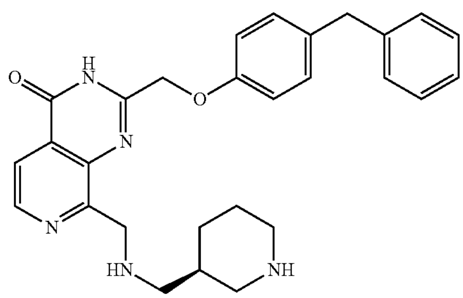 [SMILES: O=c1[nH]c(COc2ccc(Cc3ccccc3)cc2)nc2c(CNC[C@H]3CCCNC3)nccc12] | (S)-2-((4-benzylphenoxy)methyl)-8-(((piperidin-3-ylmethyl)amino)methyl)pyrido[3,4-d]pyrimidin-4(3H)-one |
| 154 | 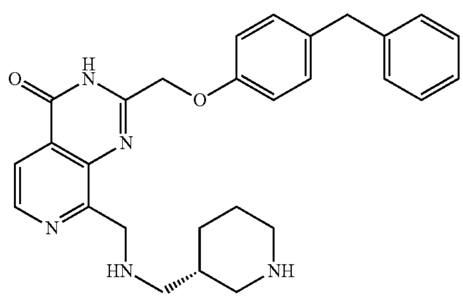 | (R)-2-((4-benzylphenoxy)methyl)-8-(((piperidin-3-ylmethyl)amino)methyl)pyrido[3,4-d]pyrimidin-4(3H)-one |
| 155 | 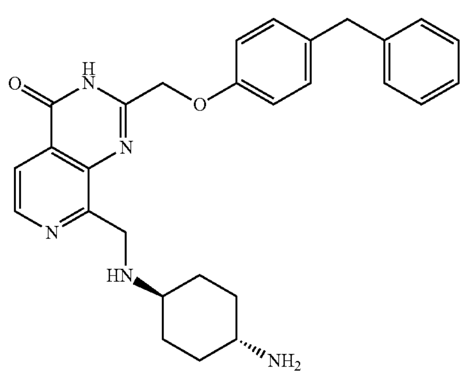 [SMILES: N[C@H]1CC[C@H](NCc2nccc3c(=O)[nH]c(COc4ccc(Cc5ccccc5)cc4)nc23)CC1] | 8-((((1r,4r)-4-aminocyclohexyl)amino)methyl)-2-((4-benzylphenoxy)methyl)pyrido[3,4-d]pyrimidin-4(3H)-one |

TABLE 1-continued

| No. | Chemical Structure | Chemical Name |
|---|---|---|
| 156 | 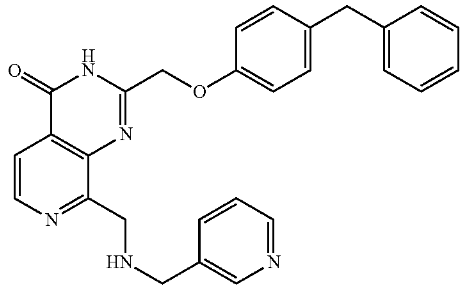 [SMILES: O=c1[nH]c(COc2ccc(Cc3ccccc3)cc2)nc2c(CNCc3cccnc3)nccc12] | 2-((4-benzylphenoxy)methyl)-8-(((pyridin-3-ylmethyl)amino)methyl)pyrido[3,4-d]pyrimidin-4(3H)-one |
| 157 | 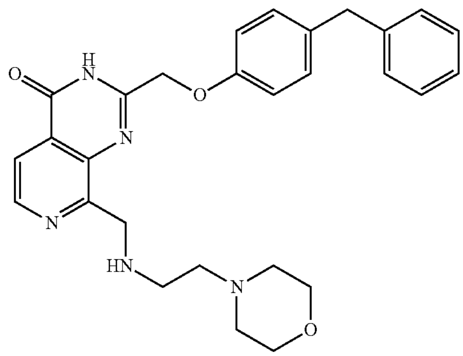 [SMILES: O=c1[nH]c(COc2ccc(Cc3ccccc3)cc2)nc2c(CNCCN3CCOCC3)nccc12] | 2-((4-benzylphenoxy)methyl)-8-(((2-morpholinoethyl)amino)methyl)pyrido[3,4-d]pyrimidin-4(3H)-one |
| 158 | 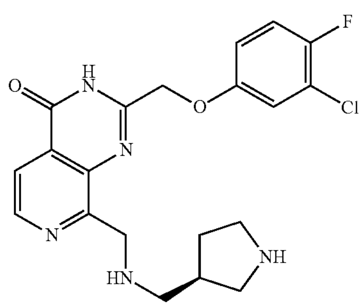 [SMILES: O=c1[nH]c(COc2ccc(F)c(Cl)c2)nc2c(CNC[C@H]3CCNC3)nccc12] | (S)-2-((3-chloro-4-fluorophenoxy)methyl)-8-(((pyrrolidin-3-ylmethyl)amino)methyl)pyrido[3,4-d]pyrimidin-4(3H)-one |
| 159 | 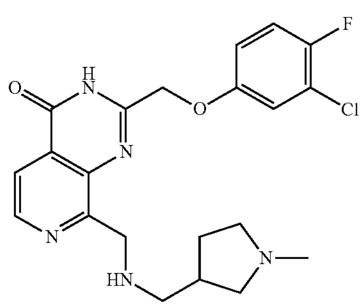 [SMILES: CN1CCC(CNCc2nccc3c(=O)[nH]c(COc4ccc(F)c(Cl)c4)nc23)C1] | 2-((3-chloro-4-fluorophenoxy)methyl)-8-((((1-methylpyrrolidin-3-yl)methyl)amino)methyl)pyrido[3,4-d]pyrimidin-4(3H)-one |
| 160 | 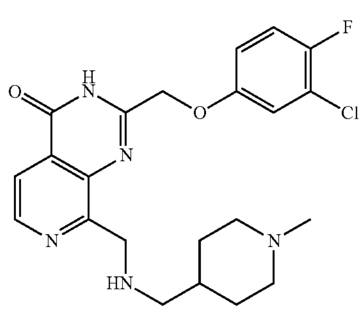 [SMILES: CN1CCC(CNCc2nccc3c(=O)[nH]c(COc4ccc(F)c(Cl)c4)nc23)CC1] | 2-((3-chloro-4-fluorophenoxy)methyl)-8-((((1-methylpiperidin-4-yl)methyl)amino)methyl)pyrido[3,4-d]pyrimidin-4(3H)-one |

TABLE 1-continued

| No. | Chemical Structure | Chemical Name |
|---|---|---|
| 161 | 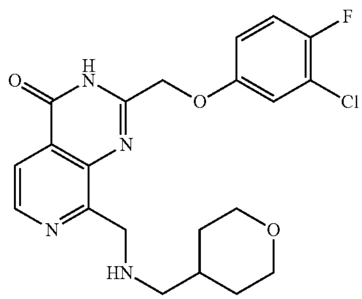 [SMILES: O=c1[nH]c(COc2ccc(F)c(Cl)c2)nc2c(CNCC3CCOCC3)nccc12] | 2-((3-chloro-4-fluorophenoxy)methyl)-8-(((((tetrahydro-2H-pyran-4-yl)methyl)amino)methyl)pyrido[3,4-d]pyrimidin-4(3H)-one |
| 162 | 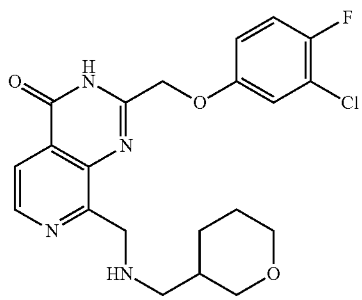 [SMILES: O=c1[nH]c(COc2ccc(F)c(Cl)c2)nc2c(CNCC3CCCOC3)nccc12] | 2-((3-chloro-4-fluorophenoxy)methyl)-8-(((((tetrahydro-2H-pyran-3-yl)methyl)amino)methyl)pyrido[3,4-d]pyrimidin-4(3H)-one |
| 163 | 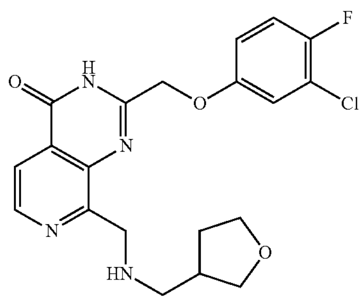 [SMILES: O=c1[nH]c(COc2ccc(F)c(Cl)c2)nc2c(CNCC3CCOC3)nccc12] | 2-((3-chloro-4-fluorophenoxy)methyl)-8-(((((tetrahydrofuran-3-yl)methyl)amino)methyl)pyrido[3,4-d]pyrimidin-4(3H)-one |
| 164 | 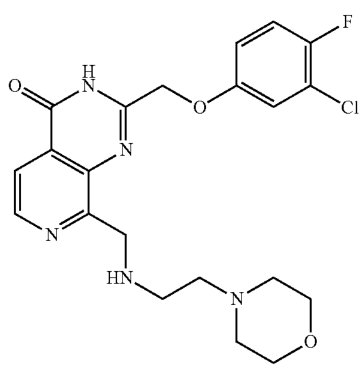 [SMILES: O=c1[nH]c(COc2ccc(F)c(Cl)c2)nc2c(CNCCN3CCOCC3)nccc12] | 2-((3-chloro-4-fluorophenoxy)methyl)-8-(((2-morpholinoethyl)amino)methyl)pyrido[3,4-d]pyrimidin-4(3H)-one |
| 165 | 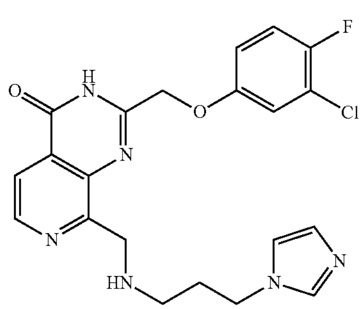 [SMILES: O=c1[nH]c(COc2ccc(F)c(Cl)c2)nc2c(CNCCCn3ccnc3)nccc12] | 8-(((3-(1H-imidazol-1-yl)propyl)amino)methyl)-2-((3-chloro-4-fluorophenoxy)methyl)pyrido[3,4-d]pyrimidin-4(3H)-one |

TABLE 1-continued

| No. | Chemical Structure | Chemical Name |
|---|---|---|
| 166 | 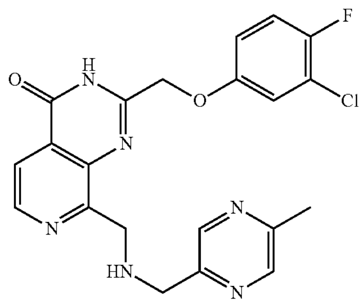 [SMILES: Cc1cnc(CNCc2nccc3c(=O)[nH]c(COc4ccc(F)c(Cl)c4)nc23)cn1] | 2-((3-chloro-4-fluorophenoxy)methyl)-8-((((5-methylpyrazin-2-yl)methyl)amino)methyl)pyrido[3,4-d]pyrimidin-4(3H)-one |
| 167 | 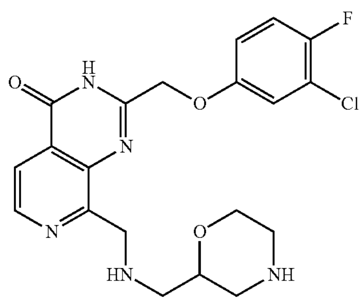 | 2-((3-chloro-4-fluorophenoxy)methyl)-8-(((morpholin-2-ylmethyl)amino)methyl)pyrido[3,4-d]pyrimidin-4(3H)-one |
| 168 | 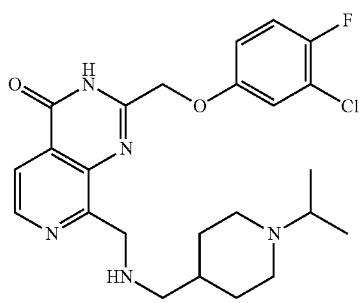 [SMILES: CC(C)N1CCC(CNCc2nccc3c(=O)[nH]c(COc4ccc(F)c(Cl)c4)nc23)CC1] | 2-((3-chloro-4-fluorophenoxy)methyl)-8-((((1-isopropylpiperidin-4-yl)methyl)amino)methyl)pyrido[3,4-d]pyrimidin-4(3H)-one |
| 169 | 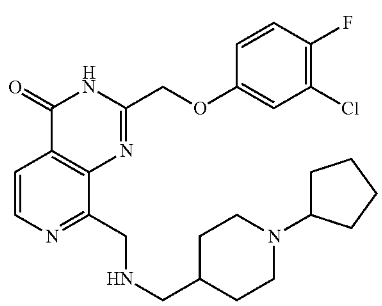 [SMILES: O=c1[nH]c(COc2ccc(F)c(Cl)c2)nc2c(CNCC3CCN(C4CCCC4)CC3)nccc12] | 2-((3-chloro-4-fluorophenoxy)methyl)-8-((((1-cyclopentylpiperidin-4-yl)methyl)amino)methyl)pyrido[3,4-d]pyrimidin-4(3H)-one |
| 170 | 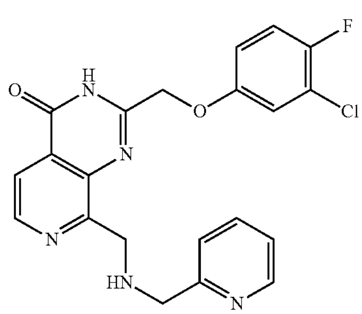 [SMILES: O=c1[nH]c(COc2ccc(F)c(Cl)c2)nc2c(CNCc3ccccn3)nccc12] | 2-((3-chloro-4-fluorophenoxy)methyl)-8-(((pyridin-2-ylmethyl)amino)methyl)pyrido[3,4-d]pyrimidin-4(3H)-one |

TABLE 1-continued

| No. | Chemical Structure | Chemical Name |
|---|---|---|
| 171 | 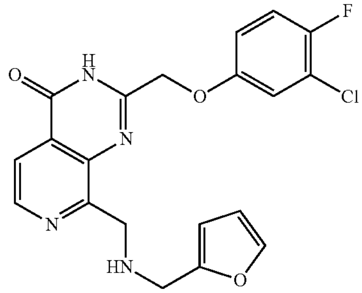 | 2-((3-chloro-4-fluorophenoxy)methyl)-8-(((furan-2-ylmethyl)amino)methyl)pyrido[3,4-d]pyrimidin-4(3H)-one |
| 172 | 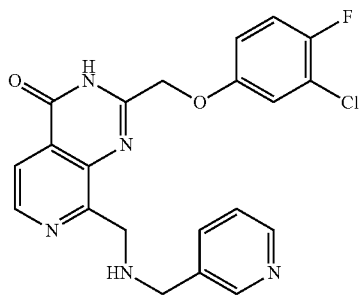 [SMILES: O=c1[nH]c(COc2ccc(F)c(Cl)c2)nc2c(CNCc3cccnc3)nccc12] | 2-((3-chloro-4-fluorophenoxy)methyl)-8-(((pyridin-3-ylmethyl)amino)methyl)pyrido[3,4-d]pyrimidin-4(3H)-one |
| 173 | 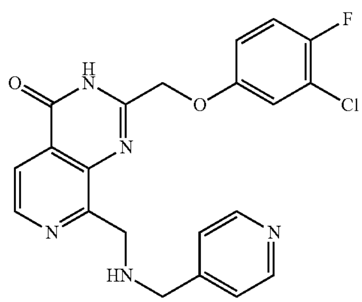 [SMILES: O=c1[nH]c(COc2ccc(F)c(Cl)c2)nc2c(CNCc3ccncc3)nccc12] | 2-((3-chloro-4-fluorophenoxy)methyl)-8-(((pyridin-4-ylmethyl)amino)methyl)pyrido[3,4-d]pyrimidin-4(3H)-one |
| 174 | 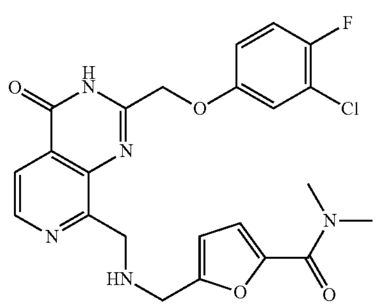 [SMILES: CN(C)C(=O)c1ccc(CNCc2nccc3c(=O)[nH]c(COc4ccc(F)c(Cl)c4)nc23)o1] | 5-((((2-((3-chloro-4-fluorophenoxy)methyl)-4-oxo-3,4-dihydropyrido[3,4-d]pyrimidin-8-yl)methyl)amino)methyl)-N,N-dimethylfuran-2-carboxamide |
| 175 | 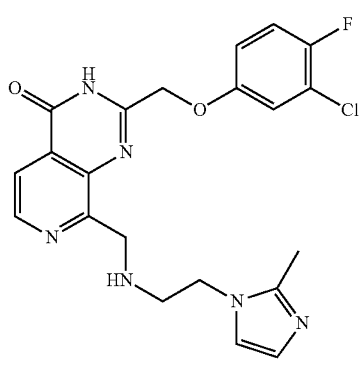 [SMILES: Cc1nccn1CCNCc1nccc2c(=O)[nH]c(COc3ccc(F)c(Cl)c3)nc12] | 2-((3-chloro-4-fluorophenoxy)methyl)-8-(((2-(2-methyl-1H-imidazol-1-yl)ethyl)amino)methyl)pyrido[3,4-d]pyrimidin-4(3H)-one |

TABLE 1-continued

| No. | Chemical Structure | Chemical Name |
|-----|-------------------|---------------|
| 176 | 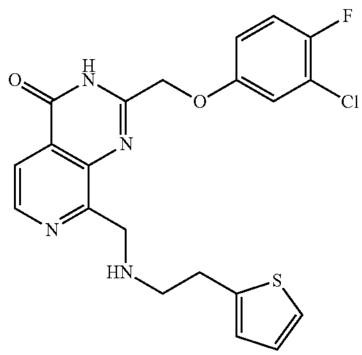 [SMILES: O=c1[nH]c(COc2ccc(F)c(Cl)c2)nc2c(CNCCc3cccs3)nccc12] | 2-((3-chloro-4-fluorophenoxy)methyl)-8-(((2-(thiophen-2-yl)ethyl)amino)methyl)pyrido[3,4-d]pyrimidin-4(3H)-one |
| 177 | 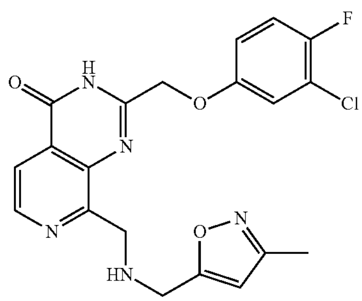 [SMILES: Cc1cc(CNCc2nccc3c(=O)[nH]c(COc4ccc(F)c(Cl)c4)nc23)on1] | 2-((3-chloro-4-fluorophenoxy)methyl)-8-((((3-methylisoxazol-5-yl)methyl)amino)methyl)pyrido[3,4-d]pyrimidin-4(3H)-one |
| 178 | 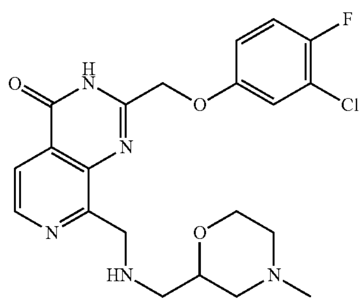 [SMILES: CN1CCOC(CNCc2nccc3c(=O)[nH]c(COc4ccc(F)c(Cl)c4)nc23)C1] | 2-((3-chloro-4-fluorophenoxy)methyl)-8-((((4-methylmorpholin-2-yl)methyl)amino)methyl)pyrido[3,4-d]pyrimidin-4(3H)-one |
| 179 | 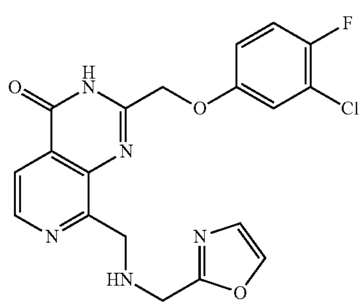 [SMILES: O=c1[nH]c(COc2ccc(F)c(Cl)c2)nc2c(CNCc3ncco3)nccc12] | 2-((3-chloro-4-fluorophenoxy)methyl)-8-(((oxazol-2-ylmethyl)amino)methyl)pyrido[3,4-d]pyrimidin-4(3H)-one |
| 180 | 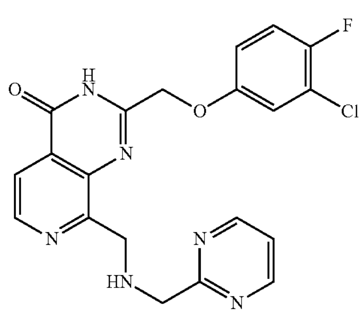 [SMILES: O=c1[nH]c(COc2ccc(F)c(Cl)c2)nc2c(CNCc3ncccn3)nccc12] | 2-((3-chloro-4-fluorophenoxy)methyl)-8-((((pyrimidin-2-ylmethyl)amino)methyl)pyrido[3,4-d]pyrimidin-4(3H)-one |

TABLE 1-continued

| No. | Chemical Structure | Chemical Name |
|---|---|---|
| 181 | 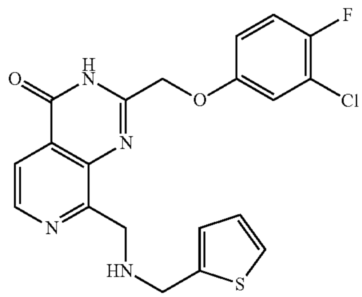 [SMILES: O=c1[nH]c(COc2ccc(F)c(Cl)c2)nc2c(CNCc3cccs3)nccc12] | 2-((3-chloro-4-fluorophenoxy)methyl)-8-(((thiophen-2-ylmethyl)amino)methyl)pyrido[3,4-d]pyrimidin-4(3H)-one |
| 182 | 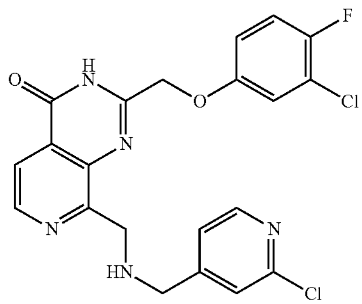 [SMILES: O=c1[nH]c(COc2ccc(F)c(Cl)c2)nc2c(CNCc3ccnc(Cl)c3)nccc12] | 2-((3-chloro-4-fluorophenoxy)methyl)-8-((((2-chloropyridin-4-yl)methyl)amino)methyl)pyrido[3,4-d]pyrimidin-4(3H)-one |
| 183 | 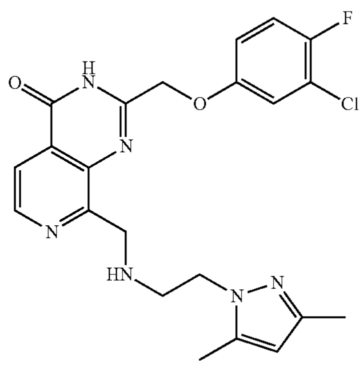 [SMILES: Cc1cc(C)n(CCNCc2nccc3c(=O)[nH]c(COc4ccc(F)c(Cl)c4)nc23)n1] | 2-((3-chloro-4-fluorophenoxy)methyl)-8-(((2-(3,5-dimethyl-1H-pyrazol-1-yl)ethyl)amino)methyl)pyrido[3,4-d]pyrimidin-4(3H)-one |
| 184 | 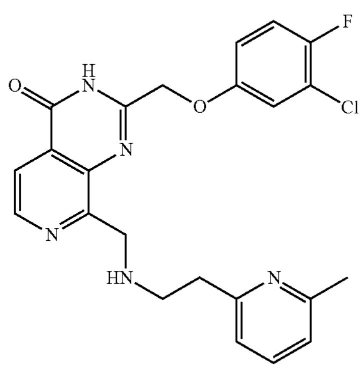 [SMILES: Cc1cccc(CCNCc2nccc3c(=O)[nH]c(COc4ccc(F)c(Cl)c4)nc23)n1] | 2-((3-chloro-4-fluorophenoxy)methyl)-8-(((2-(6-methylpyridin-2-yl)ethyl)amino)methyl)pyrido[3,4-d]pyrimidin-4(3H)-one |

| No. | Chemical Structure | Chemical Name |
|---|---|---|
| 185 | 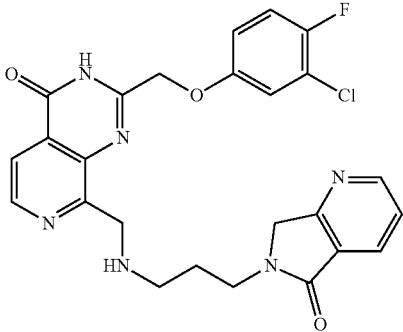 [SMILES: O=C1c2cccnc2CN1CCCNCc1nccc2c(=O)[nH]c(COc3ccc(F)c(Cl)c3)nc12] | 2-((3-chloro-4-fluorophenoxy)methyl)-8-(((3-(5-oxo-5,7-dihydro-6H-pyrrolo[3,4-b]pyridin-6-yl)propyl)amino)methyl)pyrido[3,4-d]pyrimidin-4(3H)-one |
| 186 | 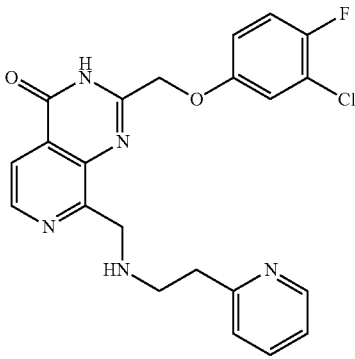 [SMILES: O=c1[nH]c(COc2ccc(F)c(Cl)c2)nc2c(CNCCc3ccccn3)nccc12] | 2-((3-chloro-4-fluorophenoxy)methyl)-8-(((2-(pyridin-2-yl)ethyl)amino)methyl)pyrido[3,4-d]pyrimidin-4(3H)-one |
| 187 | 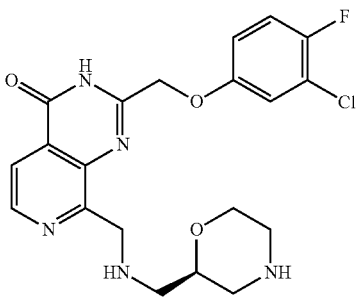 [SMILES: O=c1[nH]c(COc2ccc(F)c(Cl)c2)nc2c(CNC[C@@H]3CNCCO3)nccc12] | (R)-2-((3-chloro-4-fluorophenoxy)methyl)-8-(((morpholin-2-ylmethyl)amino)methyl)pyrido[3,4-d]pyrimidin-4(3H)-one |
| 188 | 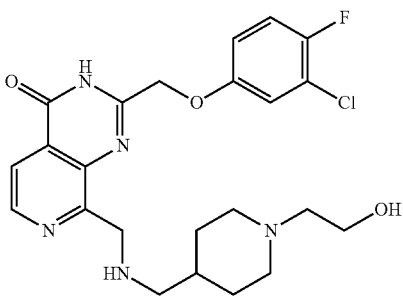 [SMILES: O=c1[nH]c(COc2ccc(F)c(Cl)c2)nc2c(CNCC3CCN(CCO)CC3)nccc12] | 2-((3-chloro-4-fluorophenoxy)methyl)-8-((((1-(2-hydroxyethyl)piperidin-4-yl)methyl)amino)methyl)pyrido[3,4-d]pyrimidin-4(3H)-one |
| 189 | 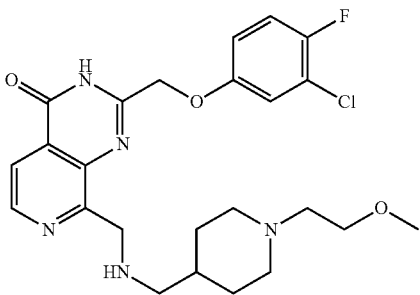 [SMILES: COCCN1CCC(CNCc2nccc3c(=O)[nH]c(COc4ccc(F)c(Cl)c4)nc23)CC1] | 2-((3-chloro-4-fluorophenoxy)methyl)-8-((((1-(2-methoxyethyl)piperidin-4-yl)methyl)amino)methyl)pyrido[3,4-d]pyrimidin-4(3H)-one |

TABLE 1-continued

| No. | Chemical Structure | Chemical Name |
|---|---|---|
| 190 | 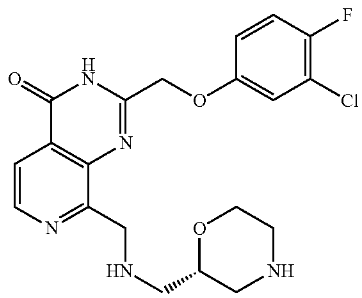 [SMILES: O=c1[nH]c(COc2ccc(F)c(Cl)c2)nc2c(CNC[C@H]3CNCCO3)nccc12] | (S)-2-((3-chloro-4-fluorophenoxy)methyl)-8-(((morpholin-2-ylmethyl)amino)methyl)pyrido[3,4-d]pyrimidin-4(3H)-one |
| 191 | 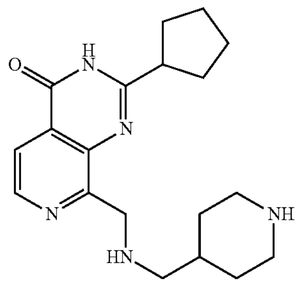 | 2-cyclopentyl-8-(((piperidin-4-ylmethyl)amino)methyl)pyrido[3,4-d]pyrimidin-4(3H)-one |
| 192 | 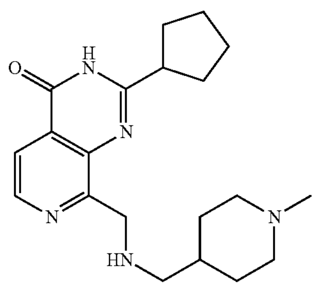 [SMILES: CN1CCC(CNCc2nccc3c(=O)[nH]c(C4CCCC4)nc23)CC1] | 2-cyclopentyl-8-((((1-methylpiperidin-4-yl)methyl)amino)methyl)pyrido[3,4-d]pyrimidin-4(3H)-one |
| 193 | 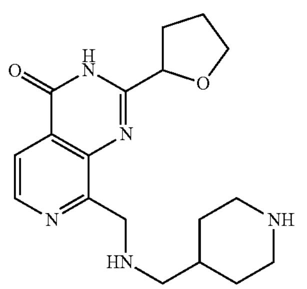 | 8-(((piperidin-4-ylmethyl)amino)methyl)-2-(tetrahydrofuran-2-yl)pyrido[3,4-d]pyrimidin-4(3H)-one |
| 194 | 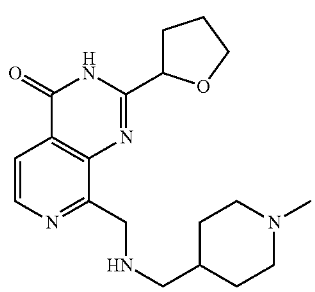 [SMILES: CN1CCC(CNCc2nccc3c(=O)[nH]c(C4CCCO4)nc23)CC1] | 8-((((1-methylpiperidin-4-yl)methyl)amino)methyl)-2-(tetrahydrofuran-2-yl)pyrido[3,4-d]pyrimidin-4(3H)-one |

TABLE 1-continued

| No. | Chemical Structure | Chemical Name |
|---|---|---|
| 195 | 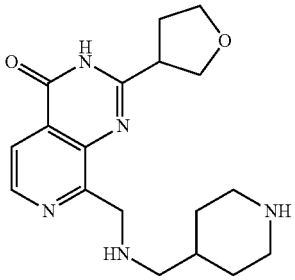 | 8-(((piperidin-4-ylmethyl)amino)methyl)-2-(tetrahydrofuran-3-yl)pyrido[3,4-d]pyrimidin-4(3H)-one |
| 196 | 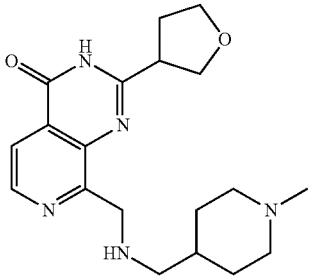 [SMILES: CN1CCC(CNCc2nccc3c(=O)[nH]c(C4CCOC4)nc23)CC1] | 8-((((1-methylpiperidin-4-yl)methyl)amino)methyl)-2-(tetrahydrofuran-3-yl)pyrido[3,4-d]pyrimidin-4(3H)-one |
| 197 | 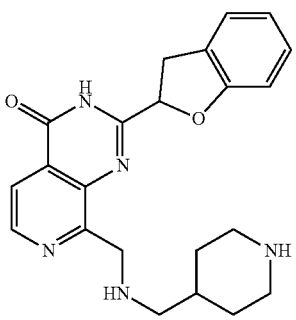 [SMILES: O=c1[nH]c(C2Cc3ccccc3O2)nc2c(CNCC3CCNCC3)nccc12] | 2-(2,3-dihydrobenzofuran-2-yl)-8-(((piperidin-4-ylmethyl)amino)methyl)pyrido[3,4-d]pyrimidin-4(3H)-one |
| 198 | 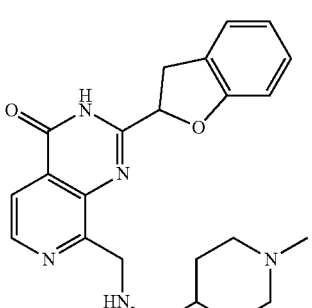 | 2-(2,3-dihydrobenzofuran-2-yl)-8-((((1-methylpiperidin-4-yl)methyl)amino)methyl)pyrido[3,4-d]pyrimidin-4(3H)-one |
| 199 | 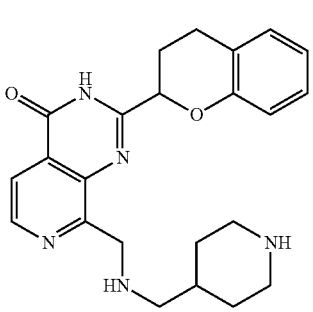 [SMILES: O=c1[nH]c(C2CCc3ccccc3O2)nc2c(CNCC3CCNCC3)nccc12] | 2-(chroman-2-yl)-8-(((piperidin-4-ylmethyl)amino)methyl)pyrido[3,4-d]pyrimidin-4(3H)-one |

TABLE 1-continued

| No. | Chemical Structure | Chemical Name |
|---|---|---|
| 200 | 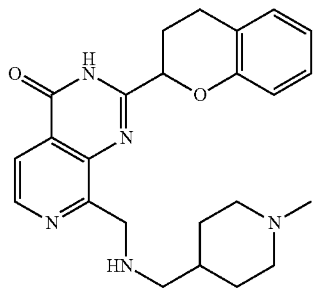 [SMILES: CN1CCC(CNCc2nccc3c(=O)[nH]c(C4CCc5ccccc5O4)nc23)CC1] | 2-(chroman-2-yl)-8-((((1-methylpiperidin-4-yl)methyl)amino)methyl)pyrido[3,4-d]pyrimidin-4(3H)-one |
| 201 | 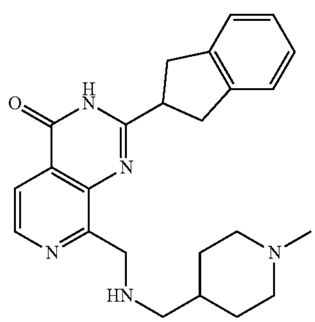 | 2-(2,3-dihydro-1H-inden-2-yl)-8-((((1-methylpiperidin-4-yl)methyl)amino)methyl)pyrido[3,4-d]pyrimidin-4(3H)-one |
| 202 | 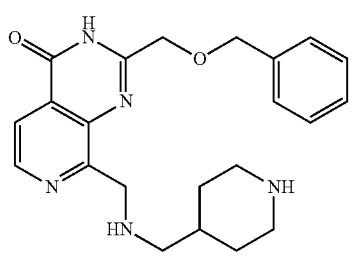 [SMILES: O=c1[nH]c(COCc2ccccc2)nc2c(CNCC3CCNCC3)nccc12] | 2-((benzyloxy)methyl)-8-(((piperidin-4-ylmethyl)amino)methyl)pyrido[3,4-d]pyrimidin-4(3H)-one |
| 203 | 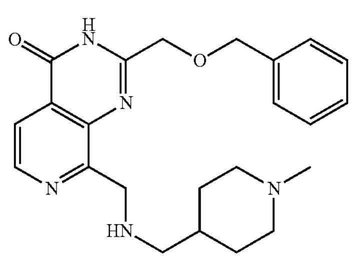 [SMILES: CN1CCC(CNCc2nccc3c(=O)[nH]c(COCc4ccccc4)nc23)CC1] | 2-((benzyloxy)methyl)-8-((((1-methylpiperidin-4-yl)methyl)amino)methyl)pyrido[3,4-d]pyrimidin-4(3H)-one |
| 204 | 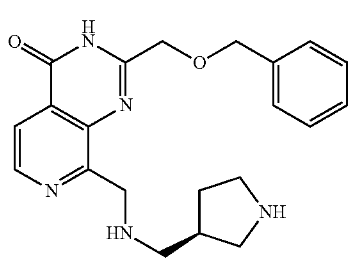 [SMILES: O=c1[nH]c(COCc2ccccc2)nc2c(CNC[C@H]3CCNC3)nccc12] | (S)-2-((benzyloxy)methyl)-8-(((pyrrolidin-3-ylmethyl)amino)methyl)pyrido[3,4-d]pyrimidin-4(3H)-one |

TABLE 1-continued

| No. | Chemical Structure | Chemical Name |
|---|---|---|
| 205 | 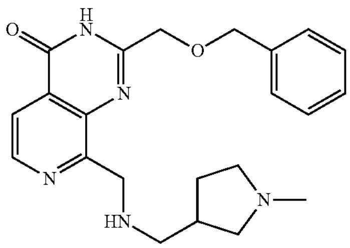 [SMILES: CN1CCC(CNCc2nccc3c(=O)[nH]c(COCc4ccccc4)nc23)C1] | 2-((benzyloxy)methyl)-8-((((1-methylpyrrolidin-3-yl)methyl)amino)methyl)pyrido[3,4-d]pyrimidin-4(3H)-one |
| 206 | 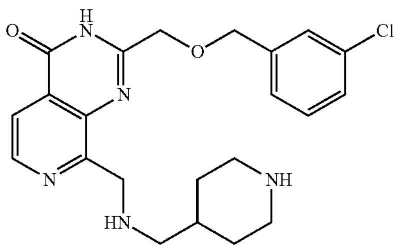 [SMILES: O=c1[nH]c(COCc2cccc(Cl)c2)nc2c(CNCC3CCNCC3)nccc12] | 2-(((3-chlorobenzyl)oxy)methyl)-8-(((piperidin-4-ylmethyl)amino)methyl)pyrido[3,4-d]pyrimidin-4(3H)-one |
| 207 | 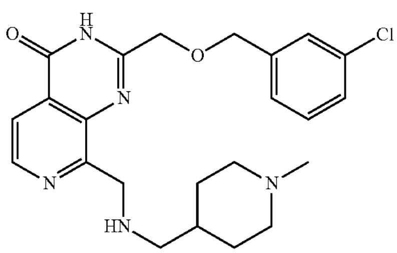 [SMILES: CN1CCC(CNCc2nccc3c(=O)[nH]c(COCc4cccc(Cl)c4)nc23)CC1] | 2-(((3-chlorobenzyl)oxy)methyl)-8-((((1-methylpiperidin-4-yl)methyl)amino)methyl)pyrido[3,4-d]pyrimidin-4(3H)-one |
| 208 | 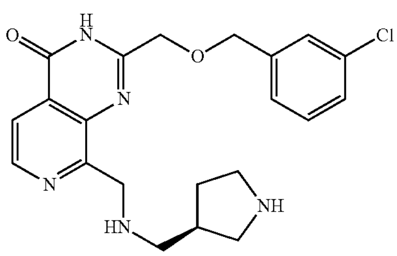 [SMILES: O=c1[nH]c(COCc2cccc(Cl)c2)nc2c(CNC[C@H]3CCNC3)nccc12] | (S)-2-(((3-chlorobenzyl)oxy)methyl)-8-(((pyrrolidin-3-ylmethyl)amino)methyl)pyrido[3,4-d]pyrimidin-4(3H)-one |
| 209 | 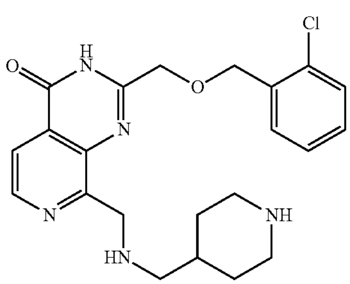 [SMILES: O=c1[nH]c(COCc2ccccc2Cl)nc2c(CNCC3CCNCC3)nccc12] | 2-(((2-chlorobenzyl)oxy)methyl)-8-(((piperidin-4-ylmethyl)amino)methyl)pyrido[3,4-d]pyrimidin-4(3H)-one |
| 210 | 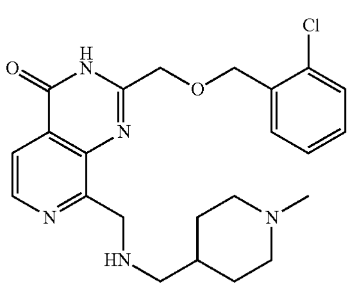 [SMILES: CN1CCC(CNCc2nccc3c(=O)[nH]c(COCc4ccccc4Cl)nc23)CC1] | 2-(((2-chlorobenzyl)oxy)methyl)-8-((((1-methylpiperidin-4-yl)methyl)amino)methyl)pyrido[3,4-d]pyrimidin-4(3H)-one |

TABLE 1-continued

| No. | Chemical Structure | Chemical Name |
|---|---|---|
| 211 | 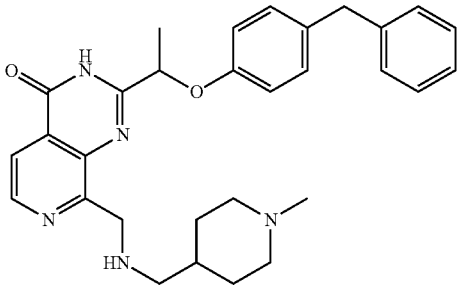 | 2-(1-(4-benzylphenoxy)ethyl)-8-((((1-methylpiperidin-4-yl)methyl)amino)methyl)pyrido[3,4-d]pyrimidin-4(3H)-one |
| 212 | 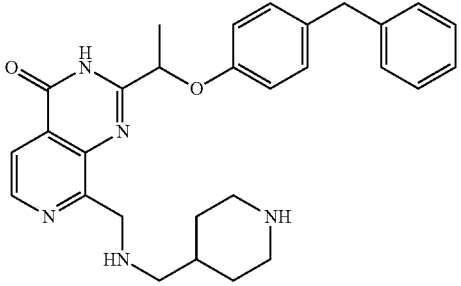 | 2-(1-(4-benzylphenoxy)ethyl)-8-(((piperidin-4-ylmethyl)amino)methyl)pyrido[3,4-d]pyrimidin-4(3H)-one |
| 213 | 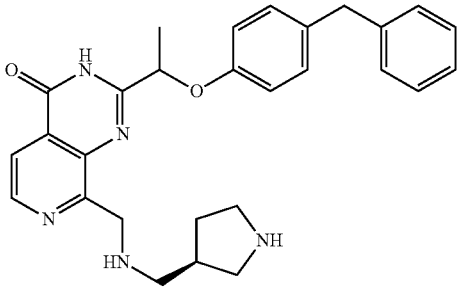 | 2-(1-(4-benzylphenoxy)ethyl)-8-(((((S)-pyrrolidin-3-yl)methyl)amino)methyl)pyrido[3,4-d]pyrimidin-4(3H)-one |
| 214 | 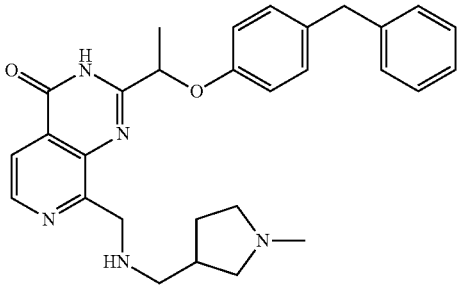 | 2-(1-(4-benzylphenoxy)ethyl)-8-((((1-methylpyrrolidin-3-yl)methyl)amino)methyl)pyrido[3,4-d]pyrimidin-4(3H)-one |
| 215 | 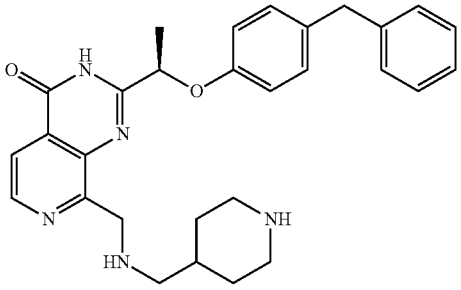 [SMILES: C[C@@H](Oc1ccc(Cc2ccccc2)cc1)c1nc2c(CNCC3CCNCC3)nccc2c(=O)[nH]1] | (R)-2-(1-(4-benzylphenoxy)ethyl)-8-(((piperidin-4-ylmethyl)amino)methyl)pyrido[3,4-d]pyrimidin-4(3H)-one |

TABLE 1-continued

| No. | Chemical Structure | Chemical Name |
|---|---|---|
| 216 | 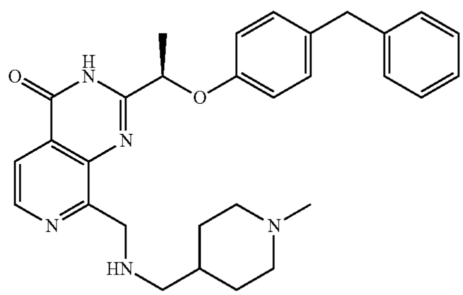 [SMILES: C[C@@H](Oc1ccc(Cc2ccccc2)cc1)c1nc2c(CNCC3CCN(C)CC3)nccc2c(=O)[nH]1] | (R)-2-(1-(4-benzylphenoxy)ethyl)-8-((((1-methylpiperidin-4-yl)methyl)amino)methyl)pyrido[3,4-d]pyrimidin-4(3H)-one |
| 217 | 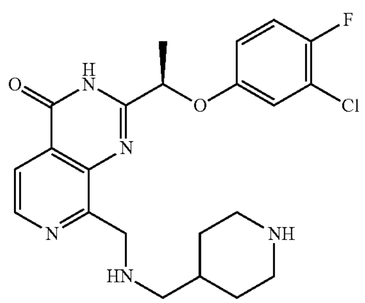 [SMILES: C[C@@H](Oc1ccc(F)c(Cl)c1)c1nc2c(CNCC3CCNCC3)nccc2c(=O)[nH]1] | (R)-2-(1-(3-chloro-4-fluorophenoxy)ethyl)-8-(((piperidin-4-ylmethyl)amino)methyl)pyrido[3,4-d]pyrimidin-4(3H)-one |
| 218 | 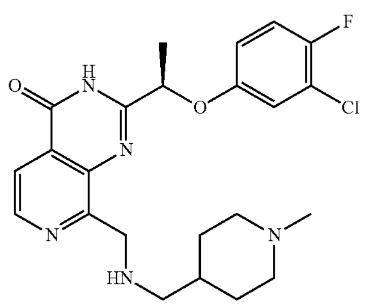 [SMILES: C[C@@H](Oc1ccc(F)c(Cl)c1)c1nc2c(CNCC3CCN(C)CC3)nccc2c(=O)[nH]1] | (R)-2-(1-(3-chloro-4-fluorophenoxy)ethyl)-8-((((1-methylpiperidin-4-yl)methyl)amino)methyl)pyrido[3,4-d]pyrimidin-4(3H)-one |
| 219 | 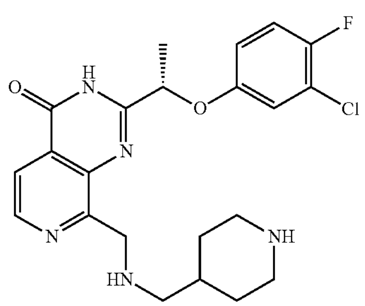 [SMILES: C[C@H](Oc1ccc(F)c(Cl)c1)c1nc2c(CNCC3CCNCC3)nccc2c(=O)[nH]1] | (S)-2-(1-(3-chloro-4-fluorophenoxy)ethyl)-8-(((piperidin-4-ylmethyl)amino)methyl)pyrido[3,4-d]pyrimidin-4(3H)-one |
| 220 | 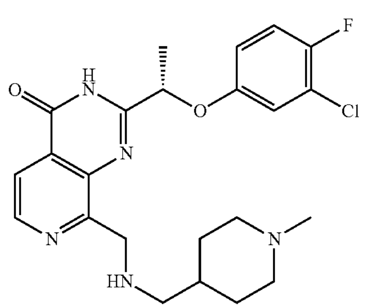 [SMILES: C[C@H](Oc1ccc(F)c(Cl)c1)c1nc2c(CNCC3CCN(C)CC3)nccc2c(=O)[nH]1] | (S)-2-(1-(3-chloro-4-fluorophenoxy)ethyl)-8-((((1-methylpiperidin-4-yl)methyl)amino)methyl)pyrido[3,4-d]pyrimidin-4(3H)-one |

TABLE 1-continued

| No. | Chemical Structure | Chemical Name |
|---|---|---|
| 221 | 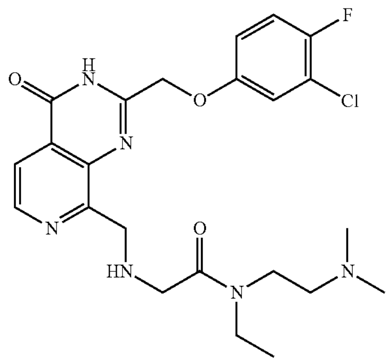 [SMILES: CCN(CCN(C)C)C(=O)CNCc1nccc2c(=O)[nH]c(COc3ccc(F)c(Cl)c3)nc12] | 2-(((2-((3-chloro-4-fluorophenoxy)methyl)-4-oxo-3,4-dihydropyrido[3,4-d]pyrimidin-8-yl)methyl)amino)-N-(2-(dimethylamino)ethyl)-N-ethylacetamide |
| 222 | 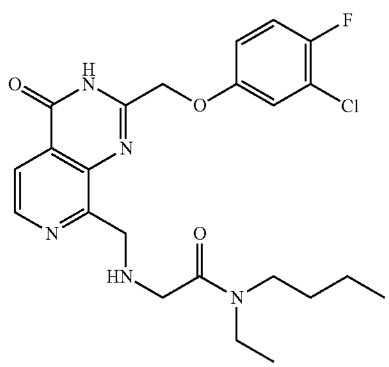 [SMILES: CCCCN(CC)C(=O)CNCc1nccc2c(=O)[nH]c(COc3ccc(F)c(Cl)c3)nc12] | N-butyl-2-(((2-((3-chloro-4-fluorophenoxy)methyl)-4-oxo-3,4-dihydropyrido[3,4-d]pyrimidin-8-yl)methyl)amino)-N-ethylacetamide |
| 223 | 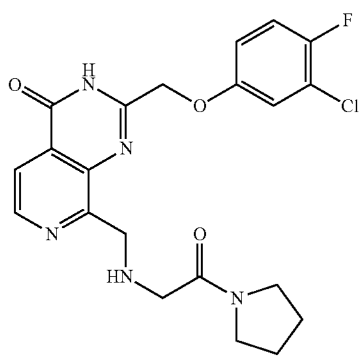 [SMILES: O=C(CNCc1nccc2c(=O)[nH]c(COc3ccc(F)c(Cl)c3)nc12)N1CCCC1] | 2-((3-chloro-4-fluorophenoxy)methyl)-8-(((2-oxo-2-(pyrrolidin-1-yl)ethyl)amino)methyl)pyrido[3,4-d]pyrimidin-4(3H)-one |
| 224 | 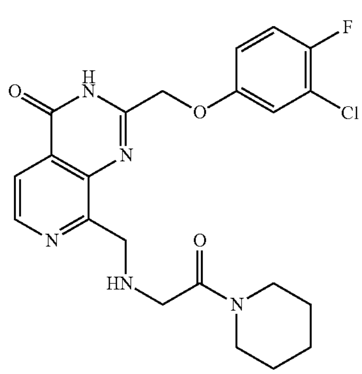 [SMILES: O=C(CNCc1nccc2c(=O)[nH]c(COc3ccc(F)c(Cl)c3)nc12)N1CCCCC1] | 2-((3-chloro-4-fluorophenoxy)methyl)-8-(((2-oxo-2-(piperidin-1-yl)ethyl)amino)methyl)pyrido[3,4-d]pyrimidin-4(3H)-one |

TABLE 1-continued

| No. | Chemical Structure | Chemical Name |
|-----|-------------------|---------------|
| 225 | 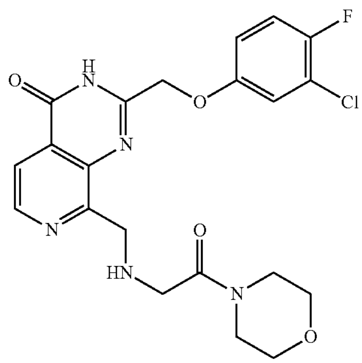 [SMILES: O=C(CNCc1nccc2c(=O)[nH]c(COc3ccc(F)c(Cl)c3)nc12)N1CCOCC1] | 2-((3-chloro-4-fluorophenoxy)methyl)-8-(((2-morpholino-2-oxoethyl)amino)methyl)pyrido[3,4-d]pyrimidin-4(3H)-one |
| 226 | 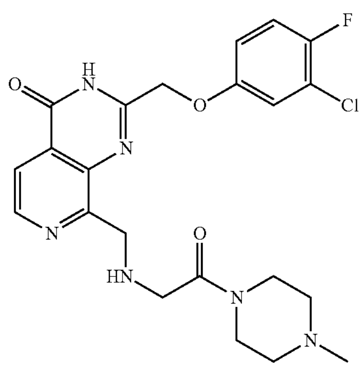 [SMILES: CN1CCN(C(=O)CNCc2nccc3c(=O)[nH]c(COc4ccc(F)c(Cl)c4)nc23)CC1] | 2-((3-chloro-4-fluorophenoxy)methyl)-8-(((2-(4-methylpiperazin-1-yl)-2-oxoethyl)amino)methyl)pyrido[3,4-d]pyrimidin-4(3H)-one |
| 227 | 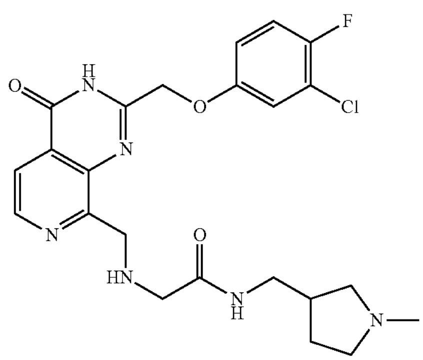 [SMILES: CN1CCC(CNC(=O)CNCc2nccc3c(=O)[nH]c(COc4ccc(F)c(Cl)c4)nc23)C1] | 2-(((2-((3-chloro-4-fluorophenoxy)methyl)-4-oxo-3,4-dihydropyrido[3,4-d]pyrimidin-8-yl)methyl)amino)-N-((1-methylpyrrolidin-3-yl)methyl)acetamide |
| 228 | 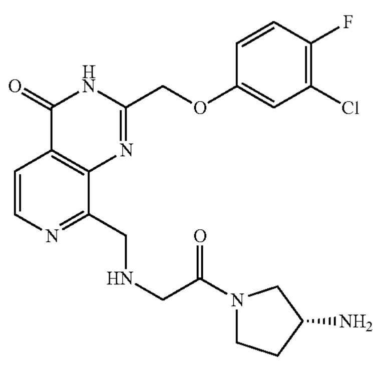 [SMILES: N[C@@H]1CCN(C(=O)CNCc2nccc3c(=O)[nH]c(COc4ccc(F)c(Cl)c4)nc23)C1] | (R)-8-(((2-(3-aminopyrrolidin-1-yl)-2-oxoethyl)amino)methyl)-2-((3-chloro-4-fluorophenoxy)methyl)pyrido[3,4-d]pyrimidin-4(3H)-one |

TABLE 1-continued

| No. | Chemical Structure | Chemical Name |
|---|---|---|
| 229 | 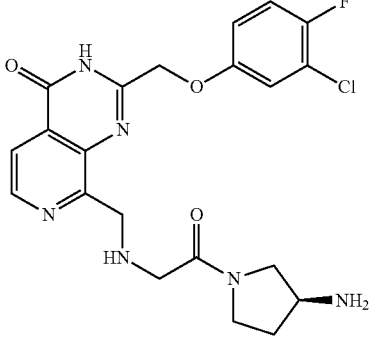 | (S)-8-(((2-(3-aminopyrrolidin-1-yl)-2-oxoethyl)amino)methyl)-2-((3-chloro-4-fluorophenoxy)methyl)pyrido[3,4-d]pyrimidin-4(3H)-one |
| 230 | 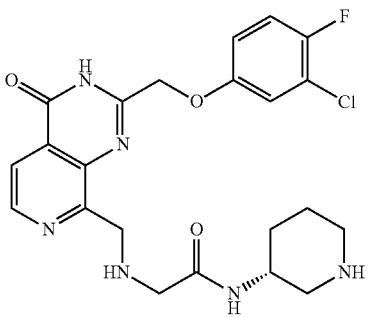 [SMILES: O=C(CNCc1nccc2c(=O)[nH]c(COc3ccc(F)c(Cl)c3)nc12)N[C@@H]1CCCNC1] | (R)-2-(((2-((3-chloro-4-fluorophenoxy)methyl)-4-oxo-3,4-dihydropyrido[3,4-d]pyrimidin-8-yl)methyl)amino)-N-(piperidin-3-yl)acetamide |
| 231 | 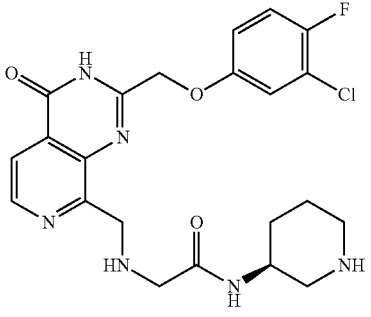 [SMILES: O=C(CNCc1nccc2c(=O)[nH]c(COc3ccc(F)c(Cl)c3)nc12)N[C@H]1CCCNC1] | (S)-2-(((2-((3-chloro-4-fluorophenoxy)methyl)-4-oxo-3,4-dihydropyrido[3,4-d]pyrimidin-8-yl)methyl)amino)-N-(piperidin-3-yl)acetamide |
| 232 | 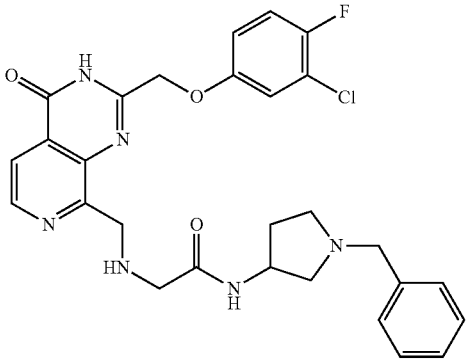 [SMILES: O=C(CNCc1nccc2c(=O)[nH]c(COc3ccc(F)c(Cl)c3)nc12)NC1CCN(Cc2ccccc2)C1] | N-(1-benzylpyrrolidin-3-yl)-2-(((2-((3-chloro-4-fluorophenoxy)methyl)-4-oxo-3,4-dihydropyrido[3,4-d]pyrimidin-8-yl)methyl)amino)acetamide |

TABLE 1-continued

| No. | Chemical Structure | Chemical Name |
|---|---|---|
| 233 | 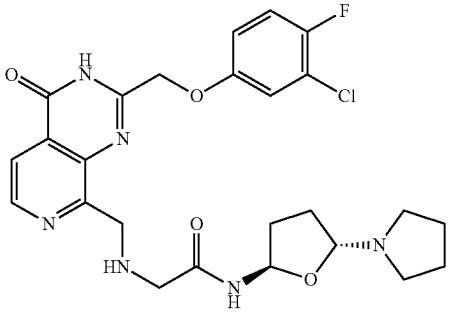 [SMILES: O=C(CNCc1nccc2c(=O)[nH]c(COc3ccc(F)c(Cl)c3)nc12)N[C@H]1CC[C@H](N2CCCC2)O1] | 2-(((2-((3-chloro-4-fluorophenoxy)methyl)-4-oxo-3,4-dihydropyrido[3,4-d]pyrimidin-8-yl)methyl)amino)-N-(trans-5-(pyrrolidin-1-yl)tetrahydrofuran-2-yl)acetamide |
| 234 | 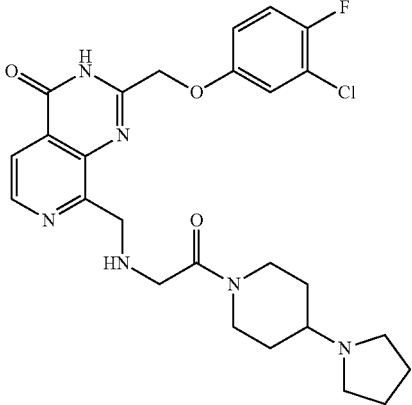 [SMILES: O=C(CNCc1nccc2c(=O)[nH]c(COc3ccc(F)c(Cl)c3)nc12)N1CCC(N2CCCC2)CC1] | 2-((3-chloro-4-fluorophenoxy)methyl)-8-(((2-oxo-2-(4-(pyrrolidin-1-yl)piperidin-1-yl)ethyl)amino)methyl)pyrido[3,4-d]pyrimidin-4(3H)-one |
| 235 | 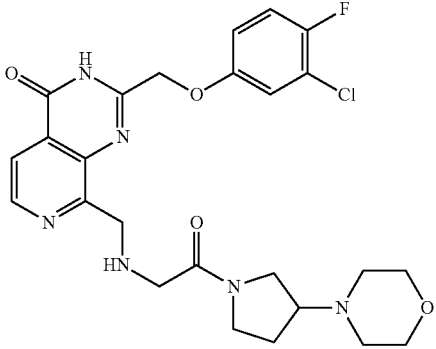 [SMILES: O=C(CNCc1nccc2c(=O)[nH]c(COc3ccc(F)c(Cl)c3)nc12)N1CCC(N2CCOCC2)C1] | 2-((3-chloro-4-fluorophenoxy)methyl)-8-(((2-(3-morpholinopyrrolidin-1-yl)-2-oxoethyl)amino)methyl)pyrido[3,4-d]pyrimidin-4(3H)-one |
| 236 | 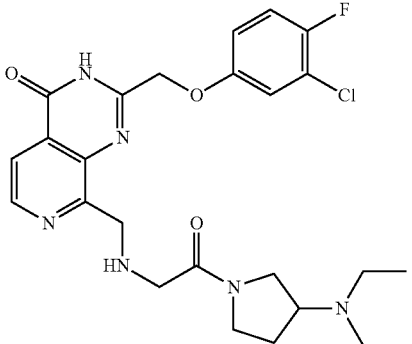 [SMILES: CCN(CC)C1CCN(C(=O)CNCc2nccc3c(=O)[nH]c(COc4ccc(F)c(Cl)c4)nc23)C1] | 2-((3-chloro-4-fluorophenoxy)methyl)-8-(((2-(3-(diethylamino)pyrrolidin-1-yl)-2-oxoethyl)amino)methyl)pyrido[3,4-d]pyrimidin-4(3H)-one |

TABLE 1-continued

| No. | Chemical Structure | Chemical Name |
|---|---|---|
| 237 | 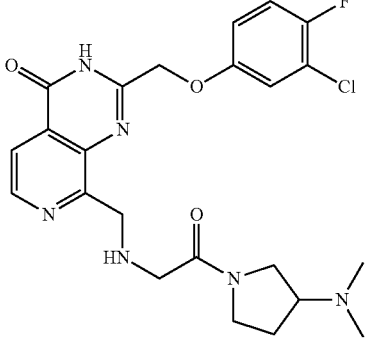 | 2-((3-chloro-4-fluorophenoxy)methyl)-8-(((2-(3-(dimethylamino)pyrrolidin-1-yl)-2-oxoethyl)amino)methyl)pyrido[3,4-d]pyrimidin-4(3H)-one |
| 238 | 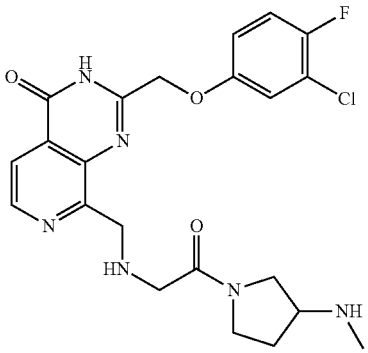 [SMILES: CNC1CCN(C(=O)CNCc2nccc3c(=O)[nH]c(COc4ccc(F)c(Cl)c4)nc23)C1] | 2-((3-chloro-4-fluorophenoxy)methyl)-8-(((2-(3-(methylamino)pyrrolidin-1-yl)-2-oxoethyl)amino)methyl)pyrido[3,4-d]pyrimidin-4(3H)-one |
| 239 | 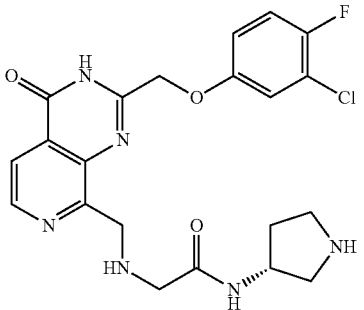 [SMILES: O=C(CNCc1nccc2c(=O)[nH]c(COc3ccc(F)c(Cl)c3)nc12)N[C@@H]1CCNC1] | (R)-2-(((2-((3-chloro-4-fluorophenoxy)methyl)-4-oxo-3,4-dihydropyrido[3,4-d]pyrimidin-8-yl)methyl)amino)-N-(pyrrolidin-3-yl)acetamide |
| 240 | 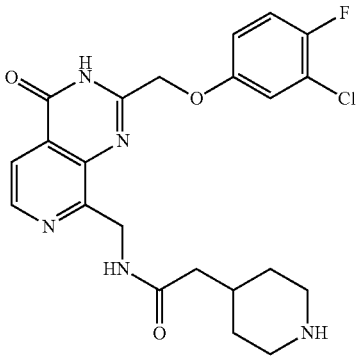 [SMILES: O=C(CC1CCNCC1)NCc1nccc2c(=O)[nH]c(COc3ccc(F)c(Cl)c3)nc12] | N-((2-((3-chloro-4-fluorophenoxy)methyl)-4-oxo-3,4-dihydropyrido[3,4-d]pyrimidin-8-yl)methyl)-2-(piperidin-4-yl)acetamide |

TABLE 1-continued

| No. | Chemical Structure | Chemical Name |
|---|---|---|
| 241 | 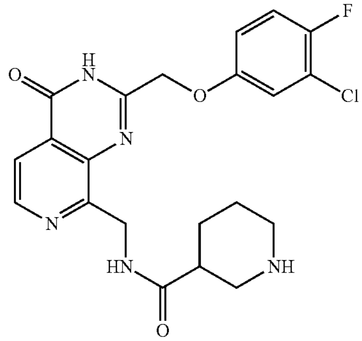 [SMILES: O=C(NCc1nccc2c(=O)[nH]c(COc3ccc(F)c(Cl)c3)nc12)C1CCCNC1] | N-((2-((3-chloro-4-fluorophenoxy)methyl)-4-oxo-3,4-dihydropyrido[3,4-d]pyrimidin-8-yl)methyl)piperidine-3-carboxamide |

Meanwhile, the compound represented by the Formula (I) may have an asymmetric carbon center, and if having the asymmetric carbon center, may exist as an optical isomer, a diastereomer or a recemate, and all forms of isomers including these may be also within the scope of the compound according to one embodiment of the present invention.

Further, a pharmaceutically acceptable salt of the compound represented by the Formula (I), or a pharmaceutically acceptable salt of the isomers of the compound represented by the Formula (I) may be also within the scope of the compound of the above described one embodiment. For example, non-limiting examples of the pharmaceutically acceptable salt of the compound represented by the Formula (I) or the isomer thereof may include a salt with an inorganic acid such as hydrochloric acid, hydrobromic acid, phosphoric acid or sulfuric acid; a salt with an organic carboxylic acid such as acetic acid, trifluoroacetic acid, citric acid, maleic acid, oxalic acid, succinic acid, benzoic acid, tartaric acid, fumaric acid, mandelic acid, ascorbic acid or malic acid, or a salt with a sulfonic acid such as methane sulfonic acid or p-toluene sulfonic acid; a salt with an alkali metal such as sodium, potassium or lithium; a salt with various acids known to be capable of forming other pharmaceutically acceptable salts, or the like.

The compound within the scope of the compound of the above Formula (I) may represent an excellent effects on modulating catalyticactivity of Histone Lysine Demethylase (KDMs), thereby having an outstanding potential for a pharmaceutical intervention of various cancer and any other diseases related to KDM dysregulation.

Further, another embodiment of the present invention provides a pharmaceutical composition including the above compound, the isomer thereof or the pharmaceutically acceptable salt thereof as an effective ingredient. More preferably, the pharmaceutical composition may be for treatment or prevention of various cancer and disease related to KDM dysregulation. In certain embodiments, the disease is a hyperproliferative disease, cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, infectious disease, pathologic immune conditions involving T cell activation, CNS disorders or a myeloproliferative disorder. More preferably, the cancer may be selected from the group consisting of embryonic carcinoma, teratoma, seminoma, germ cell tumors, prostate cancer, breast cancer, stomach cancer, gastrointestinal cancer, neuroblastoma, choriocarcinoma, yolk sac tumors, ovarian cancer, endometrial cancer, cervical cancer, retinoblastoma, kidney cancer, liver cancer, gastric cancer, brain cancer, medulloblastoma, medulloepithelioma, glioma, glioblastoma, multiple myeloma, lung cancer, bronchial cancer, mesothelioma, skin cancer, colon and rectal cancer, bladder cancer, pancreatic cancer, lip and oral cancer, laryngeal and pharyngeal cancer, melanoma, pituitary cancer, penile cancer, parathyroid cancer, thyroid cancer, pheochromocytoma and paraganglioma, thymoma and thymic carcinoma, leukemia, lymphoma, plasma cell neoplasms, myeloproliferative disorders, islet cell tumor, small intestine cancer, transitional cell cancer, pleuropulmonary blastoma, gestational trophoblastic cancer, esophageal cancer, central nervous system cancer, head and neck cancer, endocrine cancer, cardiovascular cancer, rhabdomyosarcoma, soft tissue carcinomas, carcinomas of bone, cartilage, fat, vascular, neural, and hematopoietic tissues and AIDS-related cancers.

A pharmaceutical composition including the compound represented by the Formula (I), the isomer thereof or the pharmaceutically used salt thereof, as an effective component may be used in the form of a general medicinal preparation. The medicinal preparation may be administered in various formulations such as oral and parenteral formulation, and the formulation may be variously determined depending on usage.

If the composition is formulated into various oral and parenteral formulations, it may be prepared using a generally used excipient such as a filler, a diluent, a bulking agent, a binder, a wetting agent, a disintergrating agent, a surfactant.

A solid preparation for oral administration may include tablets, pills, powders, granules, capsules, and the like, and the solid preparation may be prepared by mixing the compound represented by the Formula (I), the isomer thereof, or the pharmaceutically acceptable salt thereof with at least one excipient, for example, starch, calcium carbonate, sucrose or lactose, gelatin, and the like. Further, in addition to a simple excipient, a lubricant such as magnesium stearate and talc may be used.

Further, a liquid preparation for oral administration may be suspensions, oral liquids, emulsions, syrups, and the like, and include various excipients, for example, a wetting agent, a sweetener, an aromatic, a preservative, and the like, in addition to water and liquid paraffin which are a simple diluent to be commonly used.

The preparation for parenteral administration includes a sterile aqueous solution, a non-aqueous solvent, a suspension, an emulsion, a freeze-dried preparation, a suppository and the like. As the non-aqueous solvent and the suspension solvent, propylene glycol, polyethylene glycol, a vegetable oil such as an olive oil, injectable ester such as ethyl oleate, and the like may be used. As a base of the suppository, witepsol, microgol, tween 61, cacao butter, laurin butter, glycerogelatin, and the like may be used.

Further, the pharmaceutical composition of the present invention including the compound represented by the Formula (I), the isomer thereof or a pharmaceutically acceptable salt thereof as an effective component may have an effective amount in a dosage range of about 0.1 to about 1,000 mg. A dosage or dose may be administered in various dosages and methods, for example, in divided dosages from once to several times a day depending on a patient's weight, age, sex, a health condition, diet, administration time, an administration method, an excretion rate, and severity of a disease.

In a preferred embodiment, the compound of Formula (I) may be prepared by various processes illustrated in Schemes 1 to 16 (Methods A to P). Schemes 1 to 16 are shown in Examples.

EXAMPLES

The present invention is further explained in more detail with reference to the following examples. These examples, however, should not be interpreted as limiting the scope of the present disclosure in any manner.

1. Chemical Synthesis

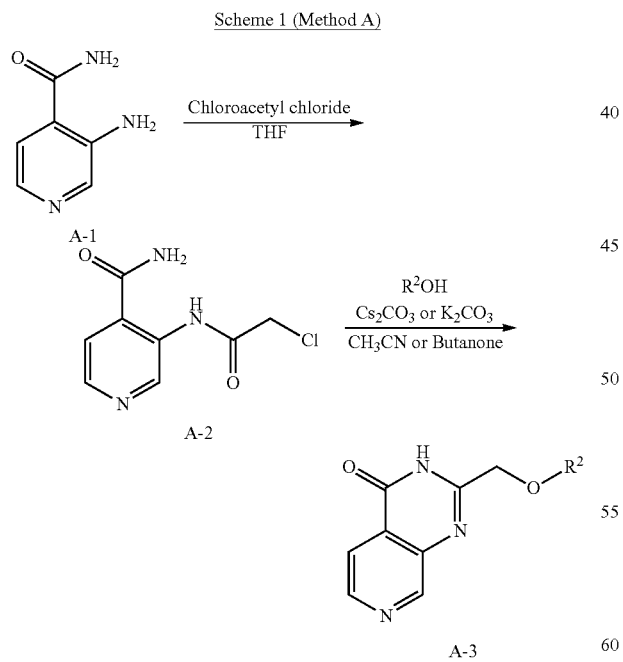

A-1, A-2, A-3

Scheme 1 (Method A)

The general synthesis of compound A-3 is illustrated in Scheme 1. 3-Aminoisonicotinamide is reacted with chloroacetyl chloride to afford the amide intermediate 2. This is followed by reaction with phenol reagent, which leads to pyridopyrimidinone compound A-3.

Example 1

Step 1

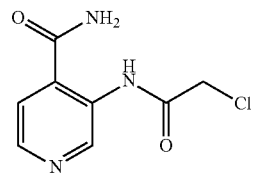 [SMILES: NC(=O)c1ccncc1NC(=O)CCl]

3-(2-chloroacetamido)isonicotinamide

To a solution of 3-aminoisonicotinamide in THF was added chloroacetyl chloride at room temperature. The mixture was allowed to stir for 2 days at room temperature and concentrated in vacuo. The crude was crystallized with EtOAc and filtered to afford the 3-(2-chloroacetamido)isonicotinamide.

MS (ESI+) m/z 214 (M+H)$^+$

Step 2

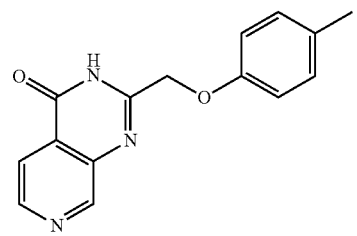 [SMILES: Cc1ccc(OCc2nc3cnccc3c(=O)[nH]2)cc1]

2-((p-tolyloxy)methyl)pyrido[3,4-d]pyrimidin-4(3H)-one

To a solution of 3-(2-chloroacetamido)isonicotinamide in $CH_3CN$ was added $Cs_2CO_3$ and p-Cresol at room temperature. The mixture was heated at reflux for 1 h. After being cooled to room temperature, the mixture was extracted with EtOAc. The combined organic layer was dried over $MgSO_4$, filtered and concentrated in vacuo. The concentrated residue was purified by preparative HPLC.

MS (ESI+) m/z 268 (M+H)$^+$

Example 2

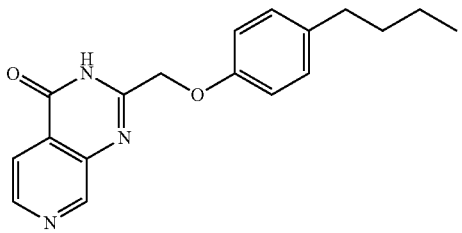 [SMILES: CCCCc1ccc(OCc2nc3cnccc3c(=O)[nH]2)cc1]

2((4-butylphenoxy)methyl)pyrido[3,4-d]pyrimidin-4(3H)—one

Using 4-butylphenol, the title compound was obtained as described in Scheme 1 (Method A).

MS (ESI+) m/z 504 (M+H)+

Example 3

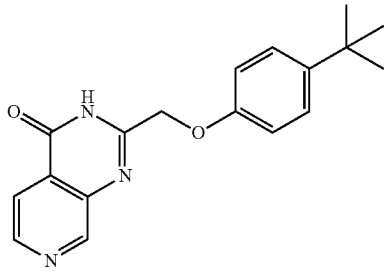 [SMILES: CC(C)(C)c1ccc(OCc2nc3cnccc3c(=O)[nH]2)cc1]

2-((4-(tert-butyl)phenoxy)methyl)pyrido[3,4-d]pyrimidin-4(3H)-one

Using 4-tert-butylphenol, the title compound was obtained as described in Scheme 1 (Method A).

$^1$H NMR (400 MHz, DMSO-d$_6$) δ 12.81 (br s, 1H), 9.02 (s, 1H), 8.65 (d, J=5.09 Hz, 1H), 7.93 (d, J=5.09 Hz, 1H), 7.30 (d, J=8.61 Hz, 2H), 6.95 (d, J=8.61 Hz, 2H), 4.98 (s, 2H), 1.21 (s, 9H)

MS (ESI+) m/z 310 (M+H)+

Example 4

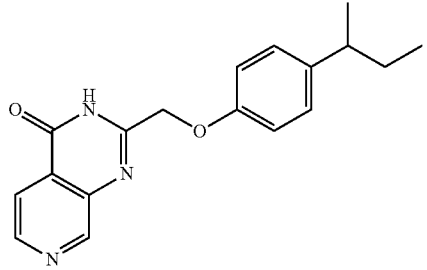 [SMILES: CCC(C)c1ccc(OCc2nc3cnccc3c(=O)[nH]2)cc1]

2-((4-(sec-butyl)phenoxy)methyl)pyrido[3,4-d]pyrimidin-4(3H)-one

Using 4-isobutylphenol, the title compound was obtained as described in Scheme 1 (Method A).

$^1$H NMR (400 MHz, DMSO-d$_6$) δ 12.80 (br s, 1H), 9.02 (s, 1H), 8.65 (d, J=5.09 Hz, 1H), 7.93 (d, J=5.09 Hz, 1H), 7.11 (d, J=8.61 Hz, 2H), 6.95 (d, J=8.61 Hz, 2H), 4.98 (S, 2H), 2.50 (m, 1H), 1.46 (m, 2H), 1.12 (d, J=7.04 Hz, 3H), 0.72 (t, J=7.24 Hz, 3H)

MS (ESI+) m/z 310 (M+H)+

Example 5

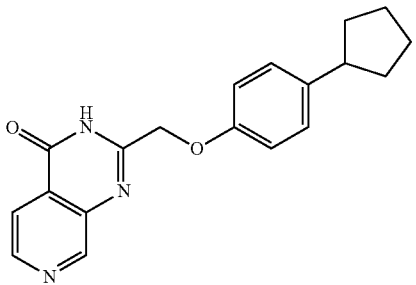 [SMILES: O=c1[nH]c(COc2ccc(C3CCCC3)cc2)nc2cnccc12]

2-((4-cyclopentylphenoxy)methyl)pyrido[3,4-d]pyrimidin-4(3H)-one

Using 4-cyclopentylphenol, the title compound was obtained as described in Scheme 1 (Method A).

$^1$H NMR (400 MHz, DMSO-d$_6$) δ 12.85 (br s, 1H), 9.01 (s, 1H), 8.63 (d, J=5.09 Hz, 1H), 7.92 (d, J=5.09 Hz, 1H), 7.14 (d, J=8.61 Hz, 2H), 6.93 (d, J=8.61 Hz, 2H), 4.97 (s, 2H), 2.68 (m, 1H), 1.93 (m, 2H), 1.70 (m, 2H), 1.58 (m, 2H), 1.43 (m, 2H)

MS (ESI+) m/z 322 (M+H)+

Example 6

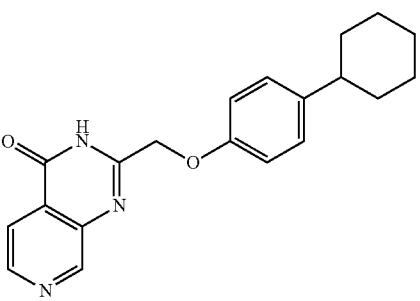 [SMILES: O=c1[nH]c(COc2ccc(C3CCCCC3)cc2)nc2cnccc12]

2-((4-cyclohexylphenoxy)methyl)pyrido[3,4-d]pyrimidin-4(3H)-one

Using 4-cyclohexylphenol, the title compound was obtained as described in Scheme 1 (Method A).

$^1$H NMR (400 MHz, DMSO-d$_6$) δ 8.97 (s, 1H), 8.61 (d, 1H), 7.91 (d, 1H), 7.16 (d, 1H), 7.09 (m, 1H), 6.98 (d, 1H), 6.90 (m, 1H), 5.01 (s, 2H), 3.24 (m, 1H), 1.73 (m, 5H), 1.32 (m, 3H), 1.20 (m, 2H)

MS (ESI+) m/z 336 (M+H)+

Example 7

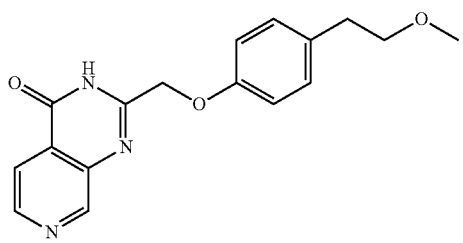 [SMILES: COCCc1ccc(OCc2nc3cnccc3c(=O)[nH]2)cc1]

2-((4-(2-methoxyethyl)phenoxy)methyl)pyrido[3,4-d]pyrimidin-4(3H)-one

Using 4-(2-methoxyethyl)phenol, the title compound was obtained as described in Scheme 1 (Method A).
$^1$H NMR (400 MHz, DMSO-$d_6$) δ 9.00 (s, 1H), 8.62 (d, J=5.09 Hz, 1H), 7.92 (d, J=5.09 Hz, 1H), 7.15 (t, J=7.83, 1H), 6.80 (m, 3H), 4.97 (s, 2H), 3.31 (m, 2H), 2.46 (m, 2H), 2.24 (s, 3H)
MS (ESI+) m/z 312 (M+H)$^+$

Example 8

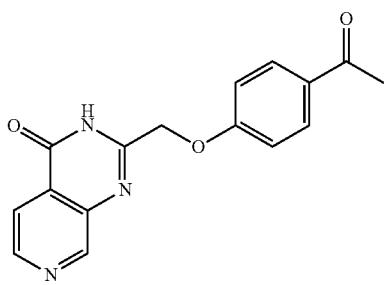 [SMILES: CC(=O)c1ccc(OCc2nc3cnccc3c(=O)[nH]2)cc1]

2-((4-acetylphenoxy)methyl)pyrido[3,4-d]pyrimidin-4(3H)-one

Using 4'-hydroxyacetophenone, the title compound was obtained as described in Scheme 1 (Method A).
$^1$H NMR (400 MHz, DMSO-$d_6$) δ 8.94 (s, 1H), 8.56 (d, 1H), 7.90 (m, 3H), 7.13 (d, 2H), 5.08 (s, 2H), 2.48 (s, 3H)
MS (ESI+) m/z 296 (M+H)$^+$

Example 9

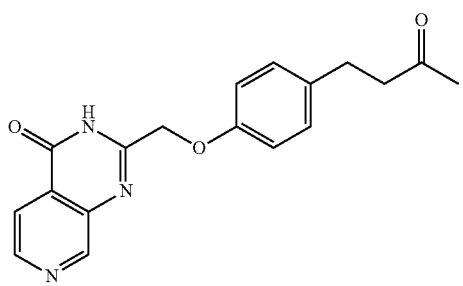 [SMILES: CC(=O)CCc1ccc(OCc2nc3cnccc3c(=O)[nH]2)cc1]

2-((4-(3-oxobutyl)phenoxy)methyl)pyrido[3,4-d]pyrimidin-4(3H)-one

Using 4-(4-hydroxyphenyl)-2-butanone, the title compound was obtained as described in Scheme 1 (Method A).
MS (ESI+) m/z 324 (M+H)$^+$

Example 10

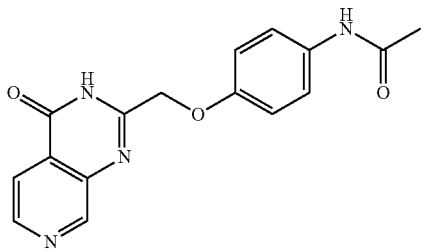 [SMILES: CC(=O)Nc1ccc(OCc2nc3cnccc3c(=O)[nH]2)cc1]

N-(4-((4-oxo-3,4-dihydropyrido[3,4-d]pyrimidin-2-yl)methoxy)phenyl)acetamide

Using 4-acetamidophenol, the title compound was obtained as described in Scheme 1 (Method A).
MS (ESI+) m/z 311 (M+H)$^+$

Example 11

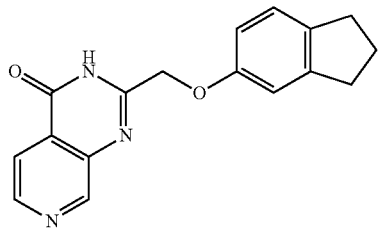 [SMILES: O=c1[nH]c(COc2ccc3c(c2)CCC3)nc2cnccc12]

2-(((2,3-dihydro-1H-inden-5-yl)oxy)methyl)pyrido[3,4-d]pyrimidin-4(3H)-one

Using 5-indanol, the title compound was obtained as described in Scheme 1 (Method A).
MS (ESI+) m/z 294 (M+H)$^+$

Example 12

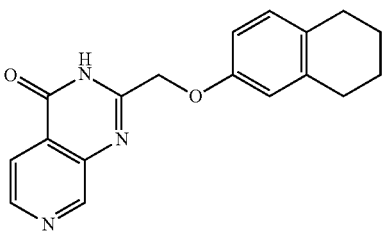 [SMILES: O=c1[nH]c(COc2ccc3c(c2)CCCC3)nc2cnccc12]

2-(((5,6,7,8-tetrahydronaphthalen-2-yl)oxy)methyl)pyrido[3,4-d]pyrimidin-4(3H)-one Using 5,6,7,8-tetrahydro-2-naphthol, the title compound was obtained as described in Scheme 1 (Method A).
MS (ESI+) m/z 308 (M+H)+

Example 13

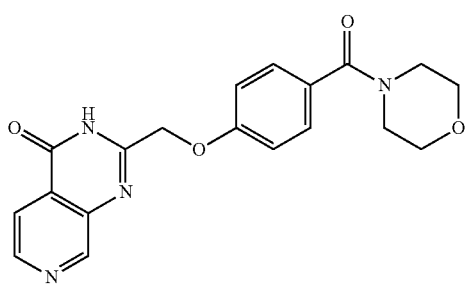 [SMILES: O=C(c1ccc(OCc2nc3cnccc3c(=O)[nH]2)cc1)N1CCOCC1]

2-((4-(morpholine-4-carbonyl)phenoxy)methyl)pyrido[3,4-d]pyrimidin-4(3H)-one

Using 4-(morpholine-4-carbonyl)phenol, the title compound was obtained as described in Scheme 1 (Method A).
MS (ESI+) m/z 367 (M+H)+

Example 14

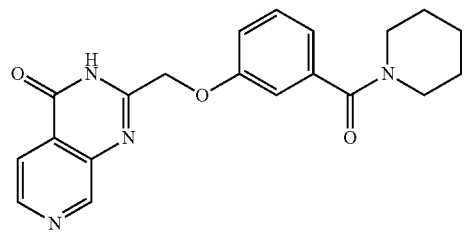 [SMILES: O=C(c1cccc(OCc2nc3cnccc3c(=O)[nH]2)c1)N1CCCCC1]

2-((3-(piperidine-1-carbonyl)phenoxy)methyl)pyrido[3,4-d]pyrimidin-4(3H)-one

Using 3-(4-morpholinylcarbonyl)phenol, the title compound was obtained as described in Scheme 1 (Method A).
MS (ESI+) m/z 365 (M+H)+

Example 15

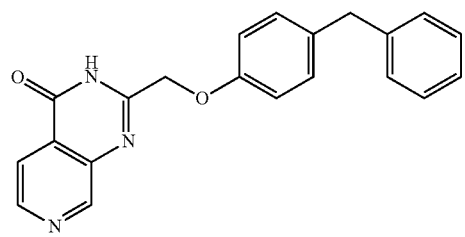 [SMILES: O=c1[nH]c(COc2ccc(Cc3ccccc3)cc2)nc2cnccc12]

2-((4-benzylphenoxy)methyl)pyrido[3,4-d]pyrimidin-4(3H)-one

Using 4-benzylphenol, the title compound was obtained as described in Scheme 1 (Method A).
$^1$H NMR (400 MHz, DMSO-$d_6$) δ 12.81 (br, 1H), 9.04 (s, 1H), 8.67 (d, 1H), 7.94 (s, 1H), 7.24 (m, 2H), 7.18 (m, 5H), 6.98 (m, 2H), 5.00 (s, 2H), 3.87 (s, 2H)
MS (ESI+) m/z 344 (M+H)+

Example 16

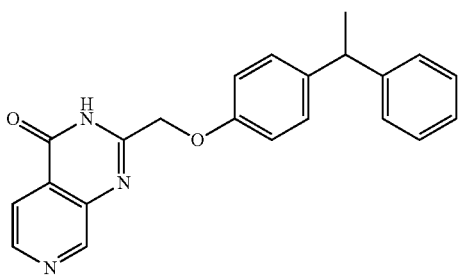 [SMILES: CC(c1ccccc1)c1ccc(OCc2nc3cnccc3c(=O)[nH]2)cc1]

2-((4-(1-phenylethyl)phenoxy)methyl)pyrido[3,4-d]pyrimidin-4(3H)-one

Using 4-(1-phenylethyl)phenol, the title compound was obtained as described in Scheme 1 (Method A).
MS (ESI+) m/z 358 (M+H)+

Example 17

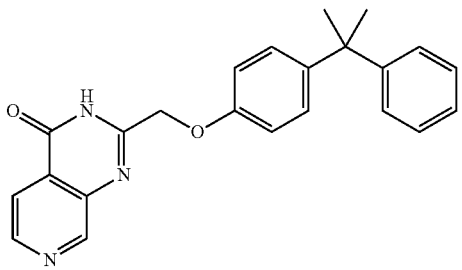 [SMILES: CC(C)(c1ccccc1)c1ccc(OCc2nc3cnccc3c(=O)[nH]2)cc1]

2-((4-(2-phenylpropan-2-yl)phenoxy)methyl)pyrido[3,4-d]pyrimidin-4(3H)-one

Using 4-cumylphenol, the title compound was obtained as described in Scheme 1 (Method A).
$^1$H NMR (400 MHz, DMSO-$d_6$) δ 9.15 (br s, 1H), 9.01 (s, 1H), 8.64 (d, J=5.09 Hz, 1H), 7.92 (d, J=5.09 Hz, 1H), 7.17 (m, 5H), 6.92 (m, 3H), 6.91 (d, J=8.61 Hz, 1H), 4.97 (s, 2H), 1.57 (s, 3H), 1.54 (s, 3H)
MS (ESI+) m/z 372 (M+H)+

Example 18

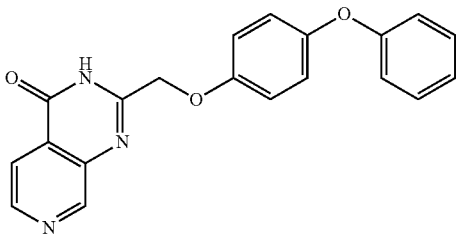 [SMILES: O=c1[nH]c(COc2ccc(Oc3ccccc3)cc2)nc2cnccc12]

2-((4-phenoxyphenoxy)methyl)pyrido[3,4-d]pyrimidin-4(3H)-one

Using 4-phenoxyphenol, the title compound was obtained as described in Scheme 1 (Method A).

$^1$H NMR (400 MHz, DMSO-d$_6$) δ 12.83 (br s, 1H), 9.02 (s, 1H), 8.65 (d, J=5.09 Hz, 1H), 7.93 (d, J=5.09 Hz, 1H), 7.31 (t, J=8.02 Hz, 2H), 7.03 (m, 5H), 6.89 (m, 2H), 5.01 (s, 2H)
MS (ESI+) m/z 346 (M+H)$^+$

Example 19

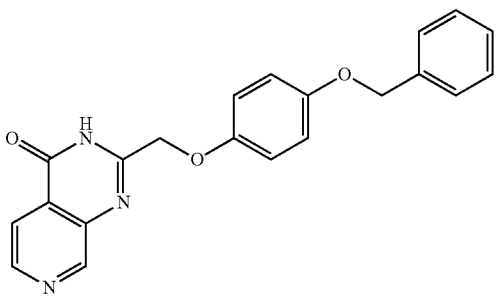 [SMILES: O=c1[nH]c(COc2ccc(OCc3ccccc3)cc2)nc2cnccc12]

2-((4-(benzyloxy)phenoxy)methyl)pyrido[3,4-d]pyrimidin-4(3H)-one

Using 4-benzyloxyphenol, the title compound was obtained as described in Scheme 1 (Method A).

$^1$H NMR (400 MHz, DMSO-d$_6$) δ 12.79 (br s, 1H), 9.01 (s, 1H), 8.64 (d, J=5.09 Hz, 1H), 7.93 (d, J=5.09 Hz, 1H), 7.34 (m, 5H), 6.96 (m, 4H), 5.00 (s, 2H), 4.94 (s, 2H)
MS (ESI+) m/z 360 (M+H)$^+$

Example 20

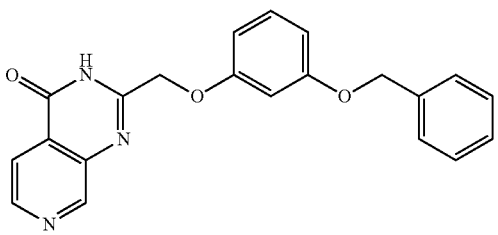 [SMILES: O=c1[nH]c(COc2cccc(OCc3ccccc3)c2)nc2cnccc12]

2-((3-(benzyloxy)phenoxy)methyl)pyrido[3,4-d]pyrimidin-4(3H)-one

Using 3-benzyloxyphenol, the title compound was obtained as described in Scheme 1 (Method A).

$^1$H NMR (400 MHz, DMSO-d$_6$) δ 9.39 (br s, 1H), 9.00 (s, 1H), 8.63 (d, J=5.09 Hz, 1H), 7.92 (d, J=5.09 Hz, 1H), 7.38 (m, 5H), 7.17 (t, J=8.02 Hz, 1H), 6.69 (s, 1H), 6.61 (d, J=8.22 Hz, 2H), 5.05 (s, 2H), 4.99 (s, 2H)
MS (ESI+) m/z 360 (M+H)$^+$

Example 21

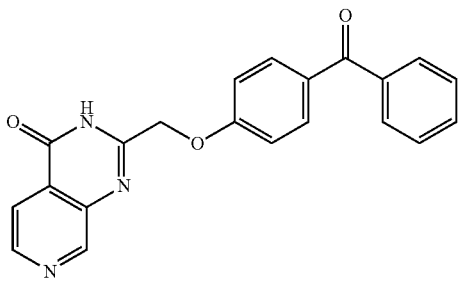 [SMILES: O=C(c1ccccc1)c1ccc(OCc2nc3cnccc3c(=O)[nH]2)cc1]

2-((4-benzoylphenoxy)methyl)pyrido[3,4-d]pyrimidin-4(3H)-one

Using 4-benzoylphenol, the title compound was obtained as described in Scheme 1 (Method A).

$^1$H NMR (400 MHz, DMSO-d$_6$) δ 8.96 (s, 1H), 8.55 (d, 1H), 7.87 (d, 1H), 7.71 (d, 2H), 7.63 (d, 3H), 7.50 (t, 2H), 7.16 (d, 2H), 5.10 (s, 2H)
MS (ESI+) m/z 358 (M+H)$^+$

Example 22

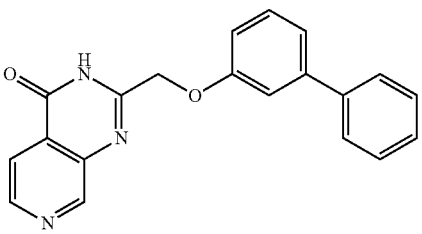 [SMILES: O=c1[nH]c(COc2cccc(-c3ccccc3)c2)nc2cnccc12]

2-(([1,1'-biphenyl]-3-yloxy)methyl)pyrido[3,4-d]pyrimidin-4(3H)-one

Using 3-phenylphenol, the title compound was obtained as described in Scheme 1 (Method A).
MS (ESI+) m/z 330 (M+H)$^+$

Example 23

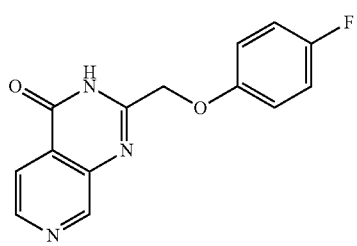 [SMILES: O=c1[nH]c(COc2ccc(F)cc2)nc2cnccc12]

2-((4-fluorophenoxy)methyl)pyrido[3,4-d]pyrimidin-4(3H)-one

Using 4-fluorophenol, the title compound was obtained as described in Scheme 1 (Method A).
$^1$H NMR (400 MHz, DMSO-$d_6$) δ 1.41 (br s, 1H), 9.01 (s, 1H), 8.64 (d, J=5.09 Hz, 1H), 7.92 (d, J=5.09 Hz, 1H), 7.12 (m, 2H), 7.06 (m, 2H), 4.99 (s, 2H)
MS (ESI+) m/z 272 (M+H)$^+$

Example 24

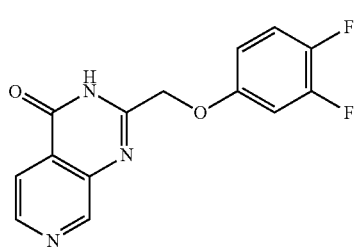 [SMILES: O=c1[nH]c(COc2ccc(F)c(F)c2)nc2cnccc12]

2-((3,4-difluorophenoxy)methyl)pyrido[3,4-d]pyrimidin-4(3H)-one

Using 3,4-difluorophenol, the title compound was obtained as described in Scheme 1 (Method A).
MS (ESI+) m/z 290 (M+H)$^+$

Example 25

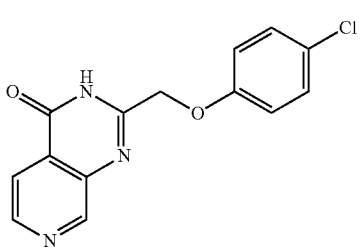 [SMILES: O=c1[nH]c(COc2ccc(Cl)cc2)nc2cnccc12]

2-((4-chlorophenoxy)methyl)pyrido[3,4-d]pyrimidin-4(3H)-one

Using 4-chlorophenol, the title compound was obtained as described in Scheme 1 (Method A).
$^1$H NMR (400 MHz, DMSO-$d_6$) δ 12.77 (br s, 1H), 9.01 (s, 1H), 8.64 (d, J=5.09 Hz, 1H), 7.91 (d, J=5.09 Hz, 1H), 7.33 (d, J=9.0 Hz, 2H), 7.06 (d, J=9.0 Hz, 2H), 5.02 (s, 2H)
MS (ESI+) m/z 288 (M+H)$^+$

Example 26

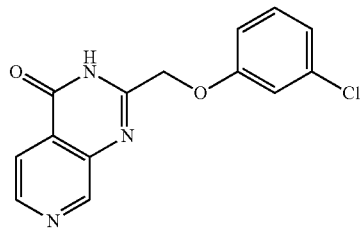 [SMILES: O=c1[nH]c(COc2cccc(Cl)c2)nc2cnccc12]

2-((3-chlorophenoxy)methyl)pyrido[3,4-d]pyrimidin-4(3H)-one

Using 3-chlorophenol, the title compound was obtained as described in Scheme 1 (Method A).
MS (ESI+) m/z 288 (M+H)$^+$

Example 27

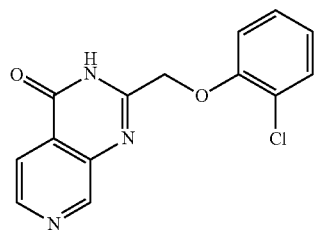 [SMILES: O=c1[nH]c(COc2ccccc2Cl)nc2cnccc12]

2-((2-chlorophenoxy)methyl)pyrido[3,4-d]pyrimidin-4(3H)-one

Using 2-chlorophenol, the title compound was obtained as described in Scheme 1 (Method A).
MS (ESI+) m/z 288 (M+H)$^+$

Example 28

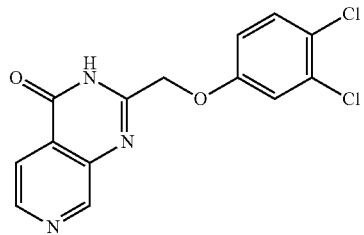 [SMILES: O=c1[nH]c(COc2ccc(Cl)c(Cl)c2)nc2cnccc12]

2-((3,4-dichlorophenoxy)methyl)pyrido[3,4-d]pyrimidin-4(3H)-one

Using 3,4-dichlorophenol, the title compound was obtained as described in Scheme 1 (Method A).
MS (ESI+) m/z 323 (M+H)$^+$ Example 29

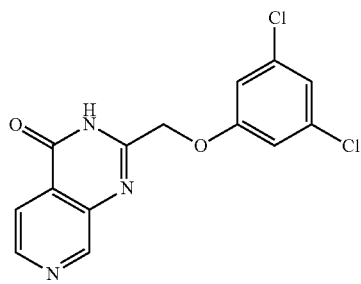 [SMILES: O=c1[nH]c(COc2cc(Cl)cc(Cl)c2)nc2cnccc12]

2-((3,5-dichlorophenoxy)methyl)pyrido[3,4-d]pyrimidin-4(3H)-one

Using 3,5-dichlorophenol, the title compound was obtained as described in Scheme 1 (Method A).
$^1$H NMR (400 MHz, DMSO-d$_6$) δ 9.01 (s, 1H), 8.66 (d, J=5.09 Hz, 1H), 8.08 (s, 1H), 7.94 (d, J=5.09 Hz, 1H), 7.19 (s, 2H), 5.09 (s, 2H)
MS (ESI+) m/z 323 (M+H)$^+$ Example 30

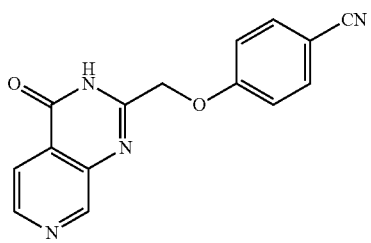 [SMILES: N#Cc1ccc(OCc2nc3cnccc3c(=O)[nH]2)cc1]

4-((4-oxo-3,4-dihydropyrido[3,4-d]pyrimidin-2-yl)methoxy)benzonitrile

Using 4-hydroxybenzonitrile, the title compound was obtained as described in Scheme 1 (Method A).
MS (ESI+) m/z 279 (M+H)$^+$ Example 31

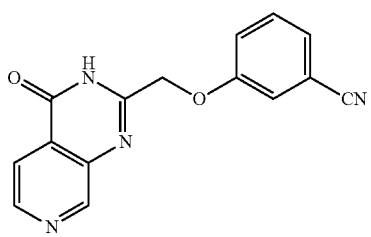 [SMILES: N#Cc1cccc(OCc2nc3cnccc3c(=O)[nH]2)c1]

3-((4-oxo-3,4-dihydropyrido[3,4-d]pyrimidin-2-yl)methoxy)benzonitrile

Using 3-hydroxybenzonitrile, the title compound was obtained as described in Scheme 1 (Method A).
$^1$H NMR (400 MHz, DMSO-d$_6$) δ 9.00 (s, 1H), 8.64 (d, J=5.09 Hz, 1H), 7.93 (d, J=5.09 Hz, 1H), 7.55 (s, 1H), 7.49 (d, 1H), 7.41 (m, 1H), 5.10 (s, 2H)
MS (ESI+) m/z 279 (M+H)$^+$ Example 32

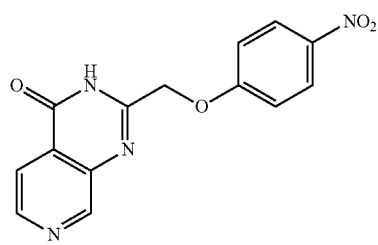 [SMILES: O=c1[nH]c(COc2ccc([N+](=O)[O-])cc2)nc2cnccc12]

2-((4-nitrophenoxy)methyl)pyrido[3,4-d]pyrimidin-4(3H)-one

Using 4-nitrophenol, the title compound was obtained as described in Scheme 1 (Method A).
$^1$H NMR (400 MHz, DMSO-d$_6$) δ 8.99 (s, 1H), 8.65 (d, J=5.09 Hz, 1H), 8.21 (d, J=9.39 Hz, 2H), 7.93 (d, J=5.48 Hz, 1H), 7.25 (d, 2H), 5.19 (s, 2H)
MS (ESI+) m/z 299 (M+H)$^+$ Example 33

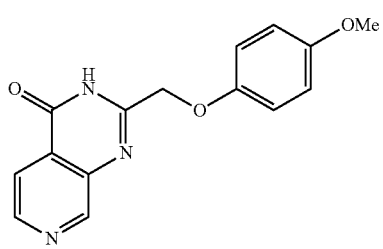 [SMILES: COc1ccc(OCc2nc3cnccc3c(=O)[nH]2)cc1]

2-((4-methoxyphenoxy)methyl)pyrido[3,4-d]pyrimidin-4(3H)-one

Using 4-methoxyphenol, the title compound was obtained as described in Scheme 1 (Method A).
MS (ESI+) m/z 284 (M+H)$^+$

Example 34

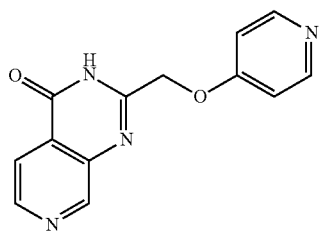 [SMILES: O=c1[nH]c(COc2ccncc2)nc2cnccc12]

2-((pyridin-4-yloxy)methyl)pyrido[3,4-d]pyrimidin-4(3H)—one

Using 4-pyridinol, the title compound was obtained as described in Scheme 1 (Method A).
MS (ESI+) m/z 255 (M+H)$^+$

Example 35

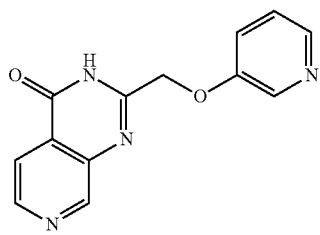 [SMILES: O=c1[nH]c(COc2cccnc2)nc2cnccc12]

2-((pyridin-3-yloxy)methyl)pyrido[3,4-d]pyrimidin-4(3H)-one

Using 3-pyridinol, the title compound was obtained as described in Scheme 1 (Method A).
$^1$H NMR (400 MHz, DMSO-d$_6$) δ 9.00 (s, 1H), 8.65 (d, J=5.09 Hz, 1H), 8.39 (d, 1H), 8.19 (d, 1H), 7.93 (d, 1H), 7.49 (m, 1H), 7.35 (m, 1H), 5.11 (s, 2H)
MS (ESI+) m/z 255 (M+H)$^+$

Example 36

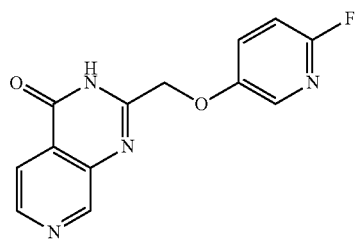 [SMILES: O=c1[nH]c(COc2ccc(F)nc2)nc2cnccc12]

2-(((6-fluoropyridin-3-yl)oxy)methyl)pyrido[3,4-d]pyrimidin-4(3H)-one

Using 2-fluoro-5-hydroxypyridine, the title compound was obtained as described in Scheme 1 (Method A).
MS (ESI+) m/z 273 (M+H)$^+$

Example 37

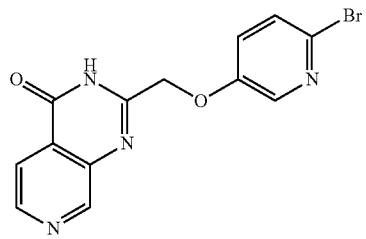 [SMILES: O=c1[nH]c(COc2ccc(Br)nc2)nc2cnccc12]

2-(((6-bromopyridin-3-yl)oxy)methyl)pyrido[3,4-d]pyrimidin-4(3H)-one

Using 2-bromo-5-hydroxypyridine, the title compound was obtained as described in Scheme 1 (Method A).
$^1$H NMR (400 MHz, DMSO-d$_6$) δ 12.84 (br s, 1H), 8.99 (s, 1H), 8.64 (d, J=5.09 Hz, 1H), 8.22 (d, J=3.13 Hz, 1H), 7.93 (d, J=5.38 Hz, 1H), 7.57 (d, 1H), 7.49 (d, 1H), 5.12 (s, 2H)
MS (ESI+) m/z 334 (M+H)$^+$

Example 38

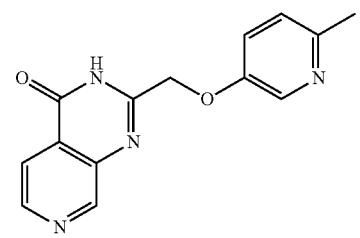

2-(((6-methylpyridin-3-yl)oxy)methyl)pyrido[3,4-d]pyrimidin-4(3H)-one

Using 3-hydroxy-6-methylpyridine, the title compound was obtained as described in Scheme 1 (Method A).
MS (ESI+) m/z 269 (M+H)$^+$

Example 39

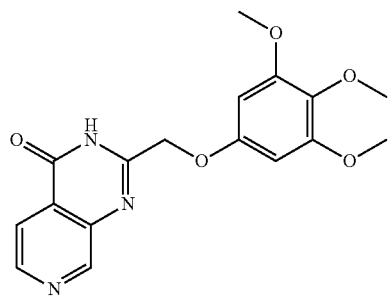 [SMILES: COc1cc(OCc2nc3cnccc3c(=O)[nH]2)cc(OC)c1OC]

2-((3,4,5-trimethoxyphenoxy)methyl)pyrido[3,4-d]pyrimidin-4(3H)-one

Using 3,4,5-trimethoxyphenol, the title compound was obtained as described in Scheme 1 (Method A).

$^1$H NMR (600 MHz, CDCl$_3$) δ 9.19 (m, 2H), 8.74 (m, 2H), 8.47 (m, 1H), 5.17 (s, 2H), 3.96 (s, 3H), 3.89 (s, 3H), 3.86 (s, 3H)

MS (ESI+) m/z 344 (M+H)$^+$

Scheme 2 (Method B)

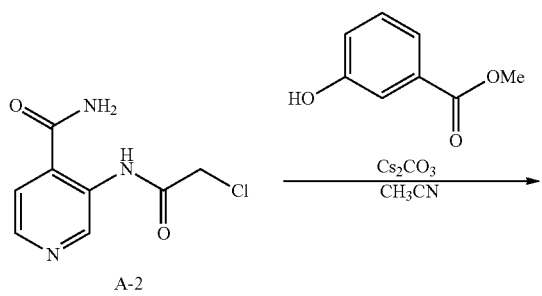

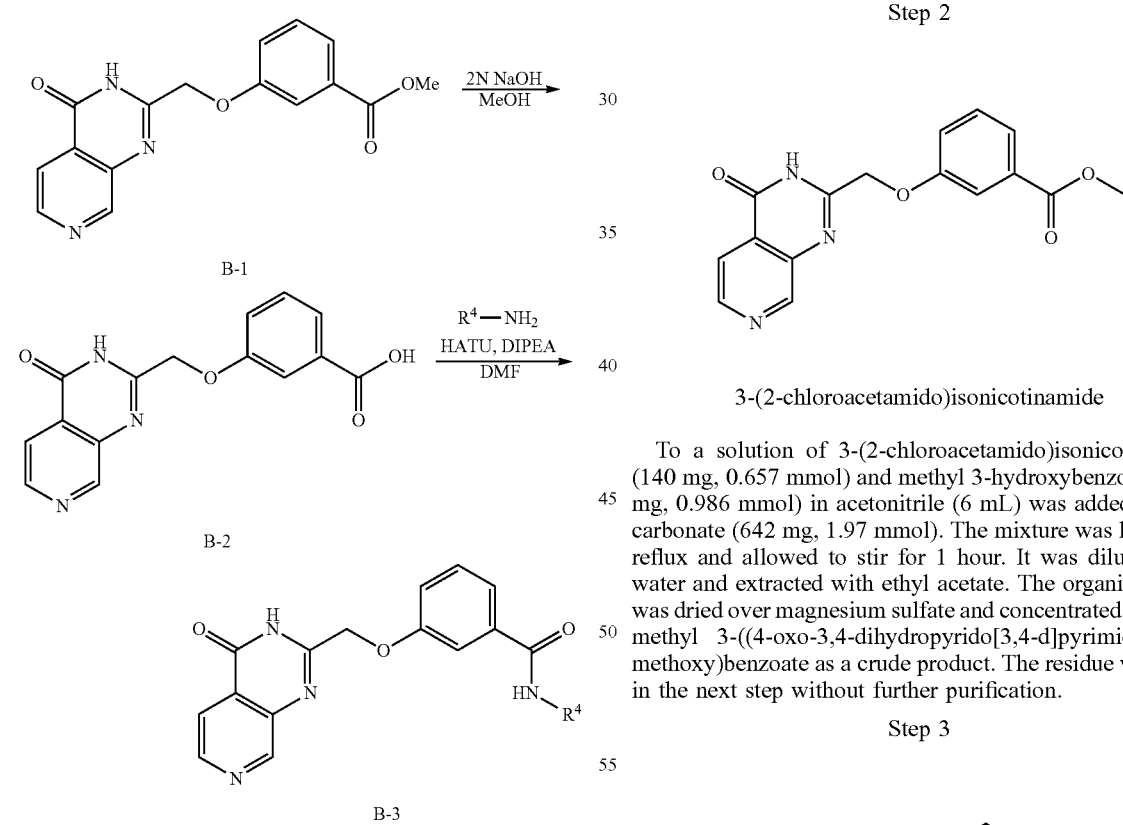

The general synthesis of compound B-3 is illustrated in Scheme 2. 3-(2-chloroacetamido)isonicotinamide is reacted with methyl 3-hydroxybenzoate to afford methyl 3-((4-oxo-3,4-dihydropyrido[3,4-d]pyrimidin-2-yl)methoxy)benzoate. The methyl ester is hydrolyzed by NaOH. Subsequent amide coupling of 3-((4-oxo-3,4-dihydropyrido[3,4-d]pyrimidin-2-yl)methoxy)benzoic acid with amine also provides compound B-3.

Example 40

Step 1

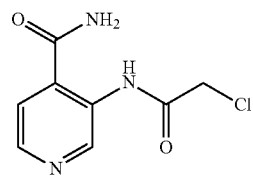 [SMILES: NC(=O)c1ccncc1NC(=O)CCl]

3-(2-chloroacetamido)isonicotinamide

To a solution of 3-aminopyridine-4-carboxamide (137 mg, 1 mmol) and N,N-diisopropylethylamine (0.53 mL, 3 mmol) in tetrahydrofuran (10 mL) was added chloroacetyl chloride (160 ul, 2 mmol) dropwise. The mixture was allowed to stir for 30 min and concentrated. The residue was diluted with water and extracted with ethyl acetate 4 times. The combined organic extract was dried over magnesium sulfate and concentrated. The residue was purified by combi-flash to afford 3-(2-chloroacetamido)isonicotinamide (140 mg, 0.657 mmol).

Step 2

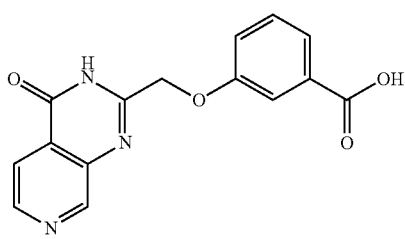 [SMILES: O=C(O)c1cccc(OCc2nc3cnccc3c(=O)[nH]2)c1]

3-(2-chloroacetamido)isonicotinamide

To a solution of 3-(2-chloroacetamido)isonicotinamide (140 mg, 0.657 mmol) and methyl 3-hydroxybenzoate (150 mg, 0.986 mmol) in acetonitrile (6 mL) was added cesium carbonate (642 mg, 1.97 mmol). The mixture was heated to reflux and allowed to stir for 1 hour. It was diluted with water and extracted with ethyl acetate. The organic extract was dried over magnesium sulfate and concentrated to afford methyl 3-((4-oxo-3,4-dihydropyrido[3,4-d]pyrimidin-2-yl)methoxy)benzoate as a crude product. The residue was used in the next step without further purification.

Step 3

3-((4-oxo-3,4-dihydropyrido[3,4-d]pyrimidin-2-yl)methoxy)benzoate

To a solution of 3-((4-oxo-3,4-dihydropyrido[3,4-d]pyrimidin-2-yl)methoxy)benzoate in methanol (3 mL) was added 2N aqueous sodium hydroxide solution (3 mL). The mixture was allowed to stir for 2 hours at ambient temperature and acidified with 2N aqueous hydrochloric acid solution to pH=4. It was extracted with ethyl acetate, dried over magnesium sulfate and concentrated in vacuo to afford 3-((4-oxo-3,4-dihydropyrido[3,4-d]pyrimidin-2-yl)methoxy)benzoic acid as a crude product (80 mg). The residue was used in the next step without further purification.

Step 4

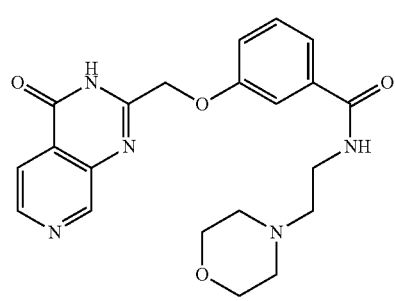 [SMILES: O=C(NCCN1CCOCC1)c1cccc(OCc2nc3cnccc3c(=O)[nH]2)c1]

N-(2-morpholinoethyl)-3-((4-oxo-3,4-dihydropyrido[3,4-d]pyrimidin-2-yl)methoxy)benzamide To a solution of 3-((4-oxo-3,4-dihydropyrido[3,4-d]pyrimidin-2-yl)methoxy)benzoate (1.0 eq) and amine (1.1 eq) in N,N-dimethylformamide were added N,N-diisopropylethylamine (2.0 eq) and HATU (1.2 eq). The mixture was allowed to stir for 30 min. It was diluted with brine and extracted with ethyl acetate twice. The combined organic extract was washed with brine twice and dried over magnesium sulfate (or extracted with UCT SPE CUBCX cartridge). It was concentrated and purified by combi-flash or preparative HPLC.

$^1$H NMR (400 MHz, CD3OD) δ 9.03 (s, 1H), 8.65 (d, J=5.2 Hz, 1H), 8.08 (d, J=5.2 Hz, 1H), 7.59 (m, 1H), 7.49 (m, 1H), 7.44 (m, 1H), 7.32 (m, 1H), 5.16 (s, 2H), 4.07 (m, 2H), 3.76 (t, J=6.0 Hz, 2H), 3.74 (m, 2H), 3.65 (m, 2H), 3.38 (t, J=6.0 Hz, 2H), 3.19 (m, 2H)

MS (ESI+) m/z 410 (M+H)$^+$

Scheme 3 (Method C)

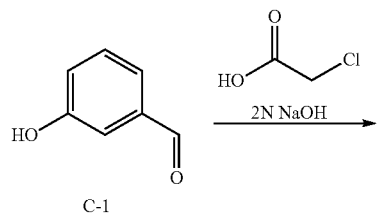

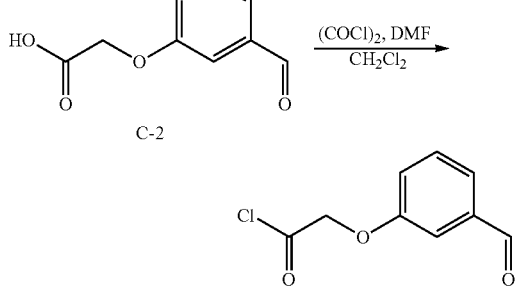

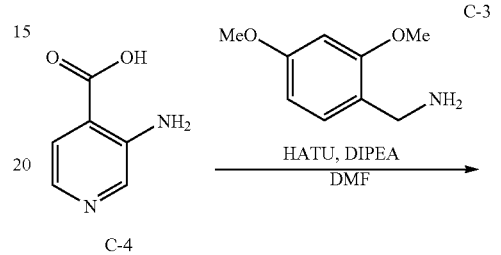

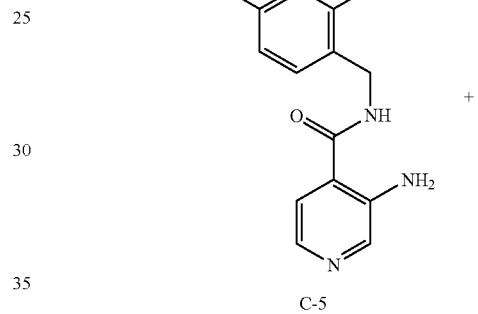

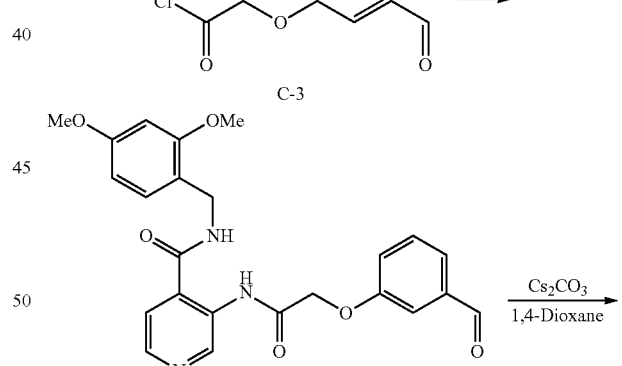

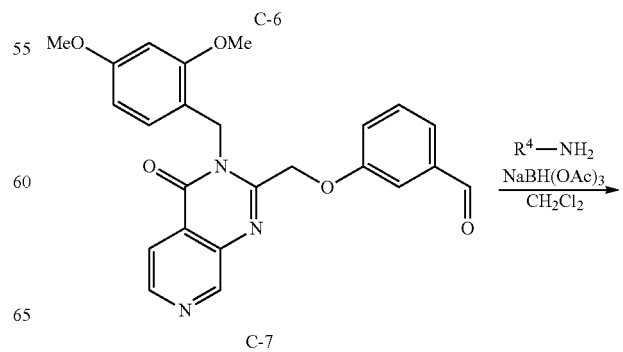

125
-continued

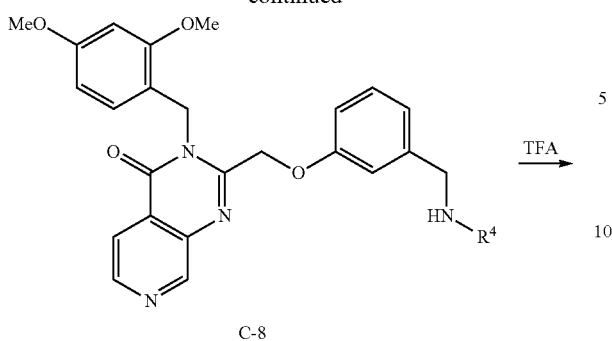

C-8

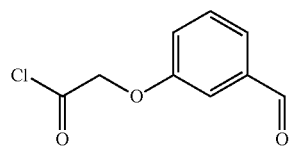 [SMILES: O=Cc1cccc(OCC(=O)Cl)c1]

TFA

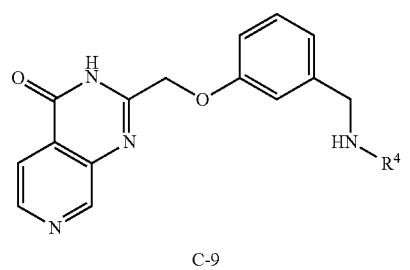

C-9

The general synthesis of compound C-9 is illustrated in Scheme 3. 2-(3-formylphenoxy)acetyl chloride is synthesized through 2 subsequent reactions which are acetic acid substitution and chlorination. 3-aminoisonicotinic acid is reacted with 2,4-dimethoxybenzylamine using HATU to afford amide intermediate C-5. The amide intermediate is coupled with intermediate C-3 to afford amide intermediate 6. Subsequent cyclization with $Cs_2CO_3$ and reductive amination with $NaBH(OAc)_3$ lead to intermediate 8. This is followed by a reaction with TFA, which leads to deprotected compound C-9.

Example 41

Step 1

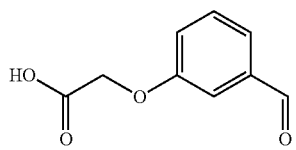

2-(3-formylphenoxy)acetic acid

To a mixture of chloroacetic acid (598 ul, 10 mmol) and 3-hydroxybenzaldehyde (1.47 g, 12 mmol) was added 2N aqueous sodium hydroxide solution (25 mL). The mixture was heated at reflux and allowed to stir overnight. It was acidified by concentrated hydrochloric acid and the precipitate was filtered off. The solid was washed with water and dried under reduced pressure to afford 2-(3-formylphenoxy) acetic acid (952 mg, 5.3 mmol).

126

Step 2

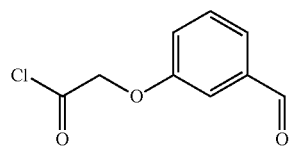 [SMILES: O=Cc1cccc(OCC(=O)Cl)c1]

2-(3-formylphenoxy)acetyl chloride

To a solution of 2-(3-formylphenoxy)acetic acid (1.0 eq) in dichloromethane were added oxalyl chloride (1.5 eq) and a few drops of N,N-dimethylformamide. The mixture was allowed to stir for 1 hour. It was concentrated in vacuo and used in the next step without further purification.

Step 3

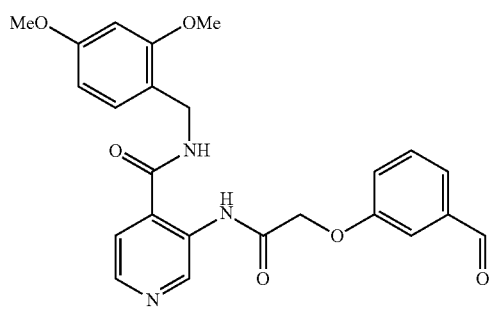 [SMILES: COc1ccc(CNC(=O)c2ccncc2NC(=O)COc2cccc(C=O)c2)c(OC)c1]

N-(2,4-dimethoxybenzyl)-3-(2-(3-formylphenoxy) acetamido)isonicotinamide

To a solution of 2-(3-formylphenoxy)acetyl chloride (1.0 eq) in tetrahydrofuran was added acyl chloride (1.5 eq). The mixture was allowed to stir overnight and then concentrated. The residue was crystallized with a proper solvent or used in the next step without further purification.

Step 4

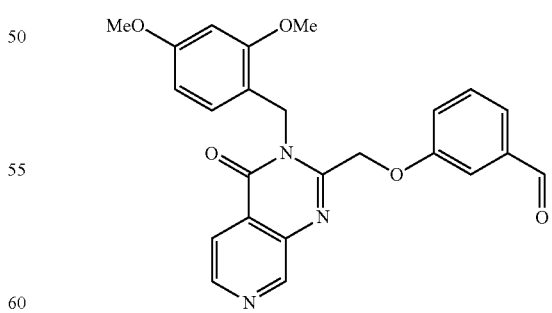

3-((3-(2,4-dimethoxybenzyl)-4-oxo-3,4-dihydro-pyrido[3,4-d]pyrimidin-2-yl)methoxy)benzaldehyde To a suspension of N-(2,4-dimethoxybenzyl)-3-(2-(3-formylphenoxy)acetamido)isonicotinamide (450 mg, 1.0 mmol) in 1,4-dioxane (6 mL) was added cesium carbonate (1.63 g, 5.0 mmol). The mixture was heated at reflux and allowed to stir for 3 days. It was diluted with water and extracted with ethyl acetate. The organic extract was dried over magnesium sulfate and concentrated. The residue was purified by combi-flash to afford 3-((3-(2,4-dimethoxybenzyl)-4-oxo-3,4-dihydropyrido[3,4-d]pyrimidin-2-yl)methoxy)benzaldehyde (56 mg, 0.13 mmol).

Step 5

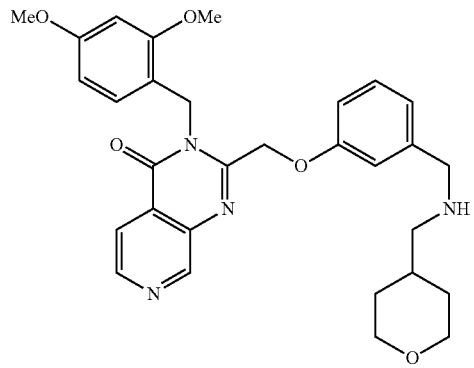 [SMILES: COc1ccc(Cn2c(COc3cccc(CNCC4CCOCC4)c3)nc3cnccc3c2=O)c(OC)c1]

3-(2,4-dimethoxybenzyl)-2-((3-((((tetrahydro-2H-pyran-4-yl)methyl)amino)methyl)phenoxy)methyl)pyrido[3,4-d]pyrimidin-4(3H)-one To a solution of 3-((3-(2,4-dimethoxybenzyl)-4-oxo-3,4-dihydropyrido[3,4-d]pyrimidin-2-yl)methoxy)benzaldehyde (1.0 eq) and amine (1.3 eq) in dichloromethane was added sodium triacetoxyborohydride (2.0 eq). The mixture was allowed to stir for 30 min. It was extracted with UCT SPE CUBCX cartridge and the extract was concentrated. The resulting residue was purified by preparative HPLC to afford the amine product.

Step 6

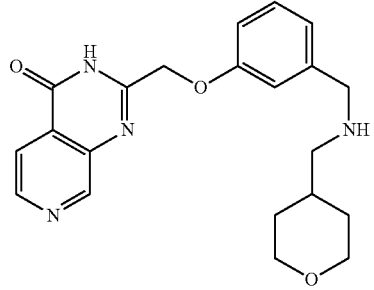 [SMILES: O=c1[nH]c(COc2cccc(CNCC3CCOCC3)c2)nc2cnccc12]

2-((3-((((tetrahydro-2H-pyran-4-yl)methyl)amino)methyl)phenoxy)methyl)pyrido[3,4-d]pyrimidin-4(3H)-one The 3-(2,4-dimethoxybenzyl)-2-((3-((((tetrahydro-2H-pyran-4-yl)methyl)amino)methyl)phenoxy)methyl)pyrido[3,4-d]pyrimidin-4(3H)-one was dissolved in trifluoroacetic acid (and dichloromethane). The mixture was allowed to stir for 1 hour at ambient temperature and concentrated in vacuo. The residue was purified by preparative HPLC to afford the final product.

$^1$H NMR (400 MHz, CD$_3$OD) δ 9.05 (s, 1H), 8.66 (d, J=4.8 Hz, 1H), 8.12 (dd, J=0.8, 5.2 Hz, 1H), 7.41 (m, 1H), 7.17 (m, 3H), 5.15 (s, 2H), 4.19 (s, 2H), 3.92 (dd, J=3.2, 10.8 Hz, 2H), 3.39 (t, J=12.0 Hz, 2H), 2.91 (d, 6.8 Hz, 2H), 1.96 (m, 1H), 1.65 (d, J=13.2 Hz, 2H), 1.30 (m, 2H)

MS (ESI+) m/z 381 (M+H)$^+$

Example 42

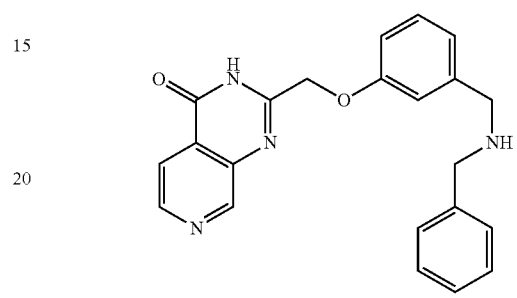

2-((3-((benzylamino)methyl)phenoxy)methyl)pyrido[3,4-d]pyrimidin-4(3H)-one

Using benzylamine, the title compound was obtained as described in Scheme 3 (Method C).

$^1$H NMR (400 MHz, CD$_3$OD) δ 9.03 (s, 1H), 8.64 (d, J=5.6 Hz, 1H), 8.09 (d, J=5.6 Hz, 1H), 7.42 (m, 6H), 7.19 (m, 2H), 7.12 (d, J=8.0 Hz, 1H), 5.14 (s, 2H), 4.21 (s, 2H), 4.20 (s, 2H)

MS (ESI+) m/z 373 (M+H)$^+$

Example 43

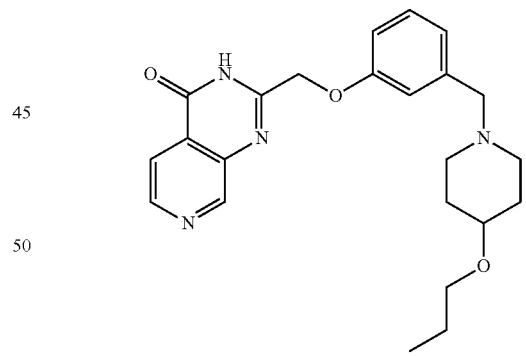

2-((3-((4-propoxypiperidin-1-yl)methyl)phenoxy)methyl)pyrido[3,4-d]pyrimidin-4(3H)-one Using 4-propoxypiperidine, the title compound was obtained as described in Scheme 3 (Method C).

$^1$H NMR (400 MHz, CD$_3$OD) δ 9.04 (s, 1H), 8.65 (d, J=4.8 Hz, 1H), 8.10 (d, J=5.2 Hz, 1H), 7.44 (m, 1H), 7.22 (m, 2H), 7.14 (m, 1H), 5.16 (s, 2H), 4.28 (s, 2H), 3.42 (m, 3H), 3.22 (m, 2H), 3.00 (m, 1H), 2.18 (m, 1H), 2.02 (m, 1H), 1.84 (m, 1H), 1.57 (m, 3H), 0.90 (t, J=7.2 Hz, 3H)

MS (ESI+) m/z 409 (M+H)$^+$

Example 44

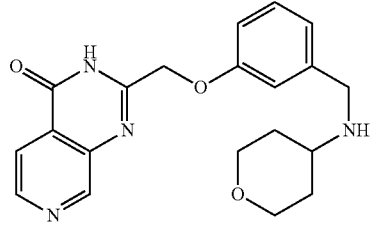 [SMILES: O=c1[nH]c(COc2cccc(CNC3CCOCC3)c2)nc2cnccc12]

2-((3-(((tetrahydro-2H-pyran-4-yl)amino)methyl)phenoxy)methyl)pyrido[3,4-d]pyrimidin-4(3H)-one Using tetrahydro-2H-pyran-4-amine, the title compound was obtained as described in Scheme 3 (Method C).
$^1$H NMR (400 MHz, CD$_3$OD) δ 9.05 (s, 1H), 8.66 (d, J=5.2 Hz, 1H), 8.11 (d, J=5.6 Hz, 1H), 7.42 (m, 1H), 7.20 (m, 2H), 7.14 (d, J=7.6 Hz, 1H), 5.21 (s, 2H), 4.22 (s, 2H), 4.01 (dd, J=4.4, 11.6 Hz, 2H), 3.39 (m, 3H), 2.06 (dd, J=2.4, 12.4 Hz, 2H), 1.67 (m, 2H)
MS (ESI+) m/z 367 (M+H)$^+$

Example 45

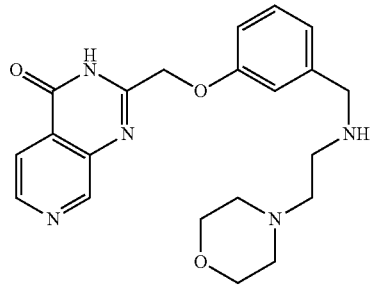 [SMILES: O=c1[nH]c(COc2cccc(CNCCN3CCOCC3)c2)nc2cnccc12]

2-((3-(((2-morpholinoethyl)amino)methyl)phenoxy)methyl)pyrido[3,4-d]pyrimidin-4(3H)-one Using 2-morpholinoethan-1-amine, the title compound was obtained as described in Scheme 3 (Method C).
$^1$H NMR (400 MHz, CD$_3$OD) δ 9.05 (s, 1H), 8.66 (d, J=4.8 Hz, 1H), 8.12 (d, J=5.2 Hz, 1H), 7.41 (m, 1H), 7.23 (m, 1H), 7.20 (m, 1H), 7.14 (d, J=7.2 Hz, 1H), 5.14 (s, 2H), 4.26 (s, 2H), 3.90 (m, 4H), 3.52 (t, J=6.4 Hz, 2H), 3.41 (t, J=7.2 Hz, 2H), 3.25 (m, 4H)
MS (ESI+) m/z 367 (M+H)$^+$ Scheme 4 (Method D)

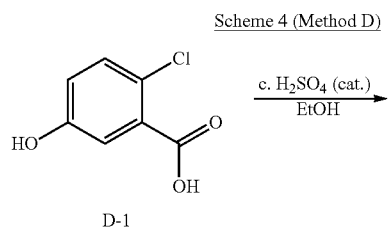

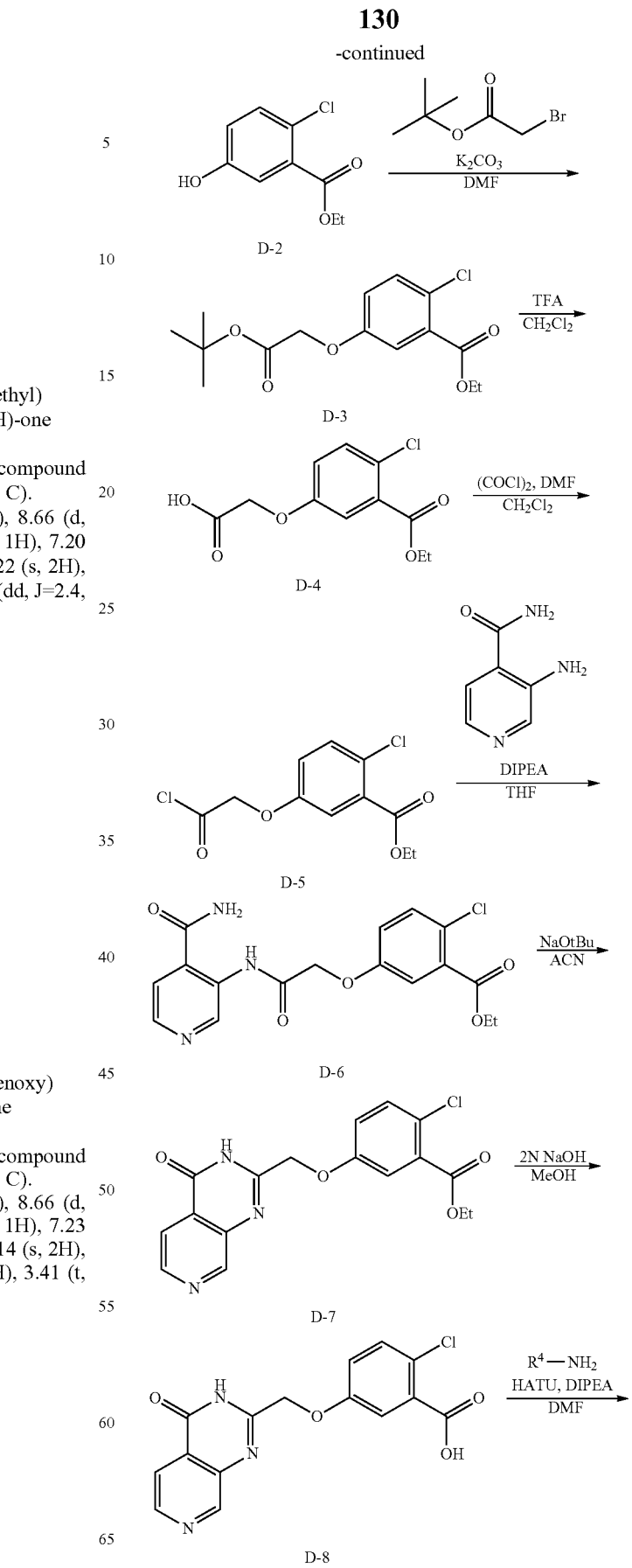

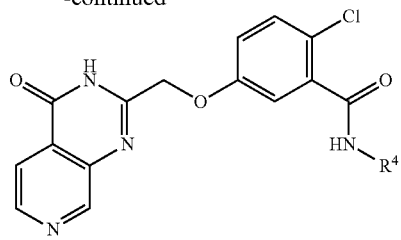

D-9

The general synthesis of compound D-9 is illustrated in Scheme 4. The carboxylic acid group of intermediate D-1 is converted to ethyl ester. The reactions of tert-butyl acetate substitution with K₂CO₃ and tert-butyl eater hydrolysis with TFA are followed to afford acetic acid intermediate D-4. The intermediate D-4 is chlorinated with oxalyl chloride and DMF and coupled with 3-aminoisonicotinamide to afford the amide intermediate D-6. Subsequent cyclization with NaOtBu and hydrolysis with NaOH lead to intermediate D-8. This is followed by amide coupling reaction with HATU, which leads to amide compound D-9.

Example 46

Step 1

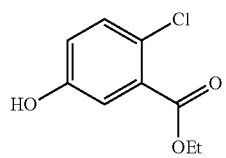 [SMILES: CCOC(=O)c1cc(O)ccc1Cl]

ethyl 2-chloro-5-hydroxybenzoate

To a solution of 2-chloro-5-hydroxybenzoic acid (5 g, 28.98 mmol) in ethanol (20 mL) was added concentrated sulfuric acid (0.5 mL) dropwise. The mixture was heated at reflux and allowed to stir overnight. It was quenched by a saturated aqueous sodium bicarbonate solution and extracted with ethyl acetate. The organic extract was dried over magnesium sulfate and concentrated to afford methyl 2-chloro-5-hydroxybenzoate as a crude product (quant.). The residue was used in the next step without further purification.

Step 2

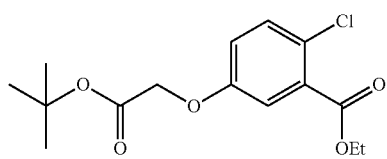 [SMILES: CCOC(=O)c1cc(OCC(=O)OC(C)(C)C)ccc1Cl]

ethyl 5-(2-(tert-butoxy)-2-oxoethoxy)-2-chlorobenzoate

To a solution of ethyl 2-chloro-5-hydroxybenzoate (crude, 34.78 mmol) and tert-butyl bromoacetate (5.1 mL, 34.78 mmol) in N,N-dimethylformamide (20 mL) was added potassium carbonate (10.6 g, 76.52 mmol). The mixture was allowed to stir for 1 hour. It was diluted with water and extracted with ethyl acetate. The combined organic extract was washed with brine twice and dried over magnesium sulfate. It was concentrated to afford ethyl 5-(2-(tert-butoxy)-2-oxoethoxy)-2-chlorobenzoate as a crude product (quant.). The residue was used in the next step without further purification Step 3

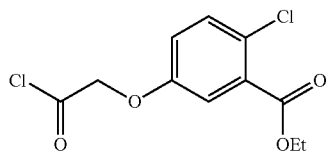 [SMILES: CCOC(=O)c1cc(OCC(=O)Cl)ccc1Cl]

2-(4-chloro-3-(ethoxycarbonyl)phenoxy)acetic acid

To a solution of ethyl 5-(2-(tert-butoxy)-2-oxoethoxy)-2-chlorobenzoate in dichloromethane (30 mL) was added trifluoroacetic acid (15 mL). The mixture was allowed to stir for 1 hour and concentrated in vacuo. The residue was crystallized with n-hexane. The precipitate was filtered off and washed with n-hexane. The solid was collected and dried at 50° C. to afford 2-(4-chloro-3-(ethoxycarbonyl)phenoxy)acetic acid (7.47 g, 28.88 mmol) as a white solid.

Step 4

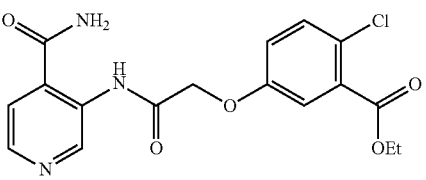 [SMILES: CCOC(=O)c1cc(OCC(=O)Nc2cnccc2C(N)=O)ccc1Cl]

ethyl 2-chloro-5-(2-chloro-2-oxoethoxy)benzoate

To a solution of carboxylic acid in dichloromethane were added oxalyl chloride (1.5 eq) and a few drops of N,N-dimethylformamide. The mixture was allowed to stir for 1 hour. It was concentrated in vacuo and used in the next step without further purification Step 5 ethyl 5-(2-((4-carbamoylpyridin-3-yl)amino)-2-oxoethoxy)-2-chlorobenzoate

To a suspension of 3-amino-2-carboxamide (1.70 g, 12.4 mmol) and ethyl 2-chloro-5-(2-chloro-2-oxoethoxy)benzoate (crude, 18.6 mmol) in tetrahydrofuran (30 mL) was added N,N-diisopropylethylamine (6.5 mL, 37.2 mmol) dropwise. The mixture was allowed to stir for 1 hour and concentrated in vacuo to afford ethyl 5-(2-((4-carbamoylpyridin-3-yl)amino)-2-oxoethoxy)-2-chlorobenzoate as a crude product. The residue was used in the next step without further purification Step 6

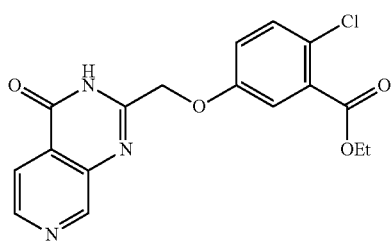 [SMILES: CCOC(=O)c1cc(OCc2nc3cnccc3c(=O)[nH]2)ccc1Cl]

ethyl 2-chloro-5-((4-oxo-3,4-dihydropyrido[3,4-d]pyrimidin-2-yl)methoxy)benzoate To a suspension of ethyl 5-(2-((4-carbamoylpyridin-3-yl)amino)-2-oxoethoxy)-2-chlorobenzoate (crude, 12.4 mmol) in acetonitrile (30 mL) was added sodium tert-butoxide (3.57 g, 37.2 mmol). The mixture was heated to reflux and allowed to stir for 4 hour. It was neutralized with 2N aqueous hydrochloric acid and extracted with ethyl acetate. The organic extract was dried over magnesium sulfate and concentrated. The residue was crystallized with isopropyl alcohol. The solid was collected and dried under reduced pressure to afford ethyl 2-chloro-5-((4-oxo-3,4-dihydropyrido[3,4-d]pyrimidin-2-yl)methoxy)benzoate (2.6 g, 7.23 mmol) as a pale brown solid.

Step 7

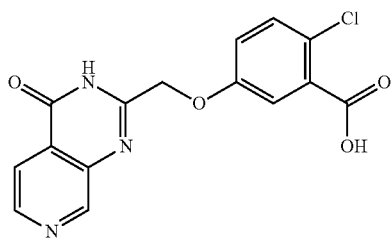 [SMILES: O=C(O)c1cc(OCc2nc3cnccc3c(=O)[nH]2)ccc1Cl]

2-chloro-5-((4-oxo-3,4-dihydropyrido[3,4-d]pyrimidin-2-yl)methoxy)benzoic acid To a solution of ethyl 2-chloro-5-((4-oxo-3,4-dihydropyrido[3,4-d]pyrimidin-2-yl)methoxy)benzoate (2.6 g, 7.23 mmol) in methanol (20 mL) was added a 2N aqueous sodium hydroxide solution (10 mL). The mixture was allowed to stir for 1 hour and neutralized with a 2N aqueous hydrochloric acid solution. The precipitate was filtered and washed with water. The solid was collected and dried under reduced pressure to afford 2-chloro-5-((4-oxo-3,4-dihydropyrido[3,4-d]pyrimidin-2-yl)methoxy)benzoic acid (2.2 g, 6.64 mmol) as a pale brown solid.

Step 8

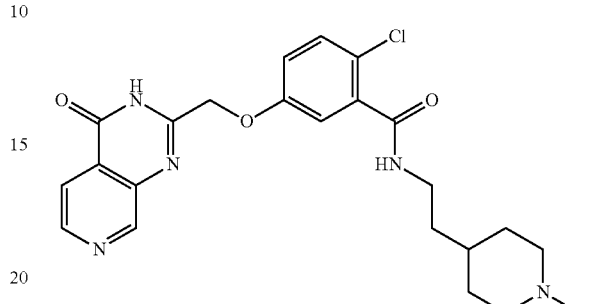

tert-butyl 4-(2-(2-chloro-5-((4-oxo-3,4-dihydropyrido[3,4-d]pyrimidin-2-yl)methoxy)benzamido)ethyl)piperidine-1-carboxylate To a solution of starting material (1.0 eq) and amine (1.1 eq) in N,N-dimethylformamide were added N,N-diisopropylethylamine (2.0 eq) and HATU (1.2 eq). The mixture was allowed to stir for 30 min. It was diluted with brine and extracted with ethyl acetate twice. The combined organic extract was washed with brine twice and dried over magnesium sulfate (or extracted with UCT SPE CUBCX cartridge). It was concentrated and purified by combi-flash or preparative HPLC.

Step 9

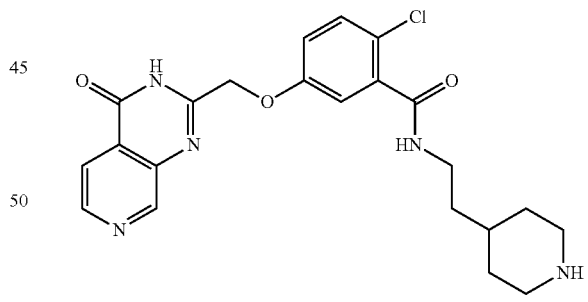

2-chloro-5-((4-oxo-3,4-dihydropyrido[3,4-d]pyrimidin-2-yl)methoxy)-N-(2-(piperidin-4-yl)ethyl)benzamide The starting material was dissolved in trifluoroacetic acid (and dichloromethane). The mixture was allowed to stir for 1 hour at ambient temperature and concentrated in vacuo. The residue was purified by preparative HPLC to afford the final product.

$^1$H NMR (600 MHz, CD$_3$OD) δ 9.04 (s, 1H), 8.66 (d, J=5.4 Hz, 1H), 8.08 (d, J=5.4 Hz, 1H), 7.41 (d, 9.0 Hz, 1H), 7.18 (m, 2H), 5.14 (s, 2H), 3.42 (m, 2H), 3.39 (m, 2H), 2.96 (m, 2H), 2.04 (m, 2H), 1.75 (m, 1H), 1.60 (m, 2H), 1.41 (m, 2H)

MS (ESI+) m/z 442 (M+H)+

Example 47

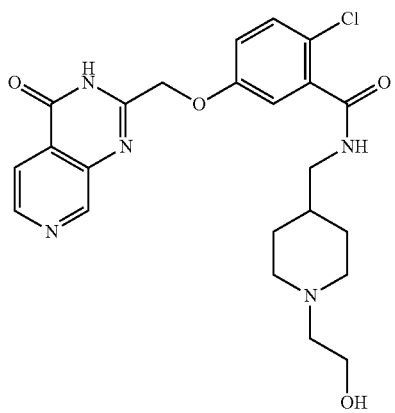 [SMILES: O=C(NCC1CCN(CCO)CC1)c1cc(OCc2nc3cnccc3c(=O)[nH]2)ccc1Cl]

2-chloro-N-((1-(2-hydroxyethyl)piperidin-4-yl)methyl)-5-((4-oxo-3,4-dihydropyrido[3,4-d]pyrimidin-2-yl)methoxy)benzamide Using 2-(4-(aminomethyl)piperidin-1-yl)ethan-1-ol, the title compound was obtained as described in Scheme 4 (Method D).

MS (ESI+) m/z 472 (M+H)+

Example 48

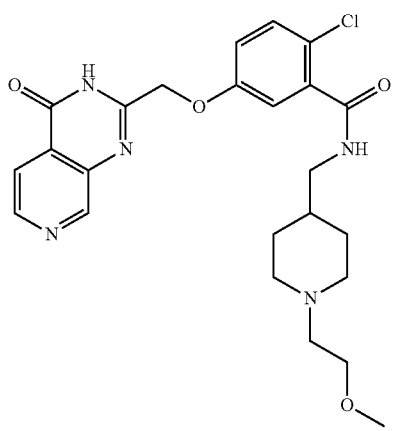 [SMILES: COCCN1CCC(CNC(=O)c2cc(OCc3nc4cnccc4c(=O)[nH]3)ccc2Cl)CC1]

2-chloro-N-((1-(2-methoxyethyl)piperidin-4-yl)methyl)-5-((4-oxo-3,4-dihydropyrido[3,4-d]pyrimidin-2-yl)methoxy)benzamide Using (1-(2-methoxyethyl)piperidin-4-yl)methanamine, the title compound was obtained as described in Scheme 4 (Method D).

MS (ESI+) m/z 486 (M+H)+

Example 49

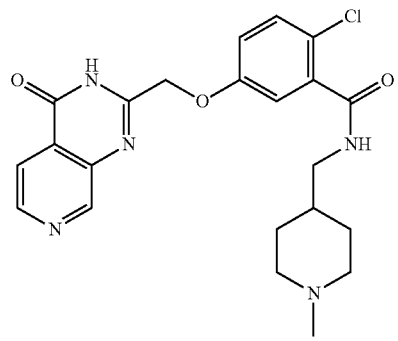 [SMILES: CN1CCC(CNC(=O)c2cc(OCc3nc4cnccc4c(=O)[nH]3)ccc2Cl)CC1]

2-chloro-N-((1-methylpiperidin-4-yl)methyl)-5-((4-oxo-3,4-dihydropyrido[3,4-d]pyrimidin-2-yl)methoxy)benzamide Using (1-methylpiperidin-4-yl)methanamine, the title compound was obtained as described in Scheme 4 (Method D).

MS (ESI+) m/z 442 (M+H)+

Example 50

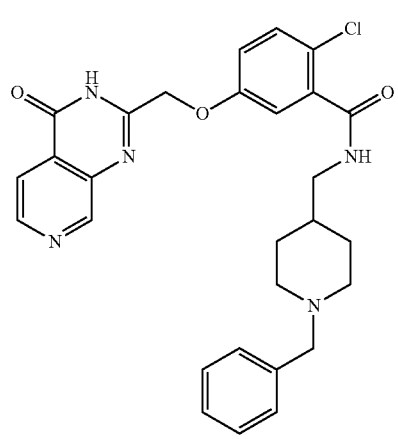 [SMILES: O=C(NCC1CCN(Cc2ccccc2)CC1)c1cc(OCc2nc3cnccc3c(=O)[nH]2)ccc1Cl]

N-((1-benzylpiperidin-4-yl)methyl)-2-chloro-5-((4-oxo-3,4-dihydropyrido[3,4-d]pyrimidin-2-yl)methoxy)benzamide Using (1-benzylpiperidin-4-yl)methanamine, the title compound was obtained as described in Scheme 4 (Method D).

MS (ESI+) m/z 518 (M+H)+

Example 51

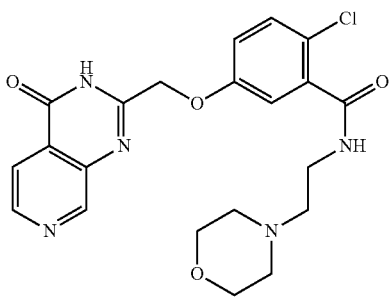 [SMILES: O=C(NCCN1CCOCC1)c1cc(OCc2nc3cnccc3c(=O)[nH]2)ccc1Cl]

2-chloro-N-(2-morpholinoethyl)-5-((4-oxo-3,4-dihydropyrido[3,4-d]pyrimidin-2-34)methoxy)benzamide Using 2-morpholinoethan-1-amine, the title compound was obtained as described in Scheme 4 (Method D).
MS (ESI+) m/z 444 (M+H)$^+$

Example 52

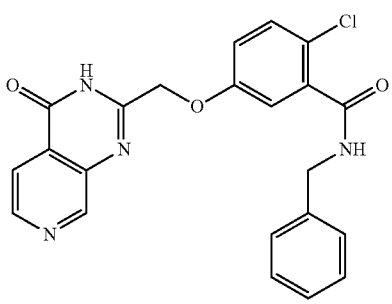 [SMILES: O=C(NCc1ccccc1)c1cc(OCc2nc3cnccc3c(=O)[nH]2)ccc1Cl]

N-benzyl-2-chloro-5-((4-oxo-3,4-dihydropyrido[3,4-d]pyrimidin-2-yl)methoxy)benz amide Using benzylamine, the title compound was obtained as described in Scheme 4 (Method D).
MS (ESI+) m/z 421 (M+H)$^+$

Example 53

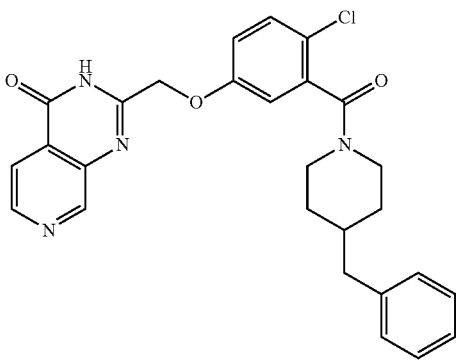 [SMILES: O=C(c1cc(OCc2nc3cnccc3c(=O)[nH]2)ccc1Cl)N1CCC(Cc2ccccc2)CC1]

2-((3-(4-benzylpiperidine-1-carbonyl)-4-chlorophenoxy)methyl)pyrido[3,4-d]pyrimidin-4(3H)-one Using 4-benzylpiperidine, the title compound was obtained as described in Scheme 4 (Method D).
MS (ESI+) m/z 489 (M+H)$^+$

Example 54

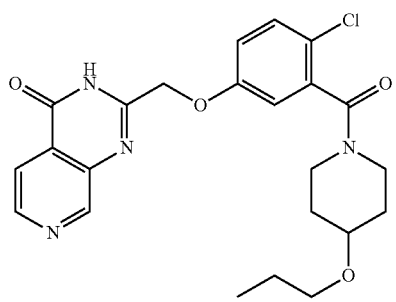 [SMILES: CCCOC1CCN(C(=O)c2cc(OCc3nc4cnccc4c(=O)[nH]3)ccc2Cl)CC1]

2-((4-chloro-3-(4-propoxypiperidine-1-carbonyl)phenoxy)methyl)pyrido[3,4-d]pyrimidin-4(3H)-one Using 4-propoxypiperidine, the title compound was obtained as described in Scheme 4 (Method D).
MS (ESI+) m/z 457 (M+H)$^+$

Example 55

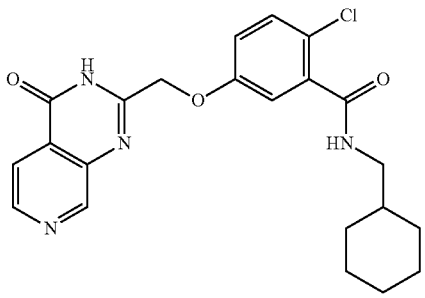 [SMILES: O=C(NCC1CCCCC1)c1cc(OCc2nc3cnccc3c(=O)[nH]2)ccc1Cl]

2-chloro-N-(cyclohexylmethyl)-5-((4-oxo-3,4-dihydropyrido[3,4-d]pyrimidin-2-yl)methoxy)benzamide Using cyclohexylmethanamine, the title compound was obtained as described in Scheme 4 (Method D).
MS (ESI+) m/z 427 (M+H)$^+$

Example 56

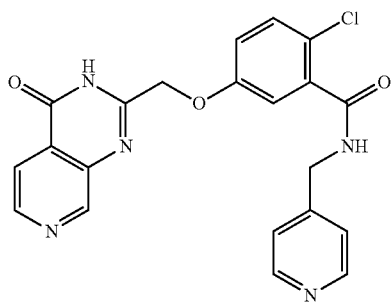 [SMILES: O=C(NCc1ccncc1)c1cc(OCc2nc3cnccc3c(=O)[nH]2)ccc1Cl]

2-chloro-5-((4-oxo-3,4-dihydropyrido[3,4-d]pyrimidin-2-yl)methoxy)-N-(pyridin-4-ylmethyl)benzamide Using 4-(aminomethyl)pyridine, the title compound was obtained as described in Scheme 4 (Method D).

$^1$H NMR (600 MHz, CD$_3$OD) δ 9.05 (s, 1H), 8.83 (d, J=7.2 Hz), 8.67 (d, J=5.4 Hz, 1H), 8.11 (d, J=5.4 Hz, 1H), 8.10 (d, J=6.6 Hz, 2H), 7.46 (d, J=9.0 Hz, 1H), 7.31 (d, J=3.0 Hz, 1H), 7.24 (dd, J=3.0, 9.0 Hz, 1H), 5.17 (s, 2H), 4.84 (s, 2H)

MS (ESI+) m/z 422 (M+H)$^+$

Example 57

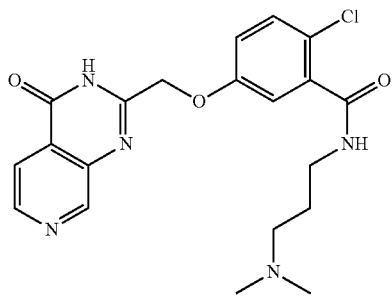 [SMILES: CN(C)CCCNC(=O)c1cc(OCc2nc3cnccc3c(=O)[nH]2)ccc1Cl]

2-chloro-N-(3-(dimethylamino)propyl)-5-((4-oxo-3,4-dihydropyrido[3,4-d]pyrimidin-2-yl)methoxy)benzamide Using N,N-dimethyl-1,3-propanediamine, the title compound was obtained as described in Scheme 4 (Method D).

$^1$H NMR (600 MHz, CD$_3$OD) δ 9.04 (s, 1H), 8.67 (d, J=5.4 Hz, 1H), 8.10 (d, J=5.4 Hz, 1H), 7.43 (d, J=9.0 Hz, 1H), 7.21 (m, 2H), 5.15 (s, 2H), 3.47 (t, J=6.6 Hz, 2H), 3.23 (m, 2H), 2.92 (s, 6H), 2.03 (m, 2H)

MS (ESI+) m/z 416 (M+H)$^+$

Example 58

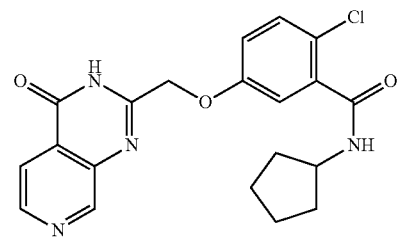 [SMILES: O=C(NC1CCCC1)c1cc(OCc2nc3cnccc3c(=O)[nH]2)ccc1Cl]

2-chloro-N-cyclopentyl-5-((4-oxo-3,4-dihydropyrido[3,4-d]pyrimidin-2-yl)methoxy)benzamide Using cyclopentylamine, the title compound was obtained as described in Scheme 4 (Method D).

$^1$H NMR (600 MHz, DMSO-d6) δ 9.03 (s, 1H), 8.67 (d, J=5.4 Hz, 1H), 8.37 (d, J=7.2 Hz, 1H), 7.95 (d, J=5.4 Hz, 1H), 7.38 (d, J=9.0 Hz, 1H), 7.10 (m, 2H), 5.08 (s, 2H), 4.14 (m, 1H), 1.83 (m, 2H), 1.62 (m, 2H), 1.48 (m, 4H)

MS (ESI+) m/z 399 (M+H)$^+$

Example 59

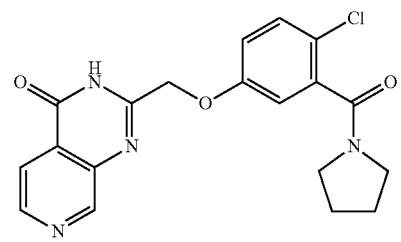 [SMILES: O=C(c1cc(OCc2nc3cnccc3c(=O)[nH]2)ccc1Cl)N1CCCC1]

2-((4-chloro-3-(pyrrolidine-1-carbonyl)phenoxy)methyl)pyrido[3,4-d]pyrimidin-4(3H)-one Using pyrrolidine, the title compound was obtained as described in Scheme 4 (Method D).

$^1$H NMR (600 MHz, CD$_3$OD) δ 9.07 (s, 1H), 8.67 (d, J=5.4 Hz, 1H), 8.13 (d, J=5.4 Hz, 1H), 7.43 (d, J=9.0 Hz, 1H), 7.17 (dd, J=3.0, 9.0 Hz, 1H), 7.11 (d, J=3.0 Hz, 1H), 5.14 (s, 2H), 3.59 (t, J=7.2 Hz, 2H), 3.21 (t, J=6.6 Hz, 2H), 1.98 (m, 2H), 1.89 (m, 2H)

MS (ESI+) m/z 385 (M+H)$^+$

Example 60

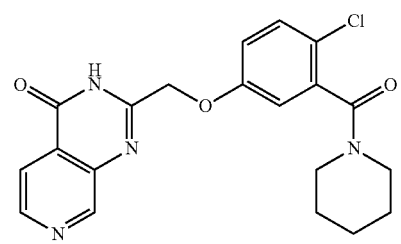

2-((4-chloro-3-(piperidine-1-carbonyl)phenoxy)methyl)pyrido[3,4-d]pyrimidin-4(3H)-one Using piperidine, the title compound was obtained as described in Scheme 4 (Method D).

$^1$H NMR (600 MHz, CD$_3$OD) δ 9.05 (s, 1H), 8.66 (d, J=5.4 Hz, 1H), 8.11 (d, J=5.4 Hz, 1H), 7.42 (d, J=9.0 Hz, 1H), 7.16 (dd, J=3.0, 9.0 Hz, 1H), 7.07 (d, J=3.0 Hz, 1H), 5.14 (s, 2H), 3.76 and 3.65 (m, 2H), 3.19 (m, 2H), 1.66 (m, 4H), 1.52 and 1.42 (m, 2H)

MS (ESI+) m/z 399 (M+H)$^+$

Example 61

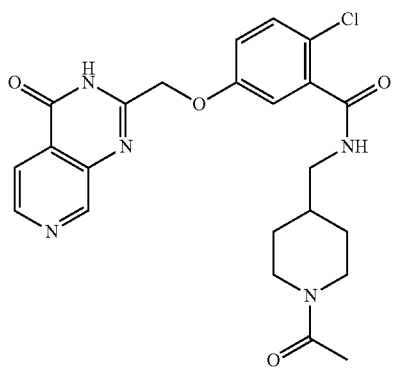 [SMILES: CC(=O)N1CCC(CNC(=O)c2cc(OCc3nc4cnccc4c(=O)[nH]3)ccc2Cl)CC1]

N-((1-acetylpiperidin-4-yl)methyl)-2-chloro-5-((4-oxo-3,4-dihydropyrido[3,4-d]pyrimidin-2-yl)methoxy)benzamide Using 1-(4-(aminomethyl)piperidin-1-yl)ethan-1-one, the title compound was obtained as described in Scheme 4 (Method D).

$^1$H NMR (600 MHz, CD$_3$OD) δ 9.15 (s, 1H), 8.71 (d, J=5.4 Hz, 1H), 8.26 (d, J=5.4 Hz, 1H), 7.41 (d, J=9.0 Hz, 1H), 7.17 (m, 2H), 5.16 (s, 2H), 4.53 (m, 1H), 3.95 (m, 1H), 3.26 and 3.22 (m, 2H), 3.11 (m, 1H), 2.63 (m, 2H), 1.92 (m, 1H), 1.84 (m, 2H), 1.27 and 1.17 (m, 2H)

MS (ESI+) m/z 470 (M+H)$^+$

Example 62

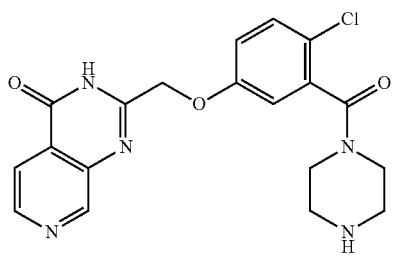 [SMILES: O=C(c1cc(OCc2nc3cnccc3c(=O)[nH]2)ccc1Cl)N1CCNCC1]

2-((4-chloro-3-(piperazine-1-carbonyl)phenoxy)methyl)pyrido[3,4-d]pyrimidin-4(3H)-one Using 1-Boc-piperazine, the title compound was obtained as described in Scheme 4 (Method D).

$^1$H NMR (600 MHz, CD$_3$OD) δ 9.06 (s, 1H), 8.68 (d, J=5.4 Hz, 1H), 8.13 (d, J=5.4 Hz, 1H), 7.47 (d, J=9.6 Hz, 1H), 7.23 (dd, J=3.0, 9.6 Hz, 1H), 7.17 (d, J=3.0 Hz, 1H), 5.15 (m, 2H), 4.01 (m, 2H), 3.54 (m, 2H), 3.34 (m, 2H), 3.22 (m, 2H)

MS (ESI+) m/z 400 (M+H)$^+$

Example 63

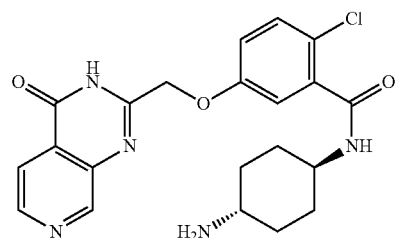

N-(trans-1,4-aminocyclohexyl)-2-chloro-5-((4-oxo-3,4-dihydropyrido[3,4-d]pyrimidin-2-yl)methoxy)benzamide Using trans-N-Boc-1,4-cyclohexanediamine, the title compound was obtained as described in Scheme 4 (Method D).

$^1$H NMR (600 MHz, CD$_3$OD) δ 9.05 (s, 1H), 8.66 (d, J=5.4 Hz, 1H), 8.10 (d, J=5.4 Hz, 1H), 7.40 (d, J=8.4 Hz, 1H), 7.16 (m, 2H), 5.14 (s, 2H), 3.83 (m, 1H), 3.09 (m, 1H), 2.11 (m, 4H), 1.54 (m, 2H), 1.42 (m, 2H)

MS (ESI+) m/z 428 (M+H)$^+$

Example 64

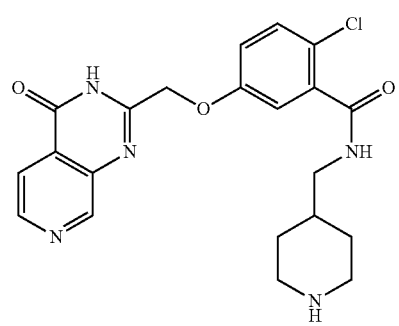 [SMILES: O=C(NCC1CCNCC1)c1cc(OCc2nc3cnccc3c(=O)[nH]2)ccc1Cl]

2-chloro-5-((4-oxo-3,4-dihydropyrido[3,4-d]pyrimidin-2-yl)methoxy)-N-(piperidin-4-ylmethyl)benzamide Using tert-butyl 4-(aminomethyl)piperidine-1-carboxylate, the title compound was obtained as described in Scheme 4 (Method D).

$^1$H NMR (600 MHz, CD$_3$OD) δ 9.06 (s, 1H), 8.67 (d, J=5.4 Hz, 1H), 8.13 (d, J=5.4 Hz, 1H), 7.41 (m, 1H), 7.18 (m, 2H), 5.15 (s, 2H), 3.42 (m, 2H), 3.32 (m, 2H), 3.00 (m, 2H), 2.01 (m, 2H), 1.96 (m, 1H), 1.48 (m, 2H)

MS (ESI+) m/z 428 (M+H)$^+$

Example 65

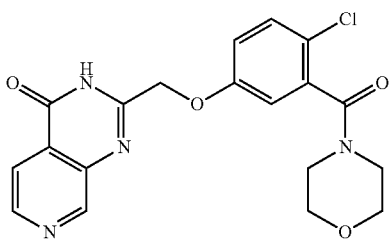

2-((4-chloro-3-(morpholine-4-carbonyl)phenoxy)methyl)pyrido[3,4-d]pyrimidin-4(3H)-one Using morpholine, the title compound was obtained as described in Scheme 4 (Method D).
$^1$H NMR (600 MHz, CD$_3$OD) δ 9.02 (s, 1H), 8.67 (d, J=4.8 Hz, 1H), 7.95 (d, J=4.8 Hz, 1H), 7.44 (d, J=8.4 Hz, 1H), 7.12 (m, 2H), 5.08 (s, 2H), 3.61 (m, 4H), 3.46 (m, 2H), 3.09 (m, 2H)
MS (ESI+) m/z 401 (M+H)$^+$

Example 66

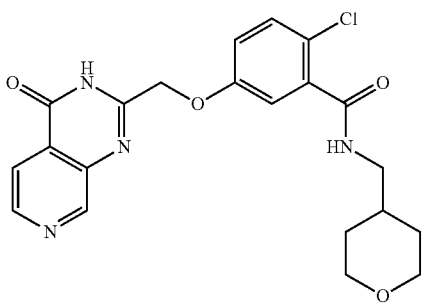 [SMILES: O=C(NCC1CCOCC1)c1cc(OCc2nc3cnccc3c(=O)[nH]2)ccc1Cl]

2-chloro-5-((4-oxo-3,4-dihydropyrido[3,4-d]pyrimidin-2-yl)methoxy)-N-((tetrahydro-2H-pyran-4-yl)methyl)benzamide Using (4-aminomethyl)tetrahydropyran, the title compound was obtained as described in Scheme 4 (Method D).
MS (ESI+) m/z 429 (M+H)$^+$

Example 67

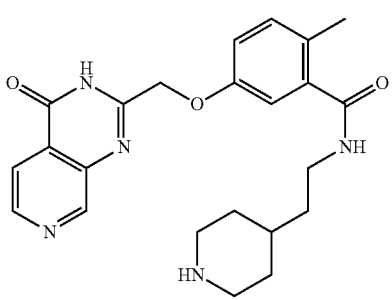 [SMILES: Cc1ccc(OCc2nc3cnccc3c(=O)[nH]2)cc1C(=O)NCCC1CCNCC1]

2-methyl-5-((4-oxo-3,4-dihydropyrido[3,4-d]pyrimidin-2-yl)methoxy)-N-(2-(piperidin-4-yl)ethyl)benzamide Using 5-hydroxy-2-methylbenzoic acid, the title compound was obtained as described in Scheme 4 (Method D).
$^1$H NMR (600 MHz, CD$_3$OD) δ 9.07 (s, 1H), 8.67 (d, J=5.4 Hz, 1H), 8.13 (d, J=5.4 Hz, 1H), 7.20 (d, J=9.0 Hz, 1H), 7.08 (m, 1H), 7.06 (d, J=3.0 Hz, 1H), 5.12 (s, 2H), 3.41 (m, 4H), 2.97 (m, 2H), 2.31 (s, 3H), 2.02 (m, 2H), 1.72 (m, 1H), 1.59 (m, 2H), 1.44 (m, 2H)
MS (ESI+) m/z 422 (M+H)$^+$

Example 68

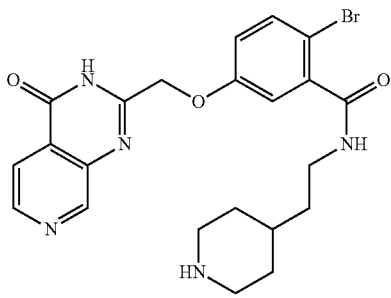 [SMILES: O=C(NCCC1CCNCC1)c1cc(OCc2nc3cnccc3c(=O)[nH]2)ccc1Br]

2-bromo-5-((4-oxo-3,4-dihydropyrido[3,4-d]pyrimidin-2-yl)methoxy)-N-(2-(piperidin-4-yl)ethyl)benzamide Using 2-bromo-5-hydroxybenzoic acid, the title compound was obtained as described in Scheme 4 (Method D).
$^1$H NMR (600 MHz, CD$_3$OD) δ 9.07 (s, 1H), 8.67 (d, J=5.4 Hz, 1H), 8.14 (d, J=5.4 Hz, 1H), 7.56 (d, J=9.0 Hz, 1H), 7.15 (d, J=3.0 Hz, 1H), 7.11 (d, J=3.0, 9.0 Hz, 1H), 5.14 (s, 2H), 3.42 (m, 2H), 3.39 (m, 2H), 2.96 (m, 2H), 2.03 (m, 2H), 1.78 (m, 1H), 1.61 (m, 2H), 1.41 (m, 2H)
MS (ESI+) m/z 422 (M+H)$^+$

Scheme 5 (Method E)

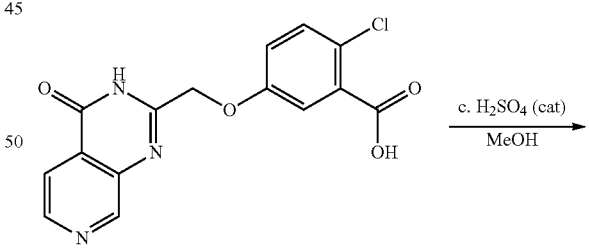

D-8

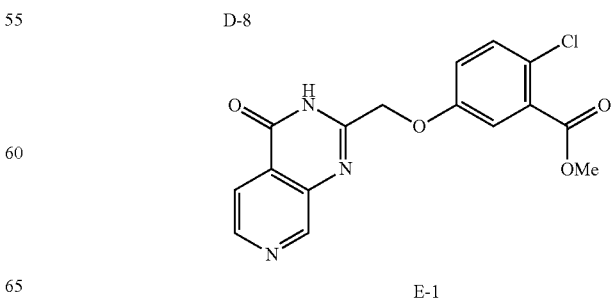

E-1

The general synthesis of compound E-1 is illustrated in Scheme 5. The above esterification reaction with MeOH and c.H$_2$SO$_4$ leads to methyl ester compound E-1.

Example 69

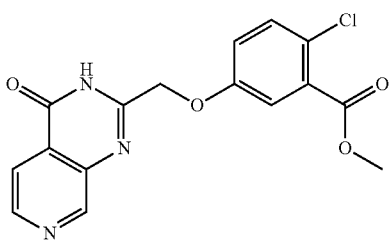 [SMILES: COC(=O)c1cc(OCc2nc3cnccc3c(=O)[nH]2)ccc1Cl]

methyl 2-chloro-5-((4-oxo-3,4-dihydropyrido[3,4-d]pyrimidin-2-yl)methoxy)benzoate To a suspension of 2-chloro-5-((4-oxo-3,4-dihydropyrido[3,4-d]pyrimidin-2-yl)methoxy)benzoic acid (20 mg) in methanol (1 mL) was added a few drops of concentrated sulfuric acid. The mixture was heated at reflux and allowed to stir overnight. It was quenched with a saturated aqueous sodium bicarbonate solution and extracted with ethyl acetate. The organic extract was dried over magnesium sulfate and concentrated. The residue was purified by preparative HPLC to afford 2-chloro-5-((4-oxo-3,4-dihydropyrido[3,4-d]pyrimidin-2-yl)methoxy)benzoate.

$^1$H NMR (600 MHz, DMSO-d6) δ 9.03 (s, 1H), 8.67 (d, J=5.4 Hz, 1H), 7.95 (d, J=5.4 Hz, 1H), 7.50 (m, 2H), 7.28 (dd, J=3.0, 9.0 Hz, 1H), 5.11 (s, 2H), 3.84 (s, 3H)

MS (ESI+) m/z 346 (M+H)$^+$

Scheme 6 (Method F)

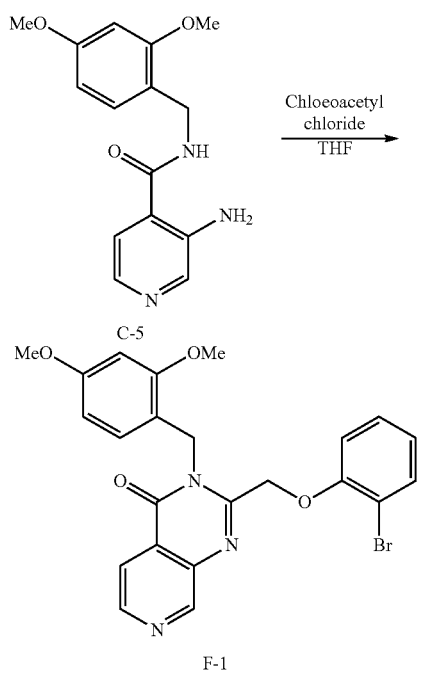

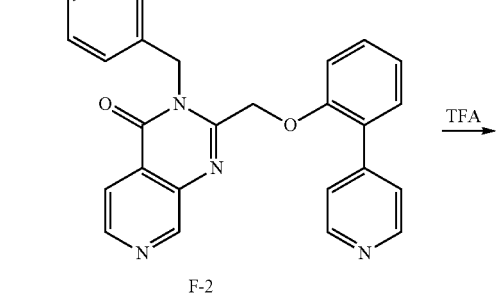

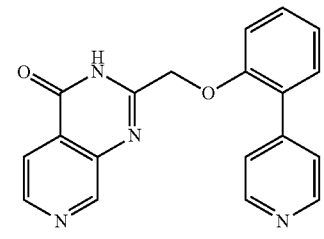

The general synthesis of compound F-3 is illustrated in Scheme 6. The intermediate 1 is synthesized through a 2-step reaction with chloroacetyl chloride and Cs$_2$CO$_3$. Subsequent Suzuki cross-coupling with boronic acid resulted in intermediate F-2, which is further deprotected with TFA to afford the desired compound F-3.

Example 70

Step 1

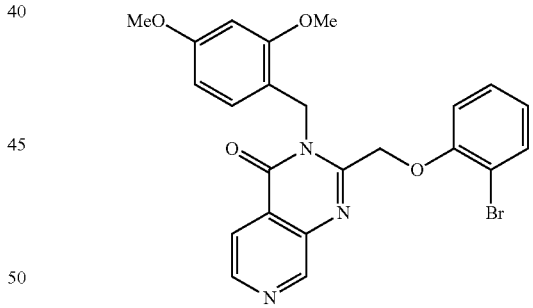

2-((2-bromophenoxy)methyl)-3-(2,4-dimethoxybenzyl)pyrido[3,4-d]pyrimidin-4(3H)-one To a suspension of 3-(2-chloroacetamido)-N-(2,4-dimethoxybenzyl)isonicotinamide (728 mg, 2 mmol) and 2-bromophenol (320 ul, 3 mmol) in acetonitrile (10 mL) was added cesium carbonate (1.95 g, 6 mmol). The mixture was heated at reflux and allowed to stir for 3 days. It was diluted with water and extracted with ethyl acetate. The organic extract was dried over magnesium sulfate and concentrated. The residue was purified by combi-flash to afford 2-((2-bromophenoxy)methyl)-3-(2,4-dimethoxybenzyl)pyrido[3,4-d]pyrimidin-4(3H)-one (116 mg, 0.24 mmol).

Step 2

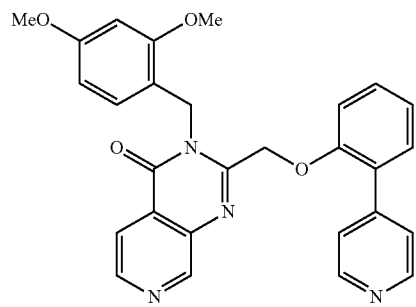 [SMILES: COc1ccc(Cn2c(COc3ccccc3-c3ccncc3)nc3cnccc3c2=O)c(OC)c1]

3-(2,4-dimethoxybenzyl)-2-((2-(pyridin-4-yl)phenoxy)methyl)pyrido[3,4-d]pyrimidin-4(3H)-one To a solution of 2-((2-bromophenoxy)methyl)-3-(2,4-dimethoxybenzyl)pyrido[3,4-d]pyrimidin-4(3H)-one (24 mg, 0.05 mmol), pyridin-4-ylboronic acid (12 mg, 0.1 mmol) and 2M aqueous potassium phosphate solution (50 ul, 0.1 mmol) was added tetrakis(triphenylphosphine)palladium(0) (6 mg, 0.005 mmol) under nitrogen atmosphere. The mixture was heated at reflux and allowed to stir overnight. It was extracted with UCT SPE CUBCX cartridge. The extract was concentrated and purified by preparative HPLC to afford 3-(2,4-dimethoxybenzyl)-2-((2-(pyridin-4-yl)phenoxy)methyl)pyrido[3,4-d]pyrimidin-4(3H)-one.

Step 3

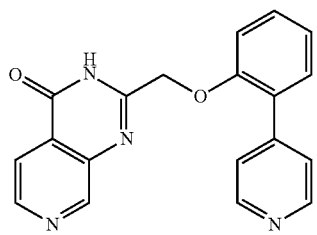 [SMILES: O=c1[nH]c(COc2ccccc2-c2ccncc2)nc2cnccc12]

2-((2-(pyridin-4-yl)phenoxy)methyl)pyrido[3,4-d]pyrimidin-4(3H)-one

The starting material was dissolved in trifluoroacetic acid (and dichloromethane). The mixture was allowed to stir for 1 hour at ambient temperature and concentrated in vacuo. The residue was purified by preparative HPLC to afford the final product.

$^1$H NMR (600 MHz, CD$_3$OD) δ 9.03 (s, 1H), 8.83 (d, J=6.6 Hz, 2H), 8.66 (d, J=5.4 Hz, 1H), 8.44 (d, J=6.6 Hz, 2H), 8.09 (d, J=5.4 Hz, 1H), 7.67 (dd, J=1.8, 7.8 Hz, 1H), 7.60 (m, 1H), 7.36 (d, J=8.4 Hz, 1H), 7.27 (t, J=7.8 Hz, 1H), 5.24 (s, 2H)

MS (ESI+) m/z 331 (M+H)$^+$

Scheme 7 (Method G)

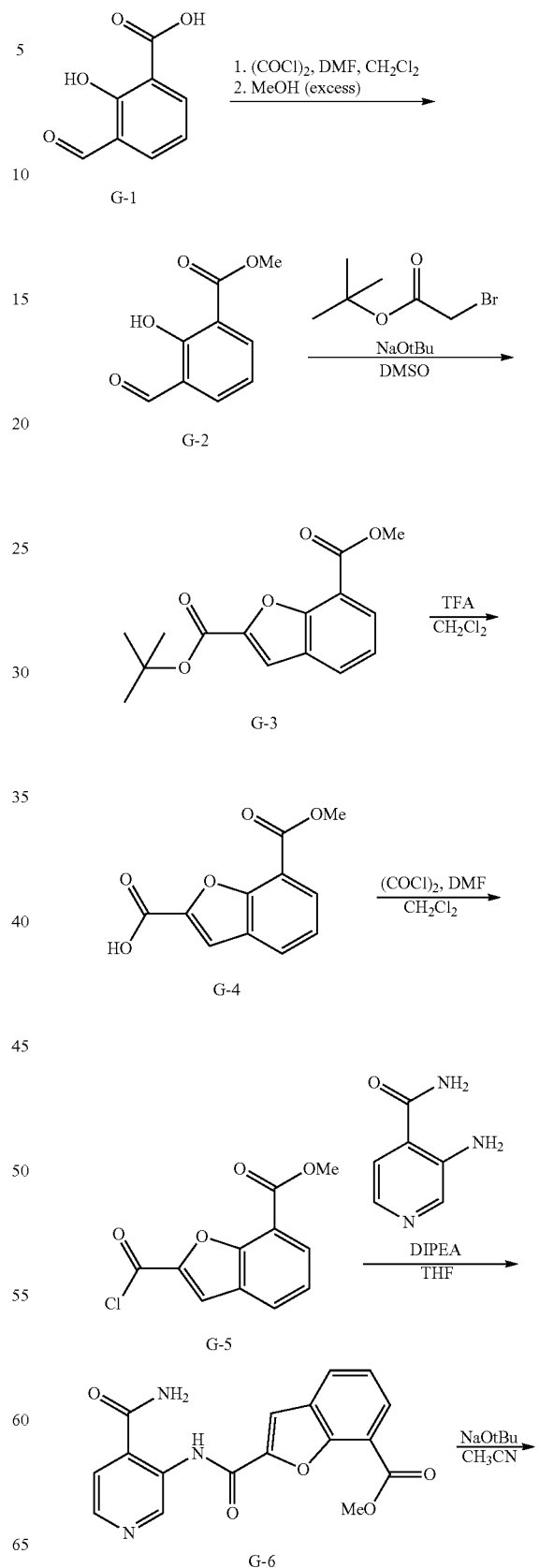

149

-continued

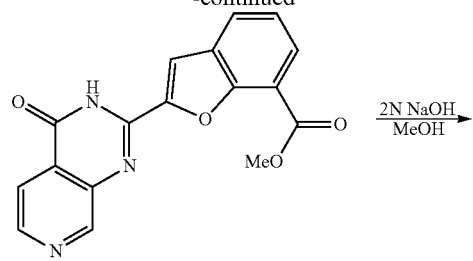

G-7

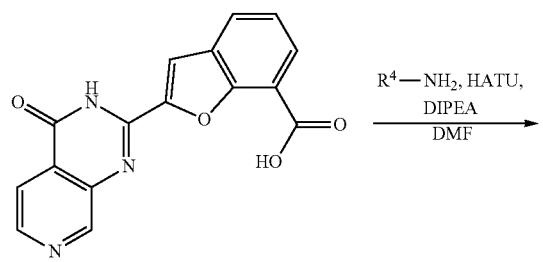

G-8

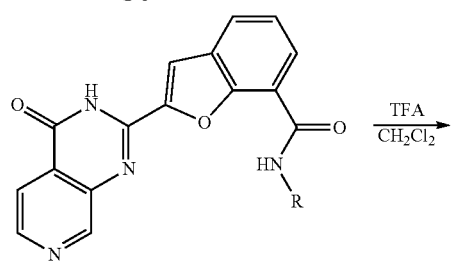

G-9

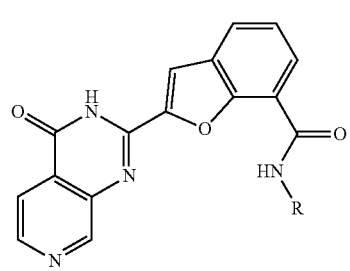

G-10
(Boc deprotected)

The general synthesis of compound G-10 is illustrated in Scheme 7. Intermediate G-2 is synthesized through a 2-step reaction of chlorination and esterification. The reactions of tert-butyl acetate substitution with NaOtBu and cyclization are followed to afford banzofuran intermediate G-3. Subsequent tert-butyl ester hydrolysis with TFA and chlorination with oxalyl chloride lead to intermediate G-5. This is followed by amide coupling reaction with HATU and cyclization with NaOtBu, which lead to pyridopyrimidinone intermediate G-7. The methyl ester group of intermediate G-7 is converted to carboxylic acid intermediate G-8. Subsequent amide coupling of intermediate G-8 with HATU and deprotection with TFA provide compound G-10.

150

Example 71

Step 1

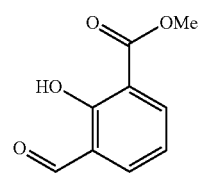 [SMILES: COC(=O)c1cccc(C=O)c1O]

methyl 3-formyl-2-hydroxybenzoate

To a suspension of 3-formyl-2-hydroxybenzoic acid (831 mg, 5 mmol) in dichloromethane (10 mL) were added oxalyl chloride (1.3 mL, 15 mmol) and a few drops of N,N-dimethylformamide. The mixture was allowed to stir for 30 min. Methanol (excess) was added and the mixture was concentrated in vacuo to afford methyl 3-formyl-2-hydroxybenzoate as a yellow solid. The residue was used in the next step without further purification.

Step 2

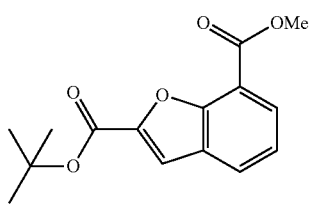 [SMILES: COC(=O)c1cccc2cc(C(=O)OC(C)(C)C)oc12]

2-(tert-butyl) 7-methyl
benzofuran-2,7-dicarboxylate

To a solution of methyl 3-formyl-2-hydroxybenzoate (crude, 5 mmol) and tert-butyl bromoacetate (0.74 mL, 5 mmol) in dimethyl sulfoxide (10 mL) was added sodium tert-butoxide (1.44 g, 15 mmol). The mixture was heated at 100° C. and allowed to stir for 3 days. It was diluted with water and extracted with ethyl acetate twice. The combined organic extract was washed with brine, and dried over magnesium sulfate and concentrated. The residue was purified by combi-flash to afford 2-(tert-butyl) 7-methyl benzofuran-2,7-dicarboxylate (261 mg, 0.945 mmol).

Step 3

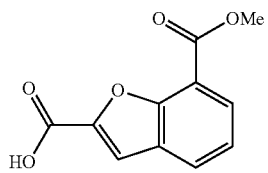 [SMILES: COC(=O)c1cccc2cc(C(=O)O)oc12]

7-(methoxycarbonyl)benzofuran-2-carboxylic acid

The starting material was dissolved in trifluoroacetic acid (and dichloromethane). The mixture was allowed to stir for 1 hour at ambient temperature and concentrated in vacuo. The residue was purified by preparative HPLC to afford 7-(methoxycarbonyl)benzofuran-2-carboxylic acid.

Step 4

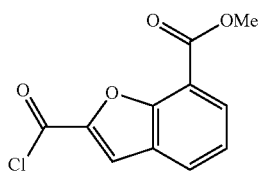 [SMILES: COC(=O)c1cccc2cc(C(=O)Cl)oc12]

methyl 2-(chlorocarbonyl)benzofuran-7-carboxylate

To a solution of 7-(methoxycarbonyl)benzofuran-2-carboxylic acid in dichloromethane were added oxalyl chloride (1.5 eq) and a few drops of N,N-dimethylformamide. The mixture was allowed to stir for 1 hour. It was concentrated in vacuo and used in the next step without further purification Step 5

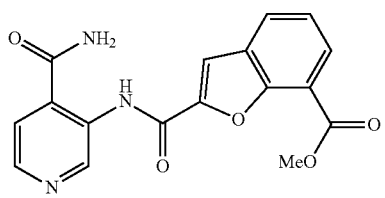 [SMILES: COC(=O)c1cccc2cc(C(=O)Nc3cnccc3C(N)=O)oc12]

methyl 2-((4-carbamoylpyridin-3-yl)carbamoyl)benzofuran-7-carboxylate

To a suspension of 3-amino-2-carboxamide (1.0 eq) and methyl 2-(chlorocarbonyl)benzofuran-7-carboxylate (1.5 eq) in tetrahydrofuran was added N,N-diisopropylethylamine (3.0 eq) dropwise. The mixture was allowed to stir for 1 hour and concentrated in vacuo to afford methyl 2-((4-carbamoylpyridin-3-yl)carbamoyl)benzofuran-7-carboxylate as a crude product. The residue was used in the next step without further purification Step 6

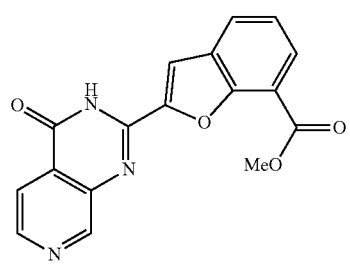 [SMILES: COC(=O)c1cccc2cc(-c3nc4cnccc4c(=O)[nH]3)oc12]

methyl 2-(4-oxo-3,4-dihydropyrido[3,4-d]pyrimidin-2-yl)benzofuran-7-carboxylate To a suspension of methyl 2-((4-carbamoylpyridin-3-yl)carbamoyl)benzofuran-7-carboxylate (1.0 eq) in acetonitrile was added sodium tert-butoxide (3.0 eq). The mixture was heated to reflux and allowed to stir for 4 hour. It was neutralized with 2N aqueous hydrochloric acid and extracted with ethyl acetate. The organic extract was dried over magnesium sulfate and concentrated. The residue was crystallized with isopropyl alcohol. The solid was collected and dried under reduced pressure to afford methyl 2-(4-oxo-3,4-dihydropyrido[3,4-d]pyrimidin-2-yl)benzofuran-7-carboxylate.

Step 7

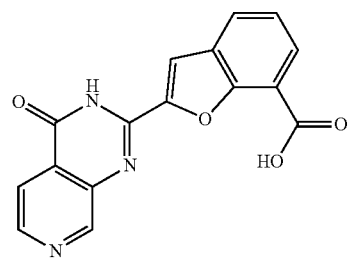

2-(4-oxo-3,4-dihydropyrido[3,4-d]pyrimidin-2-yl)benzofuran-7-carboxylic acid To a solution of methyl 2-(4-oxo-3,4-dihydropyrido[3,4-d]pyrimidin-2-yl)benzofuran-7-carboxylate (7.0 mmol) in methanol was added a 2N aqueous sodium hydroxide solution (10 mL). The mixture was allowed to stir for 1 hour and neutralized with a 2N aqueous hydrochloric acid solution. The precipitate was filtered and washed with water. The solid was collected and dried under reduced pressure to afford 2-(4-oxo-3,4-dihydropyrido[3,4-d]pyrimidin-2-yl)benzofuran-7-carboxylic acid (6.64 mmol).

Step 8

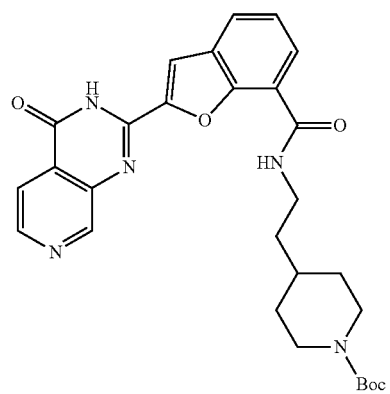 [SMILES: CC(C)(C)OC(=O)N1CCC(CCNC(=O)c2cccc3cc(-c4nc5cnccc5c(=O)[nH]4)oc23)CC1]

tert-butyl 4-(2-(2-(4-oxo-3,4-dihydropyrido[3,4-d]pyrimidin-2-yl)benzofuran-7-carboxamido)ethyl)piperidine-1-carboxylate To a solution of 2-(4-oxo-3,4-dihydropyrido[3,4-d]pyrimidin-2-yl)benzofuran-7-carboxylic acid (1.0 eq) and 4-(2-Amino-ethyl)-piperidine-1-carboxylic acid tert-butyl ester (1.1 eq) in N,N-dimethylformamide were added N,N-diisopropylethylamine (2.0 eq) and HATU (1.2 eq). The mixture was allowed to stir for 30 min. It was diluted with brine and extracted with ethyl acetate twice. The combined organic extract was washed with brine twice and dried over magnesium sulfate (or extracted with UCT SPE CUBCX cartridge). It was concentrated and purified by combi-flash or preparative HPLC.

Step 9

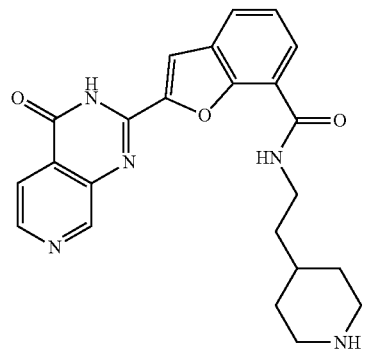 [SMILES: O=C(NCCC1CCNCC1)c1cccc2cc(-c3nc4cnccc4c(=O)[nH]3)oc12]

2-(4-oxo-3,4-dihydropyrido[3,4-d]pyrimidin-2-yl)-N-(2-(piperidin-4-yl)ethyl)benzofuran-7-carboxamide Tert-butyl 4-(2-(2-(4-oxo-3,4-dihydropyrido[3,4-d]pyrimidin-2-yl)benzofuran-7-carboxamido)ethyl)piperidine-1-carboxylate was dissolved in trifluoroacetic acid (1 ml) and dichloromethane (4 ml). The mixture was allowed to stir for 1 hour at ambient temperature and concentrated in vacuo. The residue was purified by preparative HPLC to afford 2-(4-oxo-3,4-dihydropyrido[3,4-d]pyrimidin-2-yl)-N-(2-(piperidin-4-yl)ethyl)benzofuran-7-carboxamide.

$^1$H NMR (600 MHz, CD$_3$OD) δ 9.14 (s, 1H), 8.70 (d, J=4.8 Hz, 1H), 8.55 (m, 1H), 8.11 (s, 1H), 8.01 (m, 1H), 7.93 (d, J=6.6 Hz, 1H), 7.48 (t, J=7.8 Hz, 1H), 3.48 (m, 2H), 3.24 (m, 2H), 2.84 (m, 2H), 1.94 (m, 2H), 1.70 (m, 1H), 1.60 (m, 2H), 1.31 (m, 2H)

MS (ESI+) m/z 418 (M+H)$^+$

Scheme 8 (Method H)

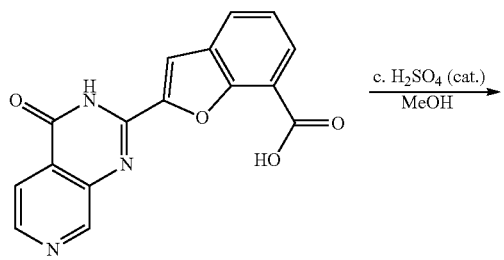

G-8

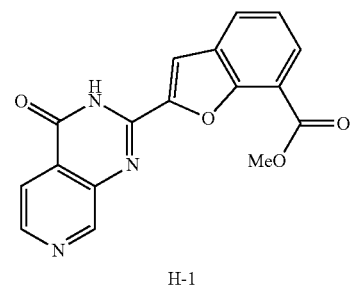

H-1

The general synthesis of compound H-1 is illustrated in Scheme 8. The above esterification reaction with MeOH and c.H$_2$SO$_4$ leads to methyl ester compound H-1.

Example 72

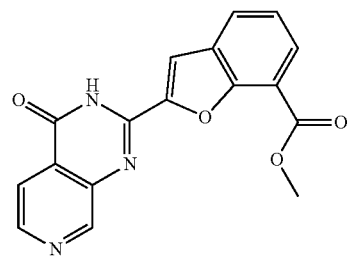

methyl 2-(4-oxo-3,4-dihydropyrido[3,4-d]pyrimidin-2-yl)benzofuran-7-carboxylate

To a suspension of 2-(4-oxo-3,4-dihydropyrido[3,4-d]pyrimidin-2-yl)benzofuran-7-carboxylic acid (20 mg) in methanol (1 mL) was added a few drops of concentrated sulfuric acid. The mixture was heated at reflux and allowed to stir overnight. It was quenched with a saturated aqueous sodium bicarbonate solution and extracted with ethyl acetate. The organic extract was dried over magnesium sulfate and concentrated. The residue was purified by preparative HPLC to afford 2-(4-oxo-3,4-dihydropyrido[3,4-d]pyrimidin-2-yl)benzofuran-7-carboxylate.

$^1$H NMR (600 MHz, DMSO-d6) δ 9.16 (s, 1H), 8.70 (d, J=5.4 Hz, 1H), 8.20 (s, 1H), 8.14 (d, J=8.4 Hz, 1H), 8.03 (d, J=7.8 Hz, 1H), 8.00 (d, J=5.4 Hz, 1H), 7.49 (t, J=7.8 Hz, 1H), 3.98 (s, 3H)

MS (ESI+) m/z 322 (M+H)$^+$

Scheme 9. (Method I)

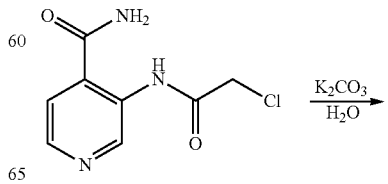

A-2

-continued

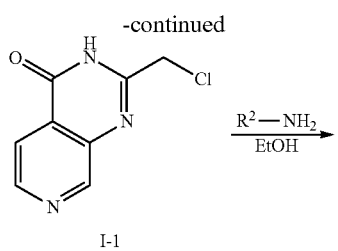

I-1

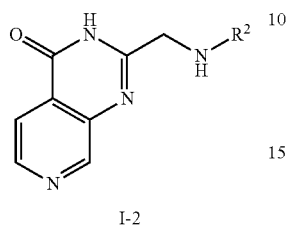

I-2

The general synthesis of compound I-2 is illustrated in Scheme 9. 3-(2-chloroacetamido)isonicotinamide is cyclized with K$_2$CO$_3$ to yield intermediate I-1. This is followed by substitution with amine, which leads to compound I-2.

Example 73

Step 1

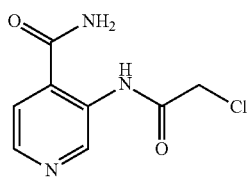 [SMILES: NC(=O)c1ccncc1NC(=O)CCl]

3-(2-chloroacetamido)isonicotinamide

To a solution of 3-aminoisonicotinamide in THF was added Chloroacetyl chloride at room temperature. The mixture was allowed to stir for 2 days at room temperature and concentrated in vacuo. The crude was crystallized with EtOAc and filtered to afford the 3-(2-chloroacetamido) isonicotinamide.
MS (ESI+) m/z 214 (M+H)$^+$ Step 2

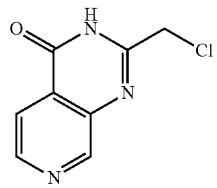 [SMILES: O=c1[nH]c(CCl)nc2cnccc12]

2-(chloromethyl)pyrido[3,4-d]pyrimidin-4(3H)-one

To a solution of 3-(2-chloroacetamido)isonicotinamide (1.0 mmol) in H$_2$O was added K$_2$CO$_3$ (1.0 mmol) at room temperature. The mixture was heated to 80° C. for 1 h in a microwave. After being cooled to room temperature, the mixture was concentrated in vacuo to afford 2-(chloromethyl)pyrido[3,4-d]pyrimidin-4(3H)-one (0.5 mmol).

Step 3

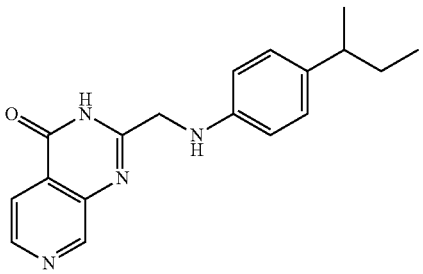 [SMILES: CCC(C)c1ccc(NCc2nc3cnccc3c(=O)[nH]2)cc1]

2-(((4-(sec-butyl)phenyl)amino)methyl)pyrido[3,4-d]pyrimidin-4(3H)-one

To a solution of 2-(chloromethyl)pyrido[3,4-d]pyrimidin-4(3H)-one (0.5 mmol) in EtOH was added 4-sec-butylaniline (0.5 mmol) at room temperature. The mixture was heated at reflux overnight. After being cooled to room temperature, the mixture was extracted with EtOAc. The combined organic layer was dried over MgSO$_4$, filtered and concentrated in vacuo. The concentrated residue was purified by preparative HPLC to afford 2-(((4-(sec-butyl)phenyl) amino)methyl)pyrido[3,4-d]pyrimidin-4(3H)-one (0.3 mmol).
MS (ESI+) m/z 309 (M+H)$^+$ Example 74

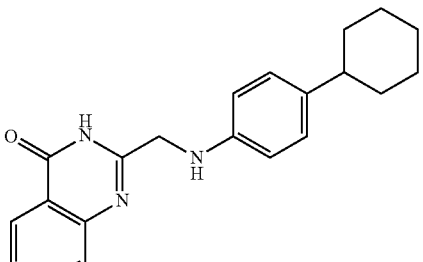

2-(((4-cyclohexylphenyl)amino)methyl)pyrido[3,4-d]pyrimidin-4(3H)-one

Using 4-cyclohexylaniline, the title compound was obtained as described in Scheme 9 (Method I).
MS (ESI+) m/z 335 (M+H)$^+$

Example 75

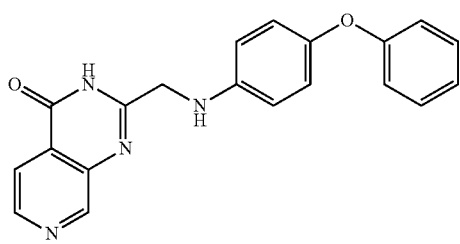 [SMILES: O=c1[nH]c(CNc2ccc(Oc3ccccc3)cc2)nc2cnccc12]

2-(((4-phenoxyphenyl)amino)methyl)pyrido[3,4-d]pyrimidin-4(3H)-one

Using 4-phenoxyaniline, the title compound was obtained as described in Scheme 9 (Method I).
$^1$H NMR (400 MHz, DMSO-d$_6$) δ 9.01 (s, 1H), 8.62 (d, J=5.48 Hz, 1H), 7.91 (d, J=5.09 Hz, 1H), 7.25 (t, J=8.02 Hz, 2H), 7.06 (d, J=8.61 Hz, 2H), 6.98 (m, 2H), 6.81 (dd, J=8.41, 5.67 Hz, 2H), 6.67 (d, J=8.61 Hz, 1H), 4.24 (s, 2H)
MS (ESI+) m/z 345 (M+H)$^+$

Example 76

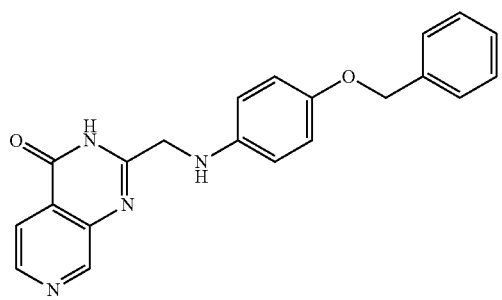 [SMILES: O=c1[nH]c(CNc2ccc(OCc3ccccc3)cc2)nc2cnccc12]

2-(((4-(benzyloxy)phenyl)amino)methyl)pyrido[3,4-d]pyrimidin-4(3H)-one

Using 4-benzyloxylaniline, the title compound was obtained as described in Scheme 9 (Method I).
MS (ESI+) m/z 359 (M+H)$^+$

Example 77

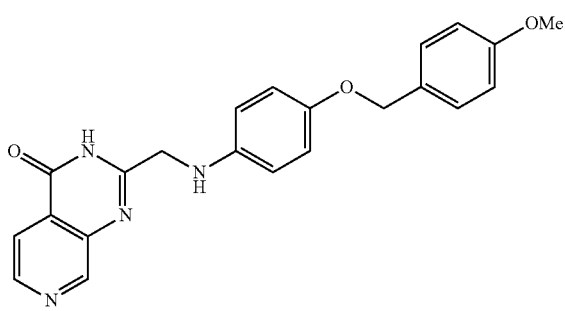 [SMILES: COc1ccc(COc2ccc(NCc3nc4cnccc4c(=O)[nH]3)cc2)cc1]

2-(((4-((4-methoxybenzyl)oxy)phenyl)amino)methyl)pyrido[3,4-d]pyrimidin-4(3H)-one Using 4-(4-methoxybenzyloxy)-phenylamine, the title compound was obtained as described in Scheme 9 (Method I).
MS (ESI+) m/z 389 (M+H)$^+$

Example 78

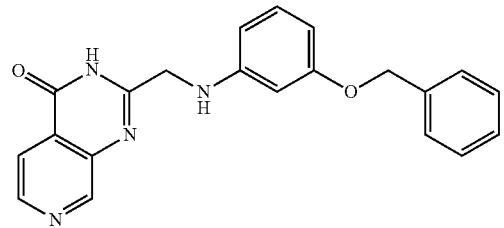 [SMILES: O=c1[nH]c(CNc2cccc(OCc3ccccc3)c2)nc2cnccc12]

2-(((3-(benzyloxy)phenyl)amino)methyl)pyrido[3,4-d]pyrimidin-4(3H)-one

Using 3-benzyloxyaniline, the title compound was obtained as described in Scheme 9 (Method I).
MS (ESI+) m/z 359 (M+H)$^+$

Example 79

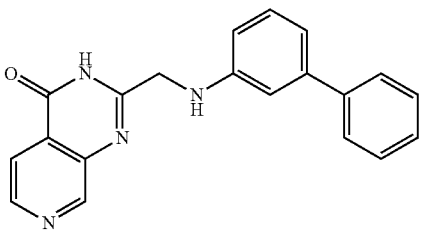 [SMILES: O=c1[nH]c(CNc2cccc(-c3ccccc3)c2)nc2cnccc12]

2-(([1,1'-biphenyl]-3-ylamino)methyl)pyrido[3,4-d]pyrimidin-4(3H)-one

Using 3-aminobiphenyl, the title compound was obtained as described in Scheme 9 (Method I).
MS (ESI+) m/z 329 (M+H)$^+$

Example 80

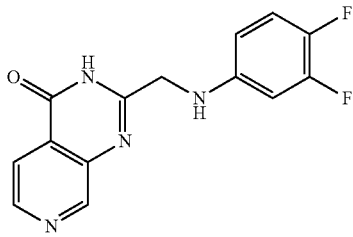 [SMILES: O=c1[nH]c(CNc2ccc(F)c(F)c2)nc2cnccc12]

2-(((3,4-difluorophenyl)amino)methyl)pyrido[3,4-d]pyrimidin-4(3H)-one

Using 3,4-difluoroaniline, the title compound was obtained as described in Scheme 9 (Method I).

$^1$H NMR (400 MHz, DMSO-$d_6$) δ 12.59 (br s, 1H), 8.98 (s, 1H), 8.61 (d, J=5.09 Hz, 1H), 7.90 (d, J=5.09 Hz, 1H), 7.09 (m, 1H), 6.62 (m, 1H), 6.37 (m, 2H), 4.23 (d, J=6.26 Hz, 2H)

MS (ESI+) m/z 289 (M+H)$^+$

Example 81

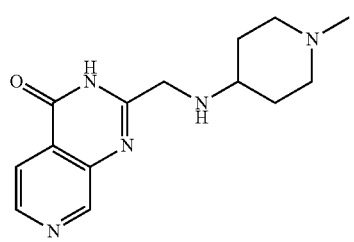 [SMILES: CN1CCC(NCc2nc3cnccc3c(=O)[nH]2)CC1]

2-(((1-methylpiperidin-4-yl)amino)methyl)pyrido[3,4-d]pyrimidin-4(3H)-one

Using 1-methyl-4-piperidineamine, the title compound was obtained as described in Scheme 9 (Method I).

MS (ESI+) m/z 274 (M+H)$^+$

Example 82

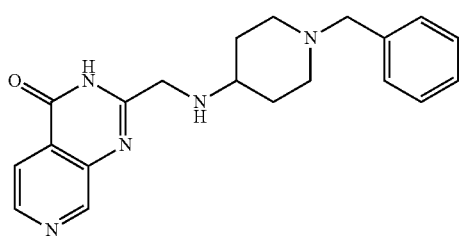 [SMILES: O=c1[nH]c(CNC2CCN(Cc3ccccc3)CC2)nc2cnccc12]

2-(((1-benzylpiperidin-4-yl)amino)methyl)pyrido[3,4-d]pyrimidin-4(3H)-one

Using 4-amino-1-benzylpiperidine, the title compound was obtained as described in Scheme 9 (Method I).

$^1$H NMR (400 MHz, DMSO-$d_6$) δ 9.00 (s, 1H), 8.6 (d, 1H), 7.8 (d, 1H), 7.24 (m, 5H), 3.42 (s, 2H), 2.73 (m, 2H), 2.63 (m, 1H), 2.46 (s, 2H), 1.93 (m, 2H), 1.66 (m, 2H), 1.32 (m, 2H)

MS (ESI+) m/z 350 (M+H)$^+$

Scheme 10 (Method J)

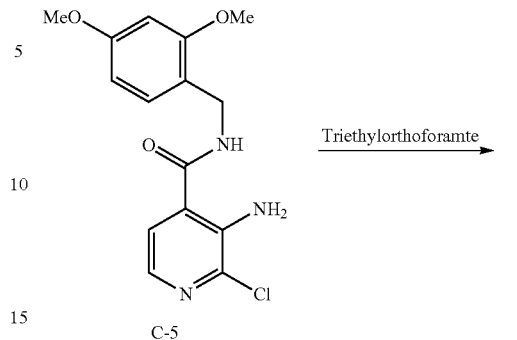

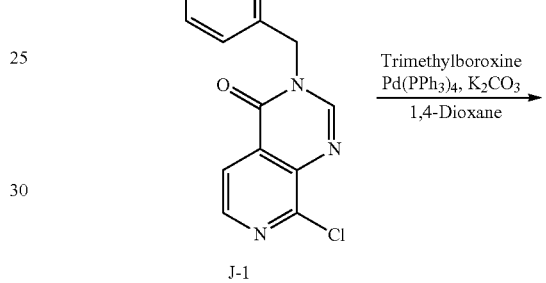

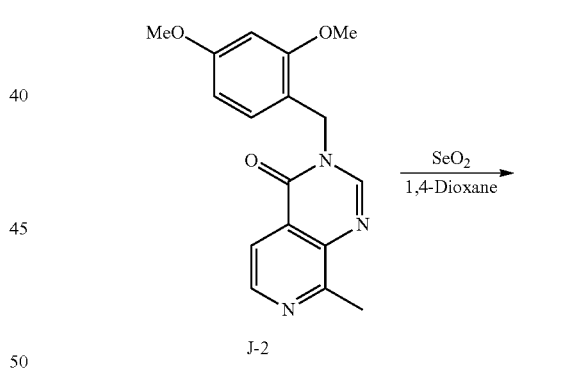

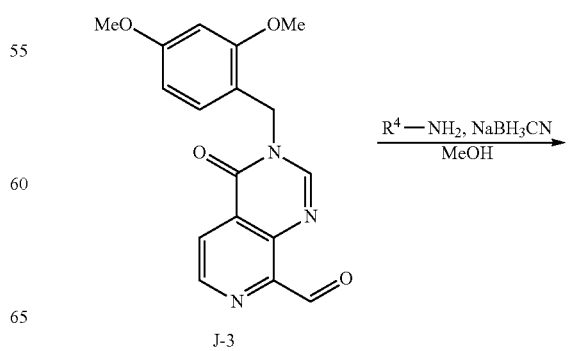

161

-continued

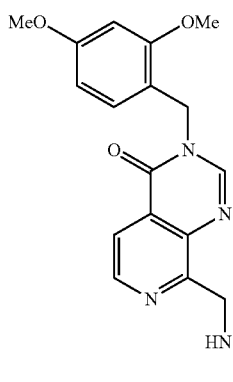

J-4

→ TFA →

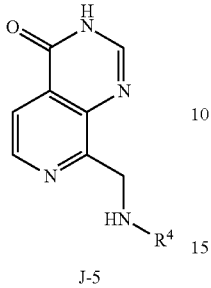

J-5

The general synthesis of compound J-5 is illustrated in Scheme 10. 3-amino-2-chloro-N-(2,4-dimethoxybenzyl) isonicotinamide is reacted with triethylorthoformate to afford the pyridopyrimidinone intermediate J-1. Suzuki cross-coupling using trimethylboroxine and oxidation using SeO₂ result in aldehyde intermediate)-3. Subsequent reductive amination using NaBH₃CN and deprotection with TFA lead to compound J-5.

Example 83

Step 1

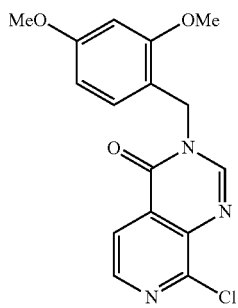 [SMILES: COc1ccc(Cn2cnc3c(Cl)nccc3c2=O)c(OC)c1]

8-chloro-3-(2,4-dimethoxybenzyl)pyrido[3,4-d]pyrimidin-4(3H)-one

The intermediate 3-5 (322 mg, 1.0 mmol) was dissolved in triethylorthoformate (4 mL). The mixture was heated at 150° C. and allowed to stir for 4 days. The solvent was concentrated in vacuo to afford the intermediate 1 (quant.) as a white solid.

¹H NMR (400 MHz, DMSO-d₆) δ 8.61 (s, 1H), 8.41 (d, J=5.2 Hz, 1H), 7.92 (d, J=5.2 Hz, 1H), 7.19 (d, J=8.8 Hz, 1H), 6.53 (d, J=2.4 Hz, 1H), 6.44 (dd, J=2.4, 8.8 Hz, 1H), 5.00 (s, 2H), 3.77 (s, 3H), 3.70 (s, 3H)

MS (ESI+) m/z 332 (M+H)⁺

162

Step 2

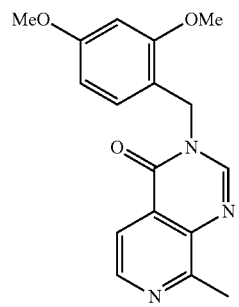 [SMILES: COc1ccc(Cn2cnc3c(C)nccc3c2=O)c(OC)c1]

3-(2,4-dimethoxybenzyl)-8-methylpyrido[3,4-d]pyrimidin-4(3H)-one

To a solution of intermediate 1 (396 mg, 1.02 mmol) in dioxane (5 ml) was added K₂CO₃ (282 mg, 2.04 mmol), trimethylboroxine (213 ul, 1.53 mmol) and Pd(PPh₃)₄ (59 mg, 0.05 mmol) under nitrogen atmosphere. The mixture was allowed to stir for 1 h at 100° C. After being cooled to room temperature, the mixture was extracted with EtOAc and washed with brine. The separated organic layer was dried over MgSO₄, filtered and concentrated in vacuo. The concentrated residue was purified by flash column chromatography to afford the intermediate 2 (301 mg, 0.815 mg) as a pale yellow oil.

Step 3

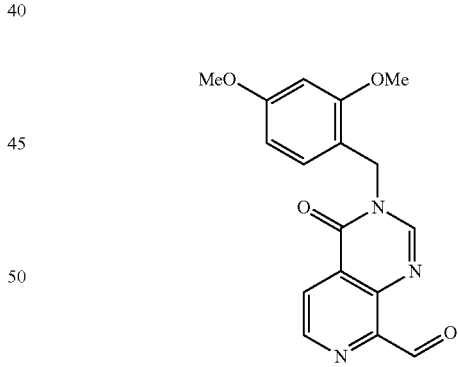

3-(2,4-dimethoxybenzyl)-4-oxo-3,4-dihydropyrido[3,4-d]pyrimidine-8-carbaldehyde

To a solution of intermediate 2 (312 mg, 1.0 mmol) in dioxane (5 mL) was added selenium dioxide (222 mg, 2.0 mmol). The reaction mixture was heated to 100° C. and allowed to stir for 3 h. After being cooled to room temperature, the mixture was filtered through celite pad. The filtrate was concentrated in vacuo.

MS (ESI+) m/z 384 (M+H)⁺

Step 4

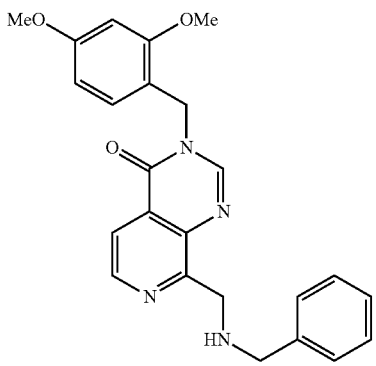 [SMILES: COc1ccc(Cn2cnc3c(CNCc4ccccc4)nccc3c2=O)c(OC)c1]

8-((benzylamino)methyl)-3-(2,4-dimethoxybenzyl)
pyrido[3,4-d]pyrimidin-4(3H)-one The intermediate 3 and (1-benzylpiperidin-4-yl)methanamine were mixed in MeOH at room temperature. The mixture was heated at reflux for 1 h. After being cooled to room temperature, the mixture was treated with NaBH$_3$CN, allowed to stir for 1 h at room temperature, quenched with 1 M NaOH and extracted with EtOAc. The separated organic layer was dried over MgSO$_4$, filtered and concentrated in vacuo. The concentrated residue was purified by preparative HPLC to afford the 8-((benzylamino)methyl)-3-(2,4-dimethoxybenzyl)pyrido[3,4-d]pyrimidin-4(3H)-one.

MS (ESI+) m/z 514 (M+H)$^+$

Step 6

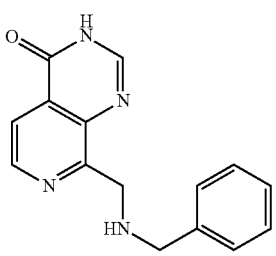 [SMILES: O=c1[nH]cnc2c(CNCc3ccccc3)nccc12]

8-((benzylamino)methyl)pyrido[3,4-d]pyrimidin-4(3H)-one

The 8-((benzylamino)methyl)-3-(2,4-dimethoxybenzyl)pyrido[3,4-d]pyrimidin-4(3H)-one was dissolved in TFA (2 ml). The mixture was allowed to stir for 1 h at 50° C. After being cooled to room temperature, the mixture was concentrated in vacuo. The concentrated residue was purified by preparative HPLC to afford the title compound.

$^1$H NMR (400 MHz, DMSO-d$_6$) δ 12.87 (br s, 1H), 8.66 (d, J=5.09 Hz, 1H), 8.28 (s, 1H), 7.97 (d, J=5.09 Hz, 1H), 7.53 (m, 2H), 7.41 (m, 3H), 4.68 (s, 2H), 4.33 (s, 2H)

MS (ESI+) m/z 267 (M+H)$^+$

Example 84

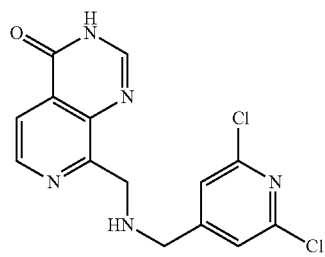 [SMILES: O=c1[nH]cnc2c(CNCc3cc(Cl)nc(Cl)c3)nccc12]

8-(((((2,6-dichloropyridin-4-yl)methyl)amino)methyl)
pyrido[3,4-d]pyrimidin-4(3H)-one Using 2,6-Dichloropyridine-4-methylamine, the title compound was obtained as described in Scheme 10 (Method J).

MS (ESI+) m/z 337 (M+H)$^+$

Example 85

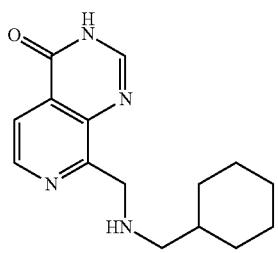 [SMILES: O=c1[nH]cnc2c(CNCC3CCCCC3)nccc12]

8-(((cyclohexylmethyl)amino)methyl)pyrido[3,4-d]
pyrimidin-4(3H)-one

Using Cyclohexanemethylamine, the title compound was obtained as described in Scheme 10 (Method J).

$^1$H NMR (400 MHz, DMSO-d$_6$) δ 8.64 (d, J=5.09 Hz, 1H), 8.29 (s, 1H), 7.97 (d, J=5.09 Hz, 1H), 4.63 (s, 2H), 2.51 (d, 2H), 1.77-1.60 (m, 5H), 1.26-0.76 (m, 6H)

MS (ESI+) m/z 273 (M+H)$^+$

Example 86

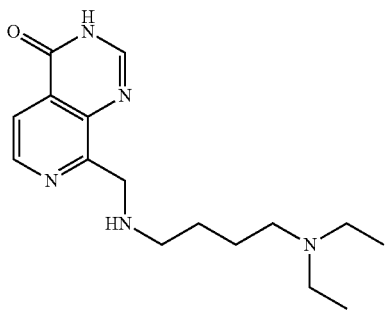 [SMILES: CCN(CC)CCCCNCc1nccc2c(=O)[nH]cnc12]

8-(((4-(diethylamino)butyl)amino)methyl)pyrido[3,4-d]pyrimidin-4(3H)-one

Using N,N-diethyl-1,4-butanediamine, the title compound was obtained as described in Scheme 10 (Method J). MS (ESI+) m/z 304 (M+H)+

Example 87

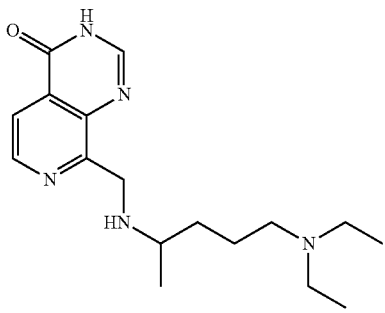 [SMILES: CCN(CC)CCCC(C)NCc1nccc2c(=O)[nH]cnc12]

8-(((5-(diethylamino)pentan-2-yl)amino)methyl)pyrido[3,4-d]pyrimidin-4(3H)-one

Using 2-amino-5-diethylaminopentane, the title compound was obtained as described in Scheme 10 (Method J). MS (ESI+) m/z 318 (M+H)+

Example 88

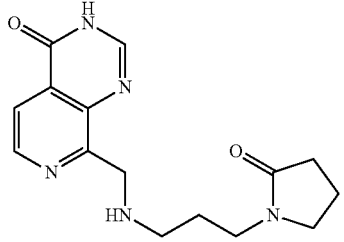 [SMILES: O=C1CCCN1CCCNCc1nccc2c(=O)[nH]cnc12]

8-(((3-(2-oxopyrrolidin-1-yl)propyl)amino)methyl)pyrido[3,4-d]pyrimidin-4(3H)-one Using N-(3-aminopropyl)-2-pyrrolidinone, the title compound was obtained as described in Scheme 10 (Method J). MS (ESI+) m/z 302 (M+H)+

Example 89

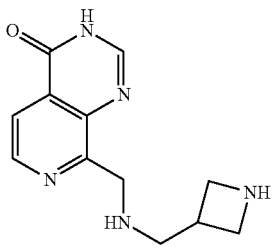 [SMILES: O=c1[nH]cnc2c(CNCC3CNC3)nccc12]

8-(((azetidin-3-ylmethyl)amino)methyl)pyrido[3,4-d]pyrimidin-4(3H)-one

Using 1-Boc-3-(aminomethyl)azetidine, the title compound was obtained as described in Scheme 10 (Method J). MS (ESI+) m/z 246 (M+H)+

Example 90

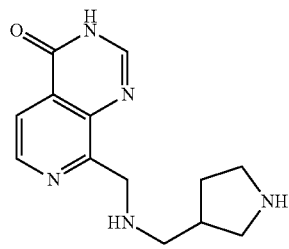 [SMILES: O=c1[nH]cnc2c(CNCC3CCNC3)nccc12]

8-(((pyrrolidin-3-ylmethyl)amino)methyl)pyrido[3,4-d]pyrimidin-4(3H)-one

Using 1-Boc-3-(aminomethyl)pyrrolidine, the title compound was obtained as described in Scheme 10 (Method J). MS (ESI+) m/z 260 (M+H)+

Example 91

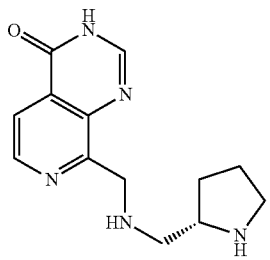 [SMILES: O=c1[nH]cnc2c(CNC[C@@H]3CCCN3)nccc12]

(S)-8-(((pyrrolidin-2-ylmethyl)amino)methyl)pyrido[3,4-d]pyrimidin-4(3H)-one

Using (S)-3-(aminomethyl)-1-Boc-pyrrolidine, the title compound was obtained as described in Scheme 10 (Method J).
MS (ESI+) m/z 260 (M+H)+

Example 92

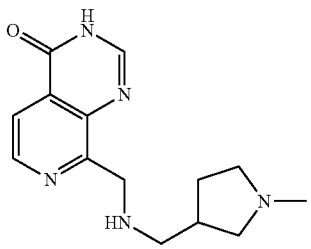 [SMILES: CN1CCC(CNCc2nccc3c(=O)[nH]cnc23)C1]

8-((((1-methylpyrrolidin-3-yl)methyl)amino)methyl)pyrido[3,4-d]pyrimidin-4(3H)-one Using 1-(1-methylpyrrolidine-3-yl)methanamine, the title compound was obtained as described in Scheme 10 (Method J).

MS (ESI+) m/z 274 (M+H)+

Example 93

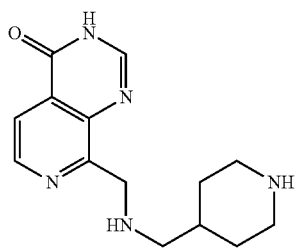 [SMILES: O=c1[nH]cnc2c(CNCC3CCNCC3)nccc12]

8-(((piperidin-4-ylmethyl)amino)methyl)pyrido[3,4-d]pyrimidin-4(3H)-one

Using 1-Boc-4-(aminomethyl)piperidine, the title compound was obtained as described in Scheme 10 (Method J).

$^1$H NMR (400 MHz, CD$_3$OD) δ 8.65 (d, 1H), 8.19 (s, 1H), 8.04 (d, 1H), 4.85 (s, 2H), 3.45 (d, 2H), 3.28 (s, 2H), 3.04 (t, 2H), 2.23 (bs, 1H), 2.10 (d, 2H), 1.56 (q, 2H)

MS (ESI+) m/z 274 (M+H)+

Example 94

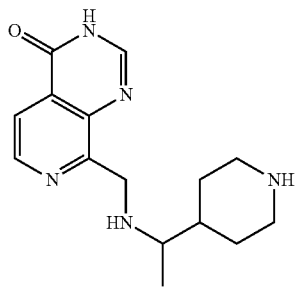 [SMILES: CC(NCc1nccc2c(=O)[nH]cnc12)C1CCNCC1]

8-(((1-(piperidin-4-yl)ethyl)amino)methyl)pyrido[3,4-d]pyrimidin-4(3H)-one

Using tert-butyl 4-(1-aminomethyl)piperidine-1-carboxylate, the title compound was obtained as described in Scheme 10 (Method J).

MS (ESI+) m/z 288 (M+H)+

Example 95

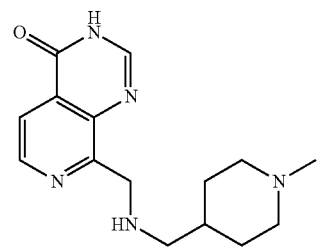 [SMILES: CN1CCC(CNCc2nccc3c(=O)[nH]cnc23)CC1]

8-((((1-methylpiperidin-4-yl)methyl)amino)methyl)pyrido[3,4-d]pyrimidin-4(3H)-one Using (1-methyl-4-pipedidinyl)methanamine, the title compound was obtained as described in Scheme 10 (Method J).

$^1$H NMR (400 MHz, DMSO-d$_6$) δ 8.65 (d, J=5.48 Hz, 1H), 8.31 (s, 1H), 7.99 (d, J=5.09 Hz, 1H), 4.74 (s, 2H), 3.06 (m, 2H), 2.96 (m, 1H), 2.73 (m, 2H), 2.5 (s, 3H), 2.49 (s, 2H), 1.99 (m, 2H), 1.39 (m, 2H)

MS (ESI+) m/z 288 (M+H)+

Example 96

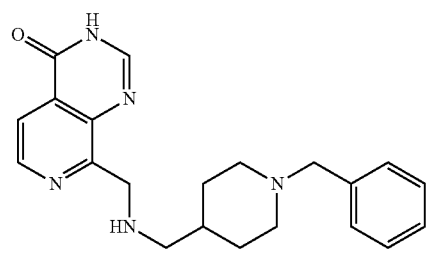 [SMILES: O=c1[nH]cnc2c(CNCC3CCN(Cc4ccccc4)CC3)nccc12]

8-((((1-benzylpiperidin-4-yl)methyl)amino)methyl)pyrido[3,4-d]pyrimidin-4(3H)-one Using 1-(1-benzylpiperidin-4-yl)methanamine, the title compound was obtained as described in Scheme 10 (Method J).

MS (ESI+) m/z 364 (M+H)+

Example 97

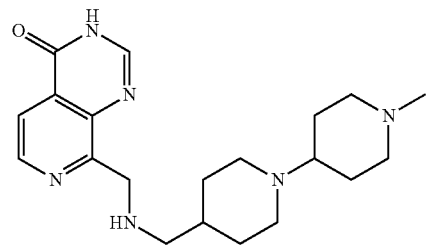 [SMILES: CN1CCC(N2CCC(CNCc3nccc4c(=O)[nH]cnc34)CC2)CC1]

8-((((1'-methyl-[1,4'-bipiperidin]-4-yl)methyl)amino)
methyl)pyrido[3,4-d]pyrimidin-4(3H)-one Using 1-(1'-methyl-1,4'-bipiperidin-4-yl)methanamine, the title compound was obtained as described in Scheme 10 (Method J).
MS (ESI+) m/z 371 (M+H)+

Example 98

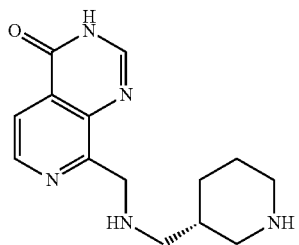 [SMILES: O=c1[nH]cnc2c(CNC[C@@H]3CCCNC3)nccc12]

(R)-8-(((piperidin-3-ylmethyl)amino)methyl)pyrido
[3,4-d]pyrimidin-4(3H)-one

Using (S)-1-Boc-3-(aminomethyl)piperidine, the title compound was obtained as described in Scheme 10 (Method J).
MS (ESI+) m/z 274 (M+H)+

Example 99

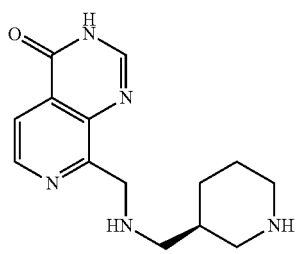 [SMILES: O=c1[nH]cnc2c(CNC[C@H]3CCCNC3)nccc12]

(S)-8-(((piperidin-3-ylmethyl)amino)methyl)pyrido
[3,4-d]pyrimidin-4(3H)-one

Using (R)-1-Boc-3-(aminomethyl)piperidine, the title compound was obtained as described in Scheme 10 (Method J).
MS (ESI+) m/z 274 (M+H)+

Example 100

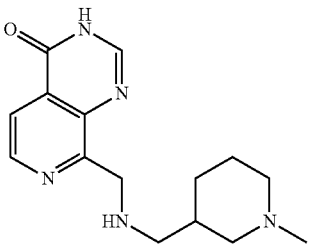 [SMILES: CN1CCCC(CNCc2nccc3c(=O)[nH]cnc23)C1]

8-((((1-methylpiperidin-3-yl)methyl)amino)methyl)
pyrido[3,4-d]pyrimidin-4(3H)-one Using 3-(aminomethyl)-1-methylpiperidine, the title compound was obtained as described in Scheme 10 (Method J).
MS (ESI+) m/z 288 (M+H)+

Example 101

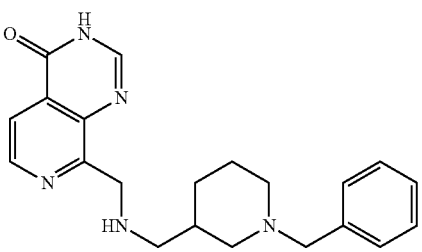 [SMILES: O=c1[nH]cnc2c(CNCC3CCCN(Cc4ccccc4)C3)nccc12]

8-((((1-benzylpiperidin-3-34)methyl)amino)methyl)
pyrido[3,4-d]pyrimidin-4(3H)-one Using (1-benzylpiperidin-3-yl)methanamine, the title compound was obtained as described in Scheme 10 (Method J).
MS (ESI+) m/z 364 (M+H)+

Example 102

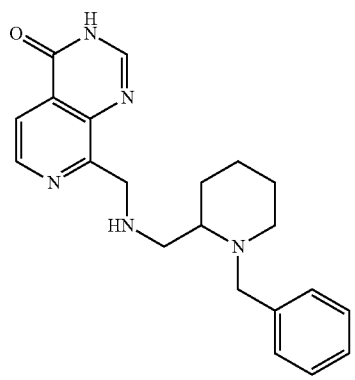 [SMILES: O=c1[nH]cnc2c(CNCC3CCCCN3Cc3ccccc3)nccc12]

8-((((1-benzylpiperidin-2-34)methyl)amino)methyl)
pyrido[3,4-d]pyrimidin-4(3H)-one Using 2-aminomethyl-1-benzylpiperidine, the title compound was obtained as described in Scheme 10 (Method J).
MS (ESI+) m/z 364 (M+H)+

Example 103

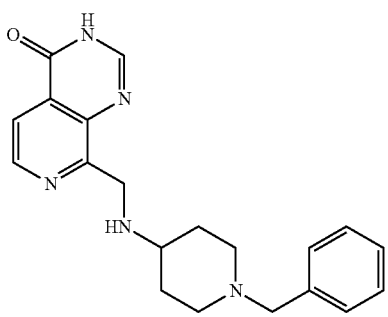 [SMILES: O=c1[nH]cnc2c(CNC3CCN(Cc4ccccc4)CC3)nccc12]

8-(((1-benzylpiperidin-4-yl)amino)methyl)pyrido[3,4-d]pyrimidin-4(3H)-one

Using 4-amino-1-benzylpiperidine, the title compound was obtained as described in Scheme 10 (Method J).
$^1$H NMR (400 MHz, DMSO-d$_6$) δ 9.72 (br s, 1H), 8.63 (d, J=5.09 Hz, 1H), 8.35 (br s, 1H), 8.30 (s, 1H), 7.97 (d, J=5.09 Hz, 1H), 7.42 (m, 5H), 4.76 (s, 2H), 4.25 (s, 2H), 3.36 (m, 2H), 3.05 (m, 2H), 2.33 (m, 2H), 2.09 (m, 2H), 1.95 (m, 1H)
MS (ESI+) m/z 350 (M+H)$^+$

Example 104

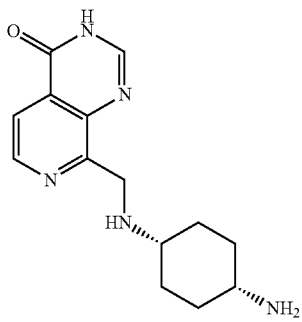 [SMILES: N[C@H]1CC[C@@H](NCc2nccc3c(=O)[nH]cnc23)CC1]

8-((((1s,4s)-4-aminocyclohexyl)amino)methyl)pyrido[3,4-d]pyrimidin-4(3H)-one

Using 1-N-Boc-cis-1,4-cyclohexyldiamine, the title compound was obtained as described in Scheme 10 (Method J).
MS (ESI+) m/z 274 (M+H)$^+$

Scheme 11 (Method K)

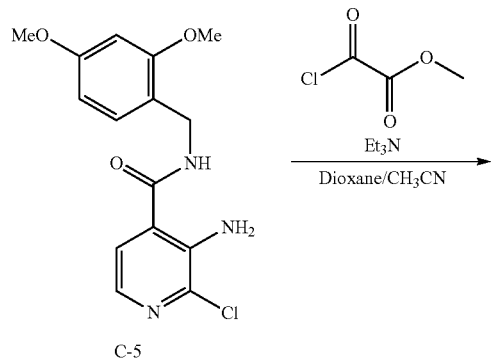

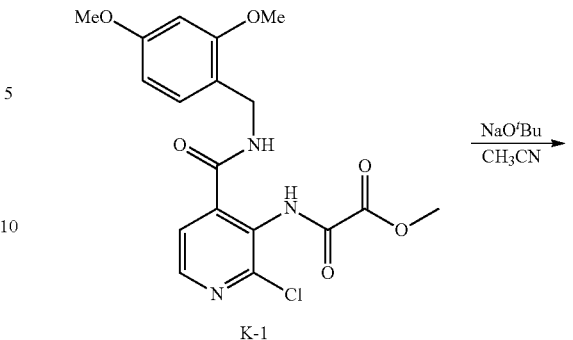

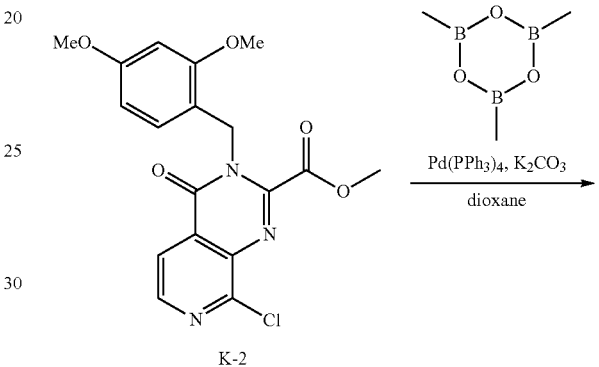

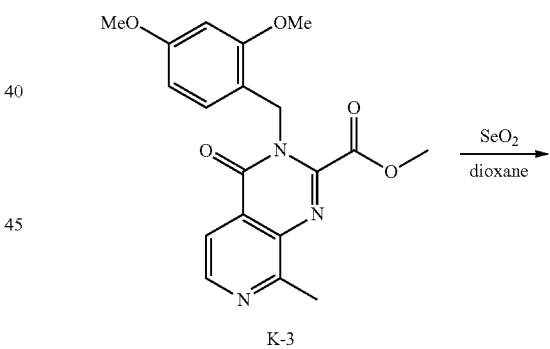

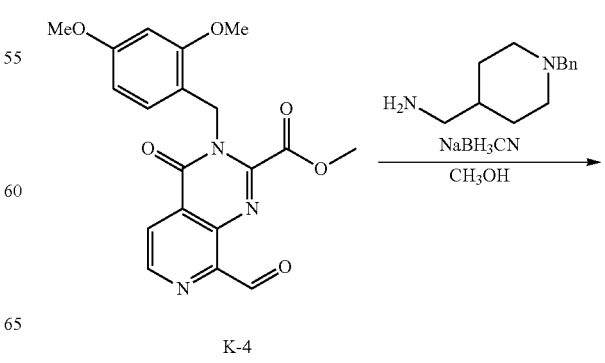

-continued

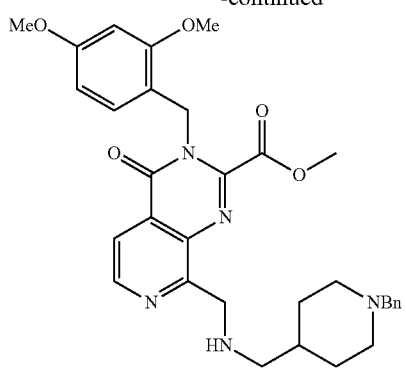
K-5

(Boc)₂O, Et₃N
—————→
CH₂Cl₂

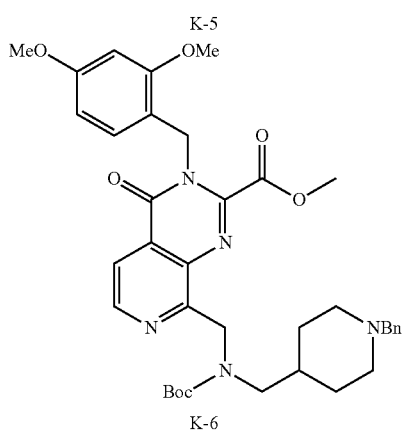
K-6

NaBH₄
—————→
CH₃OH

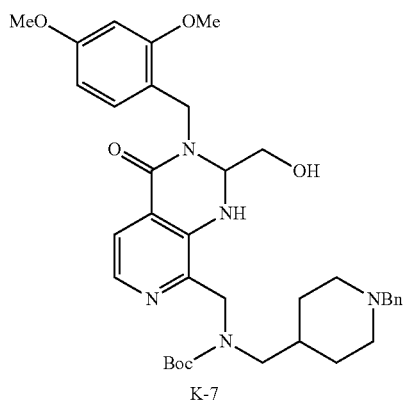
K-7

DDQ
—————→
CHCl₃

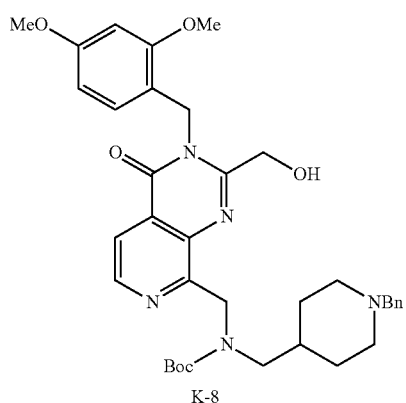
K-8

R²OH
DIAD, PPh₃
—————→
THF

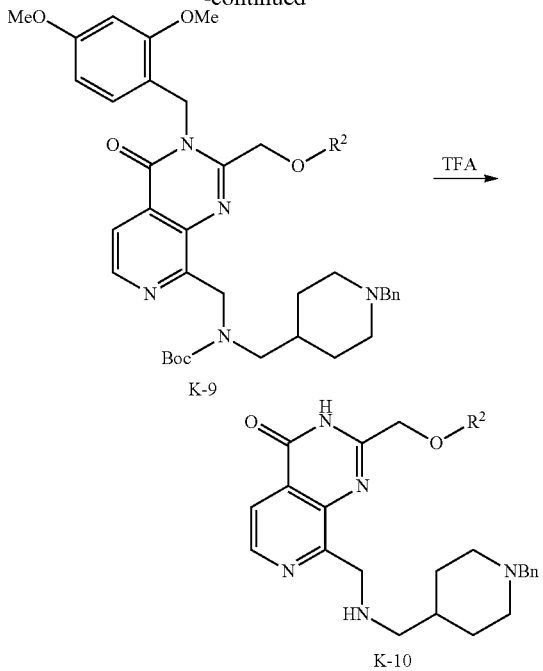
K-9

TFA
—————→

K-10

The general synthesis of compound K-10 is illustrated in Scheme 11. 3-amino-2-chloroisonicotinic acid is reacted with 2,4-dimethoxybenzylamine using HATU to afford the amide intermediate C-5. This is followed by a 2-step reaction using methyl chlorooxoacetate and NaO$^t$Bu to give the intermediate K-2. Suzuki cross-coupling using trimethylboroxine and oxidation using SeO₂ result in the aldehyde intermediate K-4. Subsequent reductive amination reaction using NaBH₃CN and Boc protection afford the intermediate K-6. The methyl ester is reduced by NaBH₄ and re-oxidized by DDQ to give the alcohol intermediate K-8. Mitsunobu reaction is performed using DIAD and PPh₃ to form ether linkage and 2,4-dimethoxybenzyl group is deprotected by TFA to afford the final product.

Example 105

Step 1

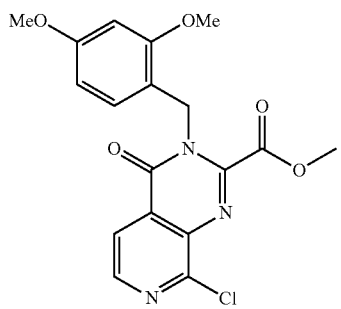 [SMILES: COC(=O)c1nc2c(Cl)nccc2c(=O)n1Cc1ccc(OC)cc1OC]

methyl 8-chloro-3-(2,4-dimethoxybenzyl)-4-oxo-3,4-dihydropyrido[3,4-d]pyrimidine-2-carboxylate To a solution of intermediate C-5 (322 mg, 1.0 mmol) and Et₃N (418 µl, 3.0 mmol) in dioxane (5 mL) and CH₃CN (5 mL) was added methyl chlorooxoacetate (276 μl, 3.0 mmol) dropwise at 0° C. under nitrogen atmosphere. The reaction mixture was warmed to ambient temperature, allowed to stir for 1 hour and concentrated in vacuo. CH$_3$CN (10 mL) and NaO$^t$Bu (192 mg, 2.0 mmol) were added to the concentrated residue. The mixture was heated at 90° C. and allowed to stir for 2 days. After cooled to ambient temperature, water (30 mL) was poured in to the mixture. The resulting mixture was extracted with EtOAc (50 mL). The organic extract was dried over MgSO$_4$, filtered and concentrated. The residue was purified by silica gel column chromatography to afford the intermediate K-2 (265 mg, 0.68 mmol) as a pale yellow oil.

$^1$H NMR (DMSO-d$_6$, 400 MHz) δ 8.50 (d, J=5.2 Hz, 1H), 7.98 (d, J=4.8 Hz, 1H), 7.08 (d, J=8.4 Hz, 1H), 6.49 (d, J=2.4 Hz, 1H), 6.42 (dd, J=2.4, 8.4 Hz, 1H), 5.19 (s, 2H), 3.85 (s, 3H), 3.69 (s, 3H), 3.66 (s, 3H)

MS (ESI+) m/z 390 (M+H)$^+$

Step 2

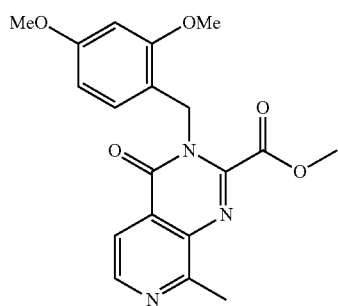 [SMILES: COC(=O)c1nc2c(C)nccc2c(=O)n1Cc1ccc(OC)cc1OC]

methyl 3-(2,4-dimethoxybenzyl)-8-methyl-4-oxo-3,4-dihydropyrido[3,4-d]pyrimidine-2-carboxylate To a solution of intermediate K-2 (396 mg, 1.02 mmol) in anhydrous dioxane (5 mL) were added K$_2$CO$_3$ (282 mg, 2.04 mmol), trimethyl boroxine (213 μl, 1.53 mmol) and Pd(PPh$_3$)$_4$ (59 mg, 0.05 mmol) under nitrogen atmosphere. The reaction mixture was heated at 100° C. and allowed to stir for 1 hour. The mixture was then diluted with EtOAc (30 mL) and washed with water (30 mL) and brine (30 mL). The organic layer was dried over MgSO$_4$, filtered and concentrated. The residue was purified by silica gel column chromatography to afford the intermediate K-3 (301 mg, 0.815 mmol) as pale yellow oil.

$^1$H NMR (DMSO-d$_6$, 400 MHz) δ 8.58 (d, J=5.2 Hz, 1H), 7.86 (d, J=5.2 Hz, 1H), 7.05 (d, J=8.0 Hz, 1H), 6.48 (d, J=2.0 Hz, 1H), 6.42 (dd, J=2.4, 8.4 Hz, 1H), 5.20 (s, 2H), 3.84 (s, 3H), 3.69 (s, 3H), 3.65 (s, 3H), 2.72 (s, 3H)

MS (ESI+) m/z 370 (M+H)$^+$

Step 3~5

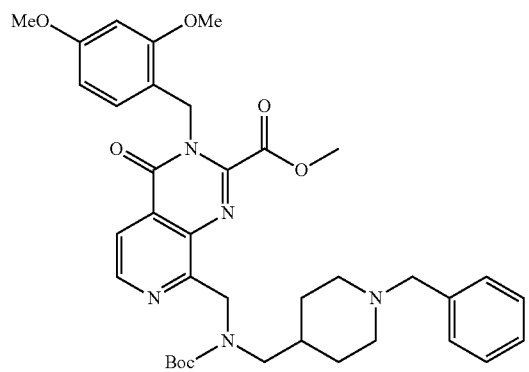 [SMILES: COC(=O)c1nc2c(CN(CC3CCN(Cc4ccccc4)CC3)C(=O)OC(C)(C)C)nccc2c(=O)n1Cc1ccc(OC)cc1OC]

methyl 8-((((1-benzylpiperidin-4-yl)methyl)(tert-butoxycarbonyl)amino)methyl)-3-(2,4-dimethoxybenzyl)-4-oxo-3,4-dihydropyrido[3,4-d]pyrimidine-2-carboxylate To a solution of intermediate K-3 (312 mg, 1.0 mmol) in dioxane (5 mL) was added SeO$_2$ (222 mg, 2.0 mmol). The reaction mixture was heated at 100° C. and allowed to stir for 3 hours. After cooled, the mixture was filtered through celite pad. The filtrate was concentrated in vacuo.

MS (ESI+) m/z 384 (M+H)$^+$

To a solution of the concentrated residue in MeOH (10 mL) were added (1-benzylpiperidin-4-yl)methanamine (225 mg, 1.1 mmol) and NaBH$_3$CN (126 mg, 2.0 mmol). After allowed to stir for 15 min, the reaction mixture was quenched with water (30 mL) and extracted with EtOAc (40 mL). The organic extract was dried over MgSO$_4$, filtered and concentrated in vacuo.

MS (ESI+) m/z 572 (M+H)$^+$

To a solution of the concentrated residue in DCM (20 mL) were added Boc$_2$O (327 mg, 1.5 mmol) and Et$_3$N (2790, 2.0 mmol). After allowed to stir for 30 min, the reaction mixture was concentrated in vacuo. The residue was purified by silica gel column chromatography to afford the intermediate K-6 (268 mg, 0.40 mmol) as a pale yellow oil.

$^1$H NMR (DMSO-d$_6$, 400 MHz) δ 8.74 (d, J=4.8 Hz, 1H), 8.05 (d, J=5.2 Hz, 1H), 7.45 (m, 5H), 7.08 (d, J=8.4 Hz, 1H), 6.50 (d, J=2.4 Hz, 1H), 6.44 (dd, J=2.4, 8.8 Hz, 1H), 5.22 (s, 2H), 4.73 (m, 2H), 4.26 (m, 2H), 3.84 (s, 3H), 3.70 (s, 3H), 3.64 (s, 3H), 3.36 (m, 2H), 3.01 (m, 2H), 2.91 (m, 2H), 2.46 (s, 9H), 1.97 (m, 2H), 1.82 (m, 1H), 1.38 (m, 2H)

MS (ESI+) m/z 672 (M+H)$^+$

Step 6~7

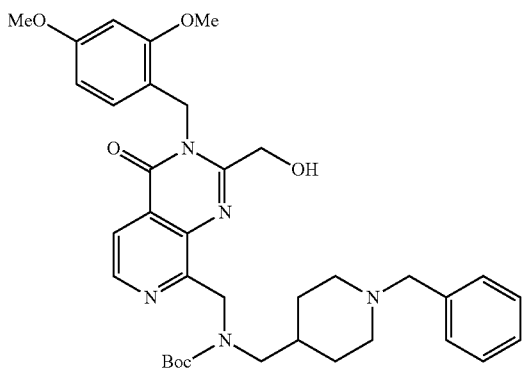 [SMILES: COc1ccc(Cn2c(CO)nc3c(CN(CC4CCN(Cc5ccccc5)CC4)C(=O)OC(C)(C)C)nccc3c2=O)c(OC)c1]

tert-butyl ((1-benzylpiperidin-4-yl)methyl)((3-(2,4-dimethoxybenzyl)-2-(hydroxymethyl)-4-oxo-3,4-dihydropyrido[3,4-d]pyrimidin-8-yl)methyl)carbamate To a solution of intermediate K-6 (200 mg, 0.298 mmol) in MeOH (10 mL) was added NaBH$_4$ (105 mg, 2.98 mmol) portionwise. After allowed to stir for 3 hours, the mixture was quenched with water (30 mL) and then extracted with EtOAc (30 mL). The organic extract was dried over MgSO$_4$, filtered and concentrated in vacuo.
MS (ESI+) m/z 646 (M+H)$^+$ To a solution of the concentrated residue in CHCl$_3$ (10 mL) was added DDQ (135 mg, 0.596 mmol). The mixture was allowed to stir for 1 hour and then diluted with DCM (30 mL). The organic layer was washed with 1N aqueous NaOH (30 mL), dried over MgSO$_4$, filtered and concentrated to afford intermediate K-8 as a crude oil (158 mg), which was used in the next step without further purification.

$^1$H NMR (CD$_3$OD, 400 MHz) δ 8.54 (m, 1H), 7.94 (m, 1H), 7.31 (m, 5H), 6.81 (m, 1H), 6.39 (m, 1H), 5.27 (m, 2H), 5.04 (m, 2H), 4.63 (m, 2H), 3.82 (s, 3H), 3.74 (m, 3H), 3.62 (m, 2H), 3.25 (m, 2H), 2.95 (m, 2H), 2.12 (m, 2H), 1.68 (m, 3H), 1.45 and 1.19 (m, 9H)
MS (ESI+) m/z 644 (M+H)$^+$

Step 8

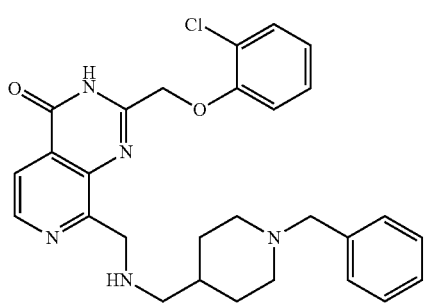

8-((((1-benzylpiperidin-4-yl)methyl)amino)methyl)-2-((2-chlorophenoxy)methyl)pyrido[3,4-d]pyrimidin-4(3H)-one To a solution of intermediate K-8 (13 mg, 0.02 mmol) in anhydrous THF (1.5 mL) were added 2-chlorophenol (0.2M in dioxane, 0.2 mL), PPh$_3$ (52 mg, 0.2 mmol) and DIAD (39 μl, 0.2 mmol). The mixture was heated to 50° C. and allowed to stir for 3 hours, and then extracted with UCT SPE CUBCX cartridge. The extract was concentrated and the residue was dissolved in TFA (1 mL). The resulting solution was heated to 50° C. and allowed to stir for 2 hours. The solution was concentrated and the residue was purified by preparative HPLC to afford the title compound (2.5 mg).

$^1$H NMR (CD$_3$OD, 400 MHz) δ 8.66 (d, J=5.2 Hz, 1H), 8.07 (d, J=5.6 Hz, 1H), 7.49 (m, 5H), 7.41 (d, J=8.0 Hz, 1H), 7.26 (m, 1H), 7.19 (m, 1H), 7.00 (t, J=7.6 Hz, 1H), 5.14 (s, 2H), 4.31 (s, 2H), 3.56 (m, 2H), 3.14 (m, 2H), 3.04 (m, 2H), 2.20 (m, 1H), 2.17 (m, 2H), 1.59 (m, 2H)

MS (ESI+) m/z 504 (M+H)$^+$

Example 106

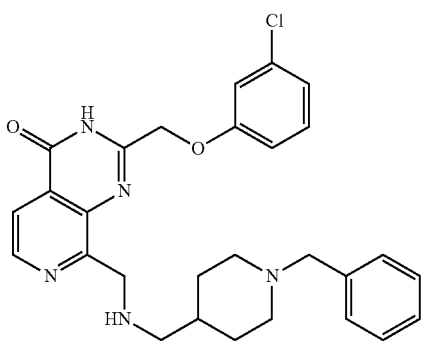 [SMILES: O=c1[nH]c(COc2cccc(Cl)c2)nc2c(CNCC3CCN(Cc4ccccc4)CC3)nccc12]

8-((((1-benzylpiperidin-4-yl)methyl)amino)methyl)-2-((3-chlorophenoxy)methyl)pyrido[3,4-d]pyrimidin-4(3H)-one Using 3-chlorophenol, the title compound was obtained (1.3 mg) as described in Scheme 11 (Method K).

$^1$H NMR (CD$_3$OD, 400 MHz) δ 8.66 (d, J=5.6 Hz, 1H), 8.07 (d, J=5.2 Hz, 1H), 7.49 (m, 5H), 7.28 (t, J=8.0 Hz, 1H), 7.13 (m, 1H), 7.01 (m, 2H), 5.14 (s, 2H), 4.31 (s, 2H), 3.53 (m, 2H), 3.14 (m, 2H), 3.04 (m, 2H), 2.17 (m, 1H), 2.13 (m, 2H), 1.56 (m, 2H)

MS (ESI+) m/z 504 (M+H)$^+$

Example 107

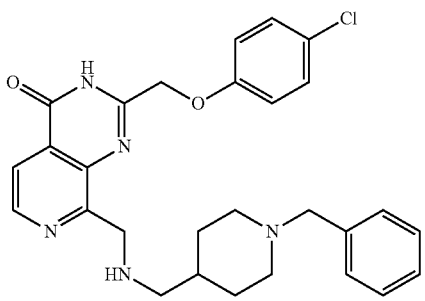

8-((((1-benzylpiperidin-4-yl)methyl)amino)methyl)-2-((4-chlorophenoxy)methyl)pyrido[3,4-d]pyrimidin-4(3H)-one Using 4-chlorophenol, the title compound was obtained (1.4 mg) as described in Scheme 11 (Method K).
$^1$H NMR (CD$_3$OD, 400 MHz) δ 8.66 (d, J=5.2 Hz, 1H), 8.06 (d, J=5.6 Hz, 1H), 7.49 (m, 5H), 7.29 (d, J=8.8 Hz, 2H), 7.05 (d, J=8.8 Hz, 2H), 5.08 (s, 2H), 4.31 (s, 2H), 3.55 (m, 2H), 3.22 (m, 2H), 3.11 (m, 2H), 2.17 (m, 1H), 2.13 (m, 2H), 1.58 (m, 2H)
MS (ESI+) m/z 504 (M+H)$^+$ Example 108

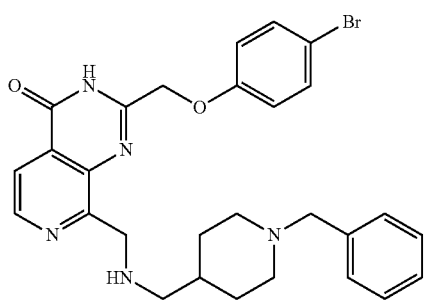

8-((((1-benzylpiperidin-4-yl)methyl)amino)methyl)-2-((4-bromophenoxy)methyl)pyrido[3,4-d]pyrimidin-4(3H)-one Using 4-bromophenol, the title compound was obtained (2.1 mg) as described in Scheme 11 (Method K).
$^1$H NMR (CD$_3$OD, 400 MHz) δ 8.65 (d, J=5.2 Hz, 1H), 8.06 (d, J=5.2 Hz, 1H), 7.49 (m, 5H), 7.43 (d, J=8.8 Hz, 2H), 7.00 (d, J=9.2 Hz, 2H), 5.08 (s, 2H), 4.32 (s, 2H), 3.55 (m, 2H), 3.15 (m, 2H), 3.05 (m, 2H), 2.17 (m, 1H), 2.13 (m, 2H), 1.57 (m, 2H)
MS (ESI+) m/z 548 (M+H)$^+$ Example 109

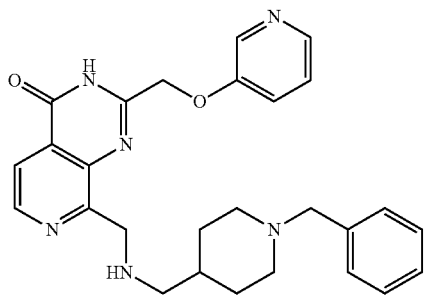 [SMILES: O=c1[nH]c(COc2cccnc2)nc2c(CNCC3CCN(Cc4ccccc4)CC3)nccc12]

8-((((1-benzylpiperidin-4-yl)methyl)amino)methyl)-2-((pyridin-3-yloxy)methyl)pyrido[3,4-d]pyrimidin-4(3H)-one Using 3-hydroxypyridine, the title compound was obtained (2.2 mg) as described in Scheme 11 (Method K).
$^1$H NMR (CD$_3$OD, 400 MHz) δ 8.66 (d, J=5.2 Hz, 1H), 8.47 (m, 1H), 8.27 (m, 1H), 8.07 (d, J=5.2 Hz, 1H), 7.71 (d, J=8.8 Hz, 1H), 7.52 (d, J=8.8 Hz, 1H), 7.49 (m, 5H), 5.23 (s, 2H), 4.33 (s, 2H), 3.57 (m, 2H), 3.15 (m, 2H), 3.06 (m, 2H), 2.17 (m, 1H), 2.14 (m, 2H), 1.58 (m, 2H)
MS (ESI+) m/z 471 (M+H)$^+$ Example 110

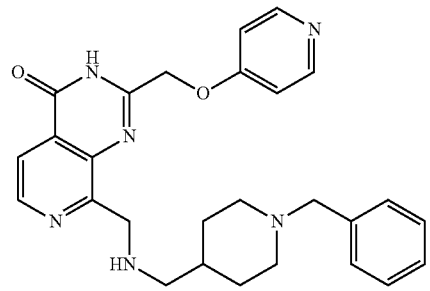 [SMILES: O=c1[nH]c(COc2ccncc2)nc2c(CNCC3CCN(Cc4ccccc4)CC3)nccc12]

8-((((1-benzylpiperidin-4-yl)methyl)amino)methyl)-2-((pyridin-4-yloxy)methyl)pyrido[3,4-d]pyrimidin-4(3H)-one Using 4-hydroxypyridine, the title compound was obtained (3.2 mg) as described in Scheme 11 (Method K).
$^1$H NMR (CD$_3$OD, 400 MHz) δ 8.70 (d, J=7.6 Hz, 2H), 8.68 (d, J=5.2 Hz, 1H), 8.07 (d, J=5.2 Hz, 1H), 7.66 (d, J=7.2 Hz, 2H), 7.49 (m, 5H), 5.46 (s, 2H), 4.32 (s, 2H), 3.54 (m, 2H), 3.15 (m, 2H), 3.06 (m, 2H), 2.17 (m, 1H), 2.13 (m, 2H), 1.60 (m, 2H)
MS (ESI+) m/z 471 (M+H)$^+$ Example 111

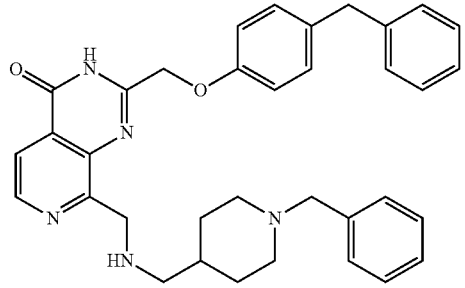 [SMILES: O=c1[nH]c(COc2ccc(Cc3ccccc3)cc2)nc2c(CNCC3CCN(Cc4ccccc4)CC3)nccc12]

2-((4-benzylphenoxy)methyl)-8-((((1-benzylpiperidin-4-yl)methyl)amino)methyl)pyrido[3,4-d]pyrimidin-4(3H)-one Using 4-benzylphenol, the title compound was obtained (3.3 mg) as described in Scheme 11 (Method K).
$^1$H NMR (CD$_3$OD, 400 MHz) δ 8.65 (d, J=5.2 Hz, 1H), 8.06 (d, J=4.8 Hz, 1H), 7.49 (m, 5H), 7.22 (m, 2H), 7.14 (m, 5H), 6.97 (m, 2H), 5.05 (s, 2H), 4.30 (s, 2H), 3.89 (s, 2H), 3.55 (m, 2H), 3.14 (m, 2H), 3.04 (m, 2H), 2.16 (m, 1H), 2.13 (m, 2H), 1.58 (m, 2H)
MS (ESI+) m/z 560 (M+H)$^+$

Scheme 12 (Method L)

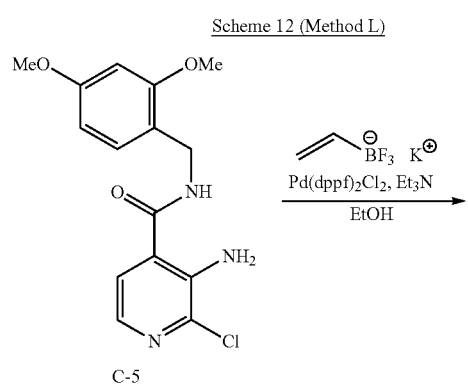

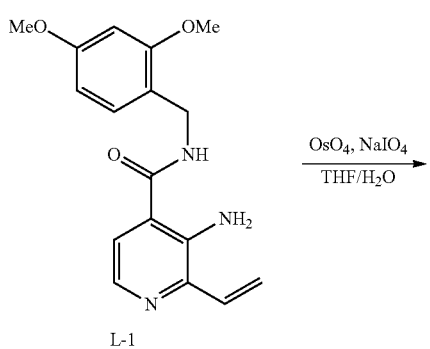

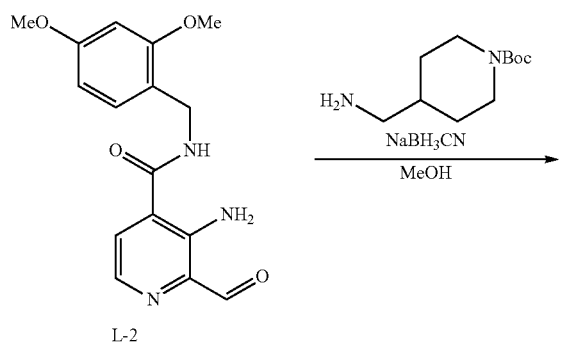

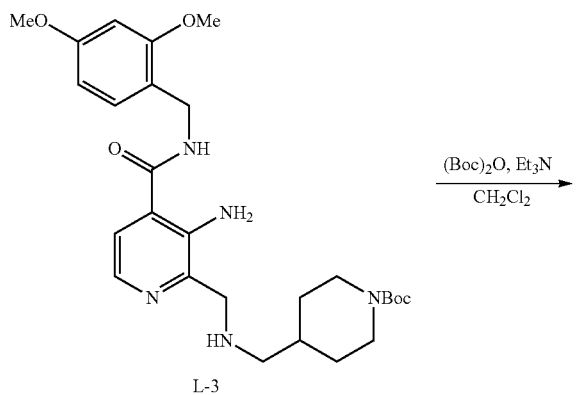

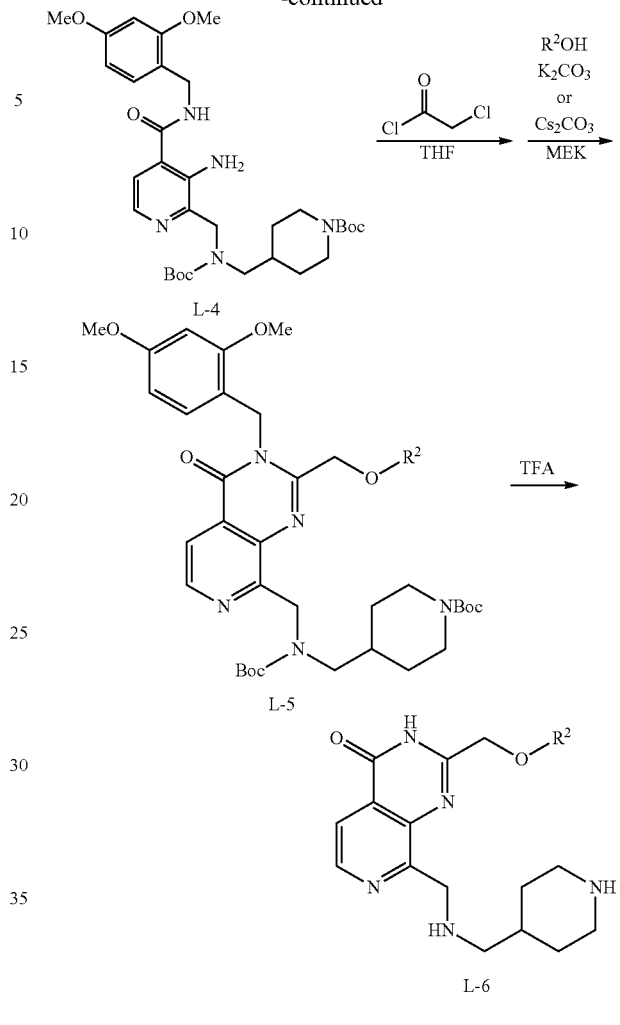

The general synthesis of compounds L-6 is illustrated in Scheme 12. The aldehyde group is introduced by Suzuki cross-coupling using potassium vinyltrifluoroborate and oxidative cleavage using $OsO_4$ and $NaIO_4$. Subsequent reductive amination using $NaBH_3CN$ and Boc protection lead to intermediate L-4. This is followed by the 2-step reaction with chloroacetyl chloride and carbonate base to give intermediate L-5. The 2,4-dimethoxybenzyl group is deprotected by TFA to afford the final product.

Example 112

Step 1

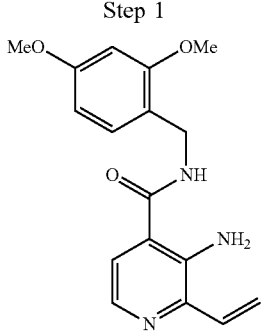

3-amino-N-(2,4-dimethoxybenzyl)-2-vinylisonicotinamide

To a solution of intermediate C-5 (644 mg, 2.0 mmol) in anhydrous EtOH (20 mL) were added potassium vinyltrifluoroborate (402 mg, 3.0 mmol), Pd(dppf)Cl$_2$ (dichloromethane adduct, 49 mg, 0.06 mmol) and Et$_3$N (1.4 mL, 10 mmol). Nitrogen flushed. After heated to 80° C. and allowed to stir for 1 hour, the reaction mixture was diluted with water (40 mL) and extracted with EtOAc (50 mL). The organic extract was dried over MgSO$_4$, filtered and concentrated. The residue was purified by silica gel column chromatography to afford the intermediate L-1 (472 mg, 1.51 mmol).

$^1$H NMR (CDCl$_3$, 400 MHz) δ 7.99 (d, J=6.0 Hz, 1H), 7.55 (d, J=5.6 Hz, 1H), 7.46 (br t, J=5.6 Hz, 1H), 7.20 (d, J=8.0 Hz, 1H), 6.75 (dd, J=12.0, 17.6 Hz, 1H), 6.44 (m, 2H), 6.32 (d, J=17.6 Hz, 1H), 6.18 (br s, 2H), 5.98 (d, J=12.0 Hz, 1H), 4.50 (d, J=5.6 Hz, 2H), 3.82 (s, 3H), 3.77 (s, 3H)

MS (ESI+) m/z 314 (M+H)$^+$

Step 2

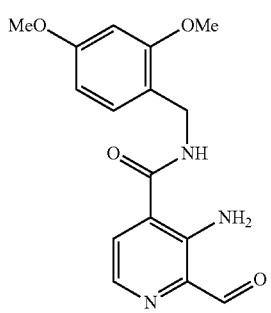 [SMILES: COc1ccc(CNC(=O)c2ccnc(C=O)c2N)c(OC)c1]

3-amino-N-(2,4-dimethoxybenzyl)-2-formylisonicotinamide

To a solution of intermediate L-1 (251 mg, 0.8 mmol) in THF (5 mL) and water (5 mL) was added OsO$_4$ (4% in water, 0.62 mL, 0.08 mmol). After a brief stirring for 5 min, NaIO$_4$ (513 mg, 2.25 mmol) was added and the reaction mixture was allowed to stir for 2 hours. The mixture was quenched with a saturated aqueous solution of NaHCO$_3$ (30 mL) and extracted with EtOAc (40 mL). The organic extract was dried over MgSO$_4$, filtered and concentrated to afford the intermediate L-2 as a crude oil. The crude oil (quant.) was used in the next step without further purification.

MS (ESI+) m/z 316 (M+H)$^+$

Step 3~4

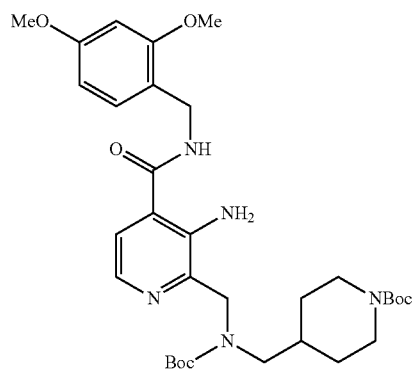 [SMILES: COc1ccc(CNC(=O)c2ccnc(CN(CC3CCN(C(=O)OC(C)(C)C)CC3)C(=O)OC(C)(C)C)c2N)c(OC)c1]

tert-butyl 4-((((3-amino-4-((2,4-dimethoxybenzyl)carbamoyl)pyridin-2-yl)methyl)(tert-butoxycarbonyl)amino)methyl)piperidine-1-carboxylate To a solution of intermediate L-2 (250 mg as crude, 0.8 mmol) in MeOH (10 mL) were added tert-butyl 4-(aminomethyl)piperidine-1-carboxylate (214 mg, 1.0 mmol) and NaBH$_3$CN (100 mg, 1.6 mmol). The reaction mixture was allowed to stir for 30 min, quenched with water (30 mL) and then extracted with DCM (30 mL). The organic extract was dried over MgSO$_4$, filtered and concentrated.

MS (ESI+) m/z 514 (M+H)$^+$

The resulting residue was diluted with DCM (10 mL), followed by the addition of Boc$_2$O (230 μl, 1.0 mmol) and Et$_3$N (223 μl, 1.6 mmol). The mixture was allowed to stir for 1 hour and concentrated in vacuo. The residue was purified by silica gel column chromatography to afford the intermediate L-4 (138 mg, 0.225 mmol).

$^1$H NMR (CD$_3$OD, 400 MHz) δ 7.73 (m, 1H), 7.30 (d, J=5.2 Hz, 1H), 7.15 (d, J=8.8 Hz, 1H), 6.52 (m, 1H), 6.46 (m, 1H), 4.54 (br s, 2H), 4.44 (s, 2H), 3.98 (m, 2H), 3.82 (s, 3H), 3.76 (s, 3H), 3.09 (m, 2H), 2.58 (m, 2H), 1.60 (m, 3H), 1.43 (m, 18H), 0.94 (m, 2H)

MS (ESI+) m/z 614 (M+H)$^+$

Step 5~6

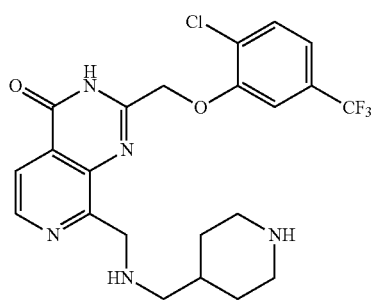 [SMILES: O=c1[nH]c(COc2cc(C(F)(F)F)ccc2Cl)nc2c(CNCC3CCNCC3)nccc12]

2-((2-chloro-5-(trifluoromethyl)phenoxy)methyl)-8-(((piperidin-4-ylmethyl)amino)methyl)pyrido[3,4-d]pyrimidin-4(3H)-one To a solution of intermediate L-4 (13.8 mg, 0.023 mmol) in THF (1 mL) was added chloroacetyl chloride (5.5 μl, 0.069 mmol). The mixture was allowed to stir for 30 min and concentrated in vacuo. The residue was diluted with MEK (1.5 mL). 2-chloro-5-trifluoromethylphenol (0.2 M in dioxane, 0.3 mL) and K₂CO₃ (9.5 mg, 0.069 mmol) were added. The reaction mixture was heated to 80° C. and allowed to stir overnight. After the mixture was extracted with UCT SPE CUBCX cartridge, the extract was concentrated and purified by preparative HPLC. The purified residue was dissolved in TFA (1 mL), heated to 50° C. and allowed to stir for 2 hours. It was concentrated in vacuo and purified by preparative HPLC to afford the title compound (2.1 mg).

$^1$H NMR (CD$_3$OD, 400 MHz) δ 8.69 (d, J=5.2 Hz, 1H), 8.09 (d, J=5.2 Hz, 1H), 7.64 (m, 1H), 7.55 (m, 1H), 7.34 (m, 1H), 5.24 (s, 2H), 4.81 (m, 2H), 3.46 (m, 2H), 3.16 (m, 2H), 3.04 (m, 2H), 2.20 (m, 1H), 2.10 (m, 2H), 1.53 (m, 2H)

MS (ESI+) m/z 482 (M+H)$^+$

Example 113

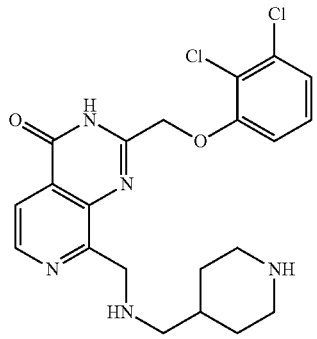 [SMILES: O=c1[nH]c(COc2cccc(Cl)c2Cl)nc2c(CNCC3CCNCC3)nccc12]

2-((2,3-dichlorophenoxy)methyl)-8-(((piperidin-4-ylmethyl)amino)methyl)pyrido[3,4-d]pyrimidin-4(3H)-one Using 2,3-dichlorophenol, the title compound was obtained (1.7 mg) as described in Scheme 12 (Method L).

$^1$H NMR (CD$_3$OD, 400 MHz) δ 8.68 (d, J=5.2 Hz, 1H), 8.08 (d, J=5.2 Hz, 1H), 7.22 (m, 3H), 5.18 (s, 2H), 4.78 (m, 2H), 3.45 (m, 2H), 3.14 (m, 2H), 3.03 (m, 2H), 2.18 (m, 1H), 2.10 (m, 2H), 1.53 (m, 2H)

MS (ESI+) m/z 448 (M+H)$^+$

Example 114

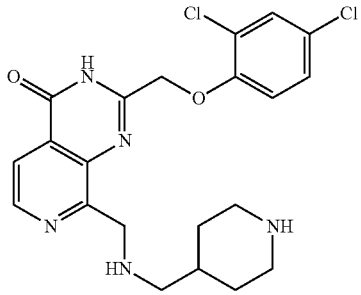 [SMILES: O=c1[nH]c(COc2ccc(Cl)cc2Cl)nc2c(CNCC3CCNCC3)nccc12]

2-((2,4-dichlorophenoxy)methyl)-8-(((piperidin-4-ylmethyl)amino)methyl)pyrido[3,4-d]pyrimidin-4(3H)-one Using 2,4-dichlorophenol, the title compound was obtained (1.4 mg) as described in Scheme 12 (Method L).

$^1$H NMR (CD$_3$OD, 400 MHz) δ 8.67 (d, J=5.6 Hz, 1H), 8.08 (d, J=5.2 Hz, 1H), 7.49 (d, J=2.4 Hz, 1H), 7.29 (dd, J=2.4, 8.8 Hz, 1H), 7.20 (d, J=8.8 Hz, 1H), 5.16 (s, 2H), 4.77 (m, 2H), 3.45 (m, 2H), 3.13 (m, 2H), 3.03 (m, 2H), 2.17 (m, 1H), 2.10 (m, 2H), 1.52 (m, 2H)

MS (ESI+) m/z 448 (M+H)$^+$

Example 115

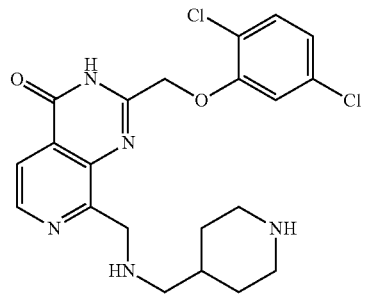

2-((2,5-dichlorophenoxy)methyl)-8-(((piperidin-4-ylmethyl)amino)methyl)pyrido[3,4-d]pyrimidin-4(3H)-one Using 2,5-dichlorophenol, the title compound was obtained (1.6 mg) as described in Scheme 12 (Method L).

$^1$H NMR (CD$_3$OD, 400 MHz) δ 8.69 (d, J=5.2 Hz, 1H), 8.09 (d, J=5.6 Hz, 1H), 7.41 (d, J=8.8 Hz, 1H), 7.33 (d, J=2.0 Hz, 1H), 7.05 (dd, J=2.4, 8.8 Hz, 1H), 5.17 (s, 2H), 4.80 (m, 2H), 3.46 (m, 2H), 3.16 (m, 2H), 3.03 (m, 2H), 2.19 (m, 1H), 2.11 (m, 2H), 1.53 (m, 2H)

MS (ESI+) m/z 448 (M+H)$^+$

Example 116

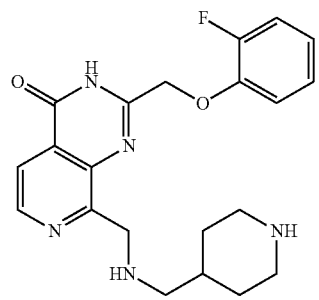

2-((2-fluorophenoxy)methyl)-8-(((piperidin-4-ylmethyl)amino)methyl)pyrido[3,4-d]pyrimidin-4(3H)-one Using 2-fluorophenol, the title compound was obtained (1.7 mg) as described in Scheme 12 (Method L).

$^1$H NMR (CD$_3$OD, 400 MHz) δ 8.67 (d, J=5.6 Hz, 1H), 8.08 (d, J=5.6 Hz, 1H), 7.13 (m, 4H) 5.14 (s, 2H), 4.81 (m, 2H), 3.46 (m, 2H), 3.16 (m, 2H), 3.04 (m, 2H), 2.21 (m, 1H), 2.11 (m, 2H), 1.53 (m, 2H)

MS (ESI+) m/z 398 (M+H)$^+$

Example 117

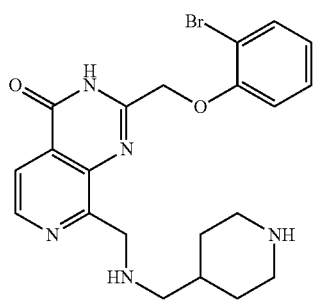

2-((2-bromophenoxy)methyl)-8-(((piperidin-4-ylmethyl)amino)methyl)pyrido[3,4-d]pyrimidin-4(3H)-one Using 2-bromophenol, the title compound was obtained (2.2 mg) as described in Scheme 12 (Method L).

$^1$H NMR (CD$_3$OD, 400 MHz) δ 8.68 (d, J=4.8 Hz, 1H), 8.09 (d, J=5.6 Hz, 1H), 7.59 (dd, J=1.2, 8.0 Hz, 1H), 7.33 (t, J=8.6 Hz, 1H), 7.17 (d, J=8.0 Hz, 1H), 6.95 (t, J=8.4 Hz, 1H), 5.15 (s, 2H), 4.81 (m, 2H), 3.46 (m, 2H), 3.15 (m, 2H), 3.04 (m, 2H), 2.19 (m, 1H), 2.10 (m, 2H), 1.53 (m, 2H)

MS (ESI+) m/z 458 (M+H)$^+$

Example 118

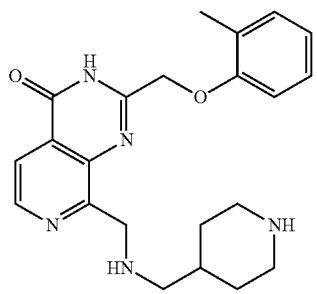 [SMILES: Cc1ccccc1OCc1nc2c(CNCC3CCNCC3)nccc2c(=O)[nH]1]

8-(((piperidin-4-ylmethyl)amino)methyl)-2-((o-tolyloxy)methyl)pyrido[3,4-d]pyrimidin-4(3H)-one Using o-cresol, the title compound was obtained (2.3 mg) as described in Scheme 12 (Method L).

$^1$H NMR (CD$_3$OD, 400 MHz) δ 8.67 (d, J=5.2 Hz, 1H), 8.08 (d, J=5.6 Hz, 1H), 7.14 (m, 2H), 6.97 (d, J=7.6 Hz, 1H), 6.90 (t, J=7.6 Hz, 1H), 5.09 (s, 2H), 4.84 (s, 2H), 3.45 (m, 2H), 3.16 (m, 2H), 3.04 (m, 2H), 2.28 (m, 3H), 2.20 (m, 1H), 2.10 (m, 2H), 1.56 (m, 2H)

MS (ESI+) m/z 394 (M+H)$^+$

Example 119

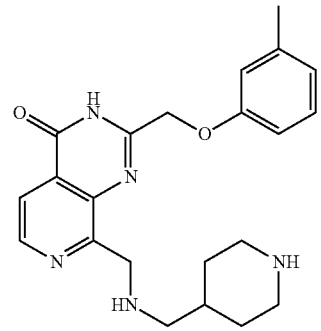 [SMILES: Cc1cccc(OCc2nc3c(CNCC4CCNCC4)nccc3c(=O)[nH]2)c1]

8-(((piperidin-4-ylmethyl)amino)methyl)-2-((m-tolyloxy)methyl)pyrido[3,4-d]pyrimidin-4(3H)-one Using m-cresol, the title compound was obtained (2.2 mg) as described in Scheme 12 (Method L).

$^1$H NMR (CD$_3$OD, 400 MHz) δ 8.66 (d, J=5.2 Hz, 1H), 8.07 (d, J=5.6 Hz, 1H), 7.17 (t, J=8.0 Hz, 2H), 6.89 (m, 1H), 6.83 (m, 1H), 5.07 (s, 2H), 4.85 (s, 2H), 3.45 (m, 2H), 3.17 (m, 2H), 3.04 (m, 2H), 2.31 (s, 3H), 2.20 (m, 1H), 2.10 (m, 2H), 1.54 (m, 2H)

MS (ESI+) m/z 394 (M+H)$^+$

Example 120

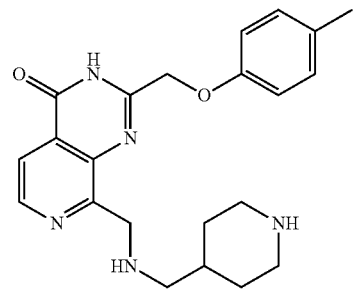 [SMILES: Cc1ccc(OCc2nc3c(CNCC4CCNCC4)nccc3c(=O)[nH]2)cc1]

8-(((piperidin-4-ylmethyl)amino)methyl)-2-((p-tolyloxy)methyl)pyrido[3,4-d]pyrimidin-4(3H)-one Using p-cresol, the title compound was obtained (2.5 mg) as described in Scheme 12 (Method L).

$^1$H NMR (CD$_3$OD, 400 MHz) δ 8.66 (d, J=5.2 Hz, 1H), 8.07 (d, J=5.6 Hz, 1H), 7.10 (d, J=8.4 Hz, 2H), 6.94 (d, J=8.4 Hz, 2H), 5.05 (s, 2H), 4.85 (s, 2H), 3.45 (m, 2H), 3.17 (m, 2H), 3.04 (m, 2H), 2.25 (s, 3H), 2.20 (m, 1H), 2.11 (m, 2H), 1.54 (m, 2H)

MS (ESI+) m/z 394 (M+H)$^+$

Example 121

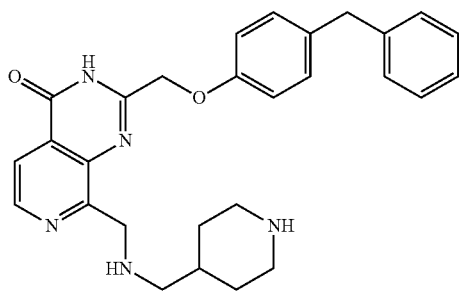 [SMILES: O=c1[nH]c(COc2ccc(Cc3ccccc3)cc2)nc2c(CNCC3CCNCC3)nccc12]

2-((4-benzylphenoxy)methyl)-8-(((piperidin-4-ylmethyl)amino)methyl)pyrido[3,4-d]pyrimidin-4(3H)-one Using 4-benzylphenol, the title compound was obtained (3.5 mg) as described in Scheme 12 (Method L).

$^1$H NMR (CD$_3$OD, 400 MHz) δ 8.66 (d, J=5.2 Hz, 1H), 8.06 (d, J=4.8 Hz, 1H), 7.22 (m, 2H), 7.14 (m, 5H), 6.98 (m, 2H), 5.06 (s, 2H), 4.84 (s, 2H), 3.45 (m, 2H), 3.16 (m, 2H), 3.03 (m, 2H), 2.20 (m, 1H), 2.10 (m, 2H), 1.53 (m, 2H)

MS (ESI+) m/z 470 (M+H)$^+$

Example 122

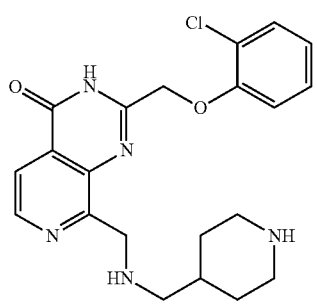

2-((2-chlorophenoxy)methyl)-8-(((piperidin-4-ylmethyl)amino)methyl)pyrido[3,4-d]pyrimidin-4(3H)-one Using 2-chlorophenol, the title compound was obtained (3.9 mg) as described in Scheme 12 (Method L).

$^1$H NMR (CD$_3$OD, 400 MHz) δ 8.67 (d, J=5.2 Hz, 1H), 8.08 (d, J=5.6 Hz, 1H), 7.42 (m, 1H), 7.28 (m, 1H), 7.20 (m, 1H), 7.01 (m, 1H), 5.15 (s, 2H), 4.81 (s, 2H), 3.45 (m, 2H), 3.15 (m, 2H), 3.03 (m, 2H), 2.19 (m, 1H), 2.09 (m, 2H), 1.53 (m, 2H)

MS (ESI+) m/z 414 (M+H)$^+$

Example 123

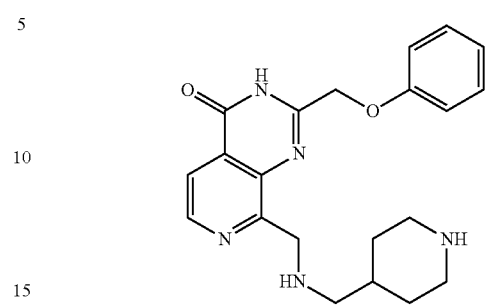

2-(phenoxymethyl)-8-(((piperidin-4-ylmethyl)amino)methyl)pyrido[3,4-d]pyrimidin-4(3H)-one Using phenol, the title compound was obtained (3.7 mg) as described in Scheme 12 (Method L).

$^1$H NMR (CD$_3$OD, 400 MHz) δ 8.66 (d, J=5.2 Hz, 1H), 8.07 (d, J=5.2 Hz, 1H), 7.31 (m, 2H), 7.06 (m, 2H), 7.00 (t, J=7.6 Hz, 1H), 5.10 (s, 2H), 4.84 (s, 2H), 3.45 (m, 2H), 3.16 (m, 2H), 3.04 (m, 2H), 2.20 (m, 1H), 2.11 (m, 2H), 1.54 (m, 2H)

MS (ESI+) m/z 380 (M+H)$^+$

Example 124

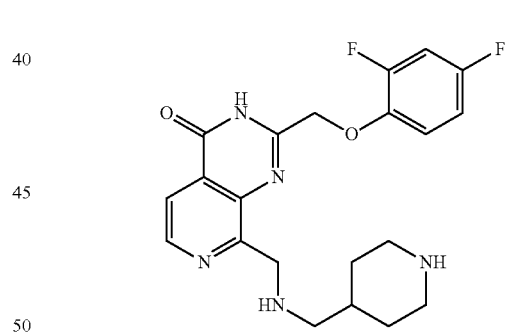

2-((2,4-difluorophenoxy)methyl)-8-(((piperidin-4-ylmethyl)amino)methyl)pyrido[3,4-d]pyrimidin-4(3H)-one Using 2,4-difluorophenol, the title compound was obtained (2.4 mg) as described in Scheme 12 (Method L).

$^1$H NMR (CD$_3$OD, 400 MHz) δ 8.67 (d, J=5.6 Hz, 1H), 8.07 (d, J=5.2 Hz, 1H), 7.23 (m, 1H), 7.05 (m, 1H), 6.92 (m, 1H), 5.12 (s, 2H), 4.81 (s, 2H), 3.45 (m, 2H), 3.16 (m, 2H), 3.04 (m, 2H), 2.20 (m, 1H), 2.11 (m, 2H), 1.54 (m, 2H)

MS (ESI+) m/z 416 (M+H)$^+$

Example 125

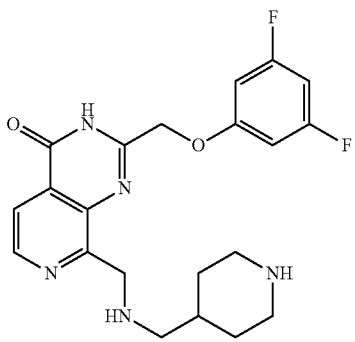 [SMILES: O=c1[nH]c(COc2cc(F)cc(F)c2)nc2c(CNCC3CCNCC3)nccc12]

2-((3,5-difluorophenoxy)methyl)-8-(((piperidin-4-ylmethyl)amino)methyl)pyrido[3,4-d]pyrimidin-4(3H)-one Using 3,5-difluorophenol, the title compound was obtained (2.5 mg) as described in Scheme 12 (Method L).

$^1$H NMR (CD$_3$OD, 400 MHz) δ 8.67 (d, J=5.2 Hz, 1H), 8.07 (d, J=5.6 Hz, 1H), 6.74 (m, 2H), 6.61 (m, 1H), 5.12 (s, 2H), 4.83 (s, 2H), 3.46 (m, 2H), 3.17 (m, 2H), 3.04 (m, 2H), 2.21 (m, 1H), 2.11 (m, 2H), 1.54 (m, 2H)

MS (ESI+) m/z 416 (M+H)$^+$

Example 126

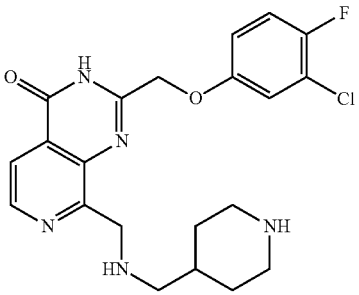

2-((3-chloro-4-fluorophenoxy)methyl)-8-(((piperidin-4-ylmethyl)amino)methyl)pyrido[3,4-d]pyrimidin-4(3H)-one Using 3-chloro-4-fluorophenol, the title compound was obtained (1.9 mg) as described in Scheme 12 (Method L).

$^1$H NMR (CD$_3$OD, 400 MHz) δ 8.67 (d, J=5.2 Hz, 1H), 8.07 (d, J=5.2 Hz, 1H), 7.23 (m, 1H), 7.19 (t, J=9.2 Hz, 1H), 7.03 (m, 1H), 5.09 (s, 2H), 4.82 (s, 2H), 3.45 (m, 2H), 3.17 (m, 2H), 3.04 (m, 2H), 2.20 (m, 1H), 2.11 (m, 2H), 1.54 (m, 2H)

MS (ESI+) m/z 432 (M+H)$^+$

Example 127

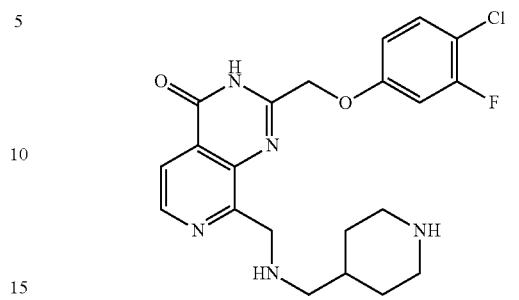

2-((4-chloro-3-fluorophenoxy)methyl)-8-(((piperidin-4-ylmethyl)amino)methyl)pyrido[3,4-d]pyrimidin-4(3H)-one Using 4-chloro-3-fluorophenol, the title compound was obtained (2.0 mg) as described in Scheme 12 (Method L).

$^1$H NMR (CD$_3$OD, 400 MHz) δ 8.67 (d, J=5.6 Hz, 1H), 8.07 (d, J=5.2 Hz, 1H), 7.39 (t, J=9.2 Hz, 1H), 7.04 (m, 1H), 6.92 (m, 1H), 5.11 (s, 2H), 4.82 (s, 2H), 3.46 (m, 2H), 3.17 (m, 2H), 3.04 (m, 2H), 2.21 (m, 1H), 2.11 (m, 2H), 1.54 (m, 2H)

MS (ESI+) m/z 432 (M+H)$^+$

Example 128

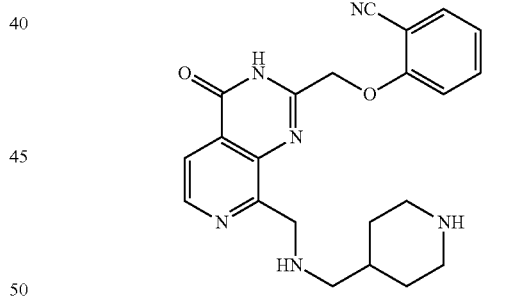

2-((4-oxo-8-(((piperidin-4-ylmethyl)amino)methyl)-3,4-dihydropyrido[3,4-d]pyrimidin-2-yl)methoxy)benzonitrile Using 2-cyanophenol, the title compound was obtained (0.3 mg) as described in Scheme 12 (Method L).

$^1$H NMR (CD$_3$OD, 400 MHz) δ 8.68 (d, J=5.2 Hz, 1H), 8.08 (d, J=5.2 Hz, 1H), 7.70 (m, 1H), 7.65 (m, 1H), 7.29 (m, 1H), 7.16 (m, 1H), 5.25 (s, 2H), 4.82 (s, 2H), 3.45 (m, 2H), 3.16 (m, 2H), 3.05 (m, 2H), 2.19 (m, 1H), 2.11 (m, 2H), 1.53 (m, 2H)

MS (ESI+) m/z 405 (M+H)$^+$

Example 129

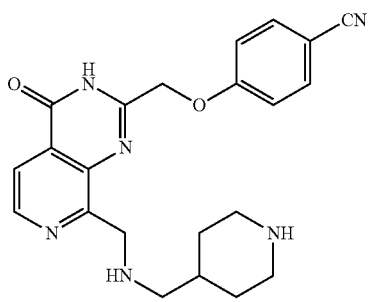 [SMILES: N#Cc1ccc(OCc2nc3c(CNCC4CCNCC4)nccc3c(=O)[nH]2)cc1]

4-((4-oxo-8-(((piperidin-4-ylmethyl)amino)methyl)-3,4-dihydropyrido[3,4-d]pyrimidin-2-yl)methoxy)benzonitrile Using 2-cyanophenol, the title compound was obtained (2.1 mg) as described in Scheme 12 (Method L).

$^1$H NMR (CD$_3$OD, 400 MHz) δ 8.67 (d, J=5.6 Hz, 1H), 8.06 (d, J=5.2 Hz, 1H), 7.71 (d, J=8.8 Hz, 2H), 7.23 (d, J=9.2 Hz, 2H), 5.20 (s, 2H), 4.81 (s, 2H), 3.45 (m, 2H), 3.16 (m, 2H), 3.04 (m, 2H), 2.20 (m, 1H), 2.11 (m, 2H), 1.55 (m, 2H)

MS (ESI+) m/z 405 (M+H)$^+$

Example 130

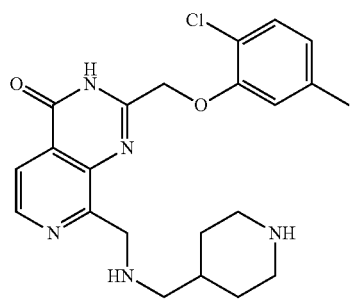 [SMILES: Cc1ccc(Cl)c(OCc2nc3c(CNCC4CCNCC4)nccc3c(=O)[nH]2)c1]

2-((2-chloro-5-methylphenoxy)methyl)-8-(((piperidin-4-ylmethyl)amino)methyl)pyrido[3,4-d]pyrimidin-4(3H)-one Using 2-chloro-5-methylphenol, the title compound was obtained (0.5 mg) as described in Scheme 12 (Method L).

$^1$H NMR (CD$_3$OD, 400 MHz) δ 8.68 (d, J=5.2 Hz, 1H), 8.09 (d, J=5.2 Hz, 1H), 7.27 (d, J=8.4 Hz, 1H), 7.03 (m, 1H), 6.84 (m, 1H), 5.12 (s, 2H), 4.82 (s, 2H), 3.45 (m, 2H), 3.16 (m, 2H), 3.03 (m, 2H), 2.32 (s, 3H), 2.19 (m, 1H), 2.10 (m, 2H), 1.53 (m, 2H)

MS (ESI+) m/z 428 (M+H)$^+$

Example 131

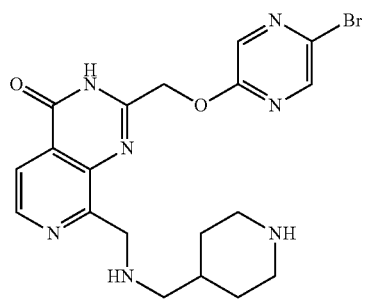 [SMILES: O=c1[nH]c(COc2cnc(Br)cn2)nc2c(CNCC3CCNCC3)nccc12]

2-(((5-bromopyrazin-2-yl)oxy)methyl)-8-(((piperidin-4-ylmethyl)amino)methyl)pyrido[3,4-d]pyrimidin-4(3H)-one Using 5-bromo-2-hydroxypyrazine, the title compound was obtained (0.4 mg) as described in Scheme 12 (Method L).

$^1$H NMR (CD$_3$OD, 400 MHz) δ 8.65 (d, J=5.6 Hz, 1H), 8.26 (s, 2H), 8.05 (d, J=5.2 Hz, 1H), 7.27 (d, J=8.4 Hz, 1H), 5.39 (s, 2H), 4.73 (s, 2H), 3.47 (m, 2H), 3.17 (m, 2H), 3.06 (m, 2H), 2.19 (m, 1H), 2.11 (m, 2H), 1.53 (m, 2H)

MS (ESI+) m/z 460 (M+H)$^+$

Example 132

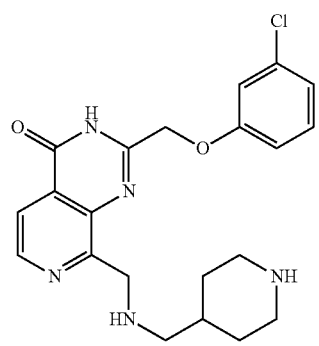 [SMILES: O=c1[nH]c(COc2cccc(Cl)c2)nc2c(CNCC3CCNCC3)nccc12]

2-((3-chlorophenoxy)methyl)-8-(((piperidin-4-ylmethyl)amino)methyl)pyrido[3,4-d]pyrimidin-4(3H)-one Using 3-chlorophenol, the title compound was obtained (0.6 mg) as described in Scheme 12 (Method L).

$^1$H NMR (CD$_3$OD, 400 MHz) δ 8.67 (d, J=5.2 Hz, 1H), 8.07 (d, J=5.2 Hz, 1H), 7.29 (t, J=8.0 Hz, 1H), 7.14 (m, 1H), 7.02 (m, 1H), 5.11 (s, 1H), 4.83 (m, 2H), 3.46 (m, 2H), 3.17 (m, 2H), 3.04 (m, 2H), 2.20 (m, 1H), 2.11 (m, 2H), 1.54 (m, 2H)

MS (ESI+) m/z 414 (M+H)$^+$

Example 133

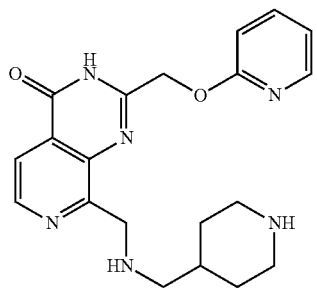 [SMILES: O=c1[nH]c(COc2ccccn2)nc2c(CNCC3CCNCC3)nccc12]

8-(((piperidin-4-ylmethyl)amino)methyl)-2-((pyridin-2-yloxy)methyl)pyrido[3,4-d]pyrimidin-4(3H)-one Using 2-hydroxypyridine, the title compound was obtained (0.6 mg) as described in Scheme 12 (Method L).

$^1$H NMR (CD$_3$OD, 400 MHz) δ 8.62 (d, J=5.2 Hz, 1H), 8.03 (d, J=5.2 Hz, 1H), 7.77 (m, 1H), 7.64 (m, 1H), 6.60 (d, J=10.0 Hz, 1H), 6.49 (m, 1H), 5.19 (s, 1H), 4.82 (m, 2H), 4.51 (s, 1H), 3.44 (m, 2H), 3.32 (m, 2H), 3.02 (m, 2H), 2.12 (m, 1H), 2.04 (m, 2H), 1.51 (m, 2H)

MS (ESI+) m/z 381 (M+H)$^+$

Example 134

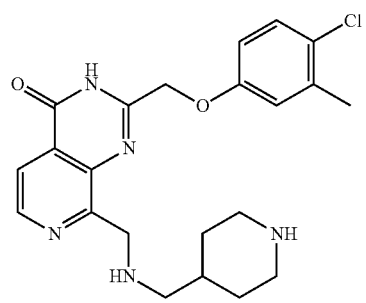 [SMILES: Cc1cc(OCc2nc3c(CNCC4CCNCC4)nccc3c(=O)[nH]2)ccc1Cl]

2-((4-chloro-3-methylphenoxy)methyl)-8-(((piperidin-4-ylmethyl)amino)methyl)pyrido[3,4-d]pyrimidin-4(3H)-one Using 4-ethylphenol, the title compound was obtained (0.9 mg) as described in Scheme 12 (Method L).

MS (ESI+) m/z 428 (M+H)$^+$

Example 135

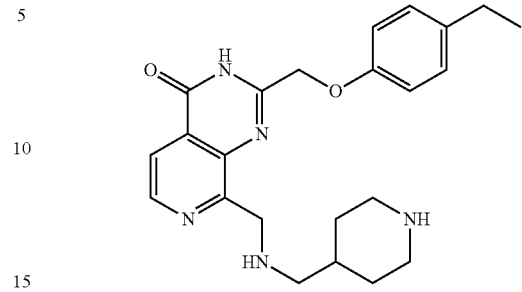

2-((4-ethylphenoxy)methyl)-8-(((piperidin-4-ylmethyl)amino)methyl)pyrido[3,4-d]pyrimidin-4(3H)-one Using 4-ethylphenol, the title compound was obtained (0.6 mg) as described in Scheme 12 (Method L).

MS (ESI+) m/z 408 (M+H)$^+$

Example 136

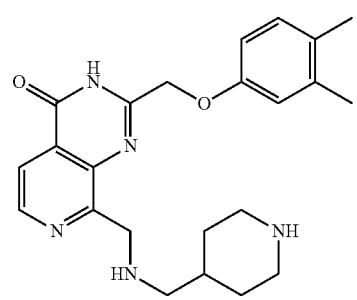 [SMILES: Cc1ccc(OCc2nc3c(CNCC4CCNCC4)nccc3c(=O)[nH]2)cc1C]

2-((3,4-dimethylphenoxy)methyl)-8-(((piperidin-4-ylmethyl)amino)methyl)pyrido[3,4-d]pyrimidin-4(3H)-one Using 3,4-dimethylphenol, the title compound was obtained (0.9 mg) as described in Scheme 12 (Method L).

MS (ESI+) m/z 408 (M+H)$^+$

Example 137

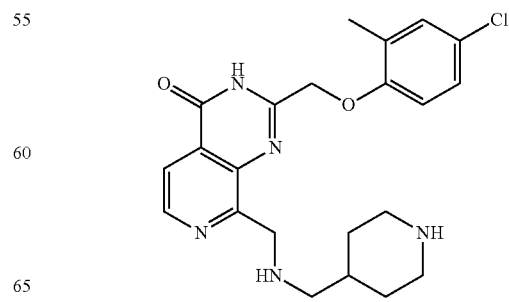

2-((4-chloro-2-methylphenoxy)methyl)-8-(((piperidin-4-ylmethyl)amino)methyl)pyrido[3,4-d]pyrimidin-4(3H)-one Using 4-chloro-2-methylphenol, the title compound was obtained (1.5 mg) as described in Scheme 12 (Method L).

MS (ESI+) m/z 428 (M+H)+

Example 138

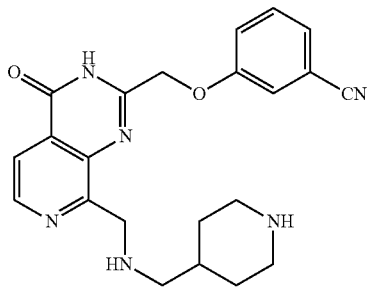 [SMILES: N#Cc1cccc(OCc2nc3c(CNCC4CCNCC4)nccc3c(=O)[nH]2)c1]

3-((4-oxo-8-(((piperidin-4-ylmethyl)amino)methyl)-3,4-dihydropyrido[3,4-d]pyrimidin-2-yl)methoxy)benzonitrile Using 3-cyanophenol, the title compound was obtained (1.9 mg) as described in Scheme 12 (Method L).

MS (ESI+) m/z 405 (M+H)+

Example 139

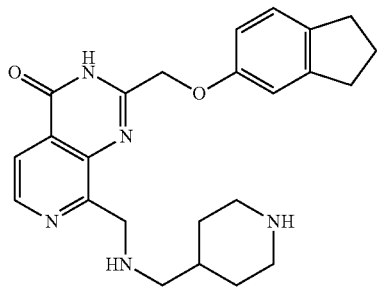 [SMILES: O=c1[nH]c(COc2ccc3c(c2)CCC3)nc2c(CNCC3CCNCC3)nccc12]

2-(((2,3-dihydro-1H-inden-5-yl)oxy)methyl)-8-(((piperidin-4-ylmethyl)amino)methyl)pyrido[3,4-d]pyrimidin-4(3H)-one Using 2,3-dihydro-1H-inden-5-ol, the title compound was obtained (0.9 mg) as described in Scheme 12 (Method L).

MS (ESI+) m/z 420 (M+H)+

Example 140

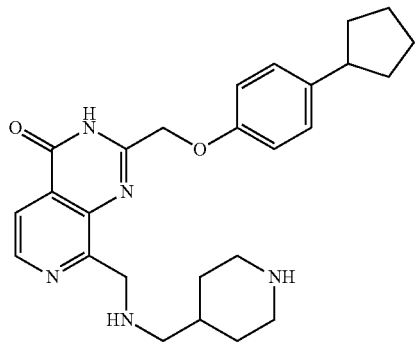 [SMILES: O=c1[nH]c(COc2ccc(C3CCCC3)cc2)nc2c(CNCC3CCNCC3)nccc12]

2-((4-cyclopentylphenoxy)methyl)-8-(((piperidin-4-ylmethyl)amino)methyl)pyrido[3,4-d]pyrimidin-4(3H)-one Using 4-cyclopentylphenol, the title compound was obtained (1.2 mg) as described in Scheme 12 (Method L).
MS (ESI+) m/z 448 (M+H)+

Example 141

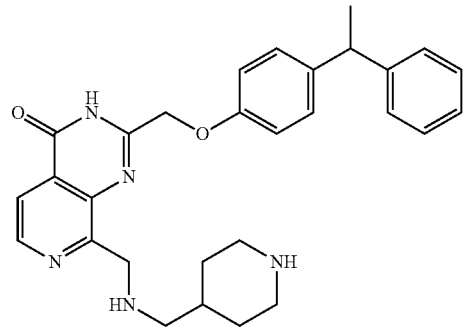 [SMILES: CC(c1ccccc1)c1ccc(OCc2nc3c(CNCC4CCNCC4)nccc3c(=O)[nH]2)cc1]

2-((4-(1-phenylethyl)phenoxy)methyl)-8-(((piperidin-4-ylmethyl)amino)methyl)pyrido[3,4-d]pyrimidin-4(3H)-one Using 4-(1-phenylethyl)phenol, the title compound was obtained (1.3 mg) as described in Scheme 12 (Method L).
MS (ESI+) m/z 484 (M+H)+

Scheme 13 (Method M)

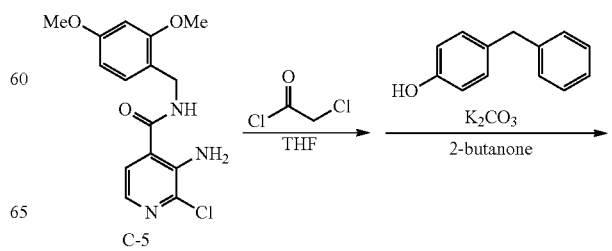

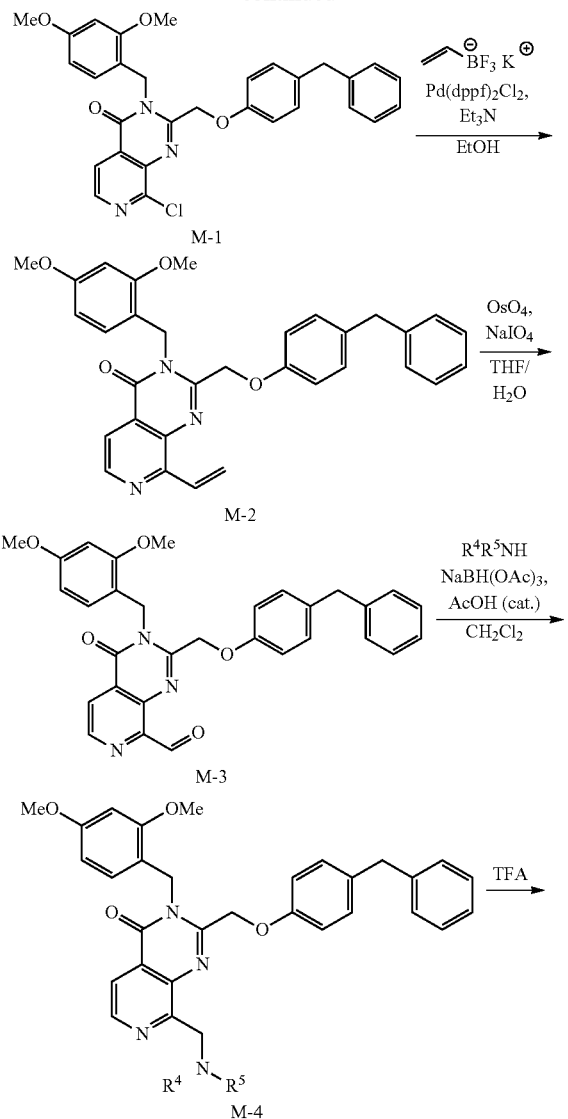

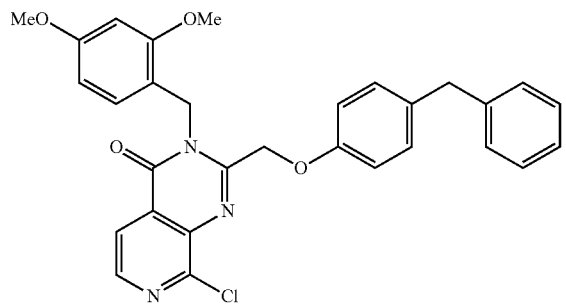 [SMILES: COc1ccc(Cn2c(COc3ccc(Cc4ccccc4)cc3)nc3c(Cl)nccc3c2=O)c(OC)c1]

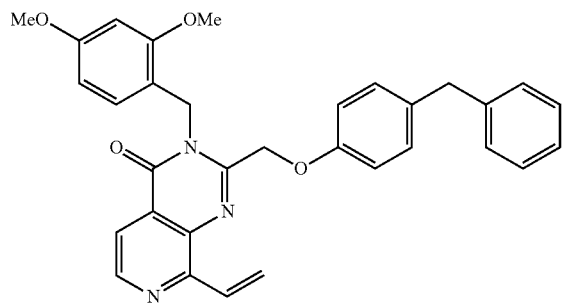 [SMILES: C=Cc1nccc2c(=O)n(Cc3ccc(OC)cc3OC)c(COc3ccc(Cc4ccccc4)cc3)nc12]

The general synthesis of compound M-5 is illustrated in Scheme 13. The intermediate M-2 is synthesized by the 2-step reaction with chloroacetyl chloride and K₂CO₃. Subsequent Suzuki cross-coupling with potassium vinyltrifluoroborate and oxidative cleavage with OsO₄/NaIO₄ introduce the aldehyde group. Reductive amination reaction and deprotection of 2,4-dimethoxybenzyl group by TFA result in the final product.

Example 142

Step 1

2-((4-benzylphenoxy)methyl)-8-chloro-3-(2,4-dimethoxybenzyl)pyrido[3,4-d]pyrimidin-4(3H)-one To a solution of Intermediate C-5 (644 mg, 2.0 mmol) in THF (20 mL) was added chloroacetyl chloride (477 µl, 6.0 mmol) dropwise under nitrogen atmosphere. The reaction mixture was allowed to stir for 2 hours and concentrated in vacuo. The residue was diluted with MEK (40 mL). 4-benzylphenol (442 mg, 2.4 mmol) and K₂CO₃ (828 mg, 6.0 mmol) were added to the suspension. The mixture was heated to reflux and allowed to stir overnight. After cooled to ambient temperature, the mixture was diluted with EtOAc (50 mL). The organic layer was washed with water (50 mL) and brine (25 mL), dried over MgSO₄, filtered and concentrated. The residue was purified by silica gel column chromatography to afford the intermediate M-1 (517 mg, 0.98 mmol).

$^1$H NMR (CDCl₃, 400 MHz) δ 8.42 (d, J=5.2 Hz, 1H), 8.00 (d, J=5.2 Hz, 1H), 7.26 (m, 2H), 7.15 (m, 3H), 7.10 (d, J=8.4 Hz, 2H), 6.98 (d, J=8.8 Hz, 1H), 6.88 (d, J=8.4 Hz, 2H), 6.37 (m, 2H), 5.43 (s, 2H), 5.16 (s, 2H), 3.91 (m, 2H), 3.74 (s, 3H), 3.58 (s, 3H)

MS (ESI+) m/z 528 (M+H)⁺

Step 2

2-((4-benzylphenoxy)methyl)-3-(2,4-dimethoxybenzyl)-8-vinylpyrido[3,4-d]pyrimidin-4(3H)-one To a solution of intermediate M-1 (600 mg, 1.14 mmol) in anhydrous EtOH (20 mL) were added potassium vinyltrifluoroborate (229 mg, 1.71 mmol), Pd(dppf)Cl₂ (dichloromethane adduct, 28 mg, 0.034 mmol) and Et$_3$N (794 µl, 5.70 mmol). Nitrogen flushed. The reaction mixture was heated to 80° C. and allowed to stir for 1 hour. After the mixture was diluted with water (30 mL) and extracted with EtOAc (40 mL), the organic extract was dried over MgSO$_4$, filtered and concentrated. The residue was purified by silica gel column chromatography to afford the intermediate M-2 (440 mg, 0.847 mmol).

$^1$H NMR (CDCl$_3$, 400 MHz) δ 8.64 (d, J=5.6 Hz, 1H), 7.96 (d, J=5.2 Hz, 1H), 7.81 (dd, J=10.8, 17.6 Hz, 1H), 7.26 (m, 2H), 7.15 (m, 3H), 7.09 (d, J=8.8 Hz, 2H), 6.94 (d, J=8.4 Hz, 1H), 6.86 (d, J=8.8 Hz, 2H), 6.59 (dd, J=2.0, 17.2 Hz, 1H), 6.36 (m, 2H), 5.64 (dd, J=2.0, 10.8 Hz, 1H), 5.42 (s, 2H), 5.10 (s, 2H), 3.91 (m, 2H), 3.74 (s, 3H), 3.58 (s, 3H)

MS (ESI+) m/z 520 (M+H)$^+$

Step 3

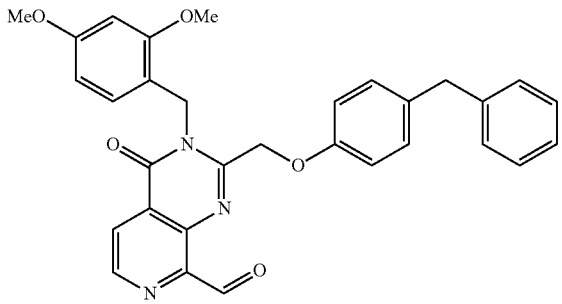 [SMILES: COc1ccc(Cn2c(COc3ccc(Cc4ccccc4)cc3)nc3c(C=O)nccc3c2=O)c(OC)c1]

2-((4-benzylphenoxy)methyl)-3-(2,4-dimethoxybenzyl)-4-oxo-3,4-dihydropyrido[3,4-d]pyrimidine-8-carbaldehyde To a solution of intermediate M-2 (390 mg, 0.75 mmol) in THF (10 mL) and water (10 mL) was added OsO$_4$ (4% in water, 0.59 mL, 0.075 mmol) dropwise. After the mixture was allowed to stir for 5 min, NaIO$_4$ (481 mg, 2.25 mmol) was added and allowed to stir for 2 hours. The reaction mixture was quenched with a saturated aqueous solution of NaHCO$_3$ (30 mL) and extracted with EtOAc (40 mL). The organic extract was dried over MgSO$_4$, filtered and concentrated to afford the intermediate M-3 (quant.) as crude oil. The crude oil was used in the next step without further purification.

MS (ESI+) m/z 522 (M+H)$^+$

Step 4~5

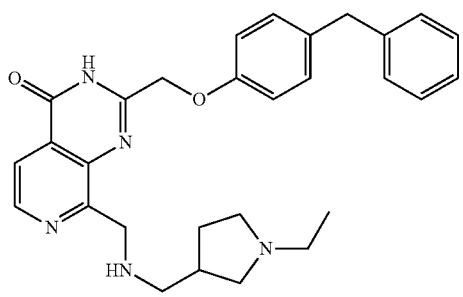 [SMILES: CCN1CCC(CNCc2nccc3c(=O)[nH]c(COc4ccc(Cc5ccccc5)cc4)nc23)C1]

2-((4-benzylphenoxy)methyl)-8-((((1-ethylpyrrolidin-3-yl)methyl)amino)methyl)pyrido[3,4-d]pyrimidin-4(3H)— one To a solution of intermediate M-3 (39 mg as a crude oil, 0.075 mmol) in DCM (1.5 mL) were added (1-ethylpyrrolidin-3-yl)methanamine (0.2M in dioxane, 0.5 mL) and AcOH (catalytic amount). After NaBH(OAc)$_3$ (32 mg, 0.15 mmol) was added, the reaction mixture was allowed to stir for 2 hours and then extracted with UCT SPE CUBCX cartridge. The extract was concentrated in vacuo and the residue was purified by preparative HPLC. The purified residue was dissolved in TFA (1.5 mL). After heated to 50° C. and allowed to stir for 3 hours, the solution was concentrated in vacuo and the resulting residue was purified by preparative HPLC to afford the titled compound (4.9 mg).

$^1$H NMR (CD$_3$OD, 400 MHz) δ 8.66 (d, J=5.6 Hz, 1H), 8.06 (d, J=4.8 Hz, 1H), 7.22 (m, 2H), 7.13 (m, 5H), 6.98 (m, 2H), 5.06 (m, 2H), 3.89 (s, 2H), 3.73 (m, 1H), 3.58 (m, 1H), 3.35 (m, 2H), 3.25 (m, 2H), 2.90 (m, 1H), 2.39 (m, 2H), 2.02 (m, 1H), 1.94 (m, 1H), 1.85 (m, 1H), 1.62 (m, 1H), 1.33 (m, 3H)

MS (ESI+) m/z 484 (M+H)$^+$

Example 143

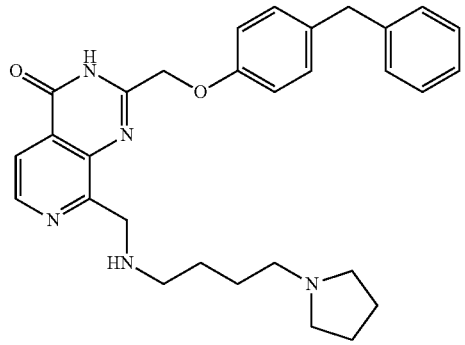 [SMILES: O=c1[nH]c(COc2ccc(Cc3ccccc3)cc2)nc2c(CNCCCCN3CCCC3)nccc12]

2-((4-benzylphenoxy)methyl)-8-(((4-(pyrrolidin-1-yl)butyl)amino)methyl)pyrido[3,4-d]pyrimidin-4(3H)-one Using 4-(pyrrolidin-1-yl)butan-1-amine, the title compound was obtained (5.5 mg) as described in Scheme 13 (Method M).

$^1$H NMR (CD$_3$OD, 400 MHz) δ 8.67 (m, 1H), 8.08 (m, 1H), 7.22 (m, 2H), 7.14 (m, 5H), 6.98 (m, 2H), 5.06 (m, 2H), 4.82 (m, 2H), 3.89 (s, 2H), 3.64 (m, 2H), 3.56 (m, 1H), 3.22 (m, 3H), 3.05 (m, 2H), 2.12 (m, 2H), 2.00 (m, 1H), 1.86 (m, 3H), 1.77 (m, 1H)

MS (ESI+) m/z 498 (M+H)$^+$

Example 144

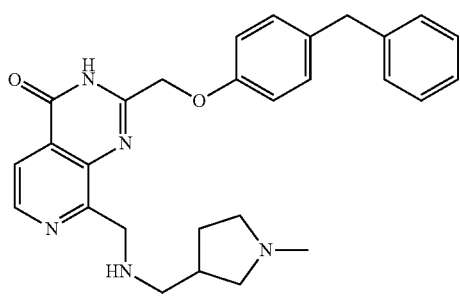 [SMILES: CN1CCC(CNCc2nccc3c(=O)[nH]c(COc4ccc(Cc5ccccc5)cc4)nc23)C1]

2-((4-benzylphenoxy)methyl)-8-((((1-methylpyrrolidin-3-yl)methyl)amino)methyl)pyrido[3,4-d]pyrimidin-4(3H)-one Using (1-methylpyrrolidin-3-yl)methanamine, the title compound was obtained (3.7 mg) as described in Scheme 13 (Method M).

$^1$H NMR (CD$_3$OD, 400 MHz) δ 8.66 (d, J=5.2 Hz, 1H), 8.06 (d, J=4.8 Hz, 1H), 7.22 (m, 2H), 7.14 (m, 5H), 6.98 (m, 2H), 5.06 (s, 2H), 3.89 (s, 2H), 3.71 (m, 1H), 3.58 (m, 1H), 3.35 (m, 2H), 2.95 (s, 3H), 2.92 (m, 1H), 2.43 (m, 2H), 2.04 (m, 1H), 1.91 (m, 2H), 1.64 (m, 1H)

MS (ESI+) m/z 470 (M+H)$^+$

Example 145

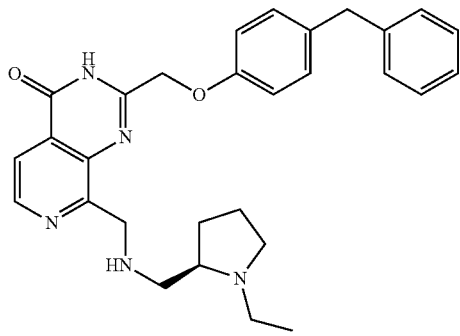 [SMILES: CCN1CCC[C@@H]1CNCc1nccc2c(=O)[nH]c(COc3ccc(Cc4ccccc4)cc3)nc12]

(R)-2-((4-benzylphenoxy)methyl)-8-((((1-ethylpyrrolidin-2-yl)methyl)amino)methyl)pyrido[3,4-d]pyrimidin-4(3H)-one Using (R)-(1-ethylpyrrolidin-2-yl)methanamine, the title compound was obtained (3.2 mg) as described in Scheme 13 (Method M).

$^1$H NMR (CD$_3$OD, 400 MHz) δ 8.65 (d, J=5.2 Hz, 1H), 8.06 (d, J=4.8 Hz, 1H), 7.22 (m, 2H), 7.13 (m, 5H), 6.97 (m, 2H), 5.06 (s, 2H), 3.89 (s, 2H), 3.83 (m, 1H), 3.71 (m, 1H), 3.63 (m, 1H), 3.47 (m, 2H), 3.18 (m, 2H), 2.45 (m, 1H), 2.17 (m, 2H), 2.12 (m, 1H), 1.36 (m, 3H)

MS (ESI+) m/z 484 (M+H)$^+$

Example 146

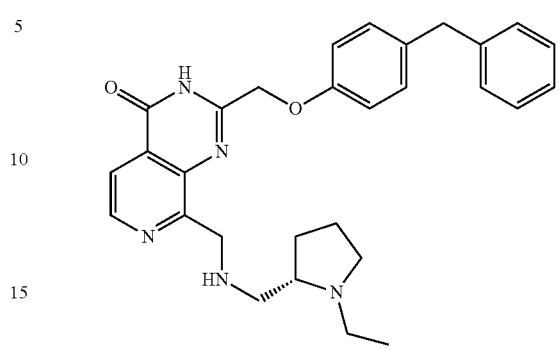

(S)-2-((4-benzylphenoxy)methyl)-8-((((1-ethylpyrrolidin-2-yl)methyl)amino)methyl)pyrido[3,4-d]pyrimidin-4(3H)-one Using (S)-(1-ethylpyrrolidin-2-yl)methanamine, the title compound was obtained (4.3 mg) as described in Scheme 13 (Method M).

$^1$H NMR (CD$_3$OD, 400 MHz) δ 8.65 (d, J=5.6 Hz, 1H), 8.06 (d, J=5.2 Hz, 1H), 7.22 (m, 2H), 7.13 (m, 5H), 6.97 (m, 2H), 5.06 (m, 2H), 3.89 (s, 2H), 3.76 (m, 1H), 3.70 (m, 2H), 3.52 (m, 2H), 3.18 (m, 2H), 3.18 (m, 2H), 2.47 (m, 1H), 2.16 (m, 2H), 2.05 (m, 1H)

MS (ESI+) m/z 484 (M+H)$^+$

Example 147

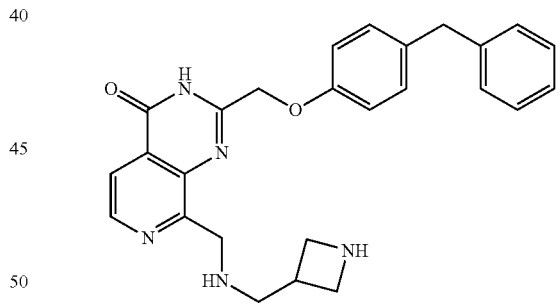

8-(((azetidin-3-ylmethyl)amino)methyl)-2-((4-benzylphenoxy)methyl)pyrido[3,4-d]pyrimidin-4(3H)-one Using tert-butyl 3-(aminomethyl)azetidine-1-carboxylate, the title compound was obtained (5.6 mg) as described in Scheme 13 (Method M).

$^1$H NMR (CD$_3$OD, 400 MHz) δ 8.65 (d, J=5.2 Hz, 1H), 8.06 (d, J=4.8 Hz, 1H), 7.22 (m, 2H), 7.14 (m, 5H), 6.98 (m, 2H), 5.06 (m, 2H), 4.83 (m, 2H), 4.22 (m, 2H), 4.04 (m, 2H), 3.89 (s, 2H), 3.53 (m, 2H), 3.42 (m, 1H)

MS (ESI+) m/z 442 (M+H)$^+$

Example 148

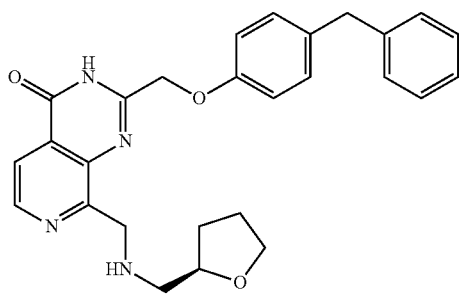 [SMILES: O=c1[nH]c(COc2ccc(Cc3ccccc3)cc2)nc2c(CNC[C@H]3CCCO3)nccc12]

(R)-2-((4-benzylphenoxy)methyl)-8-(((((tetrahydro-furan-2-yl)methyl)amino)methyl)pyrido[3,4-d]pyrimidin-4(3H)-one Using (R)-(tetrahydrofuran-2-yl)methanamine, the title compound was obtained (3.2 mg) as described in Scheme 13 (Method M).

$^1$H NMR (CD$_3$OD, 400 MHz) δ 8.66 (d, J=5.2 Hz, 1H), 8.06 (d, J=5.2 Hz, 1H), 7.22 (m, 2H), 7.13 (m, 5H), 6.98 (m, 2H), 5.07 (m, 2H), 4.81 (m, 1H), 4.25 (m, 2H), 3.92 (m, 1H), 3.89 (s, 2H), 3.82 (m, 1H), 3.33 (m, 1H), 3.12 (m, 1H), 2.13 (m, 1H), 1.96 (m, 2H), 1.62 (m, 1H)

MS (ESI+) m/z 457 (M+H)$^+$

Example 149

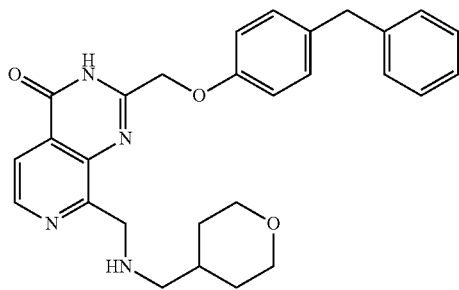 [SMILES: O=c1[nH]c(COc2ccc(Cc3ccccc3)cc2)nc2c(CNCC3CCOCC3)nccc12]

2-((4-benzylphenoxy)methyl)-8-(((((tetrahydro-2H-pyran-4-yl)methyl)amino)methyl)pyrido[3,4-d]pyrimidin-4(3H)-one Using (tetrahydro-2H-pyran-4-yl)methanamine, the title compound was obtained (4.0 mg) as described in Scheme 13 (Method M).

$^1$H NMR (CD$_3$OD, 400 MHz) δ 8.66 (d, J=5.2 Hz, 1H), 8.06 (d, J=4.8 Hz, 1H), 7.22 (m, 2H), 7.14 (m, 5H), 6.98 (m, 2H), 5.07 (s, 2H), 4.80 (m, 2H), 3.96 (m, 2H), 3.89 (m, 2H), 3.43 (m, 2H), 3.07 (m, 2H), 1.83 (m, 1H), 1.73 (m, 2H), 1.40 (m, 2H)

MS (ESI+) m/z 471 (M+H)$^+$

Example 150

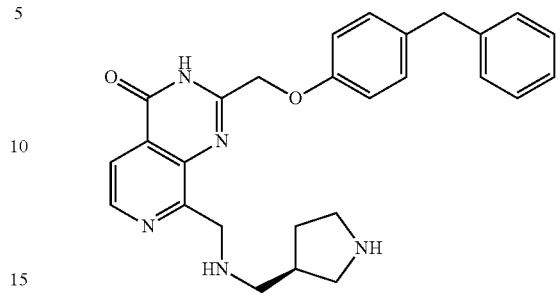

(S)-2-((4-benzylphenoxy)methyl)-8-(((pyrrolidin-3-ylmethyl)amino)methyl)pyrido[3,4-d]pyrimidin-4(3H)-one Using tert-butyl (R)-3-(aminomethyl)pyrrolidine-1-carboxylate, the title compound was obtained (9.4 mg) as described in Scheme 13 (Method M).

$^1$H NMR (CD$_3$OD, 400 MHz) δ 8.66 (d, J=5.6 Hz, 1H), 8.06 (d, J=5.2 Hz, 1H), 7.22 (m, 2H), 7.13 (m, 5H), 6.98 (m, 2H), 5.06 (s, 2H), 4.86 (s, 2H), 3.89 (s, 2H), 3.61 (m, 1H), 3.44 (m, 1H), 3.35 (m, 2H), 3.08 (m, 1H), 2.85 (m, 1H), 2.37 (m, 1H), 1.86 (m, 2H)

MS (ESI+) m/z 456 (M+H)$^+$

Example 151

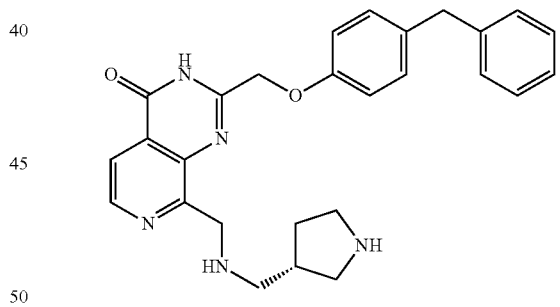

(R)-2-((4-benzylphenoxy)methyl)-8-(((pyrrolidin-3-ylmethyl)amino)methyl)pyrido[3,4-d]pyrimidin-4(3H)-one Using tert-butyl (S)-3-(aminomethyl)pyrrolidine-1-carboxylate, the title compound was obtained (8.2 mg) as described in Scheme 13 (Method M).

$^1$H NMR (CD$_3$OD, 400 MHz) δ 8.66 (d, J=5.2 Hz, 1H), 8.05 (d, J=5.2 Hz, 1H), 7.22 (m, 2H), 7.14 (m, 5H), 6.97 (m, 2H), 5.06 (s, 2H), 4.86 (s, 2H), 3.88 (s, 2H), 3.61 (m, 1H), 3.45 (m, 1H), 3.35 (m, 2H), 3.08 (m, 1H), 2.85 (m, 1H), 2.37 (m, 1H), 1.86 (m, 2H)

MS (ESI+) m/z 456 (M+H)$^+$

Example 152

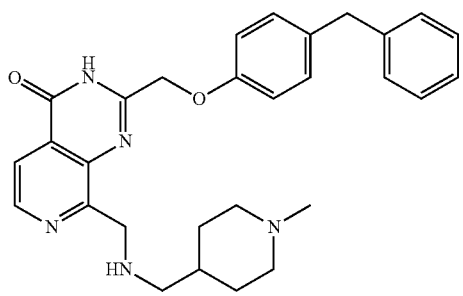 [SMILES: CN1CCC(CNCc2nccc3c(=O)[nH]c(COc4ccc(Cc5ccccc5)cc4)nc23)CC1]

2-((4-benzylphenoxy)methyl)-8-((((1-methylpiperidin-4-yl)methyl)amino)methyl)pyrido[3,4-d]pyrimidin-4(3H)-one Using (1-methylpiperidin-4-yl)methanamine, the title compound was obtained (3.2 mg) as described in Scheme 13 (Method M).

$^1$H NMR (CD$_3$OD, 400 MHz) δ 8.66 (d, J=5.2 Hz, 1H), 8.06 (d, J=4.8 Hz, 1H), 7.22 (m, 2H), 7.14 (m, 5H), 6.98 (m, 2H), 5.06 (s, 2H), 4.84 (s, 2H), 3.89 (s, 2H), 3.57 (m, 2H), 3.16 (m, 2H), 3.02 (m, 2H), 2.86 (s, 3H), 2.20 (m, 1H), 2.14 (m, 2H), 1.59 (m, 2H)

MS (ESI+) m/z 484 (M+H)$^+$

Example 153

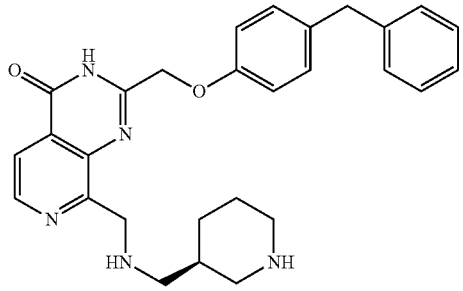 [SMILES: O=c1[nH]c(COc2ccc(Cc3ccccc3)cc2)nc2c(CNC[C@H]3CCCNC3)nccc12]

(S)-2-((4-benzylphenoxy)methyl)-8-(((piperidin-3-ylmethyl)amino)methyl)pyrido[3,4-d]pyrimidin-4(3H)-one Using tert-butyl (R)-3-(aminomethyl)piperidine-1-carboxylate, the title compound was obtained (10.6 mg) as described in Scheme 13 (Method M).

$^1$H NMR (CD$_3$OD, 400 MHz) δ 8.65 (d, J=5.6 Hz, 1H), 8.05 (d, J=5.2 Hz, 1H), 7.22 (m, 2H), 7.13 (m, 5H), 6.97 (m, 2H), 5.06 (s, 2H), 4.84 (s, 2H), 3.88 (s, 2H), 3.54 (m, 1H), 3.38 (m, 1H), 3.18 (m, 2H), 2.93 (m, 1H), 2.83 (m, 1H), 2.36 (m, 1H), 2.07 (m, 1H), 1.99 (m, 1H), 1.79 (m, 1H), 1.41 (m, 1H)

MS (ESI+) m/z 470 (M+H)$^+$

Example 154

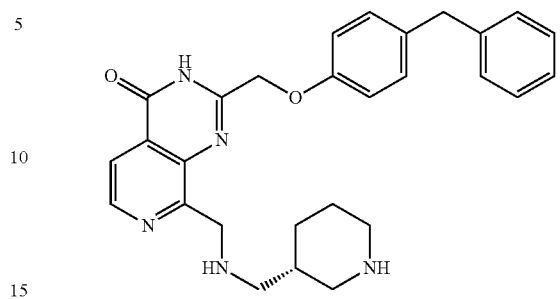

(R)-2-((4-benzylphenoxy)methyl)-8-(((piperidin-3-ylmethyl)amino)methyl)pyrido[3,4-d]pyrimidin-4(3H)-one Using tert-butyl (S)-3-(aminomethyl)piperidine-1-carboxylate, the title compound was obtained (9.0 mg) as described in Scheme 13 (Method M).

$^1$H NMR (CD$_3$OD, 400 MHz) δ 8.65 (d, J=5.2 Hz, 1H), 8.05 (d, J=4.8 Hz, 1H), 7.22 (m, 2H), 7.14 (m, 5H), 6.98 (m, 2H), 5.06 (s, 2H), 4.84 (s, 2H), 3.88 (s, 2H), 3.54 (m, 1H), 3.38 (m, 1H), 3.18 (m, 2H), 2.93 (m, 1H), 2.83 (m, 1H), 2.36 (m, 1H), 2.07 (m, 1H), 2.00 (m, 1H), 1.79 (m, 1H), 1.42 (m, 1H)

MS (ESI+) m/z 470 (M+H)$^+$

Example 155

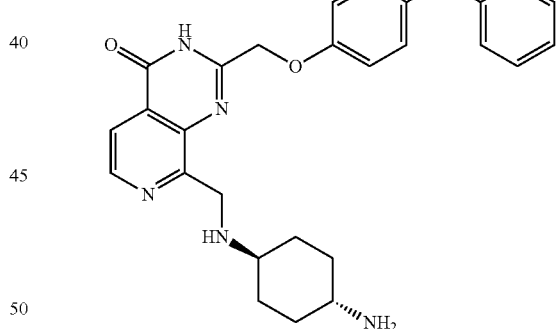

8-((((1r,4r)-4-aminocyclohexyl)amino)methyl)-2-((4-benzylphenoxy)methyl)pyrido[3,4-d]pyrimidin-4(3H)-one Using N-Boc-trans-1,4-cyclohexanediamine, the title compound was obtained (9.2 mg) as described in Scheme 13 (Method M).

$^1$H NMR (CD$_3$OD, 400 MHz) δ 8.65 (d, J=5.6 Hz, 1H), 8.05 (d, J=5.2 Hz, 1H), 7.22 (m, 2H), 7.14 (m, 5H), 6.98 (m, 2H), 5.07 (s, 2H), 4.82 (s, 2H), 3.89 (s, 2H), 3.31 (m, 1H), 3.15 (m, 1H), 2.35 (m, 2H), 2.18 (m, 2H), 1.65 (m, 2H), 1.53 (m, 2H)

MS (ESI+) m/z 470 (M+H)$^+$

Example 156

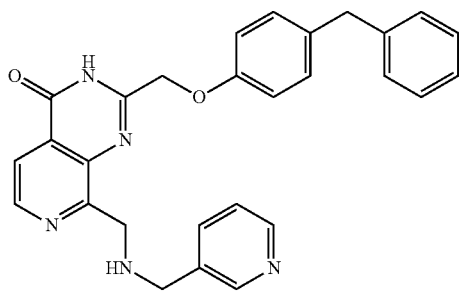 [SMILES: O=c1[nH]c(COc2ccc(Cc3ccccc3)cc2)nc2c(CNCc3cccnc3)nccc12]

2-((4-benzylphenoxy)methyl)-8-(((pyridin-3-ylmethyl)amino)methyl)pyrido[3,4-d]pyrimidin-4(3H)-one Using pyridin-3-ylmethanamine, the title compound was obtained (7.3 mg) as described in Scheme 13 (Method M).

$^1$H NMR (CD$_3$OD, 400 MHz) δ 8.76 (m, 1H), 8.67 (m, 1H), 8.15 (m, 1H), 8.05 (m, 1H), 7.63 (m, 1H), 7.23 (m, 2H), 7.14 (m, 5H), 6.97 (m, 2H), 5.06 (s, 2H), 4.86 (s, 2H), 4.48 (s, 2H), 3.88 (s, 2H)

MS (ESI+) m/z 464 (M+H)$^+$

Example 157

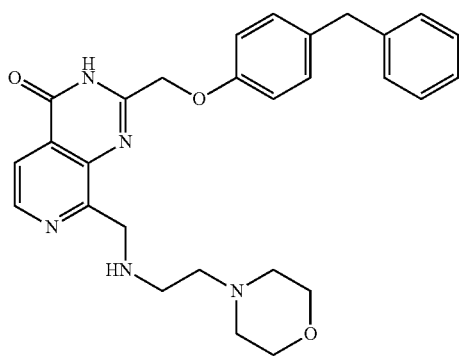 [SMILES: O=c1[nH]c(COc2ccc(Cc3ccccc3)cc2)nc2c(CNCCN3CCOCC3)nccc12]

2-((4-benzylphenoxy)methyl)-8-(((2-morpholinoethyl)amino)methyl)pyrido[3,4-d]pyrimidin-4(3H)-one Using 2-morpholinoethan-1-amine, the title compound (12.9 mg) was obtained as described in Scheme 13 (Method M).

$^1$H NMR (400 MHz, CD$_3$OD) δ 8.63 (d, J=5.2 Hz, 1H), 8.04 (d, J=5.2 Hz, 1H), 7.21 (m, 2H), 7.13 (m, 5H), 6.97 (m, 2H), 5.06 (s, 2H), 4.89 (s, 2H), 3.85 (m, 4H), 3.57 (m, 2H), 3.32 (m, 2H), 3.07 (m, 4H)

MS (ESI+) m/z 486 (M+H)$^+$

Scheme 14 (Method N)

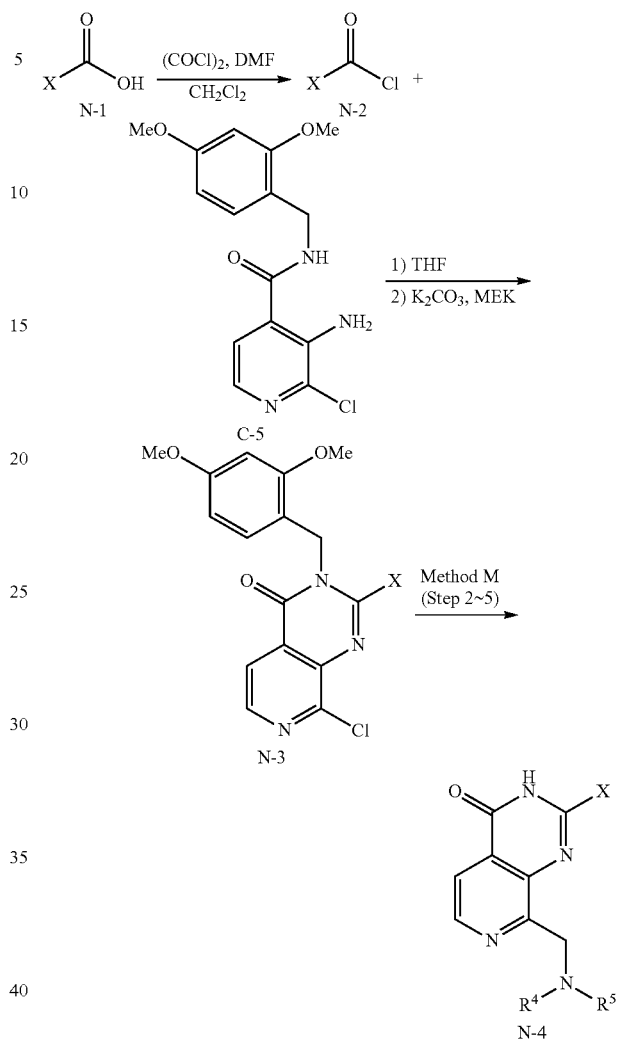

The general synthesis of compounds N-4 is illustrated in Scheme 14. Carboxylic acid is converted to the acid chloride intermediate N-2 by (COCl)$_2$. The subsequent 2-step reaction result in intermediate N-3, which is reacted by the same procedure as described in Method M (Step 2~5) to provide the final compound.

Example 158

Step 1

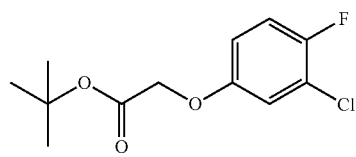 [SMILES: CC(C)(C)OC(=O)COc1ccc(F)c(Cl)c1]

tert-butyl 2-(3-chloro-4-fluorophenoxy)acetate

To a solution of tert-butyl bromoacetate (30.9 mL, 209.5 mmol, 1.0 eq) and 3-chloro-4-fluorophenol (30.7 g, 209.5 mmol, 1.0 eq) in DMF (300 mL) was added K₂CO₃ (63.6 g, 461 mmol, 2.2 eq). The mixture was stirred for 2 hours. It was diluted with EA and the organic layer was washed with brine 3 times. The organic extract was dried over MgSO₄ and concentrated to afford tert-butyl 2-(3-chloro-4-fluorophenoxy)acetate (quant.). The residue was used in the next step without further purification.

MS (ESI+) m/z 261 (M+H)⁺

Step 2

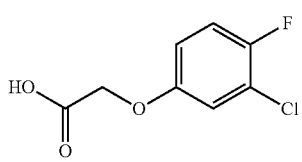 [SMILES: O=C(O)COc1ccc(F)c(Cl)c1]

2-(3-chloro-4-fluorophenoxy)acetic acid

To a solution of tert-butyl 2-(3-chloro-4-fluorophenoxy) acetate in DCM (300 mL) was added TFA (150 mL). The mixture was stirred for 2 hours and concentrated in vacuo. The residue was crystallized with n-hexane to provide the intermediate N-1 (41.3 g, 96% yield) as a white solid.

MS (ESI+) m/z 205 (M+H)⁺

Step 3

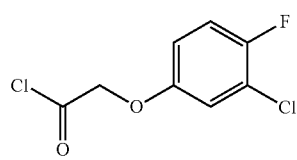 [SMILES: O=C(Cl)COc1ccc(F)c(Cl)c1]

2-(3-chloro-4-fluorophenoxy)acetyl chloride

To a suspension of intermediate N-1 (43.5 g, 213 mmol) in DCM were added (COCl)₂ (27.4 mL, 319 mmol) and DMF (1 mL) at 0° C. The mixture was allowed to stir for 3 hours and concentrated in vacuo to afford the intermediate N-2 (quant.). The residue was used in the next step without further purification.

MS (ESI+) m/z 219 (M+H)⁺

(The acyl chloride is converted to methyl ester in LC-MS sample due to MeOH as sampling solvent)

Step 4

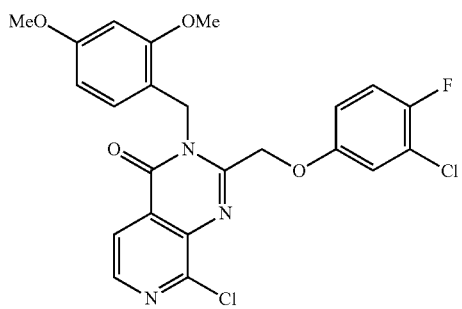 [SMILES: COc1ccc(Cn2c(COc3ccc(F)c(Cl)c3)nc3c(Cl)nccc3c2=O)c(OC)c1]

8-chloro-2-((3-chloro-4-fluorophenoxy)methyl)-3-(2,4-dimethoxybenzyl)pyrido[3,4-d]pyrimidin-4(3H)-one To intermediate N-2 (213 mmol, crude) in THF (500 mL) was added 3-amino-2-chloro-N-(2,4-dimethoxybenzyl)isonicotinamide (42.9 g, 133 mmol). The reaction mixture was allowed to stir for 2 hours. The precipitate was filtered off and washed with THF. To a suspension of the collected solid in MEK (500 mL) was added K₂CO₃ (18.4 g, 399 mmol). The mixture was heated at reflux and allowed to stir overnight. After the reaction was cooled to room temperature, water (400 mL) was poured. The mixture was allowed to stir vigorously for 30 min under ice bath. The precipitate was filtered off and washed with water. The solid was collected and dried under reduced pressure to afford the intermediate N-3 (54.5 g, 82% yield).

Step 5~8. (Same Procedure as Described in Method M)

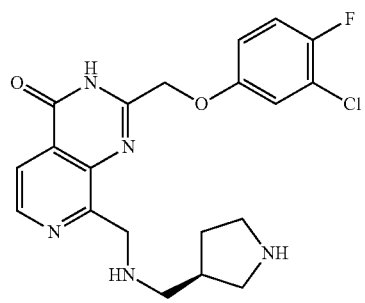 [SMILES: O=c1[nH]c(COc2ccc(F)c(Cl)c2)nc2c(CNC[C@H]3CCNC3)nccc12]

(S)-2-((3-chloro-4-fluorophenoxy)methyl)-8-(((pyrrolidin-3-ylmethyl)amino)methyl)pyrido[3,4-d]pyrimidin-4(3H)-one Using tert-butyl (R)-3-(aminomethyl)pyrrolidine-1-carboxylate, the title compound (3.4 mg) was obtained as described in Scheme 14 (Method N).

¹H NMR (400 MHz, CD₃OD) δ 8.67 (d, J=5.2 Hz, 1H), 8.07 (d, J=5.2 Hz, 1H), 7.22 (m, 1H), 7.19 (m, 1H), 7.04 (m, 1H), 5.09 (s, 2H), 4.85 (s, 2H), 3.60 (m, 1H), 3.46 (m, 1H), 3.36 (m, 2H), 3.29 (m, 1H), 3.09 (m, 1H), 2.86 (m, 1H), 2.38 (m, 1H), 1.87 (m, 1H)

MS (ESI+): m/z 418 (M+H)⁺

Example 159

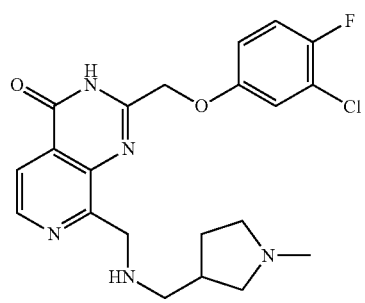 [SMILES: CN1CCC(CNCc2nccc3c(=O)[nH]c(COc4ccc(F)c(Cl)c4)nc23)C1]

2-((3-chloro-4-fluorophenoxy)methyl)-8-((((1-methylpyrrolidin-3-yl)methyl)amino)methyl)pyrido[3,4-d]pyrimidin-4(3H)-one Using (1-methylpyrrolidin-3-yl)methanamine, the title compound (5.1 mg) was obtained as described in Scheme 14 (Method N)
$^1$H NMR (400 MHz, CD$_3$OD) δ 8.67 (d, J=5.2 Hz, 1H), 8.07 (d, J=5.2 Hz, 1H), 7.24 (m, 1H), 7.19 (m, 1H), 7.03 (m, 1H), 5.09 (s, 2H), 4.85 (s, 2H), 3.60 (m, 1H), 3.46 (m, 1H), 3.42 (m, 1H), 3.36 (m, 2H), 2.96 (s, 3H), 2.45 (m, 2H), 2.04 (m, 1H), 1.95 (m, 1H), 1.64 (m, 1H)
MS (ESI+) m/z 432 (M+H)$^+$ Example 160

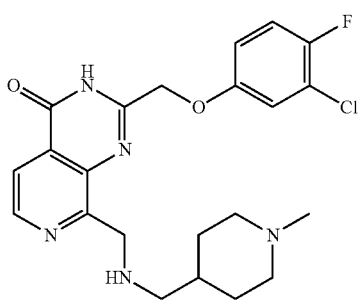 [SMILES: CN1CCC(CNCc2nccc3c(=O)[nH]c(COc4ccc(F)c(Cl)c4)nc23)CC1]

2-((3-chloro-4-fluorophenoxy)methyl)-8-((((1-methylpiperidin-4-yl)methyl)amino)methyl)pyrido[3,4-d]pyrimidin-4(3H)-one Using (1-methylpiperidin-4-yl)methanamine, the title compound (6.2 mg) was obtained as described in Scheme 14 (Method N).
$^1$H NMR (400 MHz, CD$_3$OD) δ 8.67 (d, J=5.2 Hz, 1H), 8.06 (d, J=5.2 Hz, 1H), 7.23 (m, 1H), 7.19 (m, 1H), 7.03 (m, 1H), 5.09 (s, 2H), 4.83 (s, 2H), 3.58 (m, 2H), 3.17 (m, 2H), 3.04 (m, 2H), 2.87 (s, 3H), 2.21 (m, 1H), 2.15 (m, 2H), 1.62 (m, 2H)
MS (ESI+) m/z 446 (M+H)$^+$ Example 161

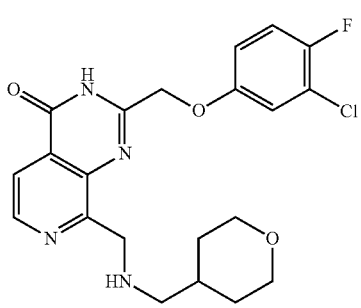 [SMILES: O=c1[nH]c(COc2ccc(F)c(Cl)c2)nc2c(CNCC3CCOCC3)nccc12]

2-((3-chloro-4-fluorophenoxy)methyl)-8-((((tetrahydro-2H-pyran-4-yl)methyl)amino)methyl)pyrido[3,4-d]pyrimidin-4(3H)-one Using (tetrahydropyran-4-yl)methanamine, the title compound (4.4 mg) was obtained as described in Scheme 14 (Method N).
$^1$H NMR (400 MHz, CD3OD) δ 8.67 (d, J=5.2 Hz, 1H), 8.06 (d, J=5.2 Hz, 1H), 7.24 (m, 1H), 7.19 (m, 1H), 7.03 (m, 1H), 5.10 (s, 2H), 4.80 (s, 2H), 3.97 (m, 2H), 3.44 (m, 2H), 3.19 (m, 2H), 3.09 (m, 2H), 2.09 (m, 1H), 1.75 (m, 2H), 1.39 (m, 2H)
MS (ESI+) m/z 433 (M+H)$^+$ Example 162

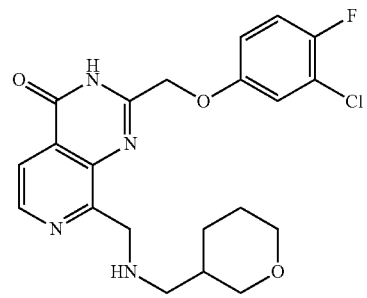 [SMILES: O=c1[nH]c(COc2ccc(F)c(Cl)c2)nc2c(CNCC3CCCOC3)nccc12]

2-((3-chloro-4-fluorophenoxy)methyl)-8-((((tetrahydro-2H-pyran-3-yl)methyl)amino)methyl)pyrido[3,4-d]pyrimidin-4(3H)-one Using (tetrahydropyran-3-yl)methanamine, the title compound (3.7 mg) was obtained as described in Scheme 14 (Method N).
$^1$H NMR (400 MHz, CD$_3$OD) δ 8.68 (d, J=5.2 Hz, 1H), 8.06 (d, J=5.2 Hz, 1H), 7.25 (m, 1H), 7.19 (m, 1H), 7.03 (m, 1H), 5.10 (s, 2H), 4.79 (s, 2H), 3.94 (m, 1H), 3.81 (m, 1H), 3.49 (m, 1H), 3.31 (m, 1H), 3.10 (m, 2H), 2.10 (m, 1H), 1.98 (m, 1H), 1.65 (m, 2H), 1.46 (m, 1H)
MS (ESI+) m/z 433 (M+H)$^+$ Example 163

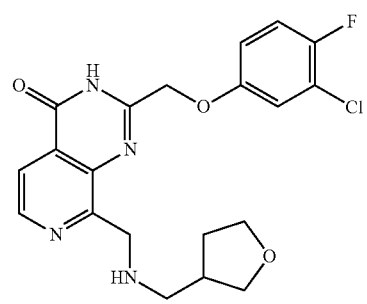 [SMILES: O=c1[nH]c(COc2ccc(F)c(Cl)c2)nc2c(CNCC3CCOC3)nccc12]

2-((3-chloro-4-fluorophenoxy)methyl)-8-((((tetrahydrofuran-3-yl)methyl)amino)methyl)pyrido[3,4-d]pyrimidin-4(3H)-one Using (tetrahydrofuran-3-yl)methanamine, the title compound (4.7 mg) was obtained as described in Scheme 14 (Method N).
$^1$H NMR (400 MHz, CD$_3$OD) δ 8.68 (d, J=5.2 Hz, 1H), 8.06 (d, J=5.2 Hz, 1H), 7.24 (m, 1H), 7.19 (m, 1H), 7.04 (m, 1H), 5.10 (s, 2H), 4.81 (s, 2H), 3.91 (m, 2H), 3.77 (m, 1H), 3.60 (m, 1H), 3.23 (m, 2H), 2.70 (m, 1H), 2.21 (m, 1H), 1.75 (m, 1H)
MS (ESI+) m/z 419 (M+H)$^+$

Example 164

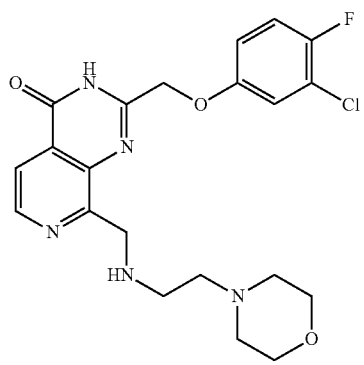 [SMILES: O=c1[nH]c(COc2ccc(F)c(Cl)c2)nc2c(CNCCN3CCOCC3)nccc12]

2-((3-chloro-4-fluorophenoxy)methyl)-8-(((2-morpholinoethyl)amino)methyl)pyrido[3,4-d]pyrimidin-4(3H)-one Using 2-morpholinoethan-1-amine, the title compound (13.3 mg) was obtained as described in Scheme 14 (Method N).

$^1$H NMR (400 MHz, CD$_3$OD) δ 8.65 (d, J=5.2 Hz, 1H), 8.06 (d, J=5.2 Hz, 1H), 7.23 (m, 1H), 7.18 (m, 1H), 7.03 (m, 1H), 5.09 (s, 2H), 4.88 (s, 2H), 3.86 (m, 4H), 3.59 (m, 2H), 3.31 (m, 2H), 3.08 (m, 4H)

MS (ESI+) m/z 448 (M+H)$^+$

Example 165

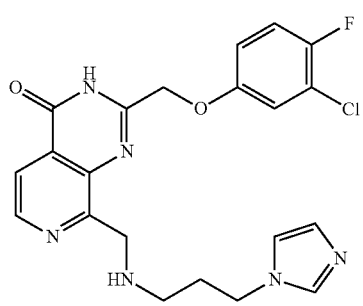 [SMILES: O=c1[nH]c(COc2ccc(F)c(Cl)c2)nc2c(CNCCCn3ccnc3)nccc12]

8-(((3-(1H-imidazol-1-yl)propyl)amino)methyl)-2-((3-chloro-4-fluorophenoxy)methyl)pyrido[3,4-d]pyrimidin-4(3H)-one Using 3-(1H-imidazol-1-yl)propan-1-amine, the title compound (14.3 mg) was obtained as described in Scheme 14 (Method N).

$^1$H NMR (400 MHz, CD$_3$OD) δ 9.00 (s, 1H), 8.65 (d, J=5.2 Hz, 1H), 8.05 (d, J=5.2 Hz, 1H), 7.70 (s, 1H), 7.60 (s, 1H), 7.23 (m, 1H), 7.18 (m, 1H), 7.04 (m, 1H), 5.08 (s, 2H), 4.83 (s, 2H), 4.43 (m, 2H), 3.29 (m, 2H), 2.43 (m, 2H)

MS (ESI+) m/z 443 (M+H)$^+$

Example 166

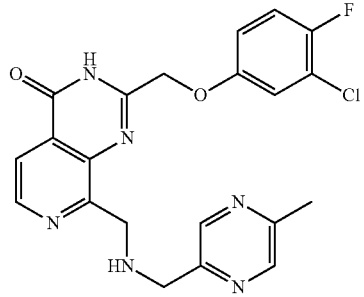 [SMILES: Cc1cnc(CNCc2nccc3c(=O)[nH]c(COc4ccc(F)c(Cl)c4)nc23)cn1]

2-((3-chloro-4-fluorophenoxy)methyl)-8-((((5-methylpyrazin-2-yl)methyl)amino)methyl)pyrido[3,4-d]pyrimidin-4(3H)-one Using (5-methylpyrazin-2-yl)methanamine, the title compound (8.4 mg) was obtained as described in Scheme 14 (Method N).

$^1$H NMR (400 MHz, CD$_3$OD) δ 8.68 (d, J=5.2 Hz, 1H), 8.58 (m, 1H), 8.53 (m, 1H), 8.06 (d, J=5.2 Hz, 1H), 7.23 (m, 1H), 7.17 (m, 1H), 7.03 (m, 1H), 5.09 (s, 2H), 4.91 (s, 2H), 4.59 (s, 2H), 2.58 (s, 3H)

MS (ESI+) m/z 441 (M+H)$^+$

Example 167

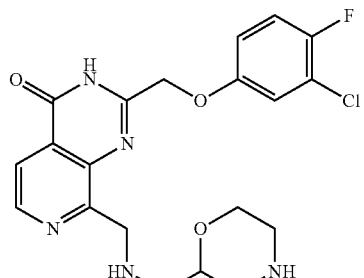

2-((3-chloro-4-fluorophenoxy)methyl)-8-(((morpholin-2-ylmethyl)amino)methyl)pyrido[3,4-d]pyrimidin-4(3H)-one Using morpholin-2-ylmethanamine, the title compound (10.7 mg) was obtained as described in Scheme 14 (Method N).

$^1$H NMR (400 MHz, CD$_3$OD) δ 8.66 (d, J=5.2 Hz, 1H), 8.05 (d, J=5.2 Hz, 1H), 7.23 (m, 1H), 7.18 (m, 1H), 7.03 (m, 1H), 5.09 (s, 2H), 4.83 (s, 2H), 4.25 (m, 1H), 4.17 (m, 1H), 3.89 (m, 1H), 3.43 (m, 1H), 3.37 (m, 1H), 3.18 (m, 2H), 3.01 (m, 1H), 1.29 (m, 1H)

MS (ESI+) m/z 434 (M+H)$^+$

Example 168

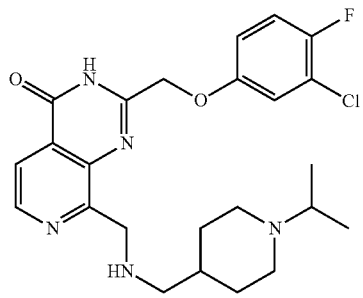 [SMILES: CC(C)N1CCC(CNCc2nccc3c(=O)[nH]c(COc4ccc(F)c(Cl)c4)nc23)CC1]

2-((3-chloro-4-fluorophenoxy)methyl)-8-((((1-isopropylpiperidin-4-yl)methyl)amino)methyl)pyrido[3,4-d]pyrimidin-4(3H)-one Using (1-isopropylpiperidin-4-yl)methanamine, the title compound (20.0 mg) was obtained as described in Scheme 14 (Method N).

$^1$H NMR (400 MHz, CD$_3$OD) δ 8.66 (d, J=5.2 Hz, 1H), 8.06 (d, J=5.2 Hz, 1H), 7.24 (m, 1H), 7.19 (m, 1H), 7.03 (m, 1H), 5.09 (s, 2H), 4.83 (s, 2H), 3.52 (m, 2H), 3.19 (m, 2H), 3.07 (m, 2H), 2.20 (m, 3H), 1.65 (m, 2H), 1.35 (m, 2H), 1.35 (d, J=6.4 Hz, 6H)

MS (ESI+) m/z 474 (M+H)$^+$

Example 169

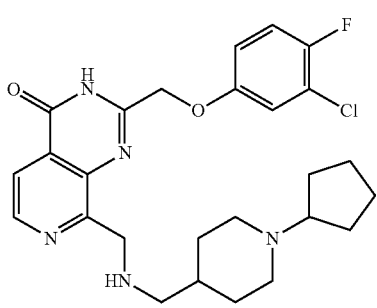 [SMILES: O=c1[nH]c(COc2ccc(F)c(Cl)c2)nc2c(CNCC3CCN(C4CCCC4)CC3)nccc12]

2-((3-chloro-4-fluorophenoxy)methyl)-8-((((1-cyclopentylpiperidin-4-yl)methyl)amino)methyl)pyrido[3,4-d]pyrimidin-4(3H)-one Using (1-cyclopentylpiperidin-4-yl)methanamine, the title compound (30.0 mg) was obtained as described in Scheme 14 (Method N).

$^1$H NMR (400 MHz, CD$_3$OD) δ 8.66 (d, J=5.2 Hz, 1H), 8.06 (d, J=5.2 Hz, 1H), 7.24 (m, 1H), 7.19 (m, 1H), 7.04 (m, 1H), 5.09 (s, 2H), 4.83 (s, 2H), 3.67 (m, 2H), 3.49 (m, 2H), 3.19 (m, 2H), 3.01 (m, 2H), 2.17 (m, 5H), 1.69 (m, 8H)

MS (ESI+) m/z 501 (M+H)$^+$

Example 170

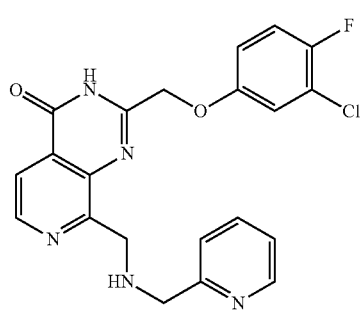 [SMILES: O=c1[nH]c(COc2ccc(F)c(Cl)c2)nc2c(CNCc3ccccn3)nccc12]

2-((3-chloro-4-fluorophenoxy)methyl)-8-(((pyridin-2-ylmethyl)amino)methyl)pyrido[3,4-d]pyrimidin-4(3H)-one Using pyridin-2-ylmethanamine, the title compound (1.7 mg) was obtained as described in Scheme 14 (Method N).

$^1$H NMR (400 MHz, CD$_3$OD) δ 8.69 (d, J=5.6 Hz, 1H), 8.63 (d, J=5.2 Hz, 1H), 8.07 (d, J=5.6 Hz, 1H), 7.86 (m, 1H), 7.44 (m, 2H), 7.22 (dd, J=2.4, 5.6 Hz, 1H), 7.17 (m, 1H), 7.03 (m, 1H), 5.09 (s, 2H), 4.88 (s, 2H), 4.55 (s, 2H)

MS (ESI+) m/z 426 (M+H)$^+$

Example 171

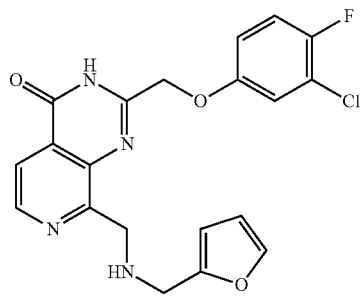

2-((3-chloro-4-fluorophenoxy)methyl)-8-(((furan-2-ylmethyl)amino)methyl)pyrido[3,4-d]pyrimidin-4(3H)-one Using furan-2-ylmethanamine, the title compound (1.5 mg) was obtained as described in Scheme 14 (Method N).

$^1$H NMR (400 MHz, CD$_3$OD) δ 8.66 (d, J=5.2 Hz, 1H), 8.05 (d, J=5.2 Hz, 1H), 7.61 (d, J=1.2 Hz, 1H), 7.23 (dd, J=3.2, 5.6 Hz, 1H), 7.18 (m, 1H), 7.02 (m, 1H), 6.63 (d, J=3.2 Hz, 1H), 6.48 (m, 1H), 5.09 (s, 2H), 4.75 (s, 2H), 4.45 (s, 2H)

MS (ESI+) m/z 415 (M+H)$^+$

Example 172

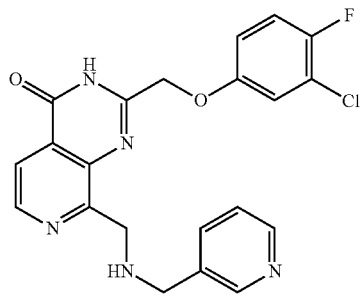 [SMILES: O=c1[nH]c(COc2ccc(F)c(Cl)c2)nc2c(CNCc3cccnc3)nccc12]

2-((3-chloro-4-fluorophenoxy)methyl)-8-(((pyridin-3-ylmethyl)amino)methyl)pyrido[3,4-d]pyrimidin-4(3H)-one Using pyridin-3-ylmethanamine (0.4 mg), the title compound was obtained as described in Scheme 14 (Method N).

$^1$H NMR (400 MHz, CD$_3$OD) δ 8.72 (s, 1H), 8.68 (d, J=5.2 Hz, 1H), 8.64 (d, J=3.2 Hz, 1H), 8.06 (m, 2H), 7.56 (m, 1H), 7.23 (dd, J=3.2, 5.6 Hz, 1H), 7.18 (m, 1H), 7.03 (m, 1H), 5.09 (s, 2H), 4.85 (s, 2H), 4.48 (s, 2H)

MS (ESI+) m/z 426 (M+H)$^+$

Example 173

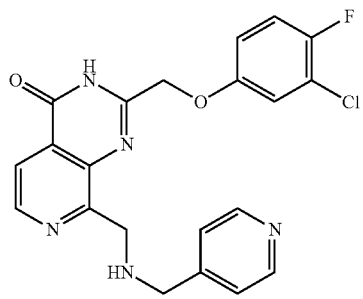 [SMILES: O=c1[nH]c(COc2ccc(F)c(Cl)c2)nc2c(CNCc3ccncc3)nccc12]

2-((3-chloro-4-fluorophenoxy)methyl)-8-(((pyridin-4-ylmethyl)amino)methyl)pyrido[3,4-d]pyrimidin-4(3H)-one Using pyridin-4-ylmethanamine, the title compound (0.6 mg) was obtained as described in Scheme 14 (Method N).

$^1$H NMR (400 MHz, CD$_3$OD) δ 8.68 (m, 3H), 8.08 (d, J=4.8 Hz, 1H), 7.63 (d, J=6.0 Hz, 2H), 7.22 (m, 1H), 7.18 (m, 1H), 7.02 (m, 1H), 5.08 (s, 2H), 4.86 (s, 2H), 4.49 (s, 2H)

MS (ESI+) m/z 426 (M+H)$^+$

Example 174

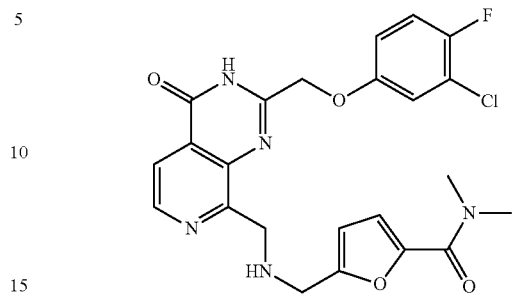

5-((((2-((3-chloro-4-fluorophenoxy)methyl)-4-oxo-3,4-dihydropyrido[3,4-d]pyrimidin-8-yl)methyl)amino)methyl)-N,N-dimethylfuran-2-carboxamide Using 5-(aminomethyl)-N,N-dimethylfuran-2-carboxamide, the title compound (1.0 mg) was obtained as described in Scheme 14 (Method N).

$^1$H NMR (400 MHz, CD$_3$OD) δ 8.65 (d, J=5.2 Hz, 1H), 8.05 (d, J=5.2 Hz, 1H), 7.23 (dd, J=3.2, 6.0 Hz, 1H), 7.18 (m, 1H), 7.02 (m, 2H), 6.74 (d, J=3.6 Hz, 1H), 5.09 (s, 2H), 4.90 (s, 2H), 4.52 (s, 2H), 3.29 (s, 6H)

MS (ESI+) m/z 486 (M+H)$^+$

Example 175

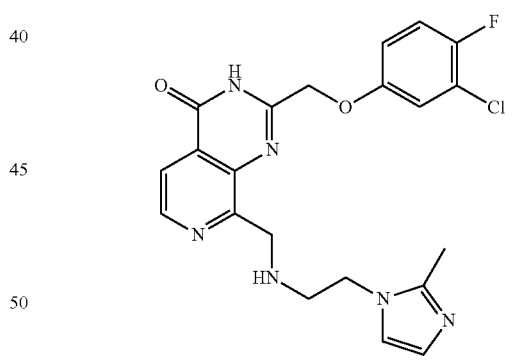

2-((3-chloro-4-fluorophenoxy)methyl)-8-(((2-(2-methyl-1H-imidazol-1-yl)ethyl)amino)methyl)pyrido[3,4-d]pyrimidin-4(3H)-one Using 2-(2-methyl-1H-imidazol-1-yl)ethan-1-amine, the title compound (0.2 mg) was obtained as described in Scheme 14 (Method N).

$^1$H NMR (600 MHz, CD$_3$OD) δ 8.82 (m, 1H), 8.06 (m, 1H), 7.25 (m, 1H), 7.20 (m, 2H), 7.05 (m, 2H), 5.10 (s, 2H), 4.89 (s, 2H), 3.20 (m, 2H), 2.67 (m, 2H), 2.15 (s, 3H)

MS (ESI+) m/z 443 (M+H)$^+$

Example 176

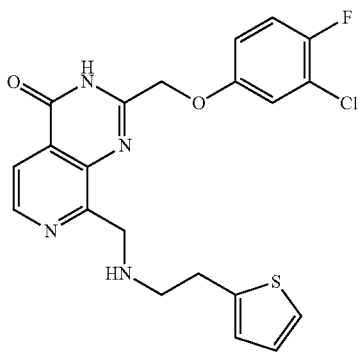 [SMILES: O=c1[nH]c(COc2ccc(F)c(Cl)c2)nc2c(CNCCc3cccs3)nccc12]

2-((3-chloro-4-fluorophenoxy)methyl)-8-(((2-(thiophen-2-yl)ethyl)amino)methyl)pyrido[3,4-d]pyrimidin-4(3H)-one Using 2-(thiophen-2-yl)ethan-1-amine, the title compound (2.9 mg) was obtained as described in Scheme 14 (Method N).

$^1$H NMR (400 MHz, CD$_3$OD) δ 8.66 (d, J=5.2 Hz, 1H), 8.06 (d, J=5.2 Hz, 1H), 7.30 (dd, J=1.2, 4.8 Hz, 1H), 7.24 (dd, J=2.8, 6.0 Hz, 1H), 7.18 (m, 1H), 7.00 (m, 3H), 5.08 (s, 2H), 4.82 (s, 2H), 3.47 (m, 2H), 3.33 (m, 2H)

MS (ESI+) m/z 445 (M+H)$^+$

Example 177

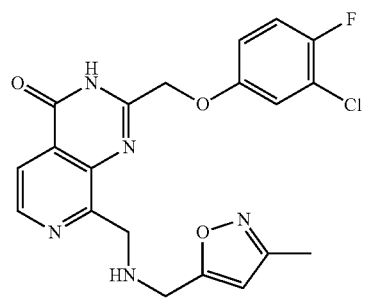 [SMILES: Cc1cc(CNCc2nccc3c(=O)[nH]c(COc4ccc(F)c(Cl)c4)nc23)on1]

2-((3-chloro-4-fluorophenoxy)methyl)-8-((((3-methylisoxazol-5-yl)methyl)amino)methyl)pyrido[3,4-d]pyrimidin-4(3H)-one Using (3-methylisoxazol-5-yl)methanamine, the title compound (2.2 mg) was obtained as described in Scheme 14 (Method N).

$^1$H NMR (400 MHz, CD$_3$OD) δ 8.67 (d, J=5.2 Hz, 1H), 8.06 (d, J=5.6 Hz, 1H), 7.23 (dd, J=3.2, 6.0 Hz, 1H), 7.19 (m, 1H), 7.03 (m, 1H), 6.51 (s, 1H), 5.09 (s, 2H), 4.84 (s, 2H), 4.59 (s, 2H), 2.30 (s, 3H)

MS (ESI+) m/z 430 (M+H)$^+$

Example 178

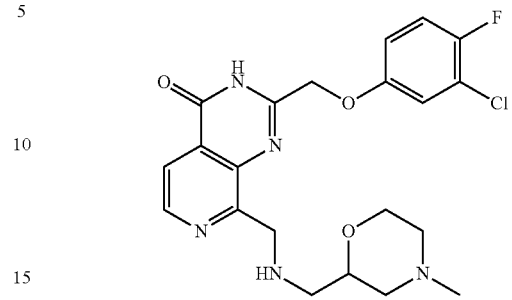

2-((3-chloro-4-fluorophenoxy)methyl)-8-((((4-methylmorpholin-2-yl)methyl)amino)methyl)pyrido[3,4-d]pyrimidin-4(3H)-one Using (4-methylmorpholin-2-yl)methanamine, the title compound (9.8 mg) was obtained as described in Scheme 14 (Method N).

$^1$H NMR (400 MHz, CD$_3$OD) δ 8.66 (d, J=5.2 Hz, 1H), 8.06 (d, J=5.2 Hz, 1H), 7.23 (m, 1H), 7.18 (m, 1H), 7.03 (m, 1H), 5.09 (s, 2H), 4.84 (s, 2H), 4.30 (m, 1H), 4.21 (m, 1H), 3.91 (m, 1H), 3.50 (m, 3H), 3.33 (m, 1H), 3.15 (m, 1H), 2.97 (m, 1H), 2.97 (s, 3H)

MS (ESI+) m/z 448 (M+H)$^+$

Example 179

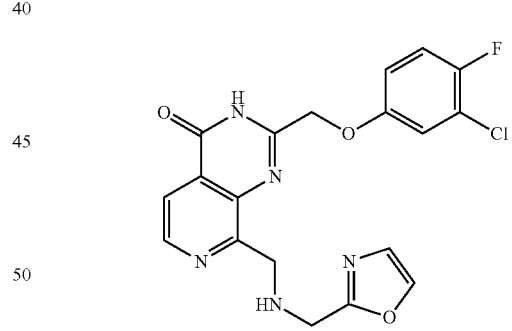

2-((3-chloro-4-fluorophenoxy)methyl)-8-(((oxazol-2-ylmethyl)amino)methyl)pyrido[3,4-d]pyrimidin-4(3H)-one Using oxazol-2-ylmethanamine, the title compound (3.2 mg) was obtained as described in Scheme 14 (Method N).

$^1$H NMR (400 MHz, CD$_3$OD) δ 8.67 (d, J=5.2 Hz, 1H), 8.06 (d, J=5.6 Hz, 1H), 8.02 (s, 1H), 7.21 (m, 3H), 7.03 (m, 1H), 5.09 (s, 2H), 4.95 (s, 2H), 4.64 (s, 2H)

MS (ESI+) m/z 416 (M+H)$^+$

Example 180

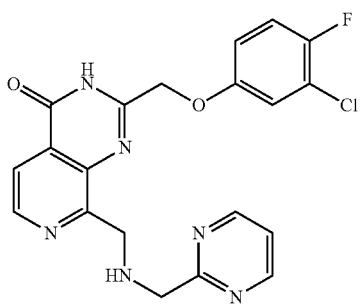 [SMILES: O=c1[nH]c(COc2ccc(F)c(Cl)c2)nc2c(CNCc3ncccn3)nccc12]

2-((3-chloro-4-fluorophenoxy)methyl)-8-(((pyrimidin-2-ylmethyl)amino)methyl)pyrido[3,4-d]pyrimidin-4(3H)-one Using pyrimidin-2-ylmethanamine, the title compound (14.3 mg) was obtained as described in Scheme 14 (Method N).

$^1$H NMR (400 MHz, CD$_3$OD) δ 8.85 (d, J=5.2 Hz, 2H), 8.69 (d, J=5.6 Hz, 1H), 8.07 (d, J=5.2 Hz, 1H), 7.49 (m, 1H), 7.23 (dd, J=2.8, 5.6 Hz, 1H), 7.17 (m, 1H), 7.03 (m, 1H) 5.09 (s, 2H), 4.98 (s, 2H), 4.69 (s, 2H)

MS (ESI+) m/z 427 (M+H)$^+$

Example 181

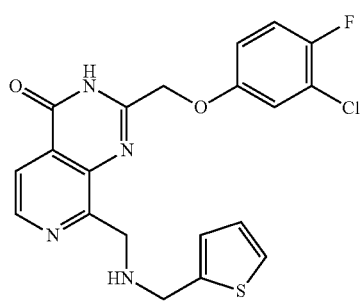

2-((3-chloro-4-fluorophenoxy)methyl)-8-(((thiophen-2-ylmethyl)amino)methyl)pyrido[3,4-d]pyrimidin-4(3H)-one Using thiophen-2-ylmethanamine, the title compound (9.3 mg) was obtained as described in Scheme 14 (Method N).

$^1$H NMR (400 MHz, CD$_3$OD) δ 8.67 (d, J=5.2 Hz, 1H), 8.05 (d, J=5.6 Hz, 1H), 7.56 (d, J=5.2 Hz, 1H), 7.31 (d, J=3.6 Hz, 1H), 7.22 (dd, J=2.8, 5.6 Hz, 1H), 7.17 (m, 1H), 7.10 (m, 1H), 7.02 (m, 1H), 5.08 (s, 2H), 4.78 (s, 2H), 4.63 (s, 2H)

MS (ESI+) m/z 431 (M+H)$^+$

Example 182

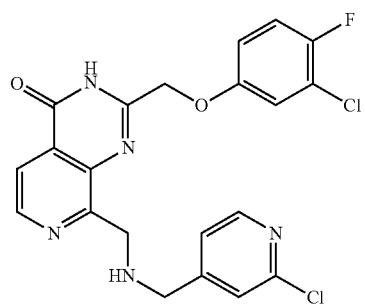 [SMILES: O=c1[nH]c(COc2ccc(F)c(Cl)c2)nc2c(CNCc3ccnc(Cl)c3)nccc12]

2-((3-chloro-4-fluorophenoxy)methyl)-8-((((2-chloropyridin-4-yl)methyl)amino)methyl)pyrido[3,4-d]pyrimidin-4(3H)-one Using (2-chloropyridin-4-yl)methanamine, the title compound (8.8 mg) was obtained as described in Scheme 14 (Method N).

$^1$H NMR (400 MHz, CD$_3$OD) δ 8.68 (d, J=5.2 Hz, 1H), 8.45 (d, J=5.2 Hz, 1H), 8.06 (d, J=5.2 Hz, 1H), 7.64 (s, 1H), 7.51 (d, J=5.2 Hz, 1H), 7.22 (dd, J=2.4, 5.6 Hz, 1H), 7.18 (m, 1H), 7.03 (m, 1H), 5.09 (s, 2H), 4.86 (s, 2H), 4.46 (s, 2H)

MS (ESI+) m/z 460 (M+H)$^+$

Example 183

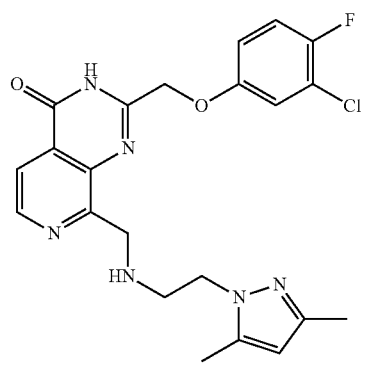 [SMILES: Cc1cc(C)n(CCNCc2nccc3c(=O)[nH]c(COc4ccc(F)c(Cl)c4)nc23)n1]

2-((3-chloro-4-fluorophenoxy)methyl)-8-(((2-(3,5-dimethyl-1H-pyrazol-1-yl)ethyl)amino)methyl)pyrido[3,4-d]pyrimidin-4(3H)-one Using 2-(3,5-dimethyl-1H-pyrazol-1-yl)ethan-1-amine, the title compound (11.5 mg) was obtained as described in Scheme 14 (Method N).

$^1$H NMR (400 MHz, CD$_3$OD) δ 8.65 (d, J=5.6 Hz, 1H), 8.05 (d, J=5.2 Hz, 1H), 7.22 (dd, J=2.8, 5.6 Hz, 1H), 7.17 (m, 1H), 7.02 (m, 1H), 5.89 (s, 1H), 5.08 (s, 2H), 4.84 (s, 2H), 4.38 (t, J=5.6 Hz, 2H), 3.62 (t, J=5.6 Hz, 2H), 2.27 (s, 3H), 2.15 (s, 3H)

MS (ESI+) m/z 457 (M+H)$^+$

Example 184

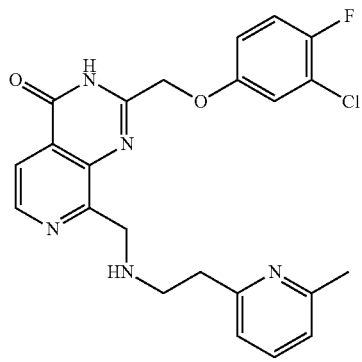 [SMILES: Cc1cccc(CCNCc2nccc3c(=O)[nH]c(COc4ccc(F)c(Cl)c4)nc23)n1]

2-((3-chloro-4-fluorophenoxy)methyl)-8-(((2-(6-methylpyridin-2-yl)ethyl)amino)methyl)pyrido[3,4-d]pyrimidin-4(3H)-one Using 2-(6-methylpyridin-2-yl)ethan-1-amine, the title compound (19.0 mg) was obtained as described in Scheme 14 (Method N).

$^1$H NMR (400 MHz, CD$_3$OD) δ 8.66 (d, J=4.8 Hz, 1H), 8.15 (m, 1H), 8.05 (d, J=5.2 Hz, 1H), 7.59 (m, 2H), 7.22 (dd, J=2.8, 6.0 Hz, 1H), 7.17 (m, 1H), 7.03 (m, 1H), 5.09 (s, 2H), 4.89 (s, 2H), 3.68 (t, J=7.6 Hz, 2H), 3.47 (t, J=7.6 Hz, 2H), 2.69 (s, 3H)

MS (ESI+) m/z 454 (M+H)$^+$

Example 185

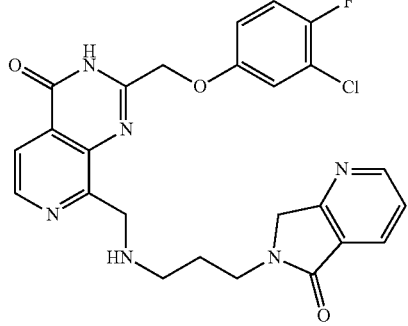

2-((3-chloro-4-fluorophenoxy)methyl)-8-(((3-(5-oxo-5,7-dihydro-6H-pyrrolo[3,4-b]pyridin-6-yl)propyl)amino)methyl)pyrido[3,4-d]pyrimidin-4(3H)-one Using 6-(3-aminopropyl)-6,7-dihydro-5H-pyrrolo[3,4-b]pyridin-5-one, the title compound (4.6 mg) was obtained as described in Scheme 14 (Method N).

MS (ESI+) m/z 509 (M+H)$^+$

Example 186

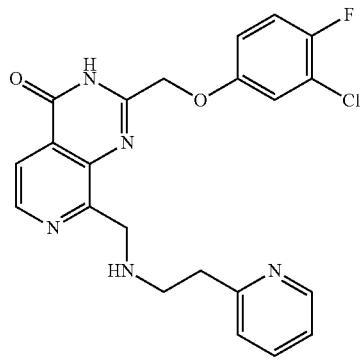 [SMILES: O=c1[nH]c(COc2ccc(F)c(Cl)c2)nc2c(CNCCc3ccccn3)nccc12]

2-((3-chloro-4-fluorophenoxy)methyl)-8-(((2-(pyridin-2-yl)ethyl)amino)methyl)pyrido[3,4-d]pyrimidin-4(3H)-one Using 2-(pyridin-2-yl)ethan-1-amine, the title compound (9.9 mg) was obtained as described in Scheme 14 (Method N).

$^1$H NMR (400 MHz, CD$_3$OD) δ 8.66 (d, J=5.2 Hz, 1H), 8.57 (d, J=4.8 Hz, 1H), 8.06 (d, J=5.6 Hz, 1H), 7.95 (m, 1H), 7.51 (d, J=8.0 Hz, 1H), 7.44 (m, 1H), 7.23 (dd, J=2.4, 5.6 Hz, 1H), 7.17 (m, 1H), 7.02 (m, 1H), 5.09 (s, 2H), 4.87 (s, 2H), 3.63 (t, J=7.2 Hz, 2H), 3.35 (t, J=6.8 Hz, 2H)

MS (ESI+) m/z 440 (M+H)$^+$

Example 187

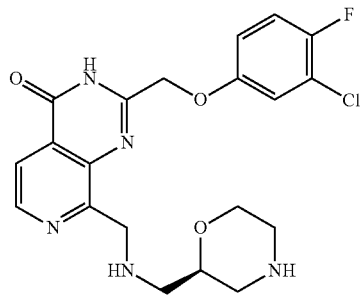 [SMILES: O=c1[nH]c(COc2ccc(F)c(Cl)c2)nc2c(CNC[C@@H]3CNCCO3)nccc12]

(R)-2-((3-chloro-4-fluorophenoxy)methyl)-8-(((morpholin-2-ylmethyl)amino)methyl)pyrido[3,4-d]pyrimidin-4(3H)-one Using (R)-morpholin-2-ylmethanamine, the title compound (11.1 mg) was obtained as described in Scheme 14 (Method N).

$^1$H NMR (400 MHz, CD$_3$OD) δ 8.66 (d, J=5.2 Hz, 1H), 8.05 (d, J=5.2 Hz, 1H), 7.23 (m, 1H), 7.18 (m, 1H), 7.03 (m, 1H), 5.09 (s, 2H), 4.83 (s, 2H), 4.25 (m, 1H), 4.17 (m, 1H), 3.89 (m, 1H), 3.43 (m, 1H), 3.37 (m, 1H), 3.18 (m, 2H), 3.01 (m, 1H), 1.29 (m, 1H)

MS (ESI+) m/z 434 (M+H)$^+$

Example 188

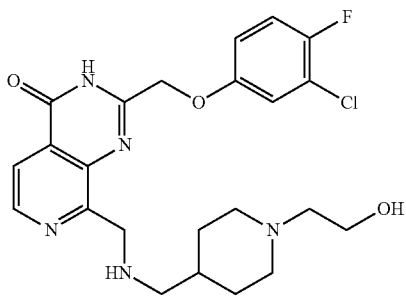 [SMILES: O=c1[nH]c(COc2ccc(F)c(Cl)c2)nc2c(CNCC3CCN(CCO)CC3)nccc12]

2-((3-chloro-4-fluorophenoxy)methyl)-8-((((1-(2-hydroxyethyl)piperidin-4-yl)methyl)amino)methyl)pyrido[3,4-d]pyrimidin-4(3H)-one Using 2-(4-(aminomethyl)piperidin-1-yl)ethan-1-ol, the title compound (13.8 mg) was obtained as described in Scheme 14 (Method N).

$^1$H NMR (400 MHz, CD$_3$OD) δ 8.66 (d, J=5.2 Hz, 1H), 8.06 (d, J=5.2 Hz, 1H), 7.24 (m, 1H), 7.18 (m, 1H), 7.03 (m, 1H), 5.09 (s, 2H), 4.83 (s, 2H), 3.87 (m, 2H), 3.71 (m, 2H), 3.24 (m, 2H), 3.18 (m, 2H), 3.07 (m, 2H), 2.21 (m, 1H), 2.16 (m, 2H), 1.67 (m, 2H)

MS (ESI+) m/z 476 (M+H)$^+$

Example 189

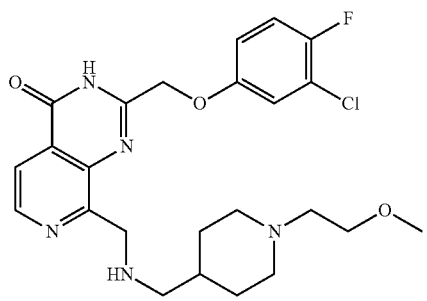 [SMILES: COCCN1CCC(CNCc2nccc3c(=O)[nH]c(COc4ccc(F)c(Cl)c4)nc23)CC1]

2-((3-chloro-4-fluorophenoxy)methyl)-8-((((1-(2-methoxyethyl)piperidin-4-yl)methyl)amino)methyl)pyrido[3,4-d]pyrimidin-4(3H)-one Using (1-(2-methoxyethyl)piperidin-4-yl)methanamine, the title compound (11.6 mg) was obtained as described in Scheme 14 (Method N).

$^1$H NMR (400 MHz, CD$_3$OD) δ 8.66 (d, J=5.2 Hz, 1H), 8.06 (d, J=5.2 Hz, 1H), 7.24 (m, 1H), 7.18 (m, 1H), 7.03 (m, 1H), 5.09 (s, 2H), 4.83 (s, 2H), 3.70 (m, 2H), 3.67 (m, 2H), 3.39 (s, 3H), 3.33 (m, 2H), 3.17 (m, 2H), 3.05 (m, 2H), 2.21 (m, 1H), 2.15 (m, 2H), 1.66 (m, 2H)

MS (ESI+) m/z 490 (M+H)$^+$

Example 190

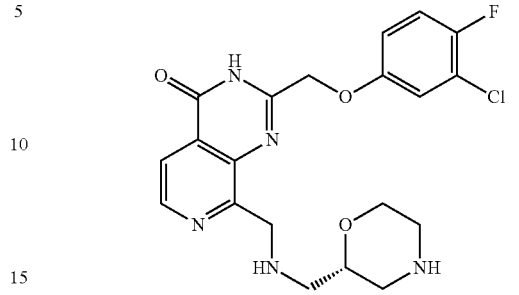

(S)-2-((3-chloro-4-fluorophenoxy)methyl)-8-(((morpholin-2-ylmethyl)amino)methyl)pyrido[3,4-d]pyrimidin-4(3H)-one Using (S)-morpholin-2-ylmethanamine, the title compound (22.8 mg) was obtained as described in Scheme 14 (Method N).

$^1$H NMR (400 MHz, CD$_3$OD) δ 8.66 (d, J=5.2 Hz, 1H), 8.05 (d, J=5.2 Hz, 1H), 7.23 (m, 1H), 7.18 (m, 1H), 7.03 (m, 1H), 5.09 (s, 2H), 4.83 (s, 2H), 4.25 (m, 1H), 4.17 (m, 1H), 3.89 (m, 1H), 3.43 (m, 1H), 3.37 (m, 1H), 3.18 (m, 2H), 3.01 (m, 1H), 1.29 (m, 1H)

MS (ESI+) m/z 434 (M+H)$^+$

Example 191

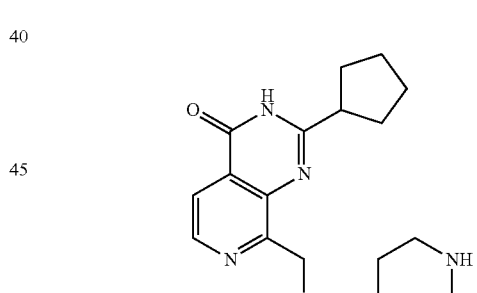

2-cyclopentyl-8-(((piperidin-4-ylmethyl)amino)methyl)pyrido[3,4-d]pyrimidin-4(3H)-one Using cyclopentanecarbonyl chloride and tert-butyl 4-(aminomethyl)piperidine-1-carboxylate, the title compound (3.2 mg) was obtained as described in Scheme 14 (Method N).

$^1$H NMR (400 MHz, CD$_3$OD) δ 8.59 (d, J=5.2 Hz, 1H), 8.01 (d, J=5.2 Hz, 1H), 4.84 (s, 2H), 3.44 (m, 2H), 3.20 (m, 2H), 3.10 (m, 1H), 3.05 (m, 2H), 2.20 (m, 1H), 2.12 (m, 2H), 2.04 (m, 4H), 1.85 (m, 2H), 1.72 (m, 2H), 1.56 (m, 2H)

MS (ESI+) m/z 342 (M+H)$^+$

Example 192

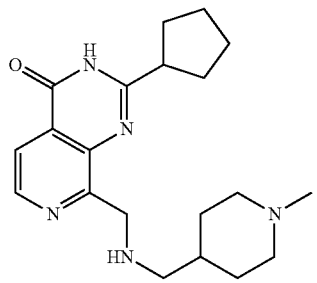

2-cyclopentyl-8-((((1-methylpiperidin-4-yl)methyl)amino)methyl)pyrido[3,4-d]pyrimidin-4(3H)-one Using cyclopentanecarbonyl chloride and (1-methylpiperidin-4-yl)methanamine, the title compound (2.6 mg) was obtained as described in Scheme 14 (Method N).

$^1$H NMR (400 MHz, CD$_3$OD) δ 8.58 (d, J=5.2 Hz, 1H), 8.02 (d, J=5.2 Hz, 1H), 4.84 (s, 2H), 3.58 (m, 2H), 3.20 (m, 2H), 3.10 (m, 1H), 3.04 (m, 2H), 2.87 (s, 3H), 2.16 (m, 3H), 2.03 (m, 4H), 1.84 (m, 2H), 1.73 (m, 2H), 1.61 (m, 2H)

MS (ESI+) m/z 356 (M+H)$^+$

Example 193

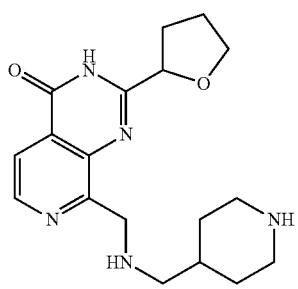 [SMILES: O=c1[nH]c(C2CCCO2)nc2c(CNCC3CCNCC3)nccc12]

8-(((piperidin-4-ylmethyl)amino)methyl)-2-(tetrahydrofuran-2-yl)pyrido[3,4-d]pyrimidin-4(3H)-one Using tetrahydrofuran-2-carboxylic acid and tert-butyl 4-(aminomethyl)piperidine-1-carboxylate, the title compound (13.0 mg) was obtained as described in Scheme 14 (Method N).

$^1$H NMR (400 MHz, CD$_3$OD) δ 8.62 (d, J=5.2 Hz, 1H), 8.03 (d, J=5.2 Hz, 1H), 4.89 (m, 1H), 4.84 (s, 2H), 4.12 (m, 1H), 3.96 (m, 1H), 3.46 (m, 2H), 3.18 (m, 2H), 3.04 (m, 2H), 2.40 (m, 1H), 2.23 (m, 2H), 2.11 (m, 2H), 2.02 (m, 2H), 1.57 (m, 2H)

MS (ESI+) m/z 344 (M+H)$^+$

Example 194

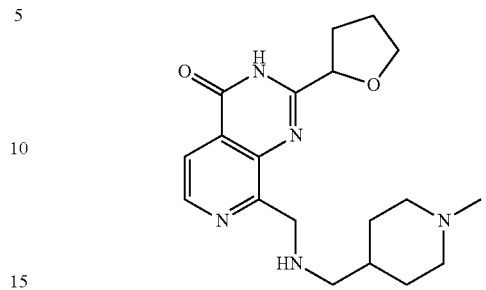

8-((((1-methylpiperidin-4-yl)methyl)amino)methyl)-2-(tetrahydrofuran-2-yl)pyrido[3,4-d]pyrimidin-4(3H)-one Using tetrahydrofuran-2-carboxylic acid and (1-methylpiperidin-4-yl)methanamine, the title compound (9.4 mg) was obtained as described in Scheme 14 (Method N).

$^1$H NMR (400 MHz, CD$_3$OD) δ 8.62 (d, J=5.2 Hz, 1H), 8.03 (d, J=5.2 Hz, 1H), 4.87 (m, 1H), 4.84 (s, 2H), 4.12 (m, 1H), 3.96 (m, 1H), 3.58 (m, 2H), 3.18 (m, 2H), 3.04 (m, 2H), 2.87 (s, 3H), 2.41 (m, 1H), 2.23 (m, 2H), 2.15 (m, 2H), 2.02 (m, 2H), 1.61 (m, 2H)

MS (ESI+) m/z 358 (M+H)$^+$

Example 195

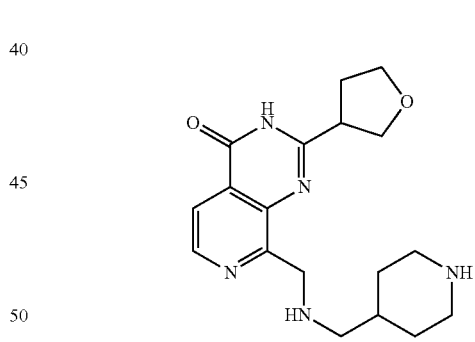

8-(((piperidin-4-ylmethyl)amino)methyl)-2-(tetrahydrofuran-3-yl)pyrido[3,4-d]pyrimidin-4(3H)-one Using tetrahydrofuran-3-carboxylic acid and tert-butyl 4-(aminomethyl)piperidine-1-carboxylate, the title compound (8.4 mg) was obtained as described in Scheme 14 (Method N).

$^1$H NMR (400 MHz, CD$_3$OD) δ 8.61 (d, J=5.2 Hz, 1H), 8.01 (d, J=5.2 Hz, 1H), 4.17 (m, 1H), 4.05 (m, 2H), 3.88 (m, 1H), 3.50 (m, 1H), 3.45 (m, 2H), 3.19 (m, 2H), 3.04 (m, 2H), 2.39 (m, 2H), 2.22 (m, 1H), 2.11 (m, 2H), 1.56 (m, 2H)

MS (ESI+) m/z 344 (M+H)$^+$

Example 196

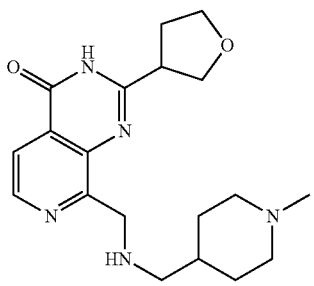 [SMILES: CN1CCC(CNCc2nccc3c(=O)[nH]c(C4CCOC4)nc23)CC1]

8-((((1-methylpiperidin-4-yl)methyl)amino)methyl)-
2-(tetrahydrofuran-3-yl)pyrido[3,4-d]pyrimidin-4
(3H)-one Using tetrahydrofuran-3-carboxylic acid and (1-methyl-piperidin-4-yl)methanamine, the title compound was obtained as described in Scheme 14 (Method N).

$^1$H NMR (400 MHz, CD$_3$OD) δ 8.61 (d, J=5.2 Hz, 1H), 8.01 (d, J=5.2 Hz, 1H), 4.17 (m, 1H), 4.05 (m, 2H), 3.88 (m, 1H), 3.57 (m, 1H), 3.49 (m, 2H), 3.19 (m, 2H), 3.04 (m, 2H), 2.87 (s, 3H), 2.37 (m, 2H), 2.21 (m, 1H), 2.14 (m, 2H), 1.63 (m, 2H)

MS (ESI+) m/z 358 (M+H)$^+$

Example 197

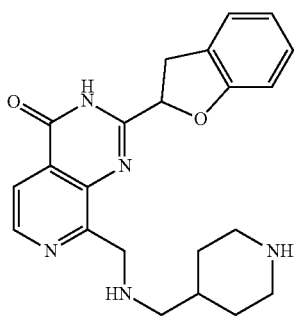 [SMILES: O=c1[nH]c(C2Cc3ccccc3O2)nc2c(CNCC3CCNCC3)nccc12]

2-(2,3-dihydrobenzofuran-2-yl)-8-(((piperidin-4-ylmethyl)amino)methyl)pyrido[3,4-d]pyrimidin-4
(3H)-one Using 2,3-dihydrobenzofuran-2-carboxylic acid and tert-butyl 4-(aminomethyl)piperidine-1-carboxylate, the title compound (11.8 mg) was obtained as described in Scheme 14 (Method N).

$^1$H NMR (400 MHz, CD$_3$OD) δ 8.64 (d, J=5.2 Hz, 1H), 8.05 (d, J=5.2 Hz, 1H), 7.24 (m, 1H), 7.14 (m, 1H), 6.89 (m, 2H), 5.70 (m, 1H), 4.84 (s, 2H), 3.84 (m, 1H), 3.64 (m, 1H), 3.44 (m, 2H), 3.16 (m, 2H), 3.03 (m, 2H), 2.19 (m, 1H), 2.09 (m, 2H), 1.55 (m, 2H)

MS (ESI+) m/z 392 (M+H)$^+$

Example 198

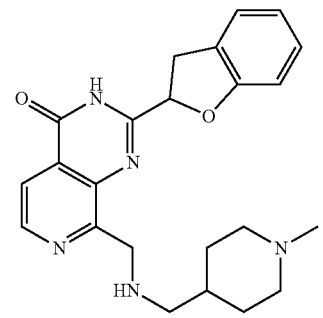

2-(2,3-dihydrobenzofuran-2-yl)-8-((((1-methylpiperidin-4-yl)methyl)amino)methyl)pyrido[3,4-d]pyrimidin-4(3H)-one Using 2,3-dihydrobenzofuran-2-carboxylic acid and (1-methylpiperidin-4-yl)methanamine, the title compound (8.9 mg) was obtained as described in Scheme 14 (Method N).

$^1$H NMR (400 MHz, CD$_3$OD) δ 8.65 (d, J=5.2 Hz, 1H), 8.05 (d, J=5.2 Hz, 1H), 7.24 (m, 1H), 7.14 (m, 1H), 6.90 (m, 2H), 5.70 (m, 1H), 4.84 (s, 2H), 3.84 (m, 1H), 3.64 (m, 1H), 3.57 (m, 2H), 3.16 (m, 2H), 3.02 (m, 2H), 2.87 (s, 3H), 2.18 (m, 1H), 2.13 (m, 2H), 1.60 (m, 2H)

MS (ESI+) m/z 406 (M+H)$^+$

Example 199

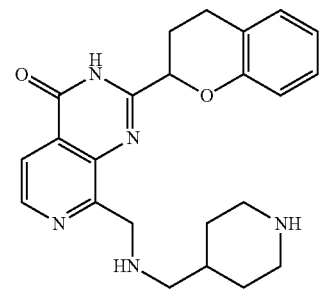 [SMILES: O=c1[nH]c(C2CCc3ccccc3O2)nc2c(CNCC3CCNCC3)nccc12]

2-(chroman-2-yl)-8-(((piperidin-4-ylmethyl)amino)methyl)pyrido[3,4-d]pyrimidin-4(3H)-one Using chromane-2-carboxylic acid and tert-butyl 4-(aminomethyl)piperidine-1-carboxylate, the title compound (18.0 mg) was obtained as described in Scheme 14 (Method N).

$^1$H NMR (400 MHz, CD$_3$OD) δ 8.67 (d, J=5.2 Hz, 1H), 8.08 (d, J=5.2 Hz, 1H), 7.10 (m, 2H), 6.91 (m, 2H), 5.10 (m, 1H), 4.82 (m, 2H), 3.44 (m, 2H), 3.18 (m, 2H), 3.04 (m, 2H), 2.94 (m, 2H), 2.47 (m, 1H), 2.30 (m, 1H), 2.20 (m, 1H), 2.09 (m, 2H), 1.55 (m, 2H)

MS (ESI+) m/z 406 (M+H)$^+$

Example 200

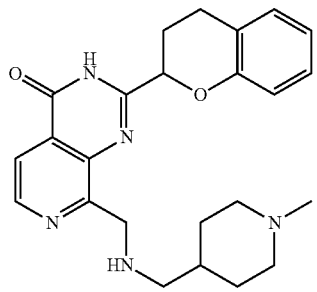 [SMILES: CN1CCC(CNCc2nccc3c(=O)[nH]c(C4CCc5ccccc5O4)nc23)CC1]

2-(chroman-2-yl)-8-((((1-methylpiperidin-4-yl)methyl)amino)methyl)pyrido[3,4-d]pyrimidin-4(3H)-one Using chromane-2-carboxylic acid and (1-methylpiperidin-4-yl)methanamine, the title compound (13.0 mg) was obtained as described in Scheme 14 (Method N).

$^1$H NMR (400 MHz, CD$_3$OD) δ 8.67 (d, J=5.2 Hz, 1H), 8.08 (d, J=5.2 Hz, 1H), 7.11 (m, 2H), 6.91 (m, 2H), 5.09 (m, 1H), 4.82 (m, 2H), 3.59 (m, 2H), 3.18 (m, 2H), 3.03 (m, 2H), 2.94 (m, 2H), 2.87 (s, 3H), 2.45 (m, 1H), 2.30 (m, 1H), 2.16 (m, 3H), 1.58 (m, 2H)

MS (ESI+) m/z 420 (M+H)$^+$

Example 201

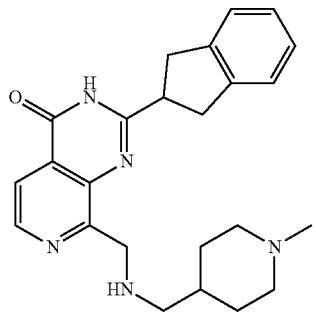 [SMILES: CN1CCC(CNCc2nccc3c(=O)[nH]c(C4Cc5ccccc5C4)nc23)CC1]

2-(2,3-dihydro-1H-inden-2-yl)-8-((((1-methylpiperidin-4-yl)methyl)amino)methyl)pyrido[3,4-d]pyrimidin-4(3H)-one Using 2,3-dihydro-1H-indene-2-carboxylic acid and (1-methylpiperidin-4-yl)methanamine, the title compound (5.2 mg) was obtained as described in Scheme 14 (Method N).

MS (ESI+) m/z 404 (M+H)$^+$

Example 202

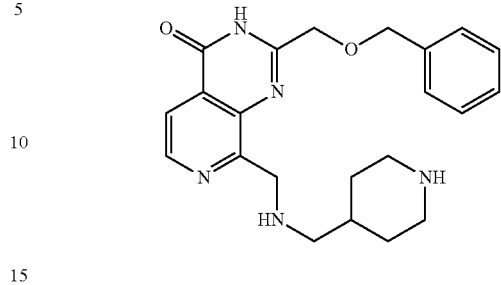

2-((benzyloxy)methyl)-8-(((piperidin-4-ylmethyl)amino)methyl)pyrido[3,4-d]pyrimidin-4(3H)-one Using 2-(benzyloxy)acetic acid and tert-butyl 4-(aminomethyl)piperidine-1-carboxylate, the title compound (3.5 mg) was obtained as described in Scheme 14 (Method N).

$^1$H NMR (400 MHz, CD$_3$OD) δ 8.64 (d, J=5.2 Hz, 1H), 8.04 (d, J=5.2 Hz, 1H), 7.40 (m, 2H), 7.33 (m, 2H), 7.29 (m, 1H), 4.82 (s, 2H), 4.70 (s, 2H), 4.53 (s, 2H), 3.45 (m, 2H), 3.15 (m, 2H), 3.03 (m, 2H), 2.20 (m, 1H), 2.09 (m, 2H), 1.54 (m, 2H)

MS (ESI+) m/z 394 (M+H)$^+$

Example 203

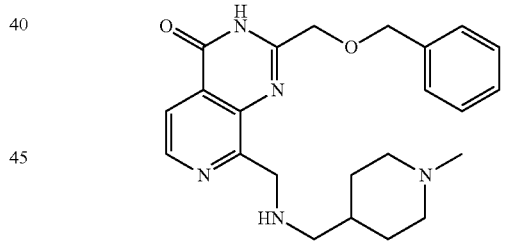

2-((benzyloxy)methyl)-8-((((1-methylpiperidin-4-yl)methyl)amino)methyl)pyrido[3,4-d]pyrimidin-4(3H)-one Using 2-(benzyloxy)acetic acid and (1-methylpiperidin-4-yl)methanamine, the title compound (3.8 mg) was obtained as described in Scheme 14 (Method N).

$^1$H NMR (400 MHz, CD$_3$OD) δ 8.64 (d, J=5.2 Hz, 1H), 8.04 (d, J=5.2 Hz, 1H), 7.40 (m, 2H), 7.33 (m, 2H), 7.29 (m, 1H), 4.82 (s, 2H), 4.70 (s, 2H), 4.53 (s, 2H), 3.57 (m, 2H), 3.15 (m, 2H), 3.02 (m, 2H), 2.86 (s, 3H), 2.18 (m, 1H), 2.14 (m, 2H), 1.58 (m, 2H)

MS (ESI+) m/z 408 (M+H)$^+$

Example 204

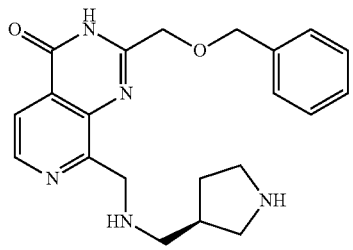 [SMILES: O=c1[nH]c(COCc2ccccc2)nc2c(CNC[C@H]3CCNC3)nccc12]

(S)-2-((benzyloxy)methyl)-8-(((pyrrolidin-3-ylmethyl)amino)methyl)pyrido[3,4-d]pyrimidin-4(3H)-one Using 2-(benzyloxy)acetic acid and tert-butyl (R)-3-(aminomethyl)pyrrolidine-1-carboxylate, the title compound (3.9 mg) was obtained as described in Scheme 14 (Method N).

$^1$H NMR (400 MHz, CD$_3$OD) δ 8.64 (d, J=5.2 Hz, 1H), 8.04 (d, J=5.2 Hz, 1H), 7.40 (m, 2H), 7.33 (m, 2H), 7.29 (m, 1H), 4.84 (s, 2H), 4.70 (s, 2H), 4.53 (s, 2H), 3.60 (m, 1H), 3.44 (m, 1H), 3.34 (m, 2H), 3.29 (m, 1H), 3.08 (m, 1H), 2.84 (m, 1H), 2.37 (m, 1H), 1.86 (m, 1H)

MS (ESI+) m/z 380 (M+H)$^+$

Example 205

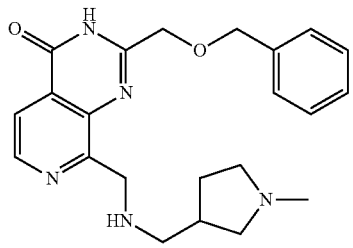 [SMILES: CN1CCC(CNCc2nccc3c(=O)[nH]c(COCc4ccccc4)nc23)C1]

2-((benzyloxy)methyl)-8-((((1-methylpyrrolidin-3-yl)methyl)amino)methyl)pyrido[3,4-d]pyrimidin-4(3H)-one Using 2-(benzyloxy)acetic acid and (1-methylpyrrolidin-3-yl)methanamine, the title compound (1.8 mg) was obtained as described in Scheme 14 (Method N).

$^1$H NMR (400 MHz, CD$_3$OD) δ 8.65 (d, J=5.2 Hz, 1H), 8.05 (d, J=5.2 Hz, 1H), 7.40 (m, 2H), 7.34 (m, 2H), 7.29 (m, 1H), 4.84 (s, 2H), 4.70 (s, 2H), 4.53 (s, 2H), 3.60 (m, 1H), 3.46 (m, 1H), 3.42 (m, 1H), 3.36 (m, 2H), 2.95 (s, 3H), 2.45 (m, 2H), 2.04 (m, 1H), 1.95 (m, 1H), 1.64 (m, 1H)

MS (ESI+) m/z 394 (M+H)$^+$

Example 206

Step 1

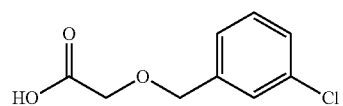 [SMILES: O=C(O)COCc1cccc(Cl)c1]

2-((3-chlorobenzyl)oxy)acetic acid

To a solution of 3-chlorobenzyl alcohol (713 mg, 5.0 mmol) in anhydrous THF (10 mL) was added NaH (60% dispersion in mineral oil, 200 mg, 5.0 mmol) in anhydrous THF (10 mL) dropwise. The mixture was allowed to stir for 30 min at ambient temperature. Bromoacetic acid (144 μl, 2.0 mmol) in anhydrous THF (2 mL) was added dropwise to the mixture and then allowed to stir overnight. The reaction was concentrated and diluted with 2N aqueous NaOH solution, water and EtOAc. The organic layer was discarded and the aqueous layer was acidified by a 2N aqueous HCl solution. The acidified aqueous layer was extracted with EA and dried over MgSO$_4$. The extract was concentrated in vacuo to afford 2-((3-chlorobenzyl)oxy)acetic acid as a crude product and the residue was used in the next step without further purification.

MS (ESI+) m/z 201 (M+H)$^+$

Step 2~7 (Same Procedure as Described in Method M)

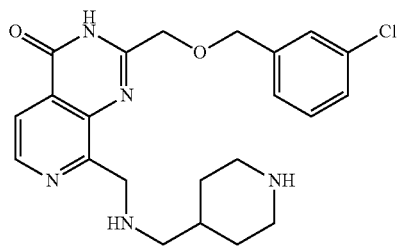 [SMILES: O=c1[nH]c(COCc2cccc(Cl)c2)nc2c(CNCC3CCNCC3)nccc12]

2-(((3-chlorobenzyl)oxy)methyl)-8-(((piperidin-4-ylmethyl)amino)methyl)pyrido[3,4-d]pyrimidin-4(3H)-one Using 2-((3-chlorobenzyl)oxy)acetic acid and tert-butyl 4-(aminomethyl)piperidine-1-carboxylate, the title compound (6.4 mg) was obtained as described in Scheme 14 (Method N).

$^1$H NMR (400 MHz, CD$_3$OD) δ 8.64 (d, J=5.2 Hz, 1H), 8.04 (d, J=5.2 Hz, 1H), 7.45 (m, 1H), 7.33 (m, 2H), 7.29 (m, 1H), 4.83 (s, 2H), 4.69 (s, 2H), 4.55 (s, 2H), 3.44 (m, 2H), 3.16 (m, 2H), 3.03 (m, 2H), 2.20 (m, 1H), 2.09 (m, 2H), 1.55 (m, 2H)

MS (ESI+) m/z 428 (M+H)$^+$

Example 207

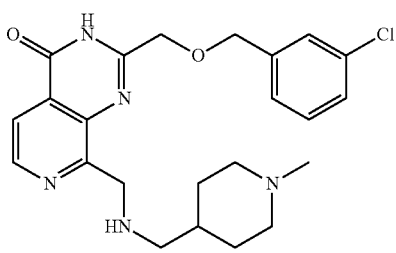 [SMILES: CN1CCC(CNCc2nccc3c(=O)[nH]c(COCc4cccc(Cl)c4)nc23)CC1]

2-(((3-chlorobenzyl)oxy)methyl)-8-((((1-methylpiperidin-4-yl)methyl)amino)methyl)pyrido[3,4-d]pyrimidin-4(3H)-one Using 2-((3-chlorobenzyl)oxy)acetic acid and (1-methylpiperidin-4-yl)methanamine, the title compound (5.3 mg) was obtained as described in Scheme 14 (Method N).

$^1$H NMR (400 MHz, CD$_3$OD) δ 8.64 (d, J=5.2 Hz, 1H), 8.04 (d, J=5.2 Hz, 1H), 7.45 (m, 1H), 7.33 (m, 2H), 7.28 (m, 1H), 4.83 (s, 2H), 4.69 (s, 2H), 4.55 (s, 2H), 3.57 (m, 2H), 3.16 (m, 2H), 3.03 (m, 2H), 2.87 (s, 3H), 2.15 (m, 3H), 1.55 (m, 2H)

MS (ESI+) m/z 442 (M+H)$^+$

Example 208

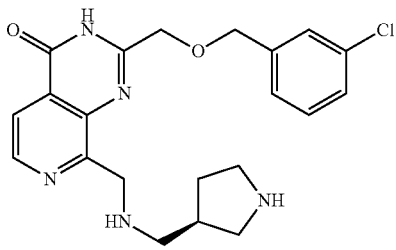 [SMILES: O=c1[nH]c(COCc2cccc(Cl)c2)nc2c(CNC[C@H]3CCNC3)nccc12]

(S)-2-(((3-chlorobenzyl)oxy)methyl)-8-(((pyrrolidin-3-ylmethyl)amino)methyl)pyrido[3,4-d]pyrimidin-4(3H)-one Using 2-((3-chlorobenzyl)oxy)acetic acid and tert-butyl (R)-3-(aminomethyl)pyrrolidine-1-carboxylate, the title compound (5.7 mg) was obtained as described in Scheme 14 (Method N).

$^1$H NMR (400 MHz, CD$_3$OD) δ 8.65 (d, J=5.2 Hz, 1H), 8.04 (d, J=5.2 Hz, 1H), 7.44 (m, 1H), 7.32 (m, 2H), 7.28 (m, 1H), 4.85 (s, 2H), 4.69 (s, 2H), 4.55 (s, 2H), 3.60 (m, 1H), 3.44 (m, 1H), 3.35 (m, 2H), 3.31 (m, 1H), 3.09 (m, 1H), 2.85 (m, 1H), 2.38 (m, 1H), 1.86 (m, 1H)

MS (ESI+) m/z 414 (M+H)$^+$

Example 209

Step 1

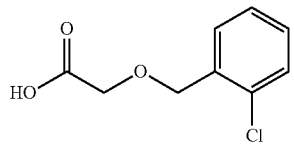 [SMILES: O=C(O)COCc1ccccc1Cl]

2-((2-chlorobenzyl)oxy)acetic acid

Using 2-chlorobenzyl alcohol, the title compound was synthesized by the same procedure as used for 2-((2-chlorobenzyl)oxy)acetic acid.

MS (ESI+) m/z 201 (M+H)$^+$

Step 2~7 (Same Procedure as Described in Method M)

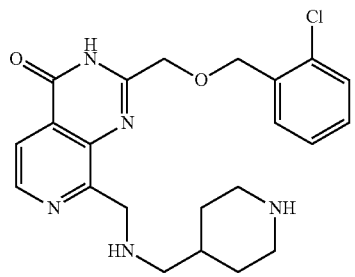

2-(((2-chlorobenzyl)oxy)methyl)-8-(((piperidin-4-ylmethyl)amino)methyl)pyrido[3,4-d]pyrimidin-4(3H)-one Using 2-((2-chlorobenzyl)oxy)acetic acid and tert-butyl 4-(aminomethyl)piperidine-1-carboxylate, the title compound (7.8 mg) was obtained as described in Scheme 14 (Method N).

$^1$H NMR (400 MHz, CD$_3$OD) δ 8.64 (d, J=5.2 Hz, 1H), 8.04 (d, J=5.2 Hz, 1H), 7.57 (d, J=7.0 Hz, 1H), 7.38 (d, J=7.0 Hz, 1H), 7.30 (m, 2H), 4.83 (s, 2H), 4.81 (s, 2H), 4.61 (s, 2H), 3.45 (m, 2H), 3.16 (m, 2H), 3.03 (m, 2H), 2.21 (m, 1H), 2.09 (m, 2H), 1.54 (m, 2H)

MS (ESI+) m/z 428 (M+H)$^+$

Example 210

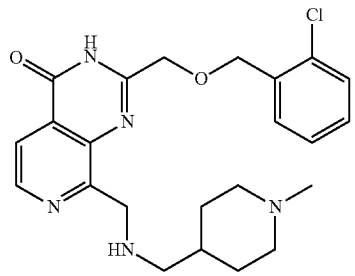 [SMILES: CN1CCC(CNCc2nccc3c(=O)[nH]c(COCc4ccccc4Cl)nc23)CC1]

2-(((2-chlorobenzyl)oxy)methyl)-8-((((1-methylpiperidin-4-yl)methyl)amino)methyl)pyrido[3,4-d]pyrimidin-4(3H)-one Using 2-((2-chlorobenzyl)oxy)acetic acid and (1-methylpiperidin-4-yl)methanamine, the title compound (7.1 mg) was obtained as described in Scheme 14 (Method N).

¹H NMR (400 MHz, CD₃OD) δ 8.64 (d, J=5.2 Hz, 1H), 8.04 (d, J=5.2 Hz, 1H), 7.57 (d, J=7.0 Hz, 1H), 7.38 (d, J=7.0 Hz, 1H), 7.29 (m, 2H), 4.83 (s, 2H), 4.81 (s, 2H), 4.61 (s, 2H), 3.57 (m, 2H), 3.16 (m, 2H), 3.03 (m, 2H), 2.86 (s, 3H), 2.15 (m, 3H), 1.61 (m, 2H)

MS (ESI+) m/z 442 (M+H)⁺

Example 211

Step 1

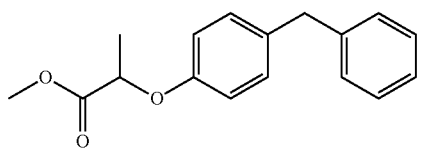 [SMILES: COC(=O)C(C)Oc1ccc(Cc2ccccc2)cc1]

methyl 2-(4-benzylphenoxy)propanoate

To a solution of methyl lactate (287 μl, 3 mmol), 4-benzylphenol (774 mg, 4.2 mmol) and PPh₃ (866 mg, 3.3 mmol) in anhydrous THF (10 mL) was added DIAD (650 μl, 3.3 mmol) dropwise. The mixture was allowed to stir overnight and concentrated in vacuo. The concentrated residue was purified by combi-flash to afford methyl 2-(4-benzylphenoxy)propanoate (quant.) as a pale yellow oil.

MS (ESI+) m/z 271 (M+H)⁺

Step 2

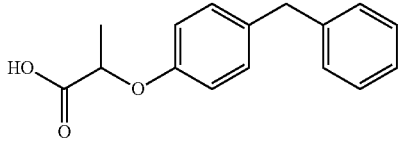 [SMILES: CC(Oc1ccc(Cc2ccccc2)cc1)C(=O)O]

2-(4-benzylphenoxy)propanoic acid

To a solution of methyl 2-(4-benzylphenoxy)propanoate in MeOH (10 mL) was added a 2N aqueous NaOH solution (3.0 mL). The mixture was allowed to stir for 2 hours at ambient temperature. A 2N aqueous HCl solution (6.0 mL) was added to quench the reaction. The mixture was concentrated, extracted with EA and dried over MgSO₄. The extract was concentrated in vacuo to afford 2-(4-benzylphenoxy)propanoic acid as a crude. The residue was used in the next step without further purification.

MS (ESI+) m/z 257 (M+H)⁺

Step 3~9 (Same Procedure as Described in Method M)

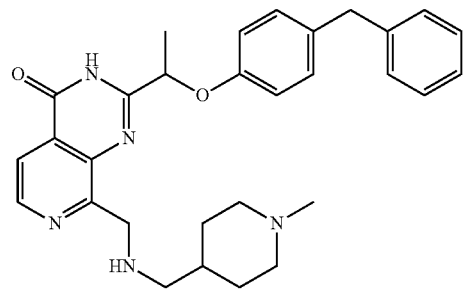 [SMILES: CC(Oc1ccc(Cc2ccccc2)cc1)c1nc2c(CNCC3CCN(C)CC3)nccc2c(=O)[nH]1]

2-(1-(4-benzylphenoxy)ethyl)-8-((((1-methylpiperidin-4-yl)methyl)amino)methyl)pyrido[3,4-d]pyrimidin-4(3H)-one Using 2-(4-benzylphenoxy)propanoic acid and (1-methylpiperidin-4-yl)methanamine, the title compound (0.6 mg) as described in Scheme 14 (Method N).

¹H NMR (400 MHz, CD₃OD) δ 8.63 (d, J=5.2 Hz, 1H), 8.02 (d, J=5.2 Hz, 1H), 7.19 (m, 2H), 7.08 (m, 5H), 6.92 (m, 2H), 5.28 (m, 1H), 4.92 (s, 2H), 3.84 (s, 2H), 3.59 (m, 2H), 3.18 (m, 2H), 3.04 (m, 2H), 2.88 (s, 3H), 2.20 (m, 1H), 2.16 (m, 2H), 1.71 (m, 2H), 1.57 (m, 2H)

MS (ESI+) m/z 498 (M+H)⁺

Example 212

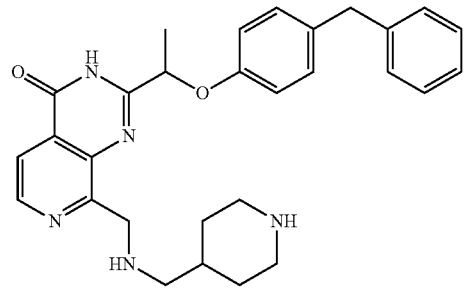 [SMILES: CC(Oc1ccc(Cc2ccccc2)cc1)c1nc2c(CNCC3CCNCC3)nccc2c(=O)[nH]1]

2-(1-(4-benzylphenoxy)ethyl)-8-(((piperidin-4-ylmethyl)amino)methyl)pyrido[3,4-d]pyrimidin-4(3H)-one Using 2-(4-benzylphenoxy)propanoic acid and tert-butyl 4-(aminomethyl)piperidine-1-carboxylate, the title compound (0.9 mg) was obtained as described in Scheme 14 (Method N).

¹H NMR (400 MHz, CD₃OD) δ 8.62 (d, J=5.2 Hz, 1H), 8.03 (d, J=5.2 Hz, 1H), 7.20 (m, 2H), 7.08 (m, 5H), 6.92 (m, 2H), 5.28 (m, 1H), 4.93 (s, 2H), 3.84 (s, 2H), 3.46 (m, 2H), 3.16 (m, 2H), 3.04 (m, 2H), 2.19 (m, 1H), 2.11 (m, 2H), 1.71 (m, 3H), 1.53 (m, 2H)

MS (ESI+) m/z 484 (M+H)⁺

Example 213

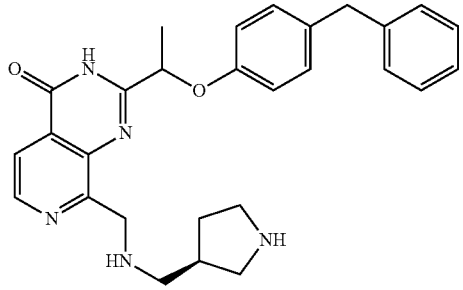 [SMILES: CC(Oc1ccc(Cc2ccccc2)cc1)c1nc2c(CNC[C@H]3CCNC3)nccc2c(=O)[nH]1]

2-(1-(4-benzylphenoxy)ethyl)-8-(((((S)-pyrrolidin-3-yl)methyl)amino)methyl)pyrido[3,4-d]pyrimidin-4(3H)-one Using 2-(4-benzylphenoxy)propanoic acid and tert-butyl (R)-3-(aminomethyl)pyrrolidine-1-carboxylate, the title compound (12.0 mg) was obtained as described in Scheme 14 (Method N).

$^1$H NMR (400 MHz, CD$_3$OD) δ 8.62 (d, J=5.2 Hz, 1H), 8.01 (d, J=5.2 Hz, 1H), 7.19 (m, 2H), 7.09 (m, 5H), 6.92 (m, 2H), 5.29 (m, 1H), 4.89 (s, 2H), 3.84 (s, 2H), 3.60 (m, 1H), 3.44 (m, 1H), 3.37 (m, 2H), 3.31 (m, 1H), 3.09 (m, 1H), 2.87 (m, 1H), 2.36 (m, 1H), 1.89 (m, 1H), 1.71 (m, 3H)

MS (ESI+) m/z 470 (M+H)$^+$

Example 214

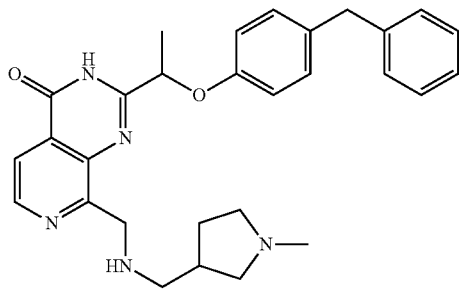 [SMILES: CC(Oc1ccc(Cc2ccccc2)cc1)c1nc2c(CNCC3CCN(C)C3)nccc2c(=O)[nH]1]

2-(1-(4-benzylphenoxy)ethyl)-8-(((((1-methylpyrrolidin-3-yl)methyl)amino)methyl)pyrido[3,4-d]pyrimidin-4(3H)-one Using 2-(4-benzylphenoxy)propanoic acid and (1-methylpyrrolidin-3-yl)methanamine, the title compound (5.4 mg) was obtained as described in Scheme 14 (Method N).

$^1$H NMR (400 MHz, CD$_3$OD) δ 8.63 (d, J=5.2 Hz, 1H), 8.02 (d, J=5.2 Hz, 1H), 7.19 (m, 2H), 7.08 (m, 5H), 6.92 (m, 2H), 5.29 (m, 1H), 4.86 (s, 2H), 3.84 (s, 2H), 3.59 (m, 1H), 3.47 (m, 1H), 3.43 (m, 1H), 3.39 (m, 2H), 2.96 (s, 3H), 2.44 (m, 2H), 2.04 (m, 1H), 1.94 (m, 1H), 1.71 (m, 3H), 1.64 (m, 1H)

MS (ESI+) m/z 484 (M+H)$^+$

Example 215

Step 1~2

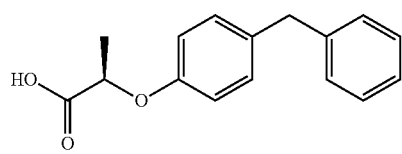 [SMILES: C[C@@H](Oc1ccc(Cc2ccccc2)cc1)C(=O)O]

(R)-2-(4-benzylphenoxy)propanoic acid

Using methyl D-lactate, the title compound was synthesized by the same procedure as described for 2-(4-benzylphenoxy)propanoic acid.

MS (ESI+) m/z 257 (M+H)$^+$

Step 3~9. (Same Procedure as Described in Method M)

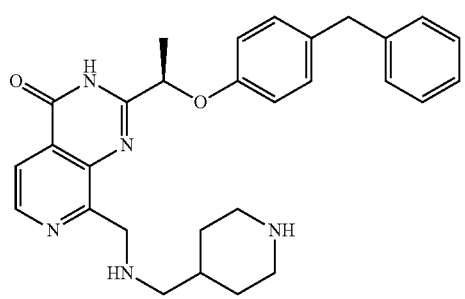

(R)-2-(1-(4-benzylphenoxy)ethyl)-8-(((piperidin-4-ylmethyl)amino)methyl)pyrido[3,4-d]pyrimidin-4(3H)-one Using (R)-2-(4-benzylphenoxy)propanoic acid and tert-butyl 4-(aminomethyl)piperidine-1-carboxylate, the title compound (2.0 mg) was obtained as described in Scheme 14 (Method N).

$^1$H NMR (400 MHz, CD$_3$OD) δ 8.63 (d, J=5.2 Hz, 1H), 8.02 (d, J=5.2 Hz, 1H), 7.19 (m, 2H), 7.08 (m, 5H), 6.92 (m, 2H), 5.28 (m, 1H), 4.87 (s, 2H), 3.84 (s, 2H), 3.44 (m, 2H), 3.18 (m, 2H), 3.04 (m, 2H), 2.21 (m, 1H), 2.09 (m, 2H), 1.71 (m, 3H), 1.56 (m, 2H)

MS (ESI+) m/z 484 (M+H)$^+$

Example 216

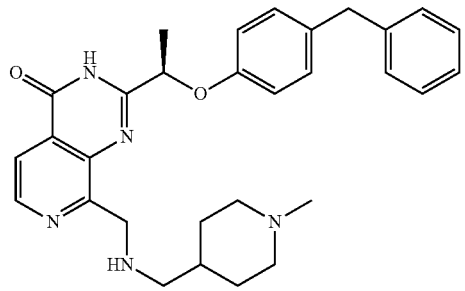 [SMILES: C[C@@H](Oc1ccc(Cc2ccccc2)cc1)c1nc2c(CNCC3CCN(C)CC3)nccc2c(=O)[nH]1]

(R)-2-(1-(4-benzylphenoxy)ethyl)-8-((((1-methylpip-
eridin-4-yl)methyl)amino)methyl)pyrido[3,4-d]py-
rimidin-4(3H)-one Using (R)-2-(4-benzylphenoxy)propanoic acid and (1-methylpiperidin-4-yl)methanamine, the title compound (1.3 mg) was obtained as described in Scheme 14 (Method N).
¹H NMR (400 MHz, CD₃OD) δ 8.63 (d, J=5.2 Hz, 1H), 8.02 (d, J=5.2 Hz, 1H), 7.19 (m, 2H), 7.08 (m, 5H), 6.92 (m, 2H), 5.30 (m, 1H), 4.87 (s, 2H), 3.84 (s, 2H), 3.59 (m, 2H), 3.18 (m, 2H), 3.05 (m, 2H), 2.87 (s, 3H), 2.17 (m, 3H), 1.71 (m, 3H), 1.61 (m, 2H)
MS (ESI+) m/z 498 (M+H)⁺

Example 217

Step 1~2

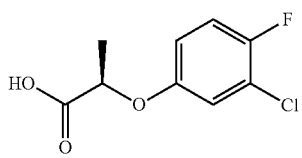

(R)-2-(3-chloro-4-fluorophenoxy)propanoic acid

Using methyl D-lactate and 3-chloro-4-fluorophenol, the title compound was synthesized by the same procedure as described for 2-(4-benzylphenoxy)propanoic acid.
MS (ESI+) m/z 219 (M+H)⁺

Step 3~9

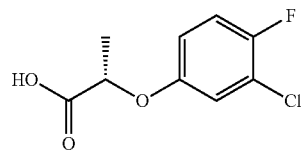

(R)-2-(1-(3-chloro-4-fluorophenoxy)ethyl)-8-(((pip-
eridin-4-ylmethyl)amino)methyl)pyrido[3,4-d]py-
rimidin-4(3H)-one Using (R)-2-(3-chloro-4-fluorophenoxy)propanoic acid and tert-butyl 4-(aminomethyl)piperidine-1-carboxylate, the title compound (13.0 mg) was obtained as described in Scheme 14 (Method N).
¹H NMR (400 MHz, CD₃OD) δ 8.64 (d, J=5.2 Hz, 1H), 8.03 (d, J=5.2 Hz, 1H), 7.18 (m, 1H), 7.12 (m, 1H), 6.98 (m, 1H), 5.32 (q, J=6.8 Hz, 1H), 4.87 (s, 2H), 3.46 (m, 2H), 3.19 (m, 2H), 3.05 (m, 2H), 2.87 (s, 3H), 2.23 (m, 1H), 2.12 (m, 2H), 1.73 (d, J=6.8 Hz, 3H), 1.56 (m, 2H)
MS (ESI+) m/z 446 (M+H)⁺

Example 218

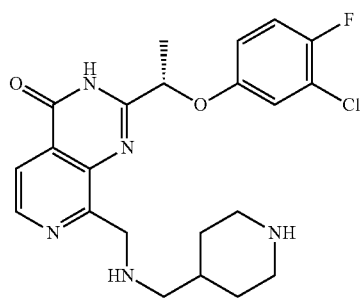 [SMILES: C[C@H](Oc1ccc(F)c(Cl)c1)c1nc2c(CNCC3CCNCC3)nccc2c(=O)[nH]1]

(R)-2-(1-(3-chloro-4-fluorophenoxy)ethyl)-8-((((1-
methylpiperidin-4-yl)methyl)amino)methyl)pyrido
[3,4-d]pyrimidin-4(3H)-one Using (R)-2-(3-chloro-4-fluorophenoxy)propanoic acid and (1-methylpiperidin-4-yl)methanamine, the title compound (10.3 mg) was obtained as described in Scheme 14 (Method N).
¹H NMR (400 MHz, CD₃OD) δ 8.64 (d, J=5.2 Hz, 1H), 8.03 (d, J=5.2 Hz, 1H), 7.18 (m, 1H), 7.12 (m, 1H), 6.98 (m, 1H), 5.32 (q, J=6.8 Hz, 1H), 4.87 (s, 2H), 3.58 (m, 2H), 3.19 (m, 2H), 3.05 (m, 2H), 2.87 (s, 3H), 2.17 (m, 3H), 1.73 (d, J=6.8 Hz, 3H), 1.62 (m, 2H)
MS (ESI+) m/z 460 (M+H)⁺

Example 219

Step 1~2

(S)-2-(3-chloro-4-fluorophenoxy)propanoic acid

Using methyl L-lactate and 3-chloro-4-fluorophenol, the title compound was synthesized by the same procedure as described for 2-(4-benzylphenoxy)propanoic acid.
MS (ESI+) m/z 219 (M+H)⁺

Step 3~9. (Same Procedure as Described in Method M)

(S)-2-(1-(3-chloro-4-fluorophenoxy)ethyl)-8-(((piperidin-4-ylmethyl)amino)methyl)pyrido[3,4-d]pyrimidin-4(3H)-one Using (S) 2 (3 chloro-4-fluorophenoxy)propanoic acid and tert-butyl 4-(aminomethyl)piperidine-1-carboxylate, the title compound (19.1 mg) was obtained as described in Scheme 14 (Method N).

$^1$H NMR (400 MHz, CD$_3$OD) δ 8.64 (d, J=5.2 Hz, 1H), 8.03 (d, J=5.2 Hz, 1H), 7.18 (m, 1H), 7.12 (m, 1H), 6.98 (m, 1H), 5.32 (q, J=6.8 Hz, 1H), 4.87 (s, 2H), 3.46 (m, 2H), 3.19 (m, 2H), 3.05 (m, 2H), 2.23 (m, 1H), 2.12 (m, 2H), 1.73 (d, J=6.8 Hz, 3H), 1.56 (m, 2H)

MS (ESI+) m/z 446 (M+H)$^+$

Example 220

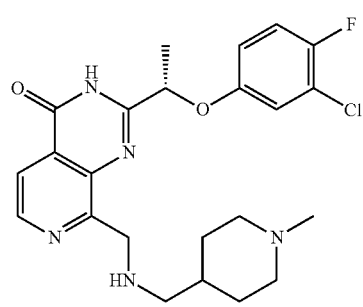 [SMILES: C[C@H](Oc1ccc(F)c(Cl)c1)c1nc2c(CNCC3CCN(C)CC3)nccc2c(=O)[nH]1]

(S)-2-(1-(3-chloro-4-fluorophenoxy)ethyl)-8-((((1-methylpiperidin-4-yl)methyl)amino)methyl)pyrido[3,4-d]pyrimidin-4(3H)-one Using (S)-2-(3-chloro-4-fluorophenoxy)propanoic acid and (1-methylpiperidin-4-yl)methanamine, the title compound (18.6 mg) was obtained as described in Scheme 14 (Method N).

$^1$H NMR (400 MHz, CD$_3$OD) δ 8.64 (d, J=5.2 Hz, 1H), 8.03 (d, J=5.2 Hz, 1H), 7.18 (m, 1H), 7.12 (m, 1H), 6.98 (m, 1H), 5.32 (q, J=6.8 Hz, 1H), 4.87 (s, 2H), 3.58 (m, 2H), 3.19 (m, 2H), 3.05 (m, 2H), 2.87 (s, 3H), 2.17 (m, 3H), 1.73 (d, J=6.8 Hz, 3H), 1.62 (m, 2H)

MS (ESI+) m/z 460 (M+H)$^+$

Scheme 15 (Method O)

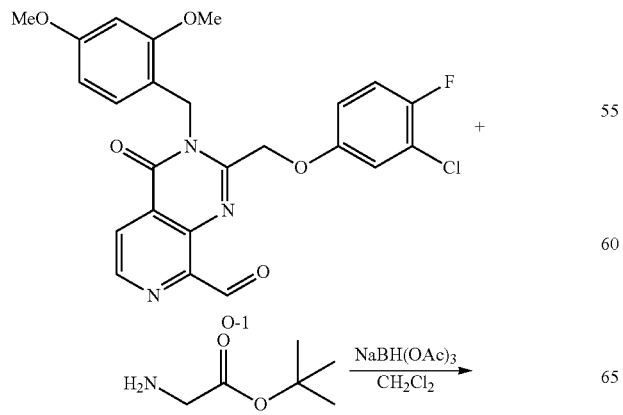

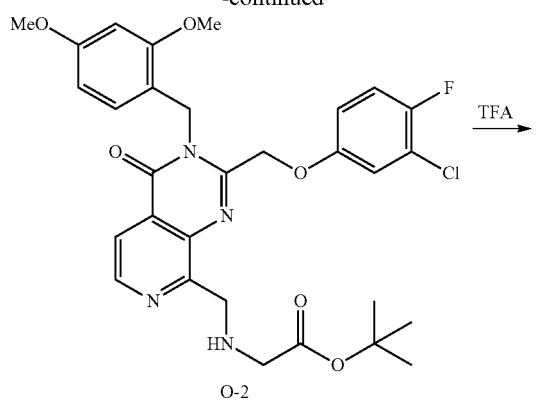

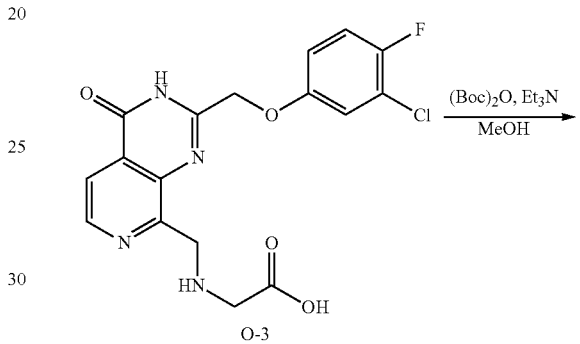

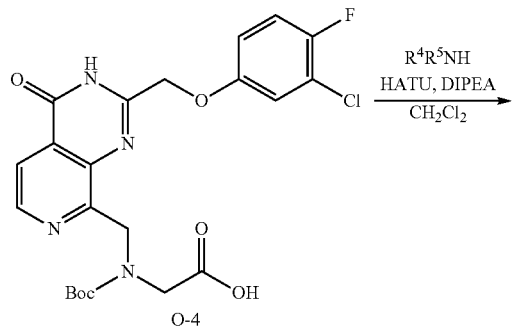

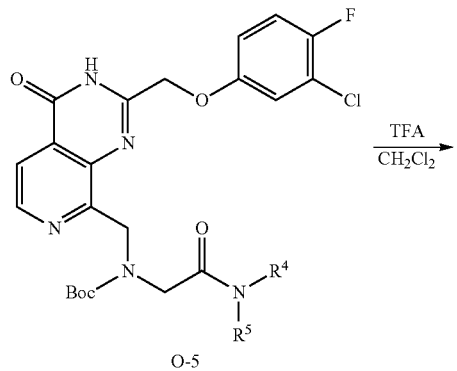

247

-continued

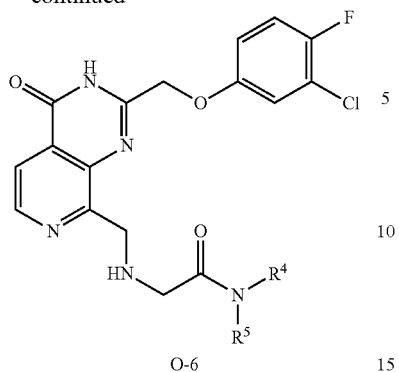

O-6

The general synthesis of compounds O-6 is illustrated in Scheme 15. Reductive amination of the aldehyde intermediate O-1 with tert-butyl glycinate leads to the intermediate O-2. Deprotection of protecting groups by TFA and Boc protection are carried out to provide the carboxylic acid intermediate O-4. Subsequent amide coupling using HATU and Boc deprotection by TFA afford the final product. (cf. O-1 is prepared by same procedure as described in Method M using 3-chloro-4-fluorophenol.)

Example 221

Step 1

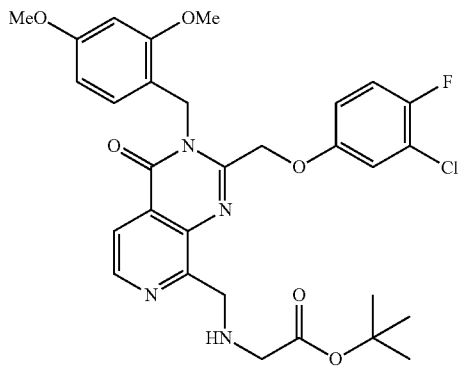 [SMILES: COc1ccc(Cn2c(COc3ccc(F)c(Cl)c3)nc3c(CNCC(=O)OC(C)(C)C)nccc3c2=O)c(OC)c1]

tert-butyl ((2-((3-chloro-4-fluorophenoxy)methyl)-3-(2,4-dimethoxybenzyl)-4-oxo-3,4-dihydropyrido[3,4-d]pyrimidin-8-yl)methyl)glycinate To a solution of intermediate O-1 (2 mmol, crude product) and tert-butyl glycinate (410 μl, 0.3 mmol) in DCM was added NaBH(OAc)$_3$ (850 mg, 0.4 mmol) portionwise. The mixture was allowed to stir for 30 min and quenched with water. It was extracted with EA and dried over MgSO$_4$. The organic extract was concentrated to afford the intermediate O-2 (quant.) as a crude product. The crude was used in the next step without further purification.

MS (ESI+) m/z 599 (M+H)$^+$

248

Step 2

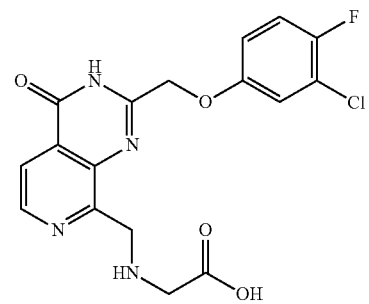 [SMILES: O=C(O)CNCc1nccc2c(=O)[nH]c(COc3ccc(F)c(Cl)c3)nc12]

((2-((3-chloro-4-fluorophenoxy)methyl)-4-oxo-3,4-dihydropyrido[3,4-d]pyrimidin-8-yl)methyl)glycine The intermediate O-2 was diluted with TFA (10 mL). The mixture was allowed to stir for 2 hours and concentrated in vacuo. The residue was diluted with MeOH and filtered. The filtrate was concentrated in vacuo to afford the intermediate O-3 (quant.) as brown solid, which was used in the next step without further purification.

MS (ESI+) m/z 393 (M+H)$^+$

Step 3

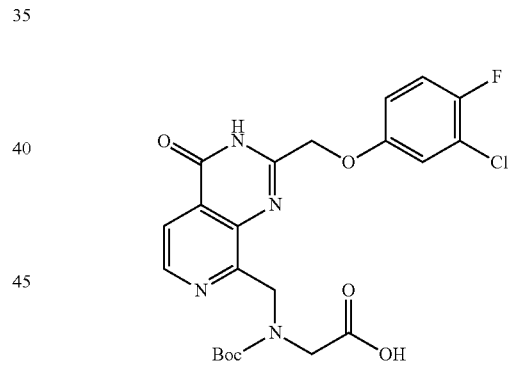

N-(tert-butoxycarbonyl)-N-((2-((3-chloro-4-fluorophenoxy)methyl)-4-oxo-3,4-dihydropyrido[3,4-d]pyrimidin-8-yl)methyl)glycine To a solution of intermediate O-3 (785 mg, 2 mmol) in MeOH (10 mL) were added Et$_3$N (1.4 mL, 10 mmol) and Boc$_2$O (1.4 mL, 6 mmol). After being allowed to stir for 1 hour, the mixture was concentrated. The residue was diluted with EtOAc and extracted with a 2N aqueous NaOH solution and water. The organic layer was discarded and the aqueous layer was neutralized with a 2N aqueous HCl solution. The precipitate was filtered off and washed with water. The collected solid was dried at 50° C. to afford the intermediate O-4 (790 mg, 1.6 mmol) as a pale brown solid.

MS (ESI+) m/z 493 (M+H)$^+$

Step 4

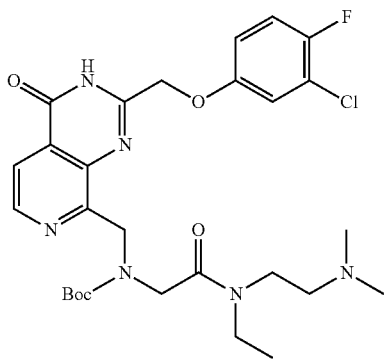 [SMILES: CCN(CCN(C)C)C(=O)CN(Cc1nccc2c(=O)[nH]c(COc3ccc(F)c(Cl)c3)nc12)C(=O)OC(C)(C)C]

tert-butyl ((2-((3-chloro-4-fluorophenoxy)methyl)-4-oxo-3,4-dihydropyrido[3,4-d]pyrimidin-8-yl)methyl)(2-((2-(dimethylamino)ethyl)(ethyl)amino)-2-oxo-ethyl)carbamate To a solution of intermediate O-4 (2 mg, 0.004 mmol) and $N^1$-ethyl-$N^2,N^2$-dimethylethane-1,2-diamine (0.2 M in dioxane, 30 µl, 0.006 mmol) in DMF were added DIPEA (0.2 M in DMF, 40 µl, 0.008 mmol) and HATU (0.2 M in DMF, 30 µk, 0.006 mmol). The mixture was allowed to stir for 30 min and extracted with UCT SPE CUBCX cartridge. The extract was concentrated in vacuo and purified by preparative HPLC to afford the intermediate O-5 (1 mg).

MS (ESI+) m/z 591 (M+H)$^+$

Step 5

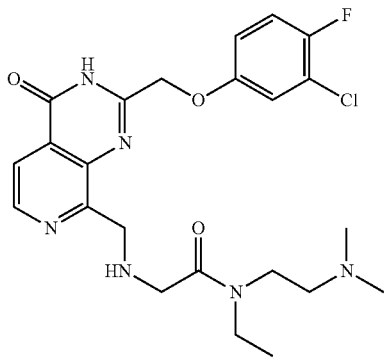 [SMILES: CCN(CCN(C)C)C(=O)CNCc1nccc2c(=O)[nH]c(COc3ccc(F)c(Cl)c3)nc12]

To a solution of intermediate O-5 in DCM (1 mL) was added TFA (0.5 mL). The mixture was allowed to stir for 30 min and concentrated in vacuo to afford the title compound (1.0 mg).

$^1$H NMR (400 MHz, CD$_3$OD) δ 8.67 (d, J=5.2 Hz, 1H), 8.07 (d, J=5.2 Hz, 1H), 7.23 (m, 1H), 7.19 (m, 1H), 7.03 (m, 1H), 5.09 (s, 2H), 4.87 (s, 2H), 4.32 (s, 2H), 3.80 (m, 2H), 3.38 (m, 4H), 2.97 (s, 6H), 1.24 (m, 3H)

MS (ESI+) m/z 491 (M+H)$^+$

Example 222

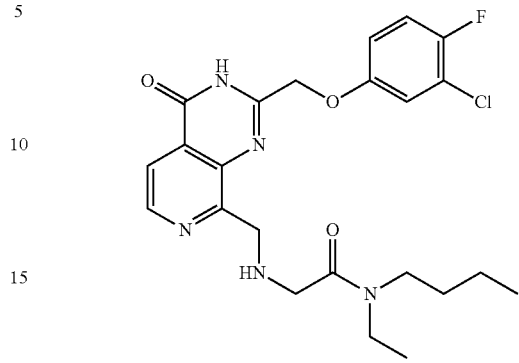

N-butyl-2-(((2-((3-chloro-4-fluorophenoxy)methyl)-4-oxo-3,4-dihydropyrido[3,4-d]pyrimidin-8-yl)methyl)amino)-N-ethylacetamide Using N-ethylbutan-1-amine, the title compound (0.2 mg) was obtained as described in Scheme 15 (Method O).

MS (ESI+) m/z 476 (M+H)$^+$

Example 223

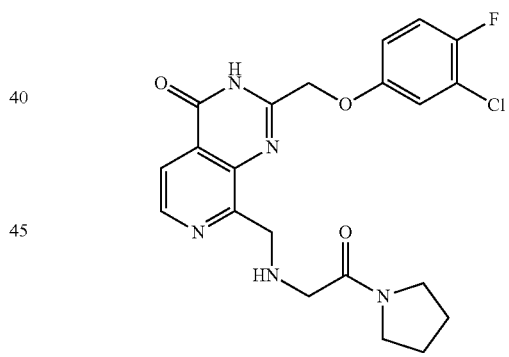

2-((3-chloro-4-fluorophenoxy)methyl)-8-(((2-oxo-2-(pyrrolidin-1-yl)ethyl)amino)methyl)pyrido[3,4-d]pyrimidin-4(3H)-one Using pyrrolidine, the title compound (1.5 mg) was obtained as described in Scheme 15 (Method O).

$^1$H NMR (400 MHz, CD$_3$OD) δ 8.68 (d, J=5.2 Hz, 1H), 8.06 (d, J=5.2 Hz, 1H), 7.24 (m, 1H), 7.19 (m, 1H), 7.03 (m, 1H), 5.09 (s, 2H), 4.85 (s, 2H), 4.15 (s, 2H), 3.49 (m, 2H), 3.43 (m, 2H), 2.01 (m, 2H), 1.91 (m, 2H)

MS (ESI+) m/z 446 (M+H)$^+$

Example 224

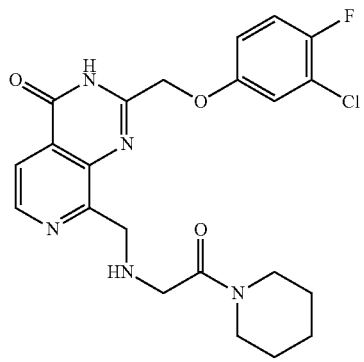 [SMILES: O=C(CNCc1nccc2c(=O)[nH]c(COc3ccc(F)c(Cl)c3)nc12)N1CCCCC1]

2-((3-chloro-4-fluorophenoxy)methyl)-8-(((2-oxo-2-(piperidin-1-yl)ethyl)amino)methyl)pyrido[3,4-d]pyrimidin-4(3H)-one Using piperidine, the title compound (0.6 mg) was obtained as described in Scheme 15 (Method O).

$^1$H NMR (400 MHz, CD$_3$OD) δ 8.68 (d, J=5.2 Hz, 1H), 8.06 (d, J=5.2 Hz, 1H), 7.24 (m, 1H), 7.18 (m, 1H), 7.04 (m, 1H), 5.09 (s, 2H), 4.83 (s, 2H), 4.24 (s, 2H), 3.58 (m, 2H), 3.36 (m, 2H), 1.68 (m, 2H), 1.60 (m, 4H)

MS (ESI+) m/z 460 (M+H)$^+$

Example 225

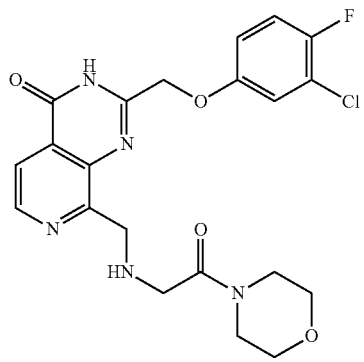 [SMILES: O=C(CNCc1nccc2c(=O)[nH]c(COc3ccc(F)c(Cl)c3)nc12)N1CCOCC1]

2-((3-chloro-4-fluorophenoxy)methyl)-8-(((2-morpholino-2-oxoethyl)amino)methyl)pyrido[3,4-d]pyrimidin-4(3H)-one Using morpholine, the title compound (0.5 mg) was obtained as described in Scheme 15 (Method O).

$^1$H NMR (400 MHz, CD$_3$OD) δ 8.68 (d, J=5.2 Hz, 1H), 8.06 (d, J=5.2 Hz, 1H), 7.24 (m, 1H), 7.18 (m, 1H), 7.04 (m, 1H), 5.09 (s, 2H), 4.84 (s, 2H), 4.26 (s, 2H), 3.68 (m, 4H), 3.62 (m, 2H), 3.43 (m, 2H)

MS (ESI+) m/z 462 (M+H)$^+$

Example 226

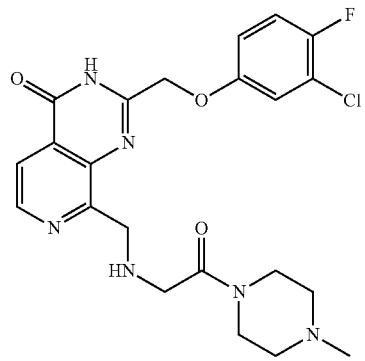 [SMILES: CN1CCN(C(=O)CNCc2nccc3c(=O)[nH]c(COc4ccc(F)c(Cl)c4)nc23)CC1]

2-((3-chloro-4-fluorophenoxy)methyl)-8-(((2-(4-methylpiperazin-1-yl)-2-oxoethyl)amino)methyl)pyrido[3,4-d]pyrimidin-4(3H)-one Using 1-methylpiperazine, the title compound (10.7 mg) was obtained as described in Scheme 15 (Method O).

$^1$H NMR (400 MHz, CD$_3$OD) δ 8.67 (d, J=5.2 Hz, 1H), 8.06 (d, J=5.2 Hz, 1H), 7.23 (m, 1H), 7.18 (m, 1H), 7.03 (m, 1H), 5.09 (s, 2H), 4.86 (s, 2H), 4.36 (s, 2H), 3.75 (m, 4H), 3.34 (m, 4H), 2.93 (s, 3H)

MS (ESI+) m/z 475 (M+H)$^+$

Example 227

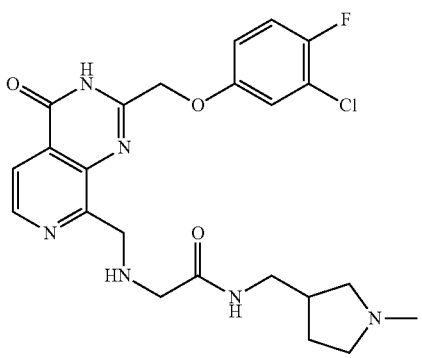 [SMILES: CN1CCC(CNC(=O)CNCc2nccc3c(=O)[nH]c(COc4ccc(F)c(Cl)c4)nc23)C1]

2-(((2-((3-chloro-4-fluorophenoxy)methyl)-4-oxo-3,4-dihydropyrido[3,4-d]pyrimidin-8-yl)methyl)amino)-N-((1-methylpyrrolidin-3-yl)methyl)acetamide Using (1-methylpyrrolidin-3-yl)methanamine, the title compound (8.7 mg) was obtained as described in Scheme 15 (Method O).

$^1$H NMR (400 MHz, CD$_3$OD) δ 8.66 (d, J=5.2 Hz, 1H), 8.06 (d, J=5.2 Hz, 1H), 7.24 (m, 1H), 7.18 (m, 1H), 7.04 (m, 1H), 5.09 (s, 2H), 4.85 (s, 2H), 4.02 (s, 2H), 3.68 (m, 2H), 3.41 (m, 1H), 3.37 (m, 2H), 3.13 (m, 1H), 2.70 (m, 1H), 2.25 (m, 1H), 1.85 (m, 1H)

MS (ESI+) m/z 489 (M+H)$^+$

Example 228

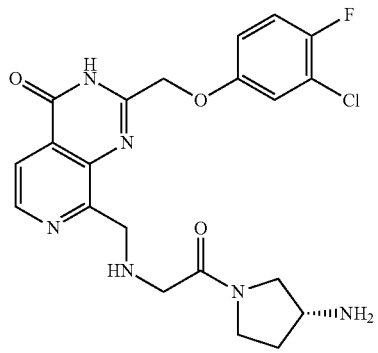 [SMILES: N[C@@H]1CCN(C(=O)CNCc2nccc3c(=O)[nH]c(COc4ccc(F)c(Cl)c4)nc23)C1]

(R)-8-(((2-(3-aminopyrrolidin-1-yl)-2-oxoethyl)
amino)methyl)-2-((3-chloro-4-fluorophenoxy)
methyl)pyrido[3,4-d]pyrimidin-4(3H)-one Using (R)-pyrrolidin-3-amine, the title compound (13.9 mg) was obtained as described in Scheme 15 (Method O).

$^1$H NMR (400 MHz, CD$_3$OD) δ 8.67 (d, J=5.2 Hz, 1H), 8.06 (d, J=5.2 Hz, 1H), 7.23 (m, 1H), 7.18 (m, 1H), 7.03 (m, 1H), 5.09 (s, 2H), 4.87 (s, 2H), 4.22 (s, 2H), 4.02 and 3.95 (m, 1H), 3.82 (m, 1H), 3.6 (m, 3H), 2.45 and 2.35 (m, 1H), 2.19 and 2.07 (m, 1H)

MS (ESI+) m/z 461 (M+H)$^+$

Example 229

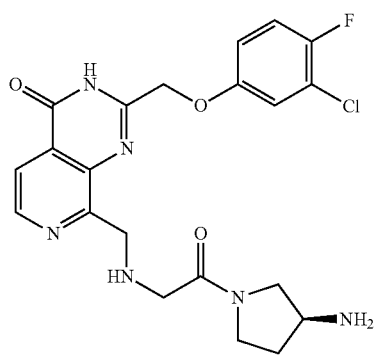 [SMILES: N[C@H]1CCN(C(=O)CNCc2nccc3c(=O)[nH]c(COc4ccc(F)c(Cl)c4)nc23)C1]

(S)-8-(((2-(3-aminopyrrolidin-1-yl)-2-oxoethyl)
amino)methyl)-2-((3-chloro-4-fluorophenoxy)
methyl)pyrido[3,4-d]pyrimidin-4(3H)-one Using (S)-pyrrolidin-3-amine, the title compound (13.4 mg) was obtained as described in Scheme 15 (Method O).

$^1$H NMR (400 MHz, CD$_3$OD) δ 8.67 (d, J=5.2 Hz, 1H), 8.06 (d, J=5.2 Hz, 1H), 7.23 (m, 1H), 7.18 (m, 1H), 7.03 (m, 1H), 5.09 (s, 2H), 4.87 (s, 2H), 4.22 (s, 2H), 4.02 and 3.95 (m, 1H), 3.82 (m, 1H), 3.6 (m, 3H), 2.45 and 2.35 (m, 1H), 2.19 and 2.07 (m, 1H)

MS (ESI+) m/z 461 (M+H)$^+$

Example 230

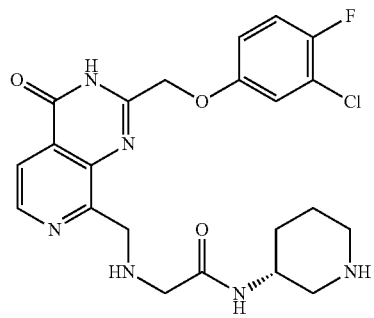 [SMILES: O=C(CNCc1nccc2c(=O)[nH]c(COc3ccc(F)c(Cl)c3)nc12)N[C@@H]1CCCNC1]

(R)-2-(((2-((3-chloro-4-fluorophenoxy)methyl)-4-
oxo-3,4-dihydropyrido[3,4-d]pyrimidin-8-yl)methyl)
amino)-N-(piperidin-3-yl)acetamide Using (R)-piperidin-3-amine, the title compound (13.0 mg) was obtained as described in Scheme 15 (Method O).

$^1$H NMR (400 MHz, CD$_3$OD) δ 8.66 (d, J=5.2 Hz, 1H), 8.05 (d, J=5.2 Hz, 1H), 7.24 (m, 1H), 7.18 (m, 1H), 7.03 (m, 1H), 5.09 (s, 2H), 4.85 (s, 2H), 4.09 (m, 1H), 4.02 (s, 2H), 3.44 (m, 1H), 3.26 (m, 1H), 2.94 (m, 2H), 2.02 (m, 2H), 1.80 (m, 1H), 1.62 (m, 1H)

MS (ESI+) m/z 475 (M+H)$^+$

Example 231

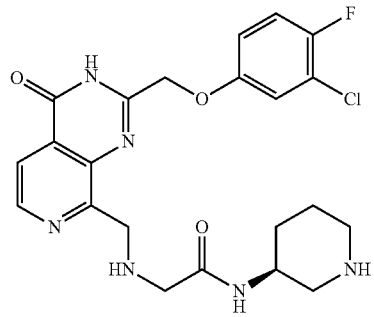 [SMILES: O=C(CNCc1nccc2c(=O)[nH]c(COc3ccc(F)c(Cl)c3)nc12)N[C@H]1CCCNC1]

(S)-2-(((2-((3-chloro-4-fluorophenoxy)methyl)-4-
oxo-3,4-dihydropyrido[3,4-d]pyrimidin-8-yl)methyl)
amino)-N-(piperidin-3-yl)acetamide Using (S)-piperidin-3-amine, the title compound (17.6 mg) was obtained as described in Scheme 15 (Method O).

$^1$H NMR (400 MHz, CD$_3$OD) δ 8.66 (d, J=5.2 Hz, 1H), 8.05 (d, J=5.2 Hz, 1H), 7.24 (m, 1H), 7.18 (m, 1H), 7.03 (m, 1H), 5.09 (s, 2H), 4.85 (s, 2H), 4.09 (m, 1H), 4.02 (s, 2H), 3.44 (m, 1H), 3.26 (m, 1H), 2.94 (m, 2H), 2.02 (m, 2H), 1.80 (m, 1H), 1.62 (m, 1H)

MS (ESI+) m/z 475 (M+H)$^+$

Example 232

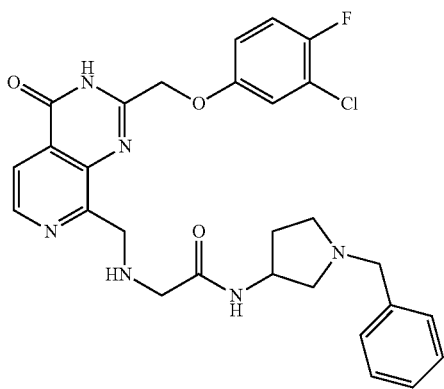 [SMILES: O=C(CNCc1nccc2c(=O)[nH]c(COc3ccc(F)c(Cl)c3)nc12)NC1CCN(Cc2ccccc2)C1]

N-(1-benzylpyrrolidin-3-yl)-2-(((2-((3-chloro-4-fluorophenoxy)methyl)-4-oxo-3,4-dihydropyrido[3,4-d]pyrimidin-8-yl)methyl)amino)acetamide Using 1-benzylpyrrolidin-3-amine, the title compound (23.4 mg) was obtained as described in Scheme 15 (Method O).
$^1$H NMR (600 MHz, CD$_3$OD) δ 8.66 (d, J=5.4 Hz, 1H), 8.05 (d, J=5.4 Hz, 1H), 7.52 (m, 2H), 7.47 (m, 3H), 7.25 (dd, J=3.0, 6.0 Hz, 1H), 7.19 (t, J=9.0 Hz, 1H), 7.04 (dt, J=3.0, 9.0 Hz), 5.10 (s, 2H), 4.85 (s, 2H), 4.58 (m, 1H), 4.46 (m, 2H), 4.37 (m, 1H), 4.02 (m, 2H), 3.71 (m, 1H), 3.54 (m, 1H), 3.44 (m, 1H), 2.58 (m, 1H), 2.10 (m, 1H)
MS (ESI+) m/z 551 (M+H)$^+$

Example 233

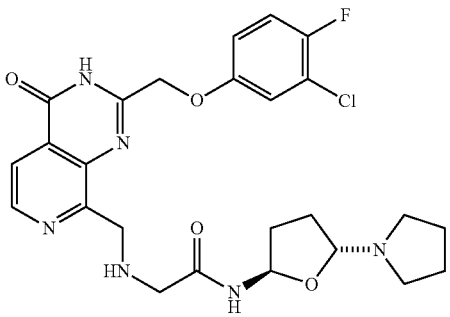 [SMILES: O=C(CNCc1nccc2c(=O)[nH]c(COc3ccc(F)c(Cl)c3)nc12)N[C@H]1CC[C@H](N2CCCC2)O1]

2-(((2-((3-chloro-4-fluorophenoxy)methyl)-4-oxo-3,4-dihydropyrido[3,4-d]pyrimidin-8-yl)methyl)amino)-N-(trans-5-(pyrrolidin-1-yl)tetrahydrofuran-2-yl)acetamide Using trans-4-(1-pyrrolidinyl)tetrahydro-3-furanamine, the title compound (18.0 mg) was obtained as described in Scheme 15 (Method O).
$^1$H NMR (600 MHz, CD$_3$OD) δ 8.68 (d, J=5.4 Hz, 1H), 8.07 (d, J=5.4 Hz, 1H), 7.25 (dd, J=3.0, 6.0 Hz, 1H), 7.20 (t, J=9.0 Hz, 1H), 7.05 (dt, J=3.0, 9.0 Hz), 5.11 (s, 2H), 4.70 (m, 2H), 4.25 (m, 1H), 4.09 (m, 4H), 4.07 (s, 2H), 3.88 (m, 1H), 3.74 (m, 1H), 3.65 (m, 1H), 3.42 (m, 1H), 3.19 (m, 1H), 2.09 (m, 4H)
MS (ESI+) m/z 531 (M+H)$^+$

Example 234

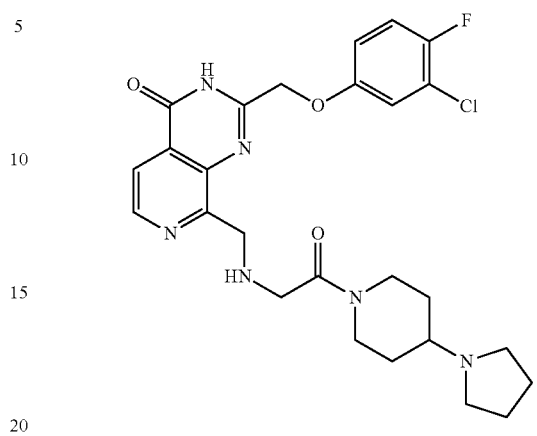

2-((3-chloro-4-fluorophenoxy)methyl)-8-(((2-oxo-2-(4-(pyrrolidin-1-yl)piperidin-1-yl)ethyl)amino)methyl)pyrido[3,4-d]pyrimidin-4(3H)-one Using 4-(pyrrolidin-1-yl)piperidine, the title compound (22.0 mg) was obtained as described in Scheme 15 (Method O).
$^1$H NMR (600 MHz, CD$_3$OD) δ 8.68 (d, J=5.4 Hz, 1H), 8.07 (d, J=5.4 Hz, 1H), 7.25 (m, 1H), 7.19 (m, 1H), 7.05 (m, 1H), 5.11 (s, 2H), 4.87 (s, 2H), 4.68 (m, 1H), 4.35 (m, 2H), 3.88 (m, 1H), 3.67 (m, 2H), 3.42 (m, 1H), 3.17 (m, 3H), 2.79 (m, 1H), 2.25 (m, 2H), 2.15 (m, 2H), 2.02 (m, 2H), 1.76 (m, 1H), 1.64 (m, 1H)
MS (ESI+) m/z 530 (M+H)$^+$

Example 235

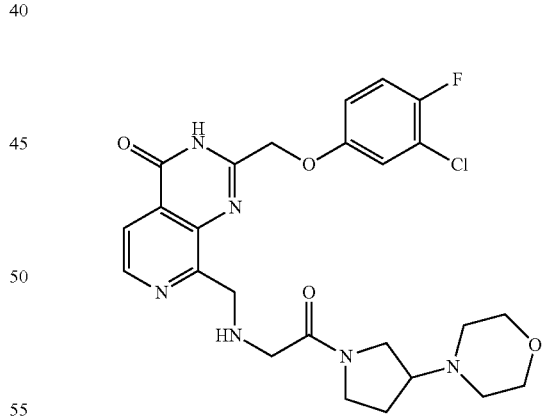

2-((3-chloro-4-fluorophenoxy)methyl)-8-(((2-(3-morpholinopyrrolidin-1-yl)-2-oxoethyl)amino)methyl)pyrido[3,4-d]pyrimidin-4(3H)-one Using 4-(pyrrolidin-3-yl)morpholine, the title compound (20.4 mg) was obtained as described in Scheme 15 (Method O).
$^1$H NMR (600 MHz, CD$_3$OD) δ 8.68 (d, J=5.4 Hz, 1H), 8.07 (d, J=5.4 Hz, 1H), 7.25 (dd, J=3.0, 6.0 Hz, 1H), 7.20 (t, J=9.0 Hz, 1H), 7.05 (dt, J=3.0, 9.0 Hz), 5.10 (m, 2H), 4.88 (m, 2H), 4.24 (m, 2H), 3.93-4.12 (m, 2H), 3.95 (m, 4H), 3.69-3.85 (m, 2H), 3.58 and 3.51 (m, 1H), 3.36 (m, 4H), 2.58 and 2.50 (m, 1H), 2.36 and 2.23 (m, 1H)

MS (ESI+) m/z 531 (M+H)+

Example 236

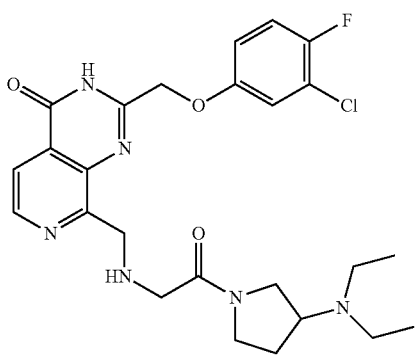 [SMILES: CCN(CC)C1CCN(C(=O)CNCc2nccc3c(=O)[nH]c(COc4ccc(F)c(Cl)c4)nc23)C1]

2-((3-chloro-4-fluorophenoxy)methyl)-8-(((2-(3-(diethylamino)pyrrolidin-1-yl)-2-oxoethyl)amino)methyl)pyrido[3,4-d]pyrimidin-4(3H)-one Using N,N-diethylpyrrolidin-3-amine, the title compound (19.2 mg) was obtained as described in Scheme 15 (Method O).

1H NMR (600 MHz, CD3OD) δ 8.68 (d, J=5.4 Hz, 1H), 8.06 (d, J=5.4 Hz, 1H), 7.25 (dd, J=3.0, 6.0 Hz, 1H), 7.20 (t, J=9.0 Hz, 1H), 7.05 (dt, J=3.0, 9.0 Hz), 5.11 (s, 2H), 4.88 (s, 2H), 4.25 (m, 2H), 4.02-4.28 (m, 4H), 3.77-3.90 (m, 2H), 3.47-3.72 (m, 3H), 2.56 and 2.49 (m, 1H), 2.30 and 2.16 (m, 1H), 1.35 (m, 6H)

MS (ESI+) m/z 517 (M+H)+

Example 237

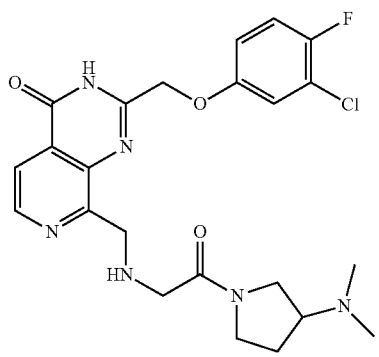 [SMILES: CN(C)C1CCN(C(=O)CNCc2nccc3c(=O)[nH]c(COc4ccc(F)c(Cl)c4)nc23)C1]

2-((3-chloro-4-fluorophenoxy)methyl)-8-(((2-(3-(dimethylamino)pyrrolidin-1-yl)-2-oxoethyl)amino)methyl)pyrido[3,4-d]pyrimidin-4(3H)-one Using N,N-dimethylpyrrolidin-3-amine, the title compound (16.8 mg) was obtained as described in Scheme 15 (Method O).

1H NMR (600 MHz, CD3OD) δ 8.68 (d, J=5.4 Hz, 1H), 8.06 (d, J=5.4 Hz, 1H), 7.24 (dd, J=3.0, 6.0 Hz, 1H), 7.19 (t, J=9.0 Hz, 1H), 7.05 (dt, J=3.0, 9.0 Hz), 5.10 (s, 2H), 4.88 (s, 2H), 4.20 (m, 2H), 4.00 (m, 2H), 3.75 (m, 2H), 3.60 (m, 1H), 2.96 (s, 6H), 2.55 and 2.49 (m, 1H), 2.33 and 2.20 (m, 1H)

MS (ESI+) m/z 489 (M+H)+

Example 238

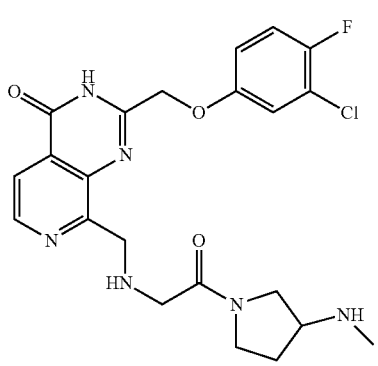 [SMILES: CNC1CCN(C(=O)CNCc2nccc3c(=O)[nH]c(COc4ccc(F)c(Cl)c4)nc23)C1]

2-((3-chloro-4-fluorophenoxy)methyl)-8-(((2-(3-(methylamino)pyrrolidin-1-yl)-2-oxoethyl)amino)methyl)pyrido[3,4-d]pyrimidin-4(3H)-one Using tert-butyl methyl(pyrrolidin-3-yl)carbamate, the title compound (25.6 mg) was obtained as described in Scheme 15 (Method O).

1H NMR (600 MHz, CD3OD) δ 8.68 (d, J=5.4 Hz, 1H), 8.06 (d, J=5.4 Hz, 1H), 7.24 (dd, J=3.0, 6.0 Hz, 1H), 7.19 (t, J=9.0 Hz, 1H), 7.05 (dt, J=3.0, 9.0 Hz), 5.10 (s, 2H), 4.89 (m, 2H), 4.25 (m, 2H), 3.95 and 3.89 (m, 2H), 3.74 (m, 2H), 3.64 (m, 1H), 2.78 (s, 3H), 2.50 and 2.40 (m, 1H), 2.30 and 2.18 (m, 1H)

MS (ESI+) m/z 475 (M+H)+

Example 239

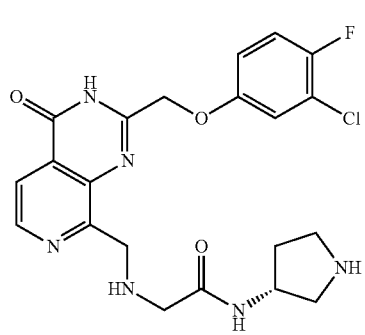 [SMILES: O=C(CNCc1nccc2c(=O)[nH]c(COc3ccc(F)c(Cl)c3)nc12)N[C@@H]1CCNC1]

(R)-2-(((2-((3-chloro-4-fluorophenoxy)methyl)-4-oxo-3,4-dihydropyrido[3,4-d]pyrimidin-8-yl)methyl)amino)-N-(pyrrolidin-3-yl)acetamide Using tert-butyl (R)-3-aminopyrrolidine-1-carboxylate, the title compound (17.5 mg) was obtained as described in Scheme 15 (Method O).

¹H NMR (600 MHz, CD₃OD) δ 8.67 (d, J=5.4 Hz, 1H), 8.06 (d, J=5.4 Hz, 1H), 7.25 (dd, J=3.0, 6.0 Hz, 1H), 7.20 (t, J=9.0 Hz, 1H), 7.05 (dt, J=3.0, 9.0 Hz), 5.11 (s, 2H), 4.88 (s, 2H), 4.51 (m, 1H), 4.04 (m, 2H), 3.55 (m, 1H), 3.48 (m, 1H), 3.36 (m, 2H), 2.35 (m, 1H), 2.07 (m, 1H)

MS (ESI+) m/z 461 (M+H)⁺

Scheme 16 (Method P)

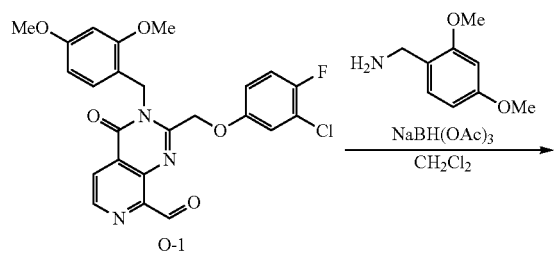

O-1

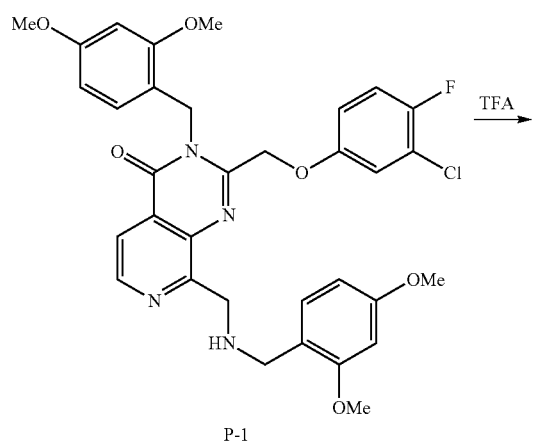

P-1

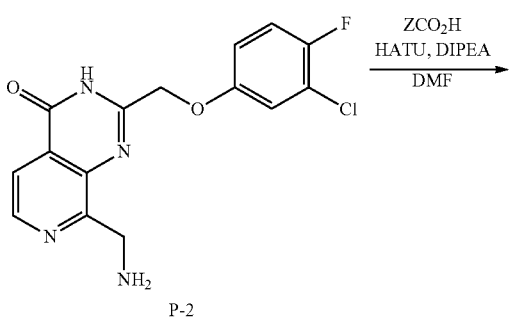

P-2

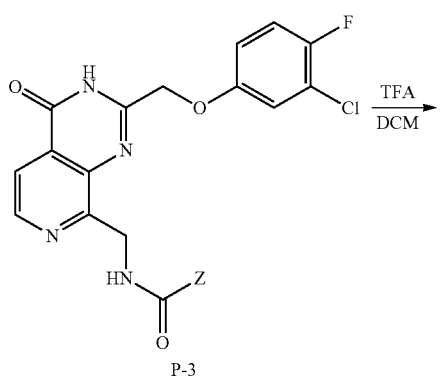

P-3

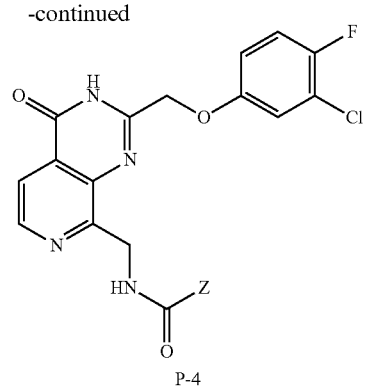

P-4

The general synthesis of compound P-4 is illustrated in Scheme 16. The aldehyde group is converted to primary amine by the 2-step reaction of reductive amination with 2,4-dimethoxybenzylamine and deprotection of 2,4-dimethoxybenzyl group by TFA. The primary amine of intermediate P-2 is converted to amide by coupling reaction using HATU to afford the intermediate P-3, whose Boc group was deprotected by TFA (optionally) to give the final products.

Example 240

Step 1

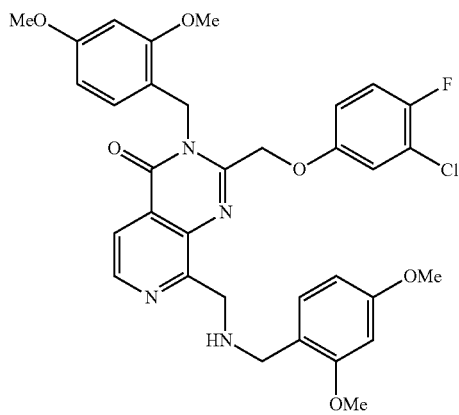 [SMILES: COc1ccc(CNCc2nccc3c(=O)n(Cc4ccc(OC)cc4OC)c(COc4ccc(F)c(Cl)c4)nc23)c(OC)c1]

2-((3-chloro-4-fluorophenoxy)methyl)-3-(2,4-dimethoxybenzyl)-8-(((2,4-dimethoxybenzyl)amino)methyl)pyrido[3,4-d]pyrimidin-4(3H)-one To a solution of intermediate O-1 (75 mg, 0.15 mmol) and 2,4-dimethoxybenzylamine (30 μl, 0.2 mmol) in DCM (5 mL) was added NaBH(OAc)₃ (64 mg, 0.3 mmol) portionwise. After being allowed to stir for 1 hour, the mixture was quenched with water. It was extracted with DCM, dried over MgSO₄ and concentrated. The residue was purified by combi-flash to afford the intermediate P-1 (64 mg, 0.10 mmol, 67% yield).

MS (ESI+) m/z 635 (M+H)⁺

Step 2

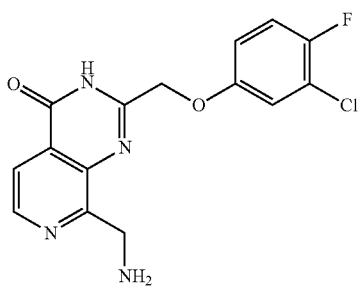 [SMILES: NCc1nccc2c(=O)[nH]c(COc3ccc(F)c(Cl)c3)nc12]

8-(aminomethyl)-2-((3-chloro-4-fluorophenoxy)methyl)pyrido[3,4-d]pyrimidin-4(3H)-one The intermediate P-1 (64 mg, 0.10 mmol) was dissolved in TFA (2 mL) and DCM (2 mL). After being allowed to stir overnight at 50° C., the mixture was concentrated in vacuo to afford the intermediate P-2 (quant.) as a crude product.

MS (ESI+) m/z 335 (M+H)$^+$

Step 3

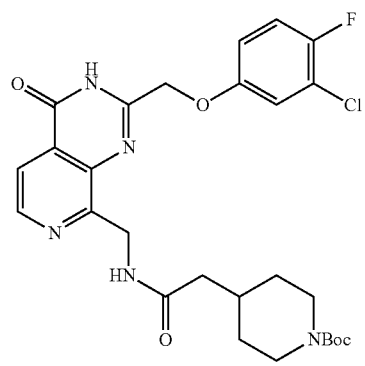 [SMILES: CC(C)(C)OC(=O)N1CCC(CC(=O)NCc2nccc3c(=O)[nH]c(COc4ccc(F)c(Cl)c4)nc23)CC1]

tert-butyl 4-(2-(((2-((3-chloro-4-fluorophenoxy)methyl)-4-oxo-3,4-dihydropyrido[3,4-d]pyrimidin-8-yl)methyl)amino)-2-oxoethyl)piperidine-1-carboxylate To a solution of intermediate P-2 (0.03 mmol, 10 mg, crude) and 2-(1-(tert-butoxycarbonyl)piperidin-4-yl)acetic acid (0.03 mmol, 7 mg) in DMF (1 mL) were added Et$_3$N (0.2 M in DMF, 300 μl, 0.06 mmol) and HATU (0.2M in DMF, 200 μl, 0.04 mmol). The mixture was allowed to stir for 1 hour. It was extracted with UCT SPE CUBCX cartridge and purified by preparative HPLC to afford the intermediate P-3 (2 mg).

MS (ESI+) m/z 560 (M+H)$^+$

Step 4

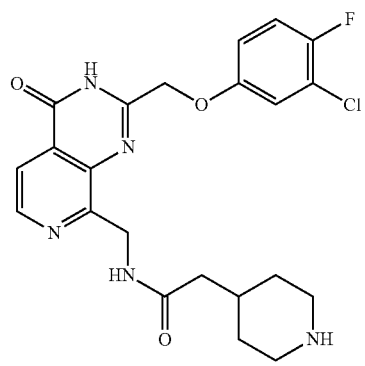 [SMILES: O=C(CC1CCNCC1)NCc1nccc2c(=O)[nH]c(COc3ccc(F)c(Cl)c3)nc12]

N-((2-((3-chloro-4-fluorophenoxy)methyl)-4-oxo-3,4-dihydropyrido[3,4-d]pyrimidin-8-yl)methyl)-2-(piperidin-4-yl)acetamide To a solution of intermediate P-3 (2 mg) in DCM (1 mL) was added TFA (0.3 mL). The mixture was allowed to stir for 30 min and concentrated in vacuo to afford the title compound (1.6 mg).

$^1$H NMR (400 MHz, CD$_3$OD) δ 8.56 (d, J=5.2 Hz, 1H), 7.95 (d, J=5.2 Hz, 1H), 7.27 (m, 1H), 7.16 (m, 1H), 7.04 (m, 1H), 5.09 (s, 2H), 4.95 (s, 2H), 3.35 (m, 2H), 2.98 (m, 2H), 2.30 (m, 2H), 2.10 (m, 1H), 2.00 (m, 2H), 1.47 (m, 2H)

MS (ESI+) m/z 460 (M+H)$^+$

Example 241

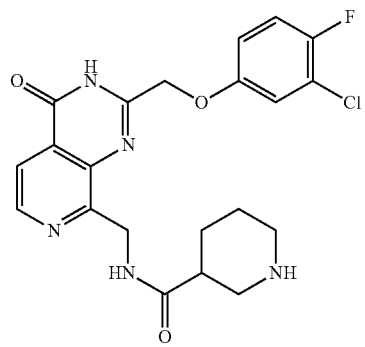 [SMILES: O=C(NCc1nccc2c(=O)[nH]c(COc3ccc(F)c(Cl)c3)nc12)C1CCCNC1]

N-((2-((3-chloro-4-fluorophenoxy)methyl)-4-oxo-3,4-dihydropyrido[3,4-d]pyrimidin-8-yl)methyl)piperidine-3-carboxamide Using 1-(tert-butoxycarbonyl)piperidine-4-carboxylic acid, the title compound (1.6 mg) was obtained as described in Scheme 16 (Method P).

$^1$H NMR (400 MHz, CD$_3$OD) δ 8.56 (d, J=5.2 Hz, 1H), 7.95 (d, J=5.2 Hz, 1H), 7.25 (m, 1H), 7.18 (m, 1H), 7.04 (m, 1H), 5.09 (s, 2H), 4.96 (s, 2H), 3.33 (m, 1H), 3.19 (m, 2H), 3.11 (m, 1H), 2.88 (m, 1H), 2.04 (m, 1H), 1.91 (m, 2H), 1.78 (m, 1H)

MS (ESI+) m/z 446 (M+H)$^+$

As used herein, the term "Ac" refers to acetyl group
As used herein, the term "Bn" refers to benzyl group.

As used herein, the term "Boc" refers to tert-butyloxycarbonyl

As used herein, the term "DCM" refers to dichloromethane

As used herein, the term "DDQ" refers to 2,3-Dichloro-5,6-Dicyanobenzoquinone.

As used herein, the term "DIPEA" refers to N,N-diisopropylethylamine.

As used herein, the term "DMF" refers to N,N-dimethylformamide.

As used herein, the term "dppf" refers to 1,1'-bis(diphenylphosphino)ferrocene.

As used herein, the term "EtOAc" refers to ethyl acetate.

As used herein, the term "Et" refers to ethyl group.

As used herein, the term "ESI" refers to Electrospray Ionization.

As used herein, the term "HATU" refers to 1-[bis(dimethylamino)methylene]-1H-1,2,3-triazolo[4,5-b]pyridinium 3-oxid hexafluorophosphate.

As used herein, the term "HPLC" refers to High-Performance Liquid Chromatography.

As used herein, the term "Me" refers to methyl group.

As used herein, the term "MEK" refers to 2-butanone.

As used herein, the term "MS" refers to mass spectroscopy.

As used herein, the term "OMe" refers to methoxy group.

As used herein, the term "Ph" refers to phenyl group.

As used herein, the term "SPE" refers to Solid-Phase Extraction.

As used herein, the term "'Bu" refers to tert-butyl group.

As used herein, the term "TFA" refers to trifluoroacetic acid.

As used herein, the term "THF" refers to tetrahydrofuran.

2. Biochemical Testing

FLAG-tagged JARID1B (also known as KDM5B) protein was screened against more than 170 compounds. For this compound screening, LANCE Ultra time-resolved fluorescence resonance energy transfer (TR-FRET) assay was employed using an europoium (Eu)-labeled antibody that can specifically recognize mono- or dimethylated peptides (H3K4me2/1) and ULight-streptavidin (ULight-SA), a small molecule fluorescent dye. When irradiated at 340 nm, the energy from the Eu donor is transferred to the ULight acceptor dye which, in turn, emits light primarily at 665 nm. The ratio between the intensity of primary emission at 665 nm and that of secondary emission at 590 nm was used to quantify the level of lysine methylation. As JARID1B removes more methyl moieties from tri-methylated substrate peptides (H3K4me3), the ratio increases until the enzyme reaction is terminated. In case, therefore, the compounds disrupt the enzymatic activity completely, the ratio becomes equal to a background value.

Recombinant human JARID1B/KDM5B (accession number NP_006609) of molecular weight 179.9 KDa was expressed in Sf9 insect cells and contains an N-terminal FLAG tag. The enzyme was obtained from Active Motif (Catalog No. 31432). The tri-methylated histone substrate peptide of purity greater than 95% was a synthetic peptide in which the first 21 amino acids correspond to the human histone H3 sequence with three extra amino acids and a biotin motif (GGK-biotin) linked to the C-terminus [sequence: ART-K (Me3)-QTARKSTGGKAPRKQLA-GGK-biotin-OH], (AnaSpec, Fremont, Calif. Catalog. No. ANA-1413). The reference inhibitory compound tranylcypromine (or trans-2-phenylcyclopropylamine hydrochloride, also known as, 2-PCPA) was purchased from Sigma (St. Louis, Mo. Cat. no. P8511). ULight-labeled streptavidin (ULight-SA, Catalog no. TRF0102), Eu-W1024-labeled anti-methyl-Histone H3 Lysine 4 (H3K4me1-2) Antibody (Catalog no. TRF0402), and LANCE detection buffer 10× (Catalog no. CR97-100) were obtained from PerkinElmer (Montreal, Quebec, Canada). The TR-FRET experiments were carried out in white, low-volume 384-wellplates purchased from PerkinElmer (ProxiPlate-384 Plus, Catalog no. 6008280).

The TR-FRET signal was measured in the presence both of the bio-H3K4me3 peptide and FLAG-JARID1B by detecting any H3K4me2/1 peptide produced in the assay system. Assays using only the bio-H3K4me2 peptide were served as a positive control. Robust enzymatic progressions were observed by using JARID1B at concentrations ranging from 10 to 30 nM. In a typical TR-FRET experiment, JARID1B was pre-incubated with or without 20 uM, 1 uM, or 0.1 uM of test-compounds (containing 1% DMSO final) for 5 mM. The enzymatic reactions were initiated by the addition of 500 nM biotinylated H3K4me3 peptide substrate plus 500 uM of 2-OG, 25 uM Fe(II) and 2 mM ascorbate. The reaction buffer also contained 50 mM Hepes (pH7.5), 0.01% (v/v) Tween 20, and 50 mM NaCl. The reaction mixture was incubated for 30 mM at room temperature before reading on an EnVision plate reader (PerkinElmer, Waltham, Mass.). Results are seen in Table 2.

TABLE 2

| No. | Chemical Name | % Inhibition at 100 nM |
|---|---|---|
| 1 | 2-((p-tolyloxy)methyl)pyrido[3,4-d]pyrimidin-4(3H)-one | N/A |
| 2 | 2-((4-butylphenoxy)methyl)pyrido[3,4-d]pyrimidin-4(3H)-one | N/A |
| 3 | 2-((4-(tert-butyl)phenoxy)methyl)pyrido[3,4-d]pyrimidin-4(3H)-one | N/A |
| 4 | 2-((4-(sec-butyl)phenoxy)methyl)pyrido[3,4-d]pyrimidin-4(3H)-one | N/A |
| 5 | 2-((4-cyclopentylphenoxy)methyl)pyrido[3,4-d]pyrimidin-4(3H)-one | N/A |
| 6 | 2-((4-cyclohexylphenoxy)methyl)pyrido[3,4-d]pyrimidin-4(3H)-one | N/A |
| 7 | 2-((4-(2-methoxyethyl)phenoxy)methyl)pyrido[3,4-d]pyrimidin-4(3H)-one | N/A |
| 8 | 2-((4-acetylphenoxy)methyl)pyrido[3,4-d]pyrimidin-4(3H)-one | N/A |
| 9 | 2-((4-(3-oxobutyl)phenoxy)methyl)pyrido[3,4-d]pyrimidin-4(3H)-one | N/A |
| 10 | N-(4-((4-oxo-3,4-dihydropyrido[3,4-d]pyrimidin-2-yl)methoxy)phenyl)acetamide | N/A |
| 11 | 2-(((2,3-dihydro-1H-inden-5-yl)oxy)methyl)pyrido[3,4-d]pyrimidin-4(3H)-one | N/A |
| 12 | 2-(((5,6,7,8-tetrahydronaphthalen-2-yl)oxy)methyl)pyrido[3,4-d]pyrimidin-4(3H)-one | N/A |
| 13 | 2-((4-(morpholine-4-carbonyl)phenoxy)methyl)pyrido[3,4-d]pyrimidin-4(3H)-one | N/A |
| 14 | 2-((3-(piperidine-1-carbonyl)phenoxy)methyl)pyrido[3,4-d]pyrimidin-4(3H)-one | N/A |

TABLE 2-continued

| No. | Chemical Name | % Inhibition at 100 nM |
|---|---|---|
| 15 | 2-((4-benzylphenoxy)methyl)pyrido[3,4-d]pyrimidin-4(3H)-one | N/A |
| 16 | 2-((4-(1-phenylethyl)phenoxy)methyl)pyrido[3,4-d]pyrimidin-4(3H)-one | N/A |
| 17 | 2-((4-(2-phenylpropan-2-yl)phenoxy)methyl)pyrido[3,4-d]pyrimidin-4(3H)-one | N/A |
| 18 | 2-((4-phenoxyphenoxy)methyl)pyrido[3,4-d]pyrimidin-4(3H)-one | N/A |
| 19 | 2-((4-(benzyloxy)phenoxy)methyl)pyrido[3,4-d]pyrimidin-4(3H)-one | N/A |
| 20 | 2-((3-(benzyloxy)phenoxy)methyl)pyrido[3,4-d]pyrimidin-4(3H)-one | N/A |
| 21 | 2-((4-benzoylphenoxy)methyl)pyrido[3,4-d]pyrimidin-4(3H)-one | N/A |
| 22 | 2-(([1,1'-biphenyl]-3-yloxy)methyl)pyrido[3,4-d]pyrimidin-4(3H)-one | N/A |
| 23 | 2-((4-fluorophenoxy)methyl)pyrido[3,4-d]pyrimidin-4(3H)-one | N/A |
| 24 | 2-((3,4-difluorophenoxy)methyl)pyrido[3,4-d]pyrimidin-4(3H)-one | N/A |
| 25 | 2-((4-chlorophenoxy)methyl)pyrido[3,4-d]pyrimidin-4(3H)-one | N/A |
| 26 | 2-((3-chlorophenoxy)methyl)pyrido[3,4-d]pyrimidin-4(3H)-one | N/A |
| 27 | 2-((2-chlorophenoxy)methyl)pyrido[3,4-d]pyrimidin-4(3H)-one | N/A |
| 28 | 2-((3,4-dichlorophenoxy)methyl)pyrido[3,4-d]pyrimidin-4(3H)-one | N/A |
| 29 | 2-((3,5-dichlorophenoxy)methyl)pyrido[3,4-d]pyrimidin-4(3H)-one | N/A |
| 30 | 4-((4-oxo-3,4-dihydropyrido[3,4-d]pyrimidin-2-yl)methoxy)benzonitrile | N/A |
| 31 | 3-((4-oxo-3,4-dihydropyrido[3,4-d]pyrimidin-2-yl)methoxy)benzonitrile | N/A |
| 32 | 2-((4-nitrophenoxy)methyl)pyrido[3,4-d]pyrimidin-4(3H)-one | N/A |
| 33 | 2-((4-methoxyphenoxy)methyl)pyrido[3,4-d]pyrimidin-4(3H)-one | N/A |
| 34 | 2-((pyridin-4-yloxy)methyl)pyrido[3,4-d]pyrimidin-4(3H)-one | N/A |
| 35 | 2-((pyridin-3-yloxy)methyl)pyrido[3,4-d]pyrimidin-4(3H)-one | N/A |
| 36 | 2-(((6-fluoropyridin-3-yl)oxy)methyl)pyrido[3,4-d]pyrimidin-4(3H)-one | N/A |
| 37 | 2-(((6-bromopyridin-3-yl)oxy)methyl)pyrido[3,4-d]pyrimidin-4(3H)-one | N/A |
| 38 | 2-(((6-methylpyridin-3-yl)oxy)methyl)pyrido[3,4-d]pyrimidin-4(3H)-one | N/A |
| 39 | 2-((3,4,5-trimethoxyphenoxy)methyl)pyrido[3,4-d]pyrimidin-4(3H)-one | + |
| 40 | N-(2-morpholinoethyl)-3-((4-oxo-3,4-dihydropyrido[3,4-d]pyrimidin-2-yl)methoxy)benzamide | + |
| 41 | 2-((3-(((((tetrahydro-2H-pyran-4-yl)methyl)amino)methyl)phenoxy)methyl)pyrido[3,4-d]pyrimidin-4(3H)-one | N/A |
| 42 | 2-((3-((benzylamino)methyl)phenoxy)methyl)pyrido[3,4-d]pyrimidin-4(3H)-one | + |
| 43 | 2-((3-((4-propoxypiperidin-1-yl)methyl)phenoxy)methyl)pyrido[3,4-d]pyrimidin-4(3H)-one | ++ |
| 44 | 2-((3-(((tetrahydro-2H-pyran-4-yl)amino)methyl)phenoxy)methyl)pyrido[3,4-d]pyrimidin-4(3H)-one | + |
| 45 | 2-((3-(((2-morpholinoethyl)amino)methyl)phenoxy)methyl)pyrido[3,4-d]pyrimidin-4(3H)-one | + |
| 46 | 2-chloro-5-((4-oxo-3,4-dihydropyrido[3,4-d]pyrimidin-2-yl)methoxy)-N-(2-(piperidin-4-yl)ethyl)benzamide | ++ |
| 47 | 2-chloro-N-((1-(2-hydroxyethyl)piperidin-4-yl)methyl)-5-((4-oxo-3,4-dihydropyrido[3,4-d]pyrimidin-2-yl)methoxy)benzamide | N/A |
| 48 | 2-chloro-N-((1-(2-methoxyethyl)piperidin-4-yl)methyl)-5-((4-oxo-3,4-dihydropyrido[3,4-d]pyrimidin-2-yl)methoxy)benzamide | N/A |
| 49 | 2-chloro-N-((1-methylpiperidin-4-yl)methyl)-5-((4-oxo-3,4-dihydropyrido[3,4-d]pyrimidin-2-yl)methoxy)benzamide | N/A |
| 50 | N-((1-benzylpiperidin-4-yl)methyl)-2-chloro-5-((4-oxo-3,4-dihydropyrido[3,4-d]pyrimidin-2-yl)methoxy)benzamide | N/A |
| 51 | 2-chloro-N-(2-morpholinoethyl)-5-((4-oxo-3,4-dihydropyrido[3,4-d]pyrimidin-2-yl)methoxy)benzamide | N/A |
| 52 | N-benzyl-2-chloro-5-((4-oxo-3,4-dihydropyrido[3,4-d]pyrimidin-2-yl)methoxy)benzamide | N/A |
| 53 | 2-((3-(4-benzylpiperidine-1-carbonyl)-4-chlorophenoxy)methyl)pyrido[3,4-d]pyrimidin-4(3H)-one | N/A |
| 54 | 2-((4-chloro-3-(4-propoxypiperidine-1-carbonyl)phenoxy)methyl)pyrido[3,4-d]pyrimidin-4(3H)-one | N/A |
| 55 | 2-chloro-N-(cyclohexylmethyl)-5-((4-oxo-3,4-dihydropyrido[3,4-d]pyrimidin-2-yl)methoxy)benzamide | N/A |
| 56 | 2-chloro-5-((4-oxo-3,4-dihydropyrido[3,4-d]pyrimidin-2-yl)methoxy)-N-(pyridin-4-ylmethyl)benzamide | N/A |
| 57 | 2-chloro-N-(3-(dimethylamino)propyl)-5-((4-oxo-3,4-dihydropyrido[3,4-d]pyrimidin-2-yl)methoxy)benzamide | N/A |
| 58 | 2-chloro-N-cyclopentyl-5-((4-oxo-3,4-dihydropyrido[3,4-d]pyrimidin-2-yl)methoxy)benzamide | N/A |
| 59 | 2-((4-chloro-3-(pyrrolidine-1-carbonyl)phenoxy)methyl)pyrido[3,4-d]pyrimidin-4(3H)-one | N/A |
| 60 | 2-((4-chloro-3-(piperidine-1-carbonyl)phenoxy)methyl)pyrido[3,4-d]pyrimidin-4(3H)-one | N/A |
| 61 | N-((1-acetylpiperidin-4-yl)methyl)-2-chloro-5-((4-oxo-3,4-dihydropyrido[3,4-d]pyrimidin-2-yl)methoxy)benzamide | N/A |
| 62 | 2-((4-chloro-3-(piperazine-1-carbonyl)phenoxy)methyl)pyrido[3,4-d]pyrimidin-4(3H)-one | N/A |
| 63 | N-(trans-1,4-aminocyclohexyl)-2-chloro-5-((4-oxo-3,4-dihydropyrido[3,4-d]pyrimidin-2-yl)methoxy)benzamide | N/A |
| 64 | 2-chloro-5-((4-oxo-3,4-dihydropyrido[3,4-d]pyrimidin-2-yl)methoxy)-N-(piperidin-4-ylmethyl)benzamide | N/A |

TABLE 2-continued

| No. | Chemical Name | % Inhibition at 100 nM |
|---|---|---|
| 65 | 2-((4-chloro-3-(morpholine-4-carbonyl)phenoxy)methyl)pyrido[3,4-d]pyrimidin-4(3H)-one | N/A |
| 66 | 2-chloro-5-((4-oxo-3,4-dihydropyrido[3,4-d]pyrimidin-2-yl)methoxy)-N-((tetrahydro-2H-pyran-4-yl)methyl)benzamide | N/A |
| 67 | 2-methyl-5-((4-oxo-3,4-dihydropyrido[3,4-d]pyrimidin-2-yl)methoxy)-N-(2-(piperidin-4-yl)ethyl)benzamide | N/A |
| 68 | 2-bromo-5-((4-oxo-3,4-dihydropyrido[3,4-d]pyrimidin-2-yl)methoxy)-N-(2-(piperidin-4-yl)ethyl)benzamide | N/A |
| 69 | methyl 2-chloro-5-((4-oxo-3,4-dihydropyrido[3,4-d]pyrimidin-2-yl)methoxy)benzoate | N/A |
| 70 | 2-((2-(pyridin-4-yl)phenoxy)methyl)pyrido[3,4-d]pyrimidin-4(3H)-one | N/A |
| 71 | 2-(4-oxo-3,4-dihydropyrido[3,4-d]pyrimidin-2-yl)-N-(2-(piperidin-4-yl)ethyl)benzofuran-7-carboxamide | N/A |
| 72 | methyl 2-(4-oxo-3,4-dihydropyrido[3,4-d]pyrimidin-2-yl)benzofuran-7-carboxylate | N/A |
| 73 | 2-(((4-(sec-butyl)phenyl)amino)methyl)pyrido[3,4-d]pyrimidin-4(3H)-one | N/A |
| 74 | 2-(((4-cyclohexylphenyl)amino)methyl)pyrido[3,4-d]pyrimidin-4(3H)-one | N/A |
| 75 | 2-(((4-phenoxyphenyl)amino)methyl)pyrido[3,4-d]pyrimidin-4(3H)-one | N/A |
| 76 | 2-(((4-(benzyloxy)phenyl)amino)methyl)pyrido[3,4-d]pyrimidin-4(3H)-one | N/A |
| 77 | 2-(((4-((4-methoxybenzyl)oxy)phenyl)amino)methyl)pyrido[3,4-d]pyrimidin-4(3H)-one | N/A |
| 78 | 2-(((3-(benzyloxy)phenyl)amino)methyl)pyrido[3,4-d]pyrimidin-4(3H)-one | N/A |
| 79 | 2-(([1,1'-biphenyl]-3-ylamino)methyl)pyrido[3,4-d]pyrimidin-4(3H)-one | N/A |
| 80 | 2-(((3,4-difluorophenyl)amino)methyl)pyrido[3,4-d]pyrimidin-4(3H)-one | N/A |
| 81 | 2-(((1-methylpiperidin-4-yl)amino)methyl)pyrido[3,4-d]pyrimidin-4(3H)-one | N/A |
| 82 | 2-(((1-benzylpiperidin-4-yl)amino)methyl)pyrido[3,4-d]pyrimidin-4(3H)-one | N/A |
| 83 | 8-((benzylamino)methyl)pyrido[3,4-d]pyrimidin-4(3H)-one | N/A |
| 84 | 8-((((2,6-dichloropyridin-4-yl)methyl)amino)methyl)pyrido[3,4-d]pyrimidin-4(3H)-one | N/A |
| 85 | 8-(((cyclohexylmethyl)amino)methyl)pyrido[3,4-d]pyrimidin-4(3H)-one | + |
| 86 | 8-(((4-(diethylamino)butyl)amino)methyl)pyrido[3,4-d]pyrimidin-4(3H)-one | + |
| 87 | 8-(((5-(diethylamino)pentan-2-yl)amino)methyl)pyrido[3,4-d]pyrimidin-4(3H)-one | + |
| 88 | 8-(((3-(2-oxopyrrolidin-1-yl)propyl)amino)methyl)pyrido[3,4-d]pyrimidin-4(3H)-one | + |
| 89 | 8-(((azetidin-3-ylmethyl)amino)methyl)pyrido[3,4-d]pyrimidin-4(3H)-one | N/A |
| 90 | 8-(((pyrrolidin-3-ylmethyl)amino)methyl)pyrido[3,4-d]pyrimidin-4(3H)-one | N/A |
| 91 | (S)-8-(((pyrrolidin-2-ylmethyl)amino)methyl)pyrido[3,4-d]pyrimidin-4(3H)-one | N/A |
| 92 | 8-((((1-methylpyrrolidin-3-yl)methyl)amino)methyl)pyrido[3,4-d]pyrimidin-4(3H)-one | ++ |
| 93 | 8-(((piperidin-4-ylmethyl)amino)methyl)pyrido[3,4-d]pyrimidin-4(3H)-one | ++ |
| 94 | 8-(((1-(piperidin-4-yl)ethyl)amino)methyl)pyrido[3,4-c]pyrimidin-4(3H)-one | + |
| 95 | 8-((((1-methylpiperidin-4-yl)methyl)amino)methyl)pyrido[3,4-d]pyrimidin-4(3H)-one | ++ |
| 96 | 8-((((1-benzylpiperidin-4-yl)methyl)amino)methyl)pyrido[3,4-d]pyrimidin-4(3H)-one | ++ |
| 97 | 8-((((1'-methyl-[1,4'-bipiperidin]-4-yl)methyl)amino)methyl)pyrido[3,4-d]pyrimidin-4(3H)-one | ++ |
| 98 | (R)-8-(((piperidin-3-ylmethyl)amino)methyl)pyrido[3,4-d]pyrimidin-4(3H)-one | + |
| 99 | (S)-8-(((piperidin-3-ylmethyl)amino)methyl)pyrido[3,4-d]pyrimidin-4(3H)-one | ++ |
| 100 | 8-((((1-methylpiperidin-3-yl)methyl)amino)methyl)pyrido[3,4-d]pyrimidin-4(3H)-one | +++ |
| 101 | 8-((((1-benzylpiperidin-3-yl)methyl)amino)methyl)pyrido[3,4-d]pyrimidin-4(3H)-one | ++ |
| 102 | 8-((((1-benzylpiperidin-2-yl)methyl)amino)methyl)pyrido[3,4-d]pyrimidin-4(3H)-one | N/A |
| 103 | 8-(((1-benzylpiperidin-4-yl)amino)methyl)pyrido[3,4-d]pyrimidin-4(3H)-one | N/A |
| 104 | 8-((((1s,4s)-4-aminocyclohexyl)amino)methyl)pyrido[3,4-d]pyrimidin-4(3H)-one | N/A |
| 105 | 8-((((1-benzylpiperidin-4-yl)methyl)amino)methyl)-2-((2-chlorophenoxy)methyl)pyrido[3,4-d]pyrimidin-4(3H)-one | +++ |

TABLE 2-continued

| No. | Chemical Name | % Inhibition at 100 nM |
|---|---|---|
| 106 | 8-((((1-benzylpiperidin-4-yl)methyl)amino)methyl)-2-((3-chlorophenoxy)methyl)pyrido[3,4-d]pyrimidin-4(3H)-one | +++ |
| 107 | 8-((((1-benzylpiperidin-4-yl)methyl)amino)methyl)-2-((4-chlorophenoxy)methyl)pyrido[3,4-d]pyrimidin-4(3H)-one | +++ |
| 108 | 8-((((1-benzylpiperidin-4-yl)methyl)amino)methyl)-2-((4-bromophenoxy)methyl)pyrido[3,4-d]pyrimidin-4(3H)-one | +++ |
| 109 | 8-((((1-benzylpiperidin-4-yl)methyl)amino)methyl)-2-((pyridin-3-yloxy)methyl)pyrido[3,4-d]pyrimidin-4(3H)-one | ++ |
| 110 | 8-((((1-benzylpiperidin-4-yl)methyl)amino)methyl)-2-((pyridin-4-yloxy)methyl)pyrido[3,4-d]pyrimidin-4(3H)-one | +++ |
| 111 | 2-((4-benzylphenoxy)methyl)-8-((((1-benzylpiperidin-4-yl)methyl)amino)methyl)pyrido[3,4-d]pyrimidin-4(3H)-one | +++ |
| 112 | 2-((2-chloro-5-(trifluoromethyl)phenoxy)methyl)-8-(((piperidin-4-ylmethyl)amino)methyl)pyrido[3,4-d]pyrimidin-4(3H)-one | ++ |
| 113 | 2-((2,3-dichlorophenoxy)methyl)-8-(((piperidin-4-ylmethyl)amino)methyl)pyrido[3,4-d]pyrimidin-4(3H)-one | ++ |
| 114 | 2-((2,4-dichlorophenoxy)methyl)-8-(((piperidin-4-ylmethyl)amino)methyl)pyrido[3,4-d]pyrimidin-4(3H)-one | ++ |
| 115 | 2-((2,5-dichlorophenoxy)methyl)-8-(((piperidin-4-ylmethyl)amino)methyl)pyrido[3,4-d]pyrimidin-4(3H)-one | ++ |
| 116 | 2-((2-fluorophenoxy)methyl)-8-(((piperidin-4-ylmethyl)amino)methyl)pyrido[3,4-d]pyrimidin-4(3H)-one | ++ |
| 117 | 2-((2-bromophenoxy)methyl)-8-(((piperidin-4-ylmethyl)amino)methyl)pyrido[3,4-d]pyrimidin-4(3H)-one | ++ |
| 118 | 8-(((piperidin-4-ylmethyl)amino)methyl)-2-((o-tolyloxy)methyl)pyrido[3,4-d]pyrimidin-4(3H)-one | ++ |
| 119 | 8-(((piperidin-4-ylmethyl)amino)methyl)-2-((m-tolyloxy)methyl)pyrido[3,4-d]pyrimidin-4(3H)-one | ++ |
| 120 | 8-(((piperidin-4-ylmethyl)amino)methyl)-2-((p-tolyloxy)methyl)pyrido[3,4-d]pyrimidin-4(3H)-one | ++ |
| 121 | 2-((4-benzylphenoxy)methyl)-8-(((piperidin-4-ylmethyl)amino)methyl)pyrido[3,4-d]pyrimidin-4(3H)-one | +++ |
| 122 | 2-((2-chlorophenoxy)methyl)-8-(((piperidin-4-ylmethyl)amino)methyl)pyrido[3,4-d]pyrimidin-4(3H)-one | ++ |
| 123 | 2-(phenoxymethyl)-8-(((piperidin-4-ylmethyl)amino)methyl)pyrido[3,4-d]pyrimidin-4(3H)-one | ++ |
| 124 | 2-((2,4-difluorophenoxy)methyl)-8-(((piperidin-4-ylmethyl)amino)methyl)pyrido[3,4-d]pyrimidin-4(3H)-one | ++ |
| 125 | 2-((3,5-difluorophenoxy)methyl)-8-(((piperidin-4-ylmethyl)amino)methyl)pyrido[3,4-d]pyrimidin-4(3H)-one | ++ |
| 126 | 2-((3-chloro-4-fluorophenoxy)methyl)-8-(((piperidin-4-ylmethyl)amino)methyl)pyrido[3,4-d]pyrimidin-4(3H)-one | +++ |
| 127 | 2-((4-chloro-3-fluorophenoxy)methyl)-8-(((piperidin-4-ylmethyl)amino)methyl)pyrido[3,4-d]pyrimidin-4(3H)-one | ++ |
| 128 | 2-((4-oxo-8-(((piperidin-4-ylmethyl)amino)methyl)-3,4-dihydropyrido[3,4-d]pyrimidin-2-yl)methoxy)benzonitrile | ++ |
| 129 | 4-((4-oxo-8-(((piperidin-4-ylmethyl)amino)methyl)-3,4-dihydropyrido[3,4-d]pyrimidin-2-yl)methoxy)benzonitrile | ++ |
| 130 | 2-((2-chloro-5-methylphenoxy)methyl)-8-(((piperidin-4-ylmethyl)amino)methyl)pyrido[3,4-d]pyrimidin-4(3H)-one | +++ |
| 131 | 2-(((5-bromopyrazin-2-yl)oxy)methyl)-8-(((piperidin-4-ylmethyl)amino)methyl)pyrido[3,4-d]pyrimidin-4(3H)-one | ++ |
| 132 | 2-((3-chlorophenoxy)methyl)-8-(((piperidin-4-ylmethyl)amino)methyl)pyrido[3,4-d]pyrimidin-4(3H)-one | +++ |
| 133 | 8-(((piperidin-4-ylmethyl)amino)methyl)-2-((pyridin-2-yloxy)methyl)pyrido[3,4-d]pyrimidin-4(3H)-one | + |
| 134 | 2-((4-chloro-3-methylphenoxy)methyl)-8-(((piperidin-4-ylmethyl)amino)methyl)pyrido[3,4-d]pyrimidin-4(3H)-one | ++ |
| 135 | 2-((4-ethylphenoxy)methyl)-8-(((piperidin-4-ylmethyl)amino)methyl)pyrido[3,4-d]pyrimidin-4(3H)-one | ++ |
| 136 | 2-((3,4-dimethylphenoxy)methyl)-8-(((piperidin-4-ylmethyl)amino)methyl)pyrido[3,4-d]pyrimidin-4(3H)-one | ++ |
| 137 | 2-((4-chloro-2-methylphenoxy)methyl)-8-(((piperidin-4-ylmethyl)amino)methyl)pyrido[3,4-d]pyrimidin-4(3H)-one | ++ |
| 138 | 3-((4-oxo-8-(((piperidin-4-ylmethyl)amino)methyl)-3,4-dihydropyrido[3,4-d]pyrimidin-2-yl)methoxy)benzonitrile | ++ |
| 139 | 2-(((2,3-dihydro-1H-inden-5-yl)oxy)methyl)-8-(((piperidin-4-ylmethyl)amino)methyl)pyrido[3,4-d]pyrimidin-4(3H)-one | ++ |
| 140 | 2-((4-cyclopentylphenoxy)methyl)-8-(((piperidin-4-ylmethyl)amino)methyl)pyrido[3,4-d]pyrimidin-4(3H)-one | ++ |
| 141 | 2-(4-(1-phenylethyl)phenoxy)methyl)-8-(((piperidin-4-ylmethyl)amino)methyl)pyrido[3,4-d]pyrimidin-4(3H)-one | ++ |
| 142 | 2-((4-benzylphenoxy)methyl)-8-((((1-ethylpyrrolidin-3-yl)methyl)amino)methyl)pyrido[3,4-d]pyrimidin-4(3H)-one | +++ |
| 143 | 2-((4-benzylphenoxy)methyl)-8-(((4-(pyrrolidin-1-yl)butyl)amino)methyl)pyrido[3,4-d]pyrimidin-4(3H)-one | ++ |
| 144 | 2-((4-benzylphenoxy)methyl)-8-((((1-methylpyrrolidin-3-yl)methyl)amino)methyl)pyrido[3,4-d]pyrimidin-4(3H)-one | +++ |

TABLE 2-continued

| No. | Chemical Name | % Inhibition at 100 nM |
|---|---|---|
| 145 | (R)-2-((4-benzylphenoxy)methyl)-8-((((1-ethylpyrrolidin-2-yl)methyl)amino)methyl)pyrido[3,4-d]pyrimidin-4(3H)-one | ++ |
| 146 | (S)-2-((4-benzylphenoxy)methyl)-8-((((1-ethylpyrrolidin-2-yl)methyl)amino)methyl)pyrido[3,4-d]pyrimidin-4(3H)-one | ++ |
| 147 | 8-(((azetidin-3-ylmethyl)amino)methyl)-2-((4-benzylphenoxy)methyl)pyrido[3,4-d]pyrimidin-4(3H)-one | +++ |
| 148 | (R)-2-((4-benzylphenoxy)methyl)-8-((((tetrahydrofuran-2-yl)methyl)amino)methyl)pyrido[3,4-d]pyrimidin-4(3H)-one | ++ |
| 149 | 2-((4-benzylphenoxy)methyl)-8-((((tetrahydro-2H-pyran-4-yl)methyl)amino)methyl)pyrido[3,4-d]pyrimidin-4(3H)-one | +++ |
| 150 | (S)-2-((4-benzylphenoxy)methyl)-8-(((pyrrolidin-3-ylmethyl)amino)methyl)pyrido[3,4-d]pyrimidin-4(3H)-one | +++ |
| 151 | (R)-2-((4-benzylphenoxy)methyl)-8-(((pyrrolidin-3-ylmethyl)amino)methyl)pyrido[3,4-d]pyrimidin-4(3H)-one | ++ |
| 152 | 2-((4-benzylphenoxy)methyl)-8-((((1-methylpiperidin-4-yl)methyl)amino)methyl)pyrido[3,4-d]pyrimidin-4(3H)-one | +++ |
| 153 | (S)-2-((4-benzylphenoxy)methyl)-8-(((piperidin-3-ylmethyl)amino)methyl)pyrido[3,4-d]pyrimidin-4(3H)-one | +++ |
| 154 | (R)-2-((4-benzylphenoxy)methyl)-8-(((piperidin-3-ylmethyl)amino)methyl)pyrido[3,4-d]pyrimidin-4(3H)-one | +++ |
| 155 | 8-((((1r,4r)-4-aminocyclohexyl)amino)methyl)-2-((4-benzylphenoxy)methyl)pyrido[3,4-d]pyrimidin-4(3H)-one | ++ |
| 156 | 2-((4-benzylphenoxy)methyl)-8-(((piperidin-3-ylmethyl)amino)methyl)pyrido[3,4-d]pyrimidin-4(3H)-one | + |
| 157 | 2-((4-benzylphenoxy)methyl)-8-(((2-morpholinoethyl)amino)methyl)pyrido[3,4-d]pyrimidin-4(3H)-one | ++ |
| 158 | (S)-((3-chloro-4-fluorophenoxy)methyl)-8-(((pyrrolidin-3-ylmethyl)amino)methyl)pyrido[3,4-d]pyrimidin-4(3H)-one | +++ |
| 159 | 2-((3-chloro-4-fluorophenoxy)methyl)-8-((((1-methylpyrrolidin-3-yl)methyl)amino)methyl)pyrido[3,4-d]pyrimidin-4(3H)-one | +++ |
| 160 | 2-((3-chloro-4-fluorophenoxy)methyl)-8-((((1-methylpiperidin-4-yl)methyl)amino)methyl)pyrido[3,4-d]pyrimidin-4(3H)-one | +++ |
| 161 | 2-((3-chloro-4-fluorophenoxy)methyl)-8-((((tetrahydro-2H-pyran-4-yl)methyl)amino)methyl)pyrido[3,4-d]pyrimidin-4(3H)-one | + |
| 162 | 2-((3-chloro-4-fluorophenoxy)methyl)-8-((((tetrahydro-2H-pyran-3-yl)methyl)amino)methyl)pyrido[3,4-d]pyrimidin-4(3H)-one | + |
| 163 | 2-((3-chloro-4-fluorophenoxy)methyl)-8-((((tetrahydrofuran-3-yl)methyl)amino)methyl)pyrido[3,4-d]pyrimidin-4(3H)-one | + |
| 164 | 2-((3-chloro-4-fluorophenoxy)methyl)-8-(((2-morpholinoethyl)amino)methyl)pyrido[3,4-d]pyrimidin-4(3H)-one | ++ |
| 165 | 8-(((3-(1H-imidazol-1-yl)propyl)amino)methyl)-2-((3-chloro-4-fluorophenoxy)methyl)pyrido[3,4-d]pyrimidin-4(3H)-one | +++ |
| 166 | 2-((3-chloro-4-fluorophenoxy)methyl)-8-((((5-methylpyrazin-2-yl)methyl)amino)methyl)pyrido[3,4-d]pyrimidin-4(3H)-one | ++ |
| 167 | 2-((3-chloro-4-fluorophenoxy)methyl)-8-(((morpholin-2-ylmethyl)amino)methyl)pyrido[3,4-d]pyrimidin-4(3H)-one | +++ |
| 168 | 2-((3-chloro-4-fluorophenoxy)methyl)-8-((((1-isopropylpiperidin-4-yl)methyl)amino)methyl)pyrido[3,4-d]pyrimidin-4(3H)-one | +++ |
| 169 | 2-((3-chloro-4-fluorophenoxy)methyl)-8-((((1-cyclopentylpiperidin-4-yl)methyl)amino)methyl)pyrido[3,4-d]pyrimidin-4(3H)-one | +++ |
| 170 | 2-((3-chloro-4-fluorophenoxy)methyl)-8-(((pyridin-2-ylmethyl)amino)methyl)pyrido[3,4-d]pyrimidin-4(3H)-one | ++ |
| 171 | 2-((3-chloro-4-fluorophenoxy)methyl)-8-(((furan-2-ylmethyl)amino)methyl)pyrido[3,4-d]pyrimidin-4(3H)-one | ++ |
| 172 | 2-((3-chloro-4-fluorophenoxy)methyl)-8-(((pyridin-3-ylmethyl)amino)methyl)pyrido[3,4-d]pyrimidin-4(3H)-one | +++ |
| 173 | 2-((3-chloro-4-fluorophenoxy)methyl)-8-(((pyridin-4-ylmethyl)amino)methyl)pyrido[3,4-d]pyrimidin-4(3H)-one | ++ |
| 174 | 5-((((2-((3-chloro-4-fluorophenoxy)methyl)-4-oxo-3,4-dihydropyrido[3,4-d]pyrimidin-8-yl)methyl)amino)methyl)-N,N-dimethylfuran-2-carboxamide | ++ |
| 175 | 2-((3-chloro-4-fluorophenoxy)methyl)-8-(((2-(2-methyl-1H-imidazol-1-yl)ethyl)amino)methyl)pyrido[3,4-d]pyrimidin-4(3H)-one | ++ |
| 176 | 2-((3-chloro-4-fluorophenoxy)methyl)-8-(((2-(thiophen-2-yl)ethyl)amino)methyl)pyrido[3,4-d]pyrimidin-4(3H)-one | ++ |
| 177 | 2-((3-chloro-4-fluorophenoxy)methyl)-8-((((3-methylisoxazol-5-yl)methyl)amino)methyl)pyrido[3,4-d]pyrimidin-4(3H)-one | ++ |
| 178 | 2-((3-chloro-4-fluorophenoxy)methyl)-8-((((4-methylmorpholin-2-yl)methyl)amino)methyl)pyrido[3,4-d]pyrimidin-4(3H)-one | ++ |
| 179 | 2-((3-chloro-4-fluorophenoxy)methyl)-8-(((oxazol-2-ylmethyl)amino)methyl)pyrido[3,4-d]pyrimidin-4(3H)-one | ++ |
| 180 | 2-((3-chloro-4-fluorophenoxy)methyl)-8-(((pyrimidin-2-ylmethyl)amino)methyl)pyrido[3,4-d]pyrimidin-4(3H)-one | ++ |
| 181 | 2-((3-chloro-4-fluorophenoxy)methyl)-8-(((thiophen-2-ylmethyl)amino)methyl)pyrido[3,4-d]pyrimidin-4(3H)-one | ++ |
| 182 | 2-((3-chloro-4-fluorophenoxy)methyl)-8-((((2-chloropyridin-4-yl)methyl)amino)methyl)pyrido[3,4-d]pyrimidin-4(3H)-one | ++ |

TABLE 2-continued

| No. | Chemical Name | % Inhibition at 100 nM |
|---|---|---|
| 183 | 2-((3-chloro-4-fluorophenoxy)methyl)-8-((((2-(3,5-dimethyl-1H-pyrazol-1-yl)ethyl)amino)methyl)pyrido[3,4-d]pyrimidin-4(3H)-one | + |
| 184 | 2-((3-chloro-4-fluorophenoxy)methyl)-8-((((2-(6-methylpyridin-2-yl)ethyl)amino)methyl)pyrido[3,4-d]pyrimidin-4(3H)-one | + |
| 185 | 2-((3-chloro-4-fluorophenoxy)methyl)-8-((((3-(5-oxo-5,7-dihydro-6H-pyrrolo[3,4-b]pyridin-6-yl)propyl)amino)methyl)pyrido[3,4-d]pyrimidin-4(3H)-one | ++ |
| 186 | 2-((3-chloro-4-fluorophenoxy)methyl)-8-((((2-(pyridin-2-yl)ethyl)amino)methyl)pyrido[3,4-d]pyrimidin-4(3H)-one | ++ |
| 187 | (R)-2-((3-chloro-4-fluorophenoxy)methyl)-8-((((morpholin-2-ylmethyl)amino)methyl)pyrido[3,4-d]pyrimidin-4(3H)-one | +++ |
| 188 | 2-((3-chloro-4-fluorophenoxy)methyl)-8-(((((1-(2-hydroxyethyl)piperidin-4-yl)methyl)amino)methyl)pyrido[3,4-d]pyrimidin-4(3H)-one | +++ |
| 189 | 2-((3-chloro-4-fluorophenoxy)methyl)-8-(((((1-(2-methoxyethyl)piperidin-4-yl)methyl)amino)methyl)pyrido[3,4-d]pyrimidin-4(3H)-one | +++ |
| 190 | (S)-2-((3-chloro-4-fluorophenoxy)methyl)-8-((((morpholin-2-ylmethyl)amino)methyl)pyrido[3,4-d]pyrimidin-4(3H)-one | +++ |
| 191 | 2-cyclopentyl-8-(((piperidin-4-ylmethyl)amino)methyl)pyrido[3,4-d]pyrimidin-4(3H)-one | + |
| 192 | 2-cyclopentyl-8-(((((1-methylpiperidin-4-yl)methyl)amino)methyl)pyrido[3,4-d]pyrimidin-4(3H)-one | + |
| 193 | 8-(((piperidin-4-ylmethyl)amino)methyl)-2-(tetrahydrofuran-2-yl)pyrido[3,4-d]pyrimidin-4(3H)-one | + |
| 194 | 8-(((((1-methylpiperidin-4-yl)methyl)amino)methyl)-2-(tetrahydrofuran-2-yl)pyrido[3,4-d]pyrimidin-4(3H)-one | + |
| 195 | 8-(((piperidin-4-ylmethyl)amino)methyl)-2-(tetrahydrofuran-3-yl)pyrido[3,4-d]pyrimidin-4(3H)-one | + |
| 196 | 8-(((((1-methylpiperidin-4-yl)methyl)amino)methyl)-2-(tetrahydrofuran-3-yl)pyrido[3,4-d]pyrimidin-4(3H)-one | + |
| 197 | 2-(2,3-dihydrobenzofuran-2-yl)-8-(((piperidin-4-ylmethyl)amino)methyl)pyrido[3,4-d]pyrimidin-4(3H)-one | ++ |
| 198 | 2-(2,3-dihydrobenzofuran-2-yl)-8-(((((1-methylpiperidin-4-yl)methyl)amino)methyl)pyrido[3,4-d]pyrimidin-4(3H)-one | ++ |
| 199 | 2-(chroman-2-yl)-8-(((piperidin-4-ylmethyl)amino)methyl)pyrido[3,4-d]pyrimidin-4(3H)-one | + |
| 200 | 2-(chroman-2-yl)-8-(((((1-methylpiperidin-4-yl)methyl)amino)methyl)pyrido[3,4-d]pyrimidin-4(3H)-one | ++ |
| 201 | 2-(2,3-dihydro-1H-inden-2-yl)-8-(((((1-methylpiperidin-4-yl)methyl)amino)methyl)pyrido[3,4-d]pyrimidin-4(3H)-one | + |
| 202 | 2-((benzyloxy)methyl)-8-(((piperidin-4-ylmethyl)amino)methyl)pyrido[3,4-d]pyrimidin-4(3H)-one | ++ |
| 203 | 2-((benzyloxy)methyl)-8-(((((1-methylpiperidin-4-yl)methyl)amino)methyl)pyrido[3,4-d]pyrimidin-4(3H)-one | +++ |
| 204 | (S)-2-((benzyloxy)methyl)-8-(((pyrrolidin-3-ylmethyl)amino)methyl)pyrido[3,4-d]pyrimidin-4(3H)-one | ++ |
| 205 | 2-((benzyloxy)methyl)-8-(((((1-methylpyrrolidin-3-yl)methyl)amino)methyl)pyrido[3,4-d]pyrimidin-4(3H)-one | ++ |
| 206 | 2-(((3-chlorobenzyl)oxy)methyl)-8-(((piperidin-4-ylmethyl)amino)methyl)pyrido[3,4-d]pyrimidin-4(3H)-one | +++ |
| 207 | 2-(((3-chlorobenzyl)oxy)methyl)-8-(((((1-methylpiperidin-4-yl)methyl)amino)methyl)pyrido[3,4-d]pyrimidin-4(3H)-one | +++ |
| 208 | (S)-2-(((3-chlorobenzyl)oxy)methyl)-8-(((pyrrolidin-3-ylmethyl)amino)methyl)pyrido[3,4-d]pyrimidin-4(3H)-one | +++ |
| 209 | 2-(((2-chlorobenzyl)oxy)methyl)-8-(((piperidin-4-ylmethyl)amino)methyl)pyrido[3,4-d]pyrimidin-4(3H)-one | +++ |
| 210 | 2-(((2-chlorobenzyl)oxy)methyl)-8-(((((1-methylpiperidin-4-yl)methyl)amino)methyl)pyrido[3,4-d]pyrimidin-4(3H)-one | +++ |
| 211 | 2-(1-(4-benzylphenoxy)ethyl)-8-(((((1-methylpiperidin-4-yl)methyl)amino)methyl)pyrido[3,4-d]pyrimidin-4(3H)-one | + |
| 212 | 2-(1-(4-benzylphenoxy)ethyl)-8-(((piperidin-4-ylmethyl)amino)methyl)pyrido[3,4-d]pyrimidin-4(3H)-one | ++ |
| 213 | 2-(1-(4-benzylphenoxy)ethyl)-8-((((((S)-pyrrolidin-3-yl)methyl)amino)methyl)pyrido[3,4-d]pyrimidin-4(3H)-one | ++ |
| 214 | 2-(1-(4-benzylphenoxy)ethyl)-8-(((((1-methylpyrrolidin-3-yl)methyl)amino)methyl)pyrido[3,4-d]pyrimidin-4(3H)-one | ++ |
| 215 | (R)-2-(1-(4-benzylphenoxy)ethyl)-8-(((piperidin-4-ylmethyl)amino)methyl)pyrido[3,4-d]pyrimidin-4(3H)-one | +++ |
| 216 | (R)-2-(1-(4-benzylphenoxy)ethyl)-8-(((((1-methylpiperidin-4-yl)methyl)amino)methyl)pyrido[3,4-d]pyrimidin-4(3H)-one | +++ |
| 217 | (R)-2-(1-(3-chloro-4-fluorophenoxy)ethyl)-8-(((piperidin-4-ylmethyl)amino)methyl)pyrido[3,4-d]pyrimidin-4(3H)-one | + |
| 218 | (R)-2-(1-(3-chloro-4-fluorophenoxy)ethyl)-8-(((((1-methylpiperidin-4-yl)methyl)amino)methyl)pyrido[3,4-d]pyrimidin-4(3H)-one | ++ |
| 219 | (S)-2-(1-(3-chloro-4-fluorophenoxy)ethyl)-8-(((piperidin-4-ylmethyl)amino)methyl)pyrido[3,4-d]pyrimidin-4(3H)-one | ++ |

TABLE 2-continued

| No. | Chemical Name | % Inhibition at 100 nM |
|---|---|---|
| 220 | (S)-2-(1-(3-chloro-4-fluorophenoxy)ethyl)-8-((((1-methylpiperidin-4-yl)methyl)amino)methyl)pyrido[3,4-d]pyrimidin-4(3H)-one | +++ |
| 221 | 2-(((2-((3-chloro-4-fluorophenoxy)methyl)-4-oxo-3,4-dihydropyrido[3,4-d]pyrimidin-8-yl)methyl)amino)-N-(2-(dimethylamino)ethyl)-N-ethylacetamide | +++ |
| 222 | N-butyl-2-(((2-((3-chloro-4-fluorophenoxy)methyl)-4-oxo-3,4-dihydropyrido[3,4-d]pyrimidin-8-yl)methyl)amino)-N-ethylacetamide | ++ |
| 223 | 2-((3-chloro-4-fluorophenoxy)methyl)-8-(((2-oxo-2-(pyrrolidin-1-yl)ethyl)amino)methyl)pyrido[3,4-d]pyrimidin-4(3H)-one | ++ |
| 224 | 2-((3-chloro-4-fluorophenoxy)methyl)-8-(((2-oxo-2-(piperidin-1-yl)ethyl)amino)methyl)pyrido[3,4-d]pyrimidin-4(3H)-one | ++ |
| 225 | 2-((3-chloro-4-fluorophenoxy)methyl)-8-(((2-morpholino-2-oxoethyl)amino)methyl)pyrido[3,4-d]pyrimidin-4(3H)-one | ++ |
| 226 | 2-((3-chloro-4-fluorophenoxy)methyl)-8-(((2-(4-methylpiperazin-1-yl)-2-oxoethyl)amino)methyl)pyrido[3,4-d]pyrimidin-4(3H)-one | +++ |
| 227 | 2-(((2-((3-chloro-4-fluorophenoxy)methyl)-4-oxo-3,4-dihydropyrido[3,4-d]pyrimidin-8-yl)methyl)amino)-N-((1-methylpyrrolidin-3-yl)methyl)acetamide | ++ |
| 228 | (R)-8-(((2-(3-aminopyrrolidin-1-yl)-2-oxoethyl)amino)methyl)-2-((3-chloro-4-fluorophenoxy)methyl)pyrido[3,4-d]pyrimidin-4(3H)-one | +++ |
| 229 | (S)-8-(((2-(3-aminopyrrolidin-1-yl)-2-oxoethyl)amino)methyl)-2-((3-chloro-4-fluorophenoxy)methyl)pyrido[3,4-d]pyrimidin-4(3H)-one | +++ |
| 230 | (R)-2-(((2-((3-chloro-4-fluorophenoxy)methyl)-4-oxo-3,4-dihydropyrido[3,4-d]pyrimidin-8-yl)methyl)amino)-N-(piperidin-3-yl)acetamide | +++ |
| 231 | (S)-2-(((2-((3-chloro-4-fluorophenoxy)methyl)-4-oxo-3,4-dihydropyrido[3,4-d]pyrimidin-8-yl)methyl)amino)-N-(piperidin-3-yl)acetamide | +++ |
| 232 | N-(1-benzylpyrrolidin-3-yl)-2-(((2-((3-chloro-4-fluorophenoxy)methyl)-4-oxo-3,4-dihydropyrido[3,4-d]pyrimidin-8-yl)methyl)amino)acetamide | +++ |
| 233 | 2-(((2-((3-chloro-4-fluorophenoxy)methyl)-4-oxo-3,4-dihydropyrido[3,4-d]pyrimidin-8-yl)methyl)amino)-N-(trans-5-(pyrrolidin-1-yl)tetrahydrofuran-2-yl)acetamide | +++ |
| 234 | 2-((3-chloro-4-fluorophenoxy)methyl)-8-(((2-oxo-2-(4-(pyrrolidin-1-yl)piperidin-1-yl)ethyl)amino)methyl)pyrido[3,4-d]pyrimidin-4(3H)-one | +++ |
| 235 | 2-((3-chloro-4-fluorophenoxy)methyl)-8-(((2-(3-morpholinopyrrolidin-1-yl)-2-oxoethyl)amino)methyl)pyrido[3,4-d]pyrimidin-4(3H)-one | ++ |
| 236 | 2-((3-chloro-4-fluorophenoxy)methyl)-8-(((2-(3-(diethylamino)pyrrolidin-1-yl)-2-oxoethyl)amino)methyl)pyrido[3,4-d]pyrimidin-4(3H)-one | +++ |
| 237 | 2-((3-chloro-4-fluorophenoxy)methyl)-8-(((2-(3-(dimethylamino)pyrrolidin-1-yl)-2-oxoethyl)amino)methyl)pyrido[3,4-d]pyrimidin-4(3H)-one | +++ |
| 238 | 2-((3-chloro-4-fluorophenoxy)methyl)-8-(((2-(3-(methylamino)pyrrolidin-1-yl)-2-oxoethyl)amino)methyl)pyrido[3,4-d]pyrimidin-4(3H)-one | +++ |
| 239 | (R)-2-(((2-((3-chloro-4-fluorophenoxy)methyl)-4-oxo-3,4-dihydropyrido[3,4-d]pyrimidin-8-yl)methyl)amino)-N-(pyrrolidin-3-yl)acetamide | +++ |
| 240 | N-((2-((3-chloro-4-fluorophenoxy)methyl)-4-oxo-3,4-dihydropyrido[3,4-d]pyrimidin-8-yl)methyl)-2-(piperidin-4-yl)acetamide | + |
| 241 | N-((2-((3-chloro-4-fluorophenoxy)methyl)-4-oxo-3,4-dihydropyrido[3,4-d]pyrimidin-8-yl)methyl)piperidine-3-carboxamide | + |

NOTE:
+++: % Inhibition > 50,
++: 50 > % Inhibition > 20,
+: 20 > % Inhibition,
N/A: Not Available As used herein, the term "2,4-PDCA" refers to 2,4-pyridinedicarboxylic acid monohydrate.

As used herein, the term "DMSO" refers to dimethyl sulfoxide.

As used herein, the term "bio" refers to biotin or biotinylated

As used herein, the term "H3K4me2" refers to dimethylated lysine 4 in histone H3

As used herein, the term "H3K4me3" refers to trimethylated lysine 4 in histone H3.

As used herein, the term "KDM5" refers to Lysine Demethylase 5

As used herein, the term "a-KG" refers to alpha-ketoglutarate, or a salt or solvate thereof.

As used herein, the term "$IC_{50}$" refers to half maximal inhibitory concentration 3. Cellular Testing In order to test the cellular inhibitory potency of compounds, the level of global trimethylation at lysine 4 on histone H3 was assessed by immunoblot analysis in a human osteosarcoma U2-OS cell line stably overexpressing KDM5B. U2-OS cells were seeded in 6-well plates at a density of $2.5 \times 10^5$ cells/well in 3 mL McCoys 5A medium containing 10% heat-inactivated fetal bovine serum and 100 U/ml penicillin/streptomycin (Invitrogen Gibco, USA) and incubated overnight. A KDM5B-expression plasmid tagged with Myc-DDK (Origene, USA) was transfected into the cells using Lipofectamine 2000 (Invitrogen, USA) according to the manufacturer's instructions. Forty-eight hours after the transfection, the cells were diluted to 1:100 for passage and neomycin-resistant clones were selected in the presence of 600 μg/ml 0418 (Gibco BRL, USA) for 2 weeks. The positive clones were picked up and expanded individually for 2 weeks. The expression of KDM5B in each clone was verified by immunoblot analysis, and the clones overexpressing KDM5B were subsequently maintained in McCoys 5A medium supplemented with 300 μg/ml G418 at 37° C. in an atmosphere of 5% $CO_2$.

For assays of compounds, U2-OS cells stably overexpressing KDM5B were seeded in 12-well plates at a density of $1.0 \times 10^5$ cells/well in 1 mL of McCoys 5A medium without 0418. The cells were incubated for 24 hours before the addition of compounds. The compounds were diluted in McCoys 5A medium and the total volume of medium in each well was 2 mL with the final concentration of DMSO 0.3%.

Twenty-four hours after the treatment with compounds, the cells were washed twice with Dulbecco's Phosphate-Buffered Saline and total cellular proteins were extracted with RIPA buffer (Simga, USA) containing protease inhibitor (Complete Protease Inhibitor Cocktail Tablets; Roche Applied Science, Switzerland). The extract was centrifuged at 14,000×g for 10 minutes, and the supernatants were recovered. The protein concentration was quantitated using BCA Protein Assay (Pierce, USA) and SoftMax pro software version 5.2 (Molecular Device, USA). After denaturation at 95° C. for 10 minutes, the total proteins (20 μg of protein/lane) were separated by SDS-PAGE on 4~12% gradient gels (Invitrogen, USA). The resolved proteins were transferred onto a 0.45-μm nitrocellulose membrane by wet electroblotting for 1 hour, and then the membrane was soaked in Tris-buffered saline containing 5% nonfat dry milk and 0.05% Tween-20 (TBS-T) for 1 hour at room temperature. The membrane was incubated with 1:2000 H3K4me3 antibodies (ab8580; Abcam) and 1:10000 H3 antibodies (ab1791; Abcam) overnight at 4° C. The membrane was washed with TBS-T three times for 30 min and then incubated with 1:5000 or 1:20000 anti-rabbit secondary antibodies for 1 hour at room temperature. Protein bands of interest were visualized by chemiluminescence (Amersham ECL prime Western Blotting Detection Reagents; GE Healthcare Lifesciences, USA). Each protein band image was acquired by a Molecular Imager ChemiDoc XRS System (Bio-Rad, USA) and quantified by using Quantity One software (ver 4.6.7). The normalized level of tri-methylation was determined by dividing an H3K4me3 band intensity by a corresponding H3 band intensity and half-maximal inhibitory concentration ($IC_{50}$) was calculated using Sigma Plot. Results are seen in Table 3.

TABLE 3

| No. | Chemical Name | $IC_{50}$ |
|---|---|---|
| 15 | 2-((4-benzylphenoxy)methyl)pyrido[3,4-d]pyrimidin-4(3H)-one | + |
| 46 | 2-chloro-5-((4-oxo-3,4-dihydropyrido[3,4-d]pyrimidin-2-yl)methoxy)-N-(2-(piperidin-4-yl)ethyl)benzamide | + |
| 49 | 2-chloro-N-((1-methylpiperidin-4-yl)methyl)-5-((4-oxo-3,4-dihydropyrido[3,4-d]pyrimidin-2-yl)methoxy)benzamide | + |
| 50 | N-((1-benzylpiperidin-4-yl)methyl)-2-chloro-5-((4-oxo-3,4-dihydropyrido[3,4-d]pyrimidin-2-yl)methoxy)benzamide | + |
| 69 | methyl 2-chloro-5-((4-oxo-3,4-dihydropyrido[3,4-d]pyrimidin-2-yl)methoxy)benzoate | + |
| 92 | 8-(((((1-methylpyrrolidin-3-yl)methyl)amino)methyl)pyrido[3,4-d]pyrimidin-4(3H)-one | + |
| 95 | 8-(((((1-methylpiperidin-4-yl)methyl)amino)methyl)pyrido[3,4-d]pyrimidin-4(3H)-one | ++ |
| 96 | 8-(((((1-benzylpiperidin-4-yl)methyl)amino)methyl)pyrido[3,4-d]pyrimidin-4(3H)-one | + |
| 98 | (R)-8-(((piperidin-3-ylmethyl)amino)methyl)pyrido[3,4-d]pyrimidin-4(3H)-one | + |
| 99 | (S)-8-(((piperidin-3-ylmethyl)amino)methyl)pyrido[3,4-d]pyrimidin-4(3H)-one | +++ |
| 100 | 8-(((((1-methylpiperidin-3-yl)methyl)amino)methyl)pyrido[3,4-d]pyrimidin-4(3H)-one | + |
| 105 | 8-(((((1-benzylpiperidin-4-yl)methyl)amino)methyl)-2-((2-chlorophenoxy)methyl)pyrido[3,4-d]pyrimidin-4(3H)-one | +++ |
| 106 | 8-(((((1-benzylpiperidin-4-yl)methyl)amino)methyl)-2-((3-chlorophenoxy)methyl)pyrido[3,4-d]pyrimidin-4(3H)-one | +++ |
| 107 | 8-(((((1-benzylpiperidin-4-yl)methyl)amino)methyl)-2-((4-chlorophenoxy)methyl)pyrido[3,4-d]pyrimidin-4(3H)-one | +++ |
| 108 | 8-(((((1-benzylpiperidin-4-yl)methyl)amino)methyl)-2-((4-bromophenoxy)methyl)pyrido[3,4-d]pyrimidin-4(3H)-one | +++ |
| 109 | 8-(((((1-benzylpiperidin-4-yl)methyl)amino)methyl)-2-((pyridin-3-yloxy)methyl)pyrido[3,4-d]pyrimidin-4(3H)-one | ++ |
| 110 | 8-(((((1-benzylpiperidin-4-yl)methyl)amino)methyl)-2-((pyridin-4-yloxy)methyl)pyrido[3,4-d]pyrimidin-4(3H)-one | + |
| 111 | 2-((4-benzylphenoxy)methyl)-8-(((((1-benzylpiperidin-4-yl)methyl)amino)methyl)pyrido[3,4-d]pyrimidin-4(3H)-one | +++ |
| 121 | 2-((4-benzylphenoxy)methyl)-8-(((piperidin-4-ylmethyl)amino)methyl)pyrido[3,4-d]pyrimidin-4(3H)-one | + |
| 126 | 2-((3-chloro-4-fluorophenoxy)methyl)-8-(((piperidin-4-ylmethyl)amino)methyl)pyrido[3,4-d]pyrimidin-4(3H)-one | ++ |
| 142 | 2-((4-benzylphenoxy)methyl)-8-(((((1-ethylpyrrolidin-3-yl)methyl)amino)methyl)pyrido[3,4-d]pyrimidin-4(3H)-one | +++ |
| 143 | 2-((4-benzylphenoxy)methyl)-8-(((4-(pyrrolidin-1-yl)butyl)amino)methyl)pyrido[3,4-d]pyrimidin-4(3H)-one | ++ |
| 144 | 2-((4-benzylphenoxy)methyl)-8-(((((1-methylpyrrolidin-3-yl)methyl)amino)methyl)pyrido[3,4-d]pyrimidin-4(3H)-one | +++ |

TABLE 3-continued

| No. | Chemical Name | IC$_{50}$ |
|---|---|---|
| 150 | (S)-2-((4-benzylphenoxy)methyl)-8-(((pyrrolidin-3-ylmethyl)amino)methyl)pyrido[3,4-d]pyrimidin-4(3H)-one | + |
| 152 | 2-((4-benzylphenoxy)methyl)-8-((((1-methylpiperidin-4-yl)methyl)amino)methyl)pyrido[3,4-d]pyrimidin-4(3H)-one | +++ |
| 155 | 8-((((1r,4r)-4-aminocyclohexyl)amino)methyl)-2-((4-benzylphenoxy)methyl)pyrido[3,4-d]pyrimidin-4(3H)-one | + |
| 157 | 2-((4-benzylphenoxy)methyl)-8-(((2-morpholinoethyl)amino)methyl)pyrido[3,4-d]pyrimidin-4(3H)-one | + |
| 158 | (S)-2-((3-chloro-4-fluorophenoxy)methyl)-8-(((pyrrolidin-3-ylmethyl)amino)methyl)pyrido[3,4-d]pyrimidin-4(3H)-one | +++ |
| 159 | 2-((3-chloro-4-fluorophenoxy)methyl)-8-((((1-methylpyrrolidin-3-yl)methyl)amino)methyl)pyrido[3,4-d]pyrimidin-4(3H)-one | ++++ |
| 160 | 2-((3-chloro-4-fluorophenoxy)methyl)-8-((((1-methylpyrrolidin-4-yl)methyl)amino)methyl)pyrido[3,4-d]pyrimidin-4(3H)-one | ++++ |
| 165 | 8-(((3-(1H-imidazol-1-yl)propyl)amino)methyl)-2-((3-chloro-4-fluorophenoxy)methyl)pyrido[3,4-d]pyrimidin-4(3H)-one | ++ |
| 167 | 2-((3-chloro-4-fluorophenoxy)methyl)-8-(((morpholin-2-ylmethyl)amino)methyl)pyrido[3,4-d]pyrimidin-4(3H)-one | +++ |
| 168 | 2-((3-chloro-4-fluorophenoxy)methyl)-8-((((1-isopropylpiperidin-4-yl)methyl)amino)methyl)pyrido[3,4-d]pyrimidin-4(3H)-one | +++ |
| 169 | 2-((3-chloro-4-fluorophenoxy)methyl)-8-((((1-cyclopentylpiperidin-4-yl)methyl)amino)methyl)pyrido[3,4-d]pyrimidin-4(3H)-one | ++++ |
| 178 | 2-((3-chloro-4-fluorophenoxy)methyl)-8-((((4-methylmorpholin-2-yl)methyl)amino)methyl)pyrido[3,4-d]pyrimidin-4(3H)-one | + |
| 188 | 2-((3-chloro-4-fluorophenoxy)methyl)-8-((((1-(2-hydroxyethyl)piperidin-4-yl)methyl)amino)methyl)pyrido[3,4-d]pyrimidin-4(3H)-one | +++ |
| 198 | 2-(2,3-dihydrobenzofuran-2-yl)-8-((((1-methylpiperidin-4-yl)methyl)amino)methyl)pyrido[3,4-d]pyrimidin-4(3H)-one | + |
| 202 | 2-((benzyloxy)methyl)-8-(((piperidin-4-ylmethyl)amino)methyl)pyrido[3,4-d]pyrimidin-4(3H)-one | + |
| 203 | 2-((benzyloxy)methyl)-8-((((1-methylpiperidin-4-yl)methyl)amino)methyl)pyrido[3,4-d]pyrimidin-4(3H)-one | ++++ |
| 204 | (S)-2-((benzyloxy)methyl)-8-(((pyrrolidin-3-ylmethyl)amino)methyl)pyrido[3,4-d]pyrimidin-4(3H)-one | + |
| 205 | 2-((benzyloxy)methyl)-8-((((1-methylpyrrolidin-3-yl)methyl)amino)methyl)pyrido[3,4-d]pyrimidin-4(3H)-one | +++ |
| 207 | 2-(((3-chlorobenzyl)oxy)methyl)-8-((((1-methylpiperidin-4-yl)methyl)amino)methyl)pyrido[3,4-d]pyrimidin-4(3H)-one | +++ |
| 210 | 2-(((2-chlorobenzyl)oxy)methyl)-8-((((1-methylpiperidin-4-yl)methyl)amino)methyl)pyrido[3,4-d]pyrimidin-4(3H)-one | +++ |
| 216 | (R)-2-(1-(4-benzylphenoxy)ethyl)-8-((((1-methylpiperidin-4-yl)methyl)amino)methyl)pyrido[3,4-d]pyrimidin-4(3H)-one | ++ |
| 221 | 2-(((2-((3-chloro-4-fluorophenoxy)methyl)-4-oxo-3,4-dihydropyrido[3,4-d]pyrimidin-8-yl)methyl)amino)-N-(2-(dimethylamino)ethyl)-N-ethylacetamide | ++ |
| 223 | 2-((3-chloro-4-fluorophenoxy)methyl)-8-(((2-oxo-2-(pyrrolidin-1-yl)ethyl)amino)methyl)pyrido[3,4-d]pyrimidin-4(3H)-one | ++ |
| 228 | (R)-8-(((2-(3-aminopyrrolidin-1-yl)-2-oxoethyl)amino)methyl)-2-((3-chloro-4-fluorophenoxy)methyl)pyrido[3,4-d]pyrimidin-4(3H)-one | +++ |
| 232 | N-(1-benzylpyrrolidin-3-yl)-2-(((2-((3-chloro-4-fluorophenoxy)methyl)-4-oxo-3,4-dihydropyrido[3,4-d]pyrimidin-8-yl)methyl)amino)acetamide | +++ |
| 233 | 2-(((2-((3-chloro-4-fluorophenoxy)methyl)-4-oxo-3,4-dihydropyrido[3,4-d]pyrimidin-8-yl)methyl)amino)-N-(trans-5-(pyrrolidin-1-yl)tetrahydrofuran-2-yl)acetamide | + |
| 234 | 2-((3-chloro-4-fluorophenoxy)methyl)-8-(((2-oxo-2-(4-(pyrrolidin-1-yl)piperidin-1-yl)ethyl)amino)methyl)pyrido[3,4-d]pyrimidin-4(3H)-one | ++ |
| 235 | 2-((3-chloro-4-fluorophenoxy)methyl)-8-(((2-(3-morpholinopyrrolidin-1-yl)-2-oxoethyl)amino)methyl)pyrido[3,4-d]pyrimidin-4(3H)-one | + |
| 236 | 2-((3-chloro-4-fluorophenoxy)methyl)-8-(((2-(3-(diethylamino)pyrrolidin-1-yl)-2-oxoethyl)amino)methyl)pyrido[3,4-d]pyrimidin-4(3H)-one | ++ |
| 237 | 2-((3-chloro-4-fluorophenoxy)methyl)-8-(((2-(3-(dimethylamino)pyrrolidin-1-yl)-2-oxoethyl)amino)methyl)pyrido[3,4-d]pyrimidin-4(3H)-one | +++ |
| 238 | 2-((3-chloro-4-fluorophenoxy)methyl)-8-(((2-(3-(methylamino)pyrrolidin-1-yl)-2-oxoethyl)amino)methyl)pyrido[3,4-d]pyrimidin-4(3H)-one | + |
| 239 | (R)-2-(((2-((3-chloro-4-fluorophenoxy)methyl)-4-oxo-3,4-dihydropyrido[3,4-d]pyrimidin-8-yl)methyl)amino)-N-(pyrrolidin-3-yl)acetamide | + |

++++: IC$_{50}$ < 1,
+++: 1 ≤ IC$_{50}$ < 10,
++: 10 ≤ IC$_{50}$ < 30,
+: IC$_{50}$ ≥ 30

4. Cell Growth Inhibition Assay

MCF-7 cells were seeded at 2000 cells/well in 100 uL complete medium in 96 well plates. Cells were incubated for 24 hours before addition of compound. Compounds were diluted in complete medium (100 uL/well) and added to the plates in duplicates. The total volume of medium in the wells was 200 uL, and the final concentration of DMSO 1%. Complete medium was DMEM with 4 mM L-glutamine containing 10% heat-inactivated fetal bovine serum and 100 U/ml penicillin/streptomycin (Invitrogen Gibco, USA) and the cells were incubated at 37° C. in an atmosphere of 5% $CO_2$.

120 hours later, 100 uL medium was discarded and 10 µl Cell Counting Kit-8 reagent (Dojindo, Japan) was added to each well and incubated at 37° C. for 4 h. The number of viable cells was assessed by measurement of absorbance at 450 nm using SpectraMax Plus384 (Molecular Devices, USA). Half-maximal growth inhibitory concentrations (GI50) values were calculated by using Sigma Plot or Prism6 software.

5. Wound Healing Assay

Breast cancer cells (MDA-MD-231) were seeded into 12-well plates (2500 cells/well), at bottom of which culture-inserts were implemented. The cells were cultured to sub-confluence in RPMI1640 medium supplemented with 0.5% FBS and 100 µg/ml penicillin/streptomycin, and then starved in serum-free media for one day at 37° C. and 5% $CO_2$. The inserts were removed to generate two cell patches separated each other by 0.9 mm of 'wound fields'. Cultures were then treated with test compounds for 24 h. The results of wound healing assays at indicated time were photographed under microscopy with ×40 magnification after generating the wound fields. Compound No. 144 suppressed MDA-MB-231 cell migration compared to DMSO and compound No. 87, an inactive compound (see FIG. 1). Similar results were obtained in three independent samples. The cancer cells were stained with 0.1% crystal violet at 24-hours time points.

6. Cell Invasion Assay

Figure 2:
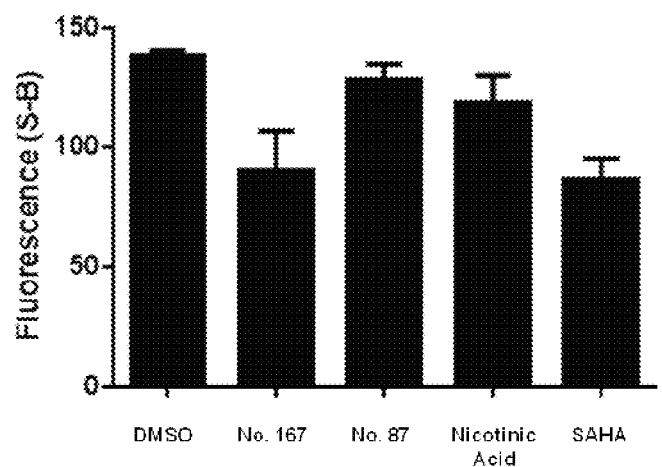
FIG. 2 shows the results of clonogenic assay of the present compounds.

The ability of MDA-MB-231 breast cancer cells to invade into the basement membrane through a layer of BME (Basement Membrane Extract) was determined by using transwell inserts in a 24-well plate. The pore size of membrane was 0.5 µm. The basement membrane was reconstituted by loading cold BME on top of the polycarbonate filter of the inserts of the transwell plate. After gelation of Matrigel at 37° C., MDA-MB-231 cells were plated into the inserts (1×105 cells/0.3 ml/well), and complete media were added to the lower wells (0.5 ml/well). To analyze the effect of 10 µM of compounds No. 87, 167, isonicotinic acid r or SAHA, was present in the cell suspensions. After a 24-h incubation, the noninvasive cells were remained within the inserts while cells that traversed through the BME and the polycarbonate filter were attached to the lower surface of the filter. The penetrated cells were then stained with 0.1% crystal violet. As shown in FIG. 2, Compound No. 167 decreased the MDA-MB-231 breast cancer cell invasion potential as well as SAHA.

What is claimed is:

1. A compound represented by following Formula 1, an isomer thereof, or a pharmaceutically acceptable salt thereof:

<Formula (I)>

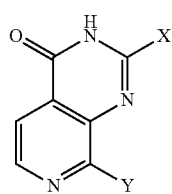

wherein,

X is selected from the group consisting of hydrogen, cycloalkyl, heterocyclyl, aryl, heteroaryl, —CH($R^1$)NH—$R^2$ and —CH($R^1$)O—$R^2$, which cycloalkyl, heterocyclyl, aryl and heteroaryl may optionally be substituted with one or more $R^3$;

Y is —$CH_2$NH-A-Z—;

A is selected from the group consisting of a single bond, $C_{1-8}$ alkylene, $C_{2-8}$ alkenylene, $C_{2-8}$ alkynylene, $C_{3-10}$ cycloalkylene, heterocyclylene, —C(=O)— and —CH($R^3$)C(=O)—, which alkylene, alkenylene, alkynylene, cycloalkylene and heterocyclylene may optionally be substituted with one or more $R^4$;

Z is selected from the group consisting of hydrogen, —N($R^4$)($R^5$), $C_{1-8}$ alkyl, $C_{2-8}$ alkenyl, $C_{2-8}$ alkynyl, $C_{3-10}$ cycloalkyl, heterocyclyl, aryl, arylalkyl and heteroaryl, which alkyl, alkenyl, alkynyl, cycloalkyl, heterocyclyl, aryl, arylalkyl and heteroaryl may optionally be substituted with one or more $R^3$;

$R^1$ is selected from the group consisting of hydrogen, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, arylalkyl, heterocyclyl and heteroarylalkyl, which heterocyclyl may optionally be substituted with one or more selected from the group consisting of halogen and $C_{1-8}$alkyl;

$R^2$ is selected from the group consisting of aryl, arylalkyl and heteroaryl, which aryl, arylalkyl and heteroaryl may optionally be substituted with one or more selected from hydrogen, halogen, $C_{1-8}$ alkyl, $C_{2-8}$ alkenyl, $C_{2-8}$ alkynyl, $C_{3-10}$ cycloalkyl, —$CF_3$, —CN, —$NO_2$, —C(=O)—O($R^4$), —C(=O)—N($R^4$)($R^5$), —O($R^4$), —$OCF_3$, —S($R^4$), —$SO_3$, —$SO_2$($R^4$), —N($R^4$)($R^5$), $C_{1-8}$ alkoxy$C_{1-8}$ alkyl, —$C_{1-8}$ alkyl-C(=O)$R^4$, —C(=O)$R^4$, —$C_{1-8}$ alkyl-$R^4$, —NH—C(=O)$R^4$ and —$C_{1-8}$alkyl-N$R^4R^5$;

$R^3$ is selected from the group consisting of hydrogen, $C_{1-8}$ alkyl, $C_{1-4}$ aminoalkyl, $C_{1-4}$ hydroxyalkyl, $C_{2-8}$ alkenyl, $C_{2-8}$ alkynyl, $C_{3-10}$ cycloalkyl, oxo, C(=O)—O($R^4$), —C(=O)—N($R^4$)($R^5$)—O($R^4$), —S($R^4$), —$SO_2$($R^4$) and —N($R^4$)($R^5$); or, alternatively two vicinal substituents are forming aryl or heteroaryl ring, which is substituted with one or more $R^4$, $R^4$ or $R^5$ is independently selected from the group consisting of hydrogen, $C_{1-6}$ alkyl, $C_{1-4}$ aminoalkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, cycloalkylalkyl, heterocyclyl, heterocyclylalkyl, heteroarylalkyl and arylalkyl, which alkyl, alkenyl, alkynyl, cycloalkyl, heterocyclyl, heteroaryl, aryl, cycloalkylalkyl, heterocyclylalkyl, heteroarylalkyl and arylalkyl may optionally be substituted with one or more independently selected $R^1$; or, alternatively germinal $R^4$ and $R^5$ are forming N-containing heterocyclyl, which is substituted with one or more $R^1$.

2. The compound of claim 1, the isomer thereof, or the pharmaceutically acceptable salt thereof, wherein X is selected from the group consisting of hydrogen, $C_{3-8}$ cycloalkyl, 4 to 10-membered heterocyclyl having 1 to 3 hetero atoms selected from the group consisting of N, O and S, phenyl, 4 to 10-membered heteroaryl having 1 to 3 hetero atoms selected from the group consisting of N, O and S, —CH($R^1$)NH—$R^2$ and CH($R^1$)O—$R^2$, which heterocyclyl may optionally be substituted with $R^3$;

A is selected from the group consisting of a single bond, $C_{1-8}$ alkylene, $C_{2-8}$ alkenylene, $C_{2-8}$ alkynylene, $C_{3-10}$ cycloalkylene, heterocyclylene, —C(=O)— and —CH($R^3$)C(=O)—, which alkylene, alkenylene, alkynylene, cycloalkylene and heterocyclylene may optionally be substituted with one or more $R^4$;

Z is selected from the group consisting of hydrogen, —N($R^4$)($R^5$), $C_{1-6}$ alkyl, $C_{2-6}$ alkenyl, $C_{2-6}$ alkynyl, $C_{3-8}$ cycloalkyl, aryl, arylalkyl, phenyl, 4 to 10-membered heterocyclyl having 1 to 3 hetero atoms selected from the group consisting of N, O and S and 4 to 10-membered heteroaryl having 1 to 3 hetero atoms selected from the group consisting of N, O and S, which alkyl, alkenyl, alkynyl, cycloalkyl, heterocyclyl, heteroaryl, and aryl may optionally be substituted independently with one or more $R^3$;

$R^1$ is selected from the group consisting of hydrogen, $C_{1-8}$ alkyl, $C_{1-3}$ aminoalkyl, $C_{1-3}$ fluoroalkyl, $C_{1-3}$ hydroxyalkyl, $C_{2-6}$ alkenyl, $C_{2-6}$ alkynyl, $C_{3-8}$ cycloalkyl, benzyl, and 4-10 membered heterocyclyl having 1 to 3 hetero atoms selected from the group consisting of N, O and S, which heterocyclyl may optionally be substituted with one or more independently selected from the group consisting of halogen and $C_{1-8}$ alkyl;

$R^2$ is selected from the group consisting of phenyl, benzyl and 4-10 membered heteroaryl having 1 to 3 hetero atoms selected from the group consisting of N, O or S, which phenyl, benzyl and heteroaryl may optionally be substituted with one or more independently selected from hydrogen, halogen, $C_{1-6}$ alkyl, $C_{2-6}$ alkenyl, $C_{2-6}$ alkynyl, $C_3$-cycloalkyl, —$CF_3$, —CN, —$NO_2$, —C(=O)—O($R^4$), —C(=O)—N($R^4$)($R^5$), —O($R^4$), —$OCF_3$, —S($R^4$), —$SO_3$, —$SO_2$($R^4$), —N($R^4$)($R^5$), $C_{1-6}$alkoxy$C_{1-6}$alkyl, —$C_{1-6}$alkyl-C(=O)$R^4$, —C(=O)$R^4$, —$C_{1-6}$alkyl-$R^4$, —NH—C(=O)$R^4$ and —$C_{1-6}$alkyl-N$R^4R^5$;

$R^3$ is selected from the group consisting of hydrogen, $C_{1-6}$ alkyl, $C_{1-4}$ aminoalkyl, $C_{1-4}$ hydroxyalkyl, $C_{2-6}$ alkenyl, $C_{2-6}$ alkynyl, $C_{3-8}$ cycloalkyl, oxo, C(=O)—O($R^4$), —C(=O)—N($R^4$)($R^5$)—O($R^4$), —S($R^4$), —$SO_2$($R^4$) and —N($R^4$)($R^5$); or, alternatively two vicinal substituents are forming phenyl or 4-10 membered heteroaryl ring, which is substituted with one or more $R^4$;

$R^4$ or $R^5$ is independently selected from the group consisting of hydrogen, $C_{1-6}$ alkyl, $C_{1-4}$ aminoalkyl, $C_{1-4}$ fluoroalkyl, $C_{1-4}$ hydroxyalkyl, $C_{2-6}$ alkenyl, $C_{2-6}$ alkynyl, $C_{3-8}$ cycloalkyl, $C_{3-8}$ cycloalkyl$C_{1-4}$ alkyl, 4-10 membered heterocyclyl having 1 to 3 hetero atoms selected from the group consisting of N, O and S, 4-10 membered heterocyclyl $C_{1-4}$ alkyl having 1 to 3 hetero atoms selected from the group consisting of N, O and S, 4-10 membered heteroarylalkyl $C_{1-4}$ alkyl having 1 to 3 hetero atoms selected from the group consisting of N, O and S, and benzyl, which alkyl, alkenyl, alkynyl, cycloalkyl, heterocyclyl, heteroaryl, aryl, cycloalkylalkyl, heterocyclylalkyl, heteroarylalkyl and arylalkyl may optionally be substituted with one or more independently selected $R^1$; or, alternatively germinal $R^4$ and $R^5$ are forming 4-10 membered N-containing heterocyclyl, which is substituted with one or more $R^1$.

3. A compound represented by following Formula 1, an isomer thereof, or a pharmaceutically acceptable salt thereof:

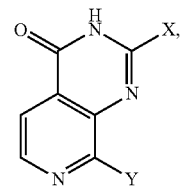

Formula (1)

wherein X is hydrogen, cyclopentyl, tetrahydrofuranyl, benzofuranyl, dihydrobenzofuranyl, chromanyl, dihydroindenyl, tetrahydronaphthalenyl, CH($R^1$)NH—$R^2$ or CH($R^1$)O—$R^2$, wherein the benzofuranyl may optionally be substituted with piperidinoethylaminocarbonyl or methoxycarbonyl;

Y is —$CH_2$NH-A-Z—;

A is a single bond, methylene, ethylene, propylene, butylene, —C(=O)— or —$CH_2$C(=O)—, which methylene, ethylene, propylene and butylene may be optionally substituted with $CH_3$;

Z is hydrogen, amino, benzyl, pyridinyl, cyclohexyl, diethylamino, azetidinyl, pyrrolidinyl, furanyl, thiophenyl, oxazolyl, isoxazolyl, pyrazolyl, imidazolyl, piperidinyl, piperazinyl, pyrimidinyl, pyrazinyl, morpholinyl, tetrahydrofuranyl, tetrahydropyranyl, dihydropyrrolopyridinyl, or piperidinylmethyl, which substituted with one or more independently selected from oxo, Cl, $CH_3$, ethyl, isopropyl, butyl, hydroxyethyl, methoxyethyl, cyclopropyl, benzyl, methylpiperidinyl, —C(=O)—N($CH_3$)$_2$, diethylamino, dimethylamino, methylamino, methylpyrrolidinylmethyl, piperidinyl, benzylpyrrolidinyl pyrrolidinyltetrahydrofuranyl and dimethylaminoethyl;

$R^1$ is hydrogen or methyl;

$R^2$ is phenyl which may optionally be substituted with one or more independently selected from the group consisting of fluoro, chloro, cyano, nitro, methyl, ethyl, butyl, trifluoromethyl, methoxy, cyclopentyl, cyclohexyl, methoxyethyl, —C(=O)—$CH_3$, —(CH$_2$)$_2$—C(=O)—$CH_3$, —NH—C(=O)—$CH_3$, pyridinyl, phenoxy, benzoyl, phenyl, propoxypiperidinylmethyl, methoxycarbonyl, benzyl optionally substituted with methyl, propoxypiperidinomethyl, aminomethyl optionally substituted with tetrahydropyranyl, benzyl, tetrahydropyranmethyl or morpholinoethyl, aminocarbonyl optionally substituted with piperidinoethyl, hydroxyethylpiperidinomethyl, methoxyethylpiperidinomethyl, methylpiperidinomethyl, benzylpiperidinomethyl, morpholinoethyl, benzyl, cyclohexylmethyl, pyridinomethyl, dimethylaminopropyl, cyclopentyl, acetylpiperidinomethyl, piperidinomethyl, aminocyclohexyl, tetrahydropyranomethyl or piperidinoethyl, pyrrolidinocarbonyl, piperidinocarbonyl optionally substituted with benzyl or propoxy, piperazinocarbonyl, morpholinocarbonyl, morpholinoethylaminocarbonyl, phenoxy, benzyloxy optionally substituted with methoxy, benzoyl, or phenyl;

piperidine optionally substituted with methyl or benzyl;

pyridinyl optionally substituted with fluoro, bromo or methyl; pyrazine optionally substituted with bromo; indenyl; or benzyl optionally substituted with chloro.

4. A compound selected from the group consisting of the following compounds:

2-((p-tolyloxy)methyl)pyrido[3,4-d]pyrimidin-4(3H)-one,
2-((4-butylphenoxy)methyl)pyrido[3,4-d]pyrimidin-4(3H)-one,
2-((4-(tert-butyl)phenoxy)methyl)pyrido[3,4-d]pyrimidin-4(3H)-one,
2-((4-(sec-butyl)phenoxy)methyl)pyrido[3,4-d]pyrimidin-4(3H)-one,
2-((4-cyclopentylphenoxy)methyl)pyrido[3,4-d]pyrimidin-4(3H)-one,
2-((4-cyclohexylphenoxy)methyl)pyrido[3,4-d]pyrimidin-4(3H)-one,
2-((4-(2-methoxyethyl)phenoxy)methyl)pyrido[3,4-d]pyrimidin-4(3H)-one,
2-((4-acetylphenoxy)methyl)pyrido[3,4-d]pyrimidin-4(3H)-one,
2-((4-(3-oxobutyl)phenoxy)methyl)pyrido[3,4-d]pyrimidin-4(3H)-one,
N-(4-((4-oxo-3,4-dihydropyrido[3,4-d]pyrimidin-2-yl)methoxy)phenyl)acetamide,
2-(((2,3-dihydro-1H-inden-5-yl)oxy)methyl)pyrido[3,4-d]pyrimidin-4(3H)-one,
2-(((5,6,7,8-tetrahydronaphthalen-2-yl)oxy)methyl)pyrido[3,4-d]pyrimidin-4(3H)-one,
2-((4-(morpholine-4-carbonyl)phenoxy)methyl)pyrido[3,4-d]pyrimidin-4(3H)-one,
2-((3-(piperidine-1-carbonyl)phenoxy)methyl)pyrido[3,4-d]pyrimidin-4(3H)-one,
2-((4-benzylphenoxy)methyl)pyrido[3,4-d]pyrimidin-4(3H)-one,
2-((4-(1-phenylethyl)phenoxy)methyl)pyrido[3,4-d]pyrimidin-4(3H)-one,
2-((4-(2-phenylpropan-2-yl)phenoxy)methyl)pyrido[3,4-d]pyrimidin-4(3H)-one,
2-((4-phenoxyphenoxy)methyl)pyrido[3,4-d]pyrimidin-4(3H)-one,
2-((4-(benzyloxy)phenoxy)methyl)pyrido[3,4-d]pyrimidin-4(3H)-one,
2-((3-(benzyloxy)phenoxy)methyl)pyrido[3,4-d]pyrimidin-4(3H)-one,
2-((4-benzoylphenoxy)methyl)pyrido[3,4-d]pyrimidin-4(3H)-one,
2-(([1,1'-biphenyl]-3-yloxy)methyl)pyrido[3,4-d]pyrimidin-4(3H)-one,
4-((4-oxo-3,4-dihydropyrido[3,4-d]pyrimidin-2-yl)methoxy)benzonitrile,
3-((4-oxo-3,4-dihydropyrido[3,4-d]pyrimidin-2-yl)methoxy)benzonitrile,
2-((4-nitrophenoxy)methyl)pyrido[3,4-d]pyrimidin-4(3H)-one,
2-((4-methoxyphenoxy)methyl)pyrido[3,4-d]pyrimidin-4(3H)-one,
2-((pyridin-4-yloxy)methyl)pyrido[3,4-d]pyrimidin-4(3H)-one,
2-((pyridin-3-yloxy)methyl)pyrido[3,4-d]pyrimidin-4(3H)-one,
2-(((6-fluoropyridin-3-yl)oxy)methyl)pyrido[3,4-d]pyrimidin-4(3H)-one,
2-(((6-bromopyridin-3-yl)oxy)methyl)pyrido[3,4-d]pyrimidin-4(3H)-one,
2-(((6-methylpyridin-3-yl)oxy)methyl)pyrido[3,4-d]pyrimidin-4(3H)-one,
2-((3,4,5-trimethoxyphenoxy)methyl)pyrido[3,4-d]pyrimidin-4(3H)-one,
N-(2-morpholinoethyl)-3-((4-oxo-3,4-dihydropyrido[3,4-d]pyrimidin-2-yl)methoxy)benzamide,
2-((3-((((tetrahydro-2H-pyran-4-yl)methyl)amino)methyl)phenoxy)methyl)pyrido[3,4-d]pyrimidin-4(3H)-one,
2-((3-((benzylamino)methyl)phenoxy)methyl)pyrido[3,4-d]pyrimidin-4(3H)-one,
2-((3-((4-propoxypiperidin-1-yl)methyl)phenoxy)methyl)pyrido[3,4-d]pyrimidin-4(3H)-one,
2-((3-(((tetrahydro-2H-pyran-4-yl)amino)methyl)phenoxy)methyl)pyrido[3,4-d]pyrimidin-4(3H)-one,
2-((3-(((2-morpholinoethyl)amino)methyl)phenoxy)methyl)pyrido[3,4-d]pyrimidin-4(3H)-one,
2-chloro-5-((4-oxo-3,4-dihydropyrido[3,4-d]pyrimidin-2-yl)methoxy)-N-(2-(piperidin-4-yl)ethyl)benzamide,
2-chloro-N-((1-(2-hydroxyethyl)piperidin-4-yl)methyl)-5-((4-oxo-3,4-dihydropyrido[3,4-d]pyrimidin-2-yl)methoxy)benzamide,
2-chloro-N-((1-(2-methoxyethyl)piperidin-4-yl)methyl)-5-((4-oxo-3,4-dihydropyrido[3,4-d]pyrimidin-2-yl)methoxy)benzamide,
2-chloro-N-((1-methylpiperidin-4-yl)methyl)-5-((4-oxo-3,4-dihydropyrido[3,4-d]pyrimidin-2-yl)methoxy)benzamide,
N-((1-benzylpipendin-4-yl)methyl)-2-chloro-5-((4-oxo-3,4-dihydropyrido[3,4-d]pyrimidin-2-yl)methoxy)benzamide,
2-chloro-N-(2-morpholinoethyl)-5-((4-oxo-3,4-dihydropyrido[3,4-d]pyrimidin-2-yl)methoxy)benzamide,
N-benzyl-2-chloro-5-((4-oxo-3,4-dihydropyrido[3,4-d]pyrimidin-2-yl)methoxy)benzamide,
2-((3-(4-benzylpipendine-1-carbonyl)-4-chlorophenoxy)methyl)pyrido[3,4-d]pyrimidin-4(3H)-one,
2-((4-chloro-3-(4-propoxypiperidine-1-carbonyl)phenoxy)methyl)pyrido[3,4-d]pyrimidin-4(3H)-one,
2-chloro-N-(cyclohexylmethyl)-5-((4-oxo-3,4-dihydropyrido[3,4-d]pyrimidin-2-yl)methoxy)benzamide,
2-chloro-5-((4-oxo-3,4-dihydropyrido[3,4-d]pyrimidin-2-yl)methoxy)-N-(pyridin-4-ylmethyl)benzamide,
2-chloro-N-(3-(dimethylamino)propyl)-5-((4-oxo-3,4-dihydropyrido[3,4-d]pyrimidin-2-yl)methoxy)benzamide,
2-chloro-N-cyclopentyl-5-((4-oxo-3,4-dihydropyrido[3,4-d]pyrimidin-2-yl)methoxy)benzamide,
2-((4-chloro-3-(pyrrolidine-1-carbonyl)phenoxy)methyl)pyrido[3,4-d]pyrimidin-4(3H)-one,
2-((4-chloro-3-(piperidine-1-carbonyl)phenoxy)methyl)pyrido[3,4-d]pyrimidin-4(3H)-one,
N-((1-acetylpipendin-4-yl)methyl)-2-chloro-5-((4-oxo-3,4-dihydropyrido[3,4-d]pyrimidin-2-yl)methoxy)benzamide,
2-((4-chloro-3-(piperazine-1-carbonyl)phenoxy)methyl)pyrido[3,4-d]pyrimidin-4(3H)-one,
N-(trans-1,4-aminocyclohexyl)-2-chloro-5-((4-oxo-3,4-dihydropyrido[3,4-d]pyrimidin-2-yl)methoxy)benzamide,
2-chloro-5-((4-oxo-3,4-dihydropyrido[3,4-d]pyrimidin-2-yl)methoxy)-N-(piperidin-4-ylmethyl)benzamide,
2-((4-chloro-3-(morpholine-4-carbonyl)phenoxy)methyl)pyrido[3,4-d]pyrimidin-4(3H)-one,
2-chloro-5-((4-oxo-3,4-dihydropyrido[3,4-d]pyrimidin-2-yl)methoxy)-N-((tetrahydro-2H-pyran-4-yl)methyl)benzamide,
2-methyl-5-((4-oxo-3,4-dihydropyrido[3,4-d]pyrimidin-2-yl)methoxy)-N-(2-(piperidin-4-yl)ethyl)benzamide,
2-bromo-5-((4-oxo-3,4-dihydropyrido[3,4-d]pyrimidin-2-yl)methoxy)-N-(2-(piperidin-4-yl)ethyl)benzamide,
methyl 2-chloro-5-((4-oxo-3,4-dihydropyrido[3,4-d]pyrimidin-2-yl)methoxy)benzoate, 2-((2-(pyridin-4-yl)phenoxy)methyl)pyrido[3,4-d]pyrimidin-4(3H)-one,
2-(4-oxo-3,4-dihydropyrido[3,4-d]pyrimidin-2-yl)-N-(2-(piperidin-4-yl)ethyl)benzofuran-7-carboxamide,
methyl 2-(4-oxo-3,4-dihydropyrido[3,4-d]pyrimidin-2-yl)benzofuran-7-carboxylate,
2-(((4-(sec-butyl)phenyl)amino)methyl)pyrido[3,4-d]pyrimidin-4(3H)-one,
2-(((4-cyclohexylphenyl)amino)methyl)pyrido[3,4-d]pyrimidin-4(3H)-one,
2-(((4-phenoxyphenyl)amino)methyl)pyrido[3,4-d]pyrimidin-4(3H)-one,
2-(((4-(benzyloxy)phenyl)amino)methyl)pyrido[3,4-d]pyrimidin-4(3H)-one,
2-(((4-((4-methoxybenzyl)oxy)phenyl)amino)methyl)pyrido[3,4-d]pyrimidin-4(3H)-one,
2-(((3-(benzyloxy)phenyl)amino)methyl)pyrido[3,4-d]pyrimidin-4(3H)-one,
2-((([1,1'-biphenyl]-3-ylamino)methyl)pyrido[3,4-d]pyrimidin-4(3H)-one,
2-(((3,4-difluorophenyl)amino)methyl)pyrido[3,4-d]pyrimidin-4(3H)-one,
2-(((1-methylpiperidin-4-yl)amino)methyl)pyrido[3,4-d]pyrimidin-4(3H)-one,
2-(((1-benzylpiperidin-4-yl)amino)methyl)pyrido[3,4-d]pyrimidin-4(3H)-one,
8-((benzylamino)methyl)pyrido[3,4-d]pyrimidin-4(3H)-one,
8-(((((2,6-dichloropyridin-4-yl)methyl)amino)methyl)pyrido[3,4-d]pyrimidin-4(3H)-one,
8-(((cyclohexylmethyl)amino)methyl)pyrido[3,4-d]pyrimidin-4(3H)-one,
8-(((4-(diethylamino)butyl)amino)methyl)pyrido[3,4-d]pyrimidin-4(3H)-one,
8-(((5-(diethylamino)pentan-2-yl)amino)methyl)pyrido[3,4-d]pyrimidin-4(3H)-one,
8-(((3-(2-oxopyrrolidin-1-yl)propyl)amino)methyl)pyrido[3,4-d]pyrimidin-4(3H)-one,
8-(((azetidin-3-ylmethyl)amino)methyl)pyrido[3,4-d]pyrimidin-4(3H)-one,
8-(((pyrrolidin-3-ylmethyl)amino)methyl)pyrido[3,4-d]pyrimidin-4(3H)-one,
(S)-8-(((pyrrolidin-2-ylmethyl)amino)methyl)pyrido[3,4-d]pyrimidin-4(3H)-one,
8-((((1-methylpyrrolidin-3-yl)methyl)amino)methyl)pyrido[3,4-d]pyrimidin-4(3H)-one,
8-(((piperidin-4-ylmethyl)amino)methyl)pyrido[3,4-d]pyrimidin-4(3H)-one,
8-(((1-(piperidin-4-yl)ethyl)amino)methyl)pyrido[3,4-d]pyrimidin-4(3H)-one,
8-((((1-methylpiperidin-4-yl)methyl)amino)methyl)pyrido[3,4-d]pyrimidin-4(3H)-one,
8-((((1-benzylpiperidin-4-yl)methyl)amino)methyl)pyrido[3,4-d]pyrimidin-4(3H)-one,
8-((((1'-methyl-[1,4'-bipiperidin]-4-yl)methyl)amino)methyl)pyrido[3,4-d]pyrimidin-4(3H)-one,
(R)-8-(((piperidin-3-ylmethyl)amino)methyl)pyrido[3,4-d]pyrimidin-4(3H)-one,
(S)-8-(((piperidin-3-ylmethyl)amino)methyl)pyrido[3,4-d]pyrimidin-4(3H)-one,
8-((((1-methylpiperidin-3-yl)methyl)amino)methyl)pyrido[3,4-d]pyrimidin-4(3H)-one,
8-((((1-benzylpiperidin-3-yl)methyl)amino)methyl)pyrido[3,4-d]pyrimidin-4(3H)-one,
8-((((1-benzylpiperidin-2-yl)methyl)amino)methyl)pyrido[3,4-d]pyrimidin-4(3H)-one,
8-((((1-benzylpiperidin-4-yl)amino)methyl)pyrido[3,4-d]pyrimidin-4(3H)-one,
8-((((1s,4s)-4-aminocyclohexyl)amino)methyl)pyrido[3,4-d]pyrimidin-4(3H)-one,
8-((((1-benzylpiperidin-4-yl)methyl)amino)methyl)-2-((2-chlorophenoxy)methyl)pyrido[3,4-d]pyrimidin-4(3H)-one,
8-((((1-benzylpiperidin-4-yl)methyl)amino)methyl)-2-((3-chlorophenoxy)methyl)pyrido[3,4-d]pyrimidin-4(3H)-one,
8-((((1-benzylpiperidin-4-yl)methyl)amino)methyl)-2-((4-chlorophenoxy)methyl)pyrido[3,4-d]pyrimidin-4(3H)-one,
8-((((1-benzylpiperidin-4-yl)methyl)amino)methyl)-2-((4-bromophenoxy)methyl)pyrido[3,4-d]pyrimidin-4(3H)-one,
8-((((1-benzylpiperidin-4-yl)methyl)amino)methyl)-2-((pyridin-3-yloxy)methyl)pyrido[3,4-d]pyrimidin-4(3H)-one,
8-((((1-benzylpiperidin-4-yl)methyl)amino)methyl)-2-((pyridin-4-yloxy)methyl)pyrido[3,4-d]pyrimidin-4(3H)-one,
2-((4-benzylphenoxy)methyl)-8-((((1-benzylpiperidin-4-yl)methyl)amino)methyl)pyrido[3,4-d]pyrimidin-4(3H)-one,
2-((2-chloro-5-(trifluoromethyl)phenoxy)methyl)-8-(((piperidin-4-ylmethyl)amino)methyl)pyrido[3,4-d]pyrimidin-4(3H)-one,
2-((2,3-dichlorophenoxy)methyl)-8-(((piperidin-4-ylmethyl)amino)methyl)pyrido[3,4-d]pyrimidin-4(3H)-one,
2-((2,4-dichlorophenoxy)methyl)-8-(((piperidin-4-ylmethyl)amino)methyl)pyrido[3,4-d]pyrimidin-4(3H)-one,
2-((2,5-dichlorophenoxy)methyl)-8-(((piperidin-4-ylmethyl)amino)methyl)pyrido[3,4-d]pyrimidin-4(3H)-one,
2-((2-fluorophenoxy)methyl)-8-(((piperidin-4-ylmethyl)amino)methyl)pyrido[3,4-d]pyrimidin-4(3H)-one,
2-((2-bromophenoxy)methyl)-8-(((piperidin-4-ylmethyl)amino)methyl)pyrido[3,4-d]pyrimidin-4(3H)-one,
8-(((piperidin-4-ylmethyl)amino)methyl)-2-((o-tolyloxy)methyl)pyrido[3,4-d]pyrimidin-4(3H)-one,
8-(((piperidin-4-ylmethyl)amino)methyl)-2-((m-tolyloxy)methyl)pyrido[3,4-d]pyrimidin-4(3H)-one,
8-(((piperidin-4-ylmethyl)amino)methyl)-2-((p-tolyloxy)methyl)pyrido[3,4-d]pyrimidin-4(3H)-one,
2-((4-benzylphenoxy)methyl)-8-(((piperidin-4-ylmethyl)amino)methyl)pyrido[3,4-d]pyrimidin-4(3H)-one,
2-((2-chlorophenoxy)methyl)-8-(((piperidin-4-ylmethyl)amino)methyl)pyrido[3,4-d]pyrimidin-4(3H)-one,
2-(phenoxymethyl)-8-(((piperidin-4-ylmethyl)amino)methyl)pyrido[3,4-d]pyrimidin-4(3H)-one,
2-((2,4-difluorophenoxy)methyl)-8-(((piperidin-4-ylmethyl)amino)methyl)pyrido[3,4-d]pyrimidin-4(3H)-one,
2-((3,5-difluorophenoxy)methyl)-8-(((piperidin-4-ylmethyl)amino)methyl)pyrido[3,4-d]pyrimidin-4(3H)-one,
2-((3-chloro-4-fluorophenoxy)methyl)-8-(((piperidin-4-ylmethyl)amino)methyl)pyrido[3,4-d]pyrimidin-4(3H)-one,
2-((4-chloro-3-fluorophenoxy)methyl)-8-(((piperidin-4-ylmethyl)amino)methyl)pyrido[3,4-d]pyrimidin-4(3H)-one, 2-((4-oxo-8-(((piperidin-4-ylmethyl)amino)methyl)-3,4-dihydropyrido[3,4-d]pyrimidin-2-yl)methoxy)benzonitrile,
4-((4-oxo-8-(((piperidin-4-ylmethyl)amino)methyl)-3,4-dihydropyrido[3,4-d]pyrimidin-2-yl)methoxy)benzonitrile,
2-((2-chloro-5-methylphenoxy)methyl)-8-(((piperidin-4-ylmethyl)amino)methyl)pyrido[3,4-d]pyrimidin-4(3H)-one,
2-(((5-bromopyrazin-2-yl)oxy)methyl)-8-(((piperidin-4-ylmethyl)amino)methyl)pyrido[3,4-d]pyrimidin-4(3H)-one,
2-((3-chlorophenoxy)methyl)-8-(((piperidin-4-ylmethyl)amino)methyl)pyrido[3,4-d]pyrimidin-4(3H)-one,
8-(((piperidin-4-ylmethyl)amino)methyl)-2-((pyridin-2-yloxy)methyl)pyrido[3,4-d]pyrimidin-4(3H)-one,
2-((4-chloro-3-methylphenoxy)methyl)-8-(((piperidin-4-ylmethyl)amino)methyl)pyrido[3,4-d]pyrimidin-4(3H)-one,
2-((4-ethylphenoxy)methyl)-8-(((piperidin-4-ylmethyl)amino)methyl)pyrido[3,4-d]pyrimidin-4(3H)-one,
2-((3,4-dimethylphenoxy)methyl)-8-(((piperidin-4-ylmethyl)amino)methyl)pyrido[3,4-d]pyrimidin-4(3H)-one,
2-((4-chloro-2-methylphenoxy)methyl)-8-(((piperidin-4-ylmethyl)amino)methyl)pyrido[3,4-d]pyrimidin-4(3H)-one,
3-((4-oxo-8-(((piperidin-4-ylmethyl)amino)methyl)-3,4-dihydropyrido[3,4-d]pyrimidin-2-yl)methoxy)benzonitrile,
2-(((2,3-dihydro-1H-inden-5-yl)oxy)methyl)-8-(((piperidin-4-ylmethyl)amino)methyl)pyrido[3,4-d]pyrimidin-4(3H)-one,
2-((4-cyclopentylphenoxy)methyl)-8-(((piperidin-4-ylmethyl)amino)methyl)pyrido[3,4-d]pyrimidin-4(3H)-one,
2-((4-(1-phenylethyl)phenoxy)methyl)-8-(((piperidin-4-ylmethyl)amino)methyl)pyrido[3,4-d]pyrimidin-4(3H)-one,
2-((4-benzylphenoxy)methyl)-8-(((((1-ethylpyrrolidin-3-yl)methyl)amino)methyl)pyrido[3,4-d]pyrimidin-4(3H)-one,
2-((4-benzylphenoxy)methyl)-8-(((4-(pyrrolidin-1-yl)butyl)amino)methyl)pyrido[3,4-d]pyrimidin-4(3H)-one,
2-((4-benzylphenoxy)methyl)-8-(((((1-methylpyrrolidin-3-yl)methyl)amino)methyl)pyrido[3,4-d]pyrimidin-4(3H)-one,
(R)-2-((4-benzylphenoxy)methyl)-8-(((((1-ethylpyrrolidin-2-yl)methyl)amino)methyl)pyrido[3,4-d]pyrimidin-4(3H)-one,
(S)-2-((4-benzylphenoxy)methyl)-8-(((((1-ethylpyrrolidin-2-yl)methyl)amino)methyl)pyrido[3,4-d]pyrimidin-4(3H)-one,
8-(((azetidin-3-ylmethyl)amino)methyl)-2-((4-benzylphenoxy)methyl)pyrido[3,4-d]pyrimidin-4(3H)-one,
(R)-2-((4-benzylphenoxy)methyl)-8-(((((tetrahydrofuran-2-yl)methyl)amino)methyl)pyrido[3,4-d]pyrimidin-4(3H)-one,
2-((4-benzylphenoxy)methyl)-8-(((((tetrahydro-2H-pyran-4-yl)methyl)amino)methyl)pyrido[3,4-d]pyrimidin-4(3H)-one,
(S)-2-((4-benzylphenoxy)methyl)-8-(((pyrrolidin-3-ylmethyl)amino)methyl)pyrido[3,4-d]pyrimidin-4(3H)-one,
(R)-2-((4-benzylphenoxy)methyl)-8-(((pyrrolidin-3-ylmethyl)amino)methyl)pyrido[3,4-d]pyrimidin-4(3H)-one,
2-((4-benzylphenoxy)methyl)-8-(((((1-methylpiperidin-4-yl)methyl)amino)methyl)pyrido[3,4-d]pyrimidin-4(3H)-one,
(S)-2-((4-benzylphenoxy)methyl)-8-(((piperidin-3-ylmethyl)amino)methyl)pyrido[3,4-d]pyrimidin-4(3H)-one,
(R)-2-((4-benzylphenoxy)methyl)-8-(((piperidin-3-ylmethyl)amino)methyl)pyrido[3,4-d]pyrimidin-4(3H)-one,
8-((((1 r,4r)-4-aminocyclohexyl)amino)methyl)-2-((4-benzylphenoxy)methyl)pyrido[3,4-d]pyrimidin-4(3H)-one,
2-((4-benzylphenoxy)methyl)-8-(((pyridin-3-ylmethyl)amino)methyl)pyrido[3,4-d]pyrimidin-4(3H)-one,
2-((4-benzylphenoxy)methyl)-8-(((2-morpholinoethyl)amino)methyl)pyrido[3,4-d]pyrimidin-4(3H)-one,
(S)-2-((3-chloro-4-fluorophenoxy)methyl)-8-(((pyrrolidin-3-ylmethyl)amino)methyl)pyrido[3,4-d]pyrimidin-4(3H)-one,
2-((3-chloro-4-fluorophenoxy)methyl)-8-(((((1-methylpyrrolidin-3-yl)methyl)amino)methyl)pyrido[3,4-d]pyrimidin-4(3H)-one,
2-((3-chloro-4-fluorophenoxy)methyl)-8-(((((1-methylpiperidin-4-yl)methyl)amino)methyl)pyrido[3,4-d]pyrimidin-4(3H)-one,
2-((3-chloro-4-fluorophenoxy)methyl)-8-(((((tetrahydro-2H-pyran-4-yl)methyl)amino)methyl)pyrido[3,4-d]pyrimidin-4(3H)-one,
2-((3-chloro-4-fluorophenoxy)methyl)-8-(((((tetrahydro-2H-pyran-3-yl)methyl)amino)methyl)pyrido[3,4-d]pyrimidin-4(3H)-one,
2-((3-chloro-4-fluorophenoxy)methyl)-8-(((((tetrahydrofuran-3-yl)methyl)amino)methyl)pyrido[3,4-d]pyrimidin-4(3H)-one,
2-((3-chloro-4-fluorophenoxy)methyl)-8-(((2-morpholinoethyl)amino)methyl)pyrido[3,4-d]pyrimidin-4(3H)-one,
8-(((3-(1H-imidazol-1-yl)propyl)amino)methyl)-2-((3-chloro-4-fluorophenoxy)methyl)pyrido[3,4-d]pyrimidin-4(3H)-one,
2-((3-chloro-4-fluorophenoxy)methyl)-8-(((((5-methylpyrazin-2-yl)methyl)amino)methyl)pyrido[3,4-d]pyrimidin-4(3H)-one,
2-((3-chloro-4-fluorophenoxy)methyl)-8-(((morpholin-2-ylmethyl)amino)methyl)pyrido[3,4-d]pyrimidin-4(3H)-one,
2-((3-chloro-4-fluorophenoxy)methyl)-8-(((((1-isopropylpiperidin-4-yl)methyl)amino)methyl)pyrido[3,4-d]pyrimidin-4(3H)-one,
2-((3-chloro-4-fluorophenoxy)methyl)-8-(((((1-cyclopentylpiperidin-4-yl)methyl)amino)methyl)pyrido[3,4-d]pyrimidin-4(3H)-one,
2-((3-chloro-4-fluorophenoxy)methyl)-8-(((pyridin-2-ylmethyl)amino)methyl)pyrido[3,4-d]pyrimidin-4(3H)-one,
2-((3-chloro-4-fluorophenoxy)methyl)-8-(((furan-2-ylmethyl)amino)methyl)pyrido[3,4-d]pyrimidin-4(3H)-one,
2-((3-chloro-4-fluorophenoxy)methyl)-8-(((pyridin-3-ylmethyl)amino)methyl)pyrido[3,4-d]pyrimidin-4(3H)-one,
2-((3-chloro-4-fluorophenoxy)methyl)-8-(((pyridin-4-ylmethyl)amino)methyl)pyrido[3,4-d]pyrimidin-4(3H)-one,
5-(((((2-((3-chloro-4-fluorophenoxy)methyl)-4-oxo-3,4-dihydropyrido[3,4-d]pyrimidin-8-yl)methyl)amino)methyl)-N,N-dimethylfuran-2-carboxamide, 2-((3-chloro-4-fluorophenoxy)methyl)-8-(((2-(2-methyl-1H-imidazol-1-yl)ethyl)amino)methyl)pyrido[3,4-d]pyrimidin-4(3H)-one, 2-((3-chloro-4-fluorophenoxy)methyl)-8-(((2-(thiophen-2-yl)ethyl)amino)methyl)pyrido[3,4-d]pyrimidin-4(3H)-one, 2-((3-chloro-4-fluorophenoxy)methyl)-8-((((3-methylisoxazol-5-yl)methyl)amino)methyl)pyrido[3,4-d]pyrimidin-4(3H)-one, 2-((3-chloro-4-fluorophenoxy)methyl)-8-((((4-methylmorpholin-2-yl)methyl)amino)methyl)pyrido[3,4-d]pyrimidin-4(3H)-one, 2-((3-chloro-4-fluorophenoxy)methyl)-8-(((oxazol-2-ylmethyl)amino)methyl)pyrido[3,4-d]pyrimidin-4(3H)-one, 2-((3-chloro-4-fluorophenoxy)methyl)-8-(((pyrimidin-2-ylmethyl)amino)methyl)pyrido[3,4-d]pyrimidin-4(3H)-one, 2-((3-chloro-4-fluorophenoxy)methyl)-8-(((thiophen-2-ylmethyl)amino)methyl)pyrido[3,4-d]pyrimidin-4(3H)-one, 2-((3-chloro-4-fluorophenoxy)methyl)-8-((((2-chloropyridin-4-yl)methyl)amino)methyl)pyrido[3,4-d]pyrimidin-4(3H)-one, 2-((3-chloro-4-fluorophenoxy)methyl)-8-(((2-(3,5-dimethyl-1H-pyrazol-1-yl)ethyl)amino)methyl)pyrido[3,4-d]pyrimidin-4(3H)-one, 2-((3-chloro-4-fluorophenoxy)methyl)-8-(((2-(6-methylpyridin-2-yl)ethyl)amino)methyl)pyrido[3,4-d]pyrimidin-4(3H)-one, 2-((3-chloro-4-fluorophenoxy)methyl)-8-(((3-(5-oxo-5,7-dihydro-6H-pyrrolo[3,4-b]pyridin-6-yl)propyl)amino)methyl)pyrido[3,4-d]pyrimidin-4(3H)-one, 2-((3-chloro-4-fluorophenoxy)methyl)-8-(((2-(pyridin-2-yl)ethyl)amino)methyl)pyrido[3,4-d]pyrimidin-4(3H)-one, (R)-2-((3-chloro-4-fluorophenoxy)methyl)-8-(((morpholin-2-ylmethyl)amino)methyl)pyrido[3,4-d]pyrimidin-4(3H)-one, 2-((3-chloro-4-fluorophenoxy)methyl)-8-((((1-(2-hydroxyethyl)piperidin-4-yl)methyl)amino)methyl)pyrido[3,4-d]pyrimidin-4(3H)-one, 2-((3-chloro-4-fluorophenoxy)methyl)-8-((((1-(2-methoxyethyl)piperidin-4-yl)methyl)amino)methyl)pyrido[3,4-d]pyrimidin-4(3H)-one, (S)-2-((3-chloro-4-fluorophenoxy)methyl)-8-(((morpholin-2-ylmethyl)amino)methyl)pyrido[3,4-d]pyrimidin-4(3H)-one, 2-cyclopentyl-8-(((piperidin-4-ylmethyl)amino)methyl)pyrido[3,4-d]pyrimidin-4(3H)-one, 2-cyclopentyl-8-((((1-methylpiperidin-4-yl)methyl)amino)methyl)pyrido[3,4-d]pyrimidin-4(3H)-one, 8-(((piperidin-4-ylmethyl)amino)methyl)-2-(tetrahydrofuran-2-yl)pyrido[3,4-d]pyrimidin-4(3H)-one, 8-((((1-methylpiperidin-4-yl)methyl)amino)methyl)-2-(tetrahydrofuran-2-yl)pyrido[3,4-d]pyrimidin-4(3H)-one, 8-(((piperidin-4-ylmethyl)amino)methyl)-2-(tetrahydrofuran-3-yl)pyrido[3,4-d]pyrimidin-4(3H)-one, 8-((((1-methylpiperidin-4-yl)methyl)amino)methyl)-2-(tetrahydrofuran-3-yl)pyrido[3,4-d]pyrimidin-4(3H)-one, 2-(2,3-dihydrobenzofuran-2-yl)-8-(((piperidin-4-ylmethyl)amino)methyl)pyrido[3,4-d]pyrimidin-4(3H)-one, 2-(2,3-dihydrobenzofuran-2-yl)-8-((((1-methylpiperidin-4-yl)methyl)amino)methyl)pyrido[3,4-d]pyrimidin-4(3H)-one, 2-(chroman-2-yl)-8-(((piperidin-4-ylmethyl)amino)methyl)pyrido[3,4-d]pyrimidin-4(3H)-one, 2-(chroman-2-yl)-8-((((1-methylpiperidin-4-yl)methyl)amino)methyl)pyrido[3,4-d]pyrimidin-4(3H)-one, 2-(2,3-dihydro-1H-inden-2-yl)-8-((((1-methylpiperidin-4-yl)methyl)amino)methyl)pyrido[3,4-d]pyrimidin-4(3H)-one, 2-((benzyloxy)methyl)-8-(((piperidin-4-ylmethyl)amino)methyl)pyrido[3,4-d]pyrimidin-4(3H)-one, 2-((benzyloxy)methyl)-8-((((1-methylpiperidin-4-yl)methyl)amino)methyl)pyrido[3,4-d]pyrimidin-4(3H)-one, (S)-2-((benzyloxy)methyl)-8-(((pyrrolidin-3-ylmethyl)amino)methyl)pyrido[3,4-d]pyrimidin-4(3H)-one, 2-((benzyloxy)methyl)-8-((((1-methylpyrrolidin-3-yl)methyl)amino)methyl)pyrido[3,4-d]pyrimidin-4(3H)-one, 2-(((3-chlorobenzyl)oxy)methyl)-8-(((piperidin-4-ylmethyl)amino)methyl)pyrido[3,4-d]pyrimidin-4(3H)-one, 2-(((3-chlorobenzyl)oxy)methyl)-8-((((1-methylpiperidin-4-yl)methyl)amino)methyl)pyrido[3,4-d]pyrimidin-4(3H)-one, (S)-2-(((3-chlorobenzyl)oxy)methyl)-8-(((pyrrolidin-3-ylmethyl)amino)methyl)pyrido[3,4-d]pyrimidin-4(3H)-one, 2-(((2-chlorobenzyl)oxy)methyl)-8-(((piperidin-4-ylmethyl)amino)methyl)pyrido[3,4-d]pyrimidin-4(3H)-one, 2-(((2-chlorobenzyl)oxy)methyl)-8-((((1-methylpiperidin-4-yl)methyl)amino)methyl)pyrido[3,4-d]pyrimidin-4(3H)-one, 2-(1-(4-benzylphenoxy)ethyl)-8-((((1-methylpiperidin-4-yl)methyl)amino)methyl)pyrido[3,4-d]pyrimidin-4(3H)-one, 2-(1-(4-benzylphenoxy)ethyl)-8-(((piperidin-4-ylmethyl)amino)methyl)pyrido[3,4-d]pyrimidin-4(3H)-one, 2-(1-(4-benzylphenoxy)ethyl)-8-(((((S)-pyrrolidin-3-yl)methyl)amino)methyl)pyrido[3,4-d]pyrimidin-4(3H)-one, 2-(1-(4-benzylphenoxy)ethyl)-8-((((1-methylpyrrolidin-3-yl)methyl)amino)methyl)pyrido[3,4-d]pyrimidin-4(3H)-one, (R)-2-(1-(4-benzylphenoxy)ethyl)-8-(((piperidin-4-ylmethyl)amino)methyl)pyrido[3,4-d]pyrimidin-4(3H)-one, (R)-2-(1-(4-benzylphenoxy)ethyl)-8-((((1-methylpiperidin-4-yl)methyl)amino)methyl)pyrido[3,4-d]pyrimidin-4(3H)-one, (R)-2-(1-(3-chloro-4-fluorophenoxy)ethyl)-8-(((piperidin-4-ylmethyl)amino)methyl)pyrido[3,4-d]pyrimidin-4(3H)-one, (R)-2-(1-(3-chloro-4-fluorophenoxy)ethyl)-8-((((1-methylpiperidin-4-yl)methyl)amino)methyl)pyrido[3,4-d]pyrimidin-4(3H)-one, (S)-2-(1-(3-chloro-4-fluorophenoxy)ethyl)-8-(((piperidin-4-ylmethyl)amino)methyl)pyrido[3,4-d]pyrimidin-4(3H)-one, (S)-2-(1-(3-chloro-4-fluorophenoxy)ethyl)-8-((((1-methylpiperidin-4-yl)methyl)amino)methyl)pyrido[3,4-d]pyrimidin-4(3H)-one, 2-(((2-((3-chloro-4-fluorophenoxy)methyl)-4-oxo-3,4-dihydropyrido[3,4-d]pyrimidin-8-yl)methyl)amino)-N-(2-(dimethylamino)ethyl)-N-ethylacetamide, N-butyl-2-(((2-((3-chloro-4-fluorophenoxy)methyl)-4-oxo-3,4-dihydropyrido[3,4-d]pyrimidin-8-yl)methyl)amino)-N-ethylacetamide,
2-((3-chloro-4-fluorophenoxy)methyl)-8-(((2-oxo-2-(pyrrolidin-1-yl)ethyl)amino)methyl)pyrido[3,4-d]pyrimidin-4(3H)-one,
2-((3-chloro-4-fluorophenoxy)methyl)-8-(((2-oxo-2-(piperidin-1-yl)ethyl)amino)methyl)pyrido[3,4-d]pyrimidin-4(3H)-one,
2-((3-chloro-4-fluorophenoxy)methyl)-8-(((2-morpholino-2-oxoethyl)amino)methyl)pyrido[3,4-d]pyrimidin-4(3H)-one,
2-((3-chloro-4-fluorophenoxy)methyl)-8-(((2-(4-methylpiperazin-1-yl)-2-oxoethyl)amino)methyl)pyrido[3,4-d]pyrimidin-4(3H)-one,
2-(((2-((3-chloro-4-fluorophenoxy)methyl)-4-oxo-3,4-dihydropyrido[3,4-d]pyrimidin-8-yl)methyl)amino)-N-((1-methylpyrrolidin-3-yl)methyl)acetamide,
(R)-8-(((2-(3-aminopyrrolidin-1-yl)-2-oxoethyl)amino)methyl)-2-((3-chloro-4-fluorophenoxy)methyl)pyrido[3,4-d]pyrimidin-4(3H)-one,
(S)-8-(((2-(3-aminopyrrolidin-1-yl)-2-oxoethyl)amino)methyl)-2-((3-chloro-4-fluorophenoxy)methyl)pyrido[3,4-d]pyrimidin-4(3H)-one,
(R)-2-(((2-((3-chloro-4-fluorophenoxy)methyl)-4-oxo-3,4-dihydropyrido[3,4-d]pyrimidin-8-yl)methyl)amino)-N-(piperidin-3-yl)acetamide,
(S)-2-(((2-((3-chloro-4-fluorophenoxy)methyl)-4-oxo-3,4-dihydropyrido[3,4-d]pyrimidin-8-yl)methyl)amino)-N-(piperidin-3-yl)acetamide,
N-(1-benzylpyrrolidin-3-yl)-2-(((2-((3-chloro-4-fluorophenoxy)methyl)-4-oxo-3,4-dihydropyrido[3,4-d]pyrimidin-8-yl)methyl)amino)acetamide,
2-(((2-((3-chloro-4-fluorophenoxy)methyl)-4-oxo-3,4-dihydropyrido[3,4-d]pyrimidin-8-yl)methyl)amino)-N-(trans-5-(pyrrolidin-1-yl)tetrahydrofuran-2-yl)acetamide,
2-((3-chloro-4-fluorophenoxy)methyl)-8-(((2-oxo-2-(4-(pyrrolidin-1-yl)piperidin-1-yl)ethyl)amino)methyl)pyrido[3,4-d]pyrimidin-4(3H)-one,
2-((3-chloro-4-fluorophenoxy)methyl)-8-(((2-(3-morpholinopyrrolidin-1-yl)-2-oxoethyl)amino)methyl)pyrido[3,4-d]pyrimidin-4(3H)-one,
2-((3-chloro-4-fluorophenoxy)methyl)-8-(((2-(3-(diethylamino)pyrrolidin-1-yl)-2-oxoethyl)amino)methyl)pyrido[3,4-d]pyrimidin-4(3H)-one,
2-((3-chloro-4-fluorophenoxy)methyl)-8-(((2-(3-(dimethylamino)pyrrolidin-1-yl)-2-oxoethyl)amino)methyl)pyrido[3,4-d]pyrimidin-4(3H)-one,
2-((3-chloro-4-fluorophenoxy)methyl)-8-(((2-(3-(methylamino)pyrrolidin-1-yl)-2-oxoethyl)amino)methyl)pyrido[3,4-d]pyrimidin-4(3H)-one,
(R)-2-(((2-((3-chloro-4-fluorophenoxy)methyl)-4-oxo-3,4-dihydropyrido[3,4-d]pyrimidin-8-yl)methyl)amino)-N-(pyrrolidin-3-yl)acetamide,
N-((2-((3-chloro-4-fluorophenoxy)methyl)-4-oxo-3,4-dihydropyrido[3,4-d]pyrimidin-8-yl)methyl)-2-(piperidin-4-yl)acetamide, and
N-((2-((3-chloro-4-fluorophenoxy)methyl)-4-oxo-3,4-dihydropyrido[3,4-d]pyrimidin-8-yl)methyl)piperidine-3-carboxamide.

5. A pharmaceutical composition comprising the compound of claim 1, the isomer thereof, or the pharmaceutically acceptable salt thereof, as an effective ingredient, and a pharmaceutically acceptable excipient.

* * * * *